US007375186B2

(12) United States Patent
Borgford

(10) Patent No.: US 7,375,186 B2
(45) **Date of Patent: *May 20, 2008**

(54) RICIN-LIKE TOXIN VARIANTS FOR TREATMENT OF CANCER, VIRAL OR PARASITIC INFECTIONS

(75) Inventor: Thor Borgford, New Westminster (CA)

(73) Assignee: Twinstrand Therapeutics Inc., Vancouver, British Columbia (CA)

( * ) Notice: Subject to any disclaimer, the term of this patent is extended or adjusted under 35 U.S.C. 154(b) by 707 days.

This patent is subject to a terminal disclaimer.

(21) Appl. No.: 10/394,511

(22) Filed: Mar. 24, 2003

(65) Prior Publication Data

US 2004/0009551 A1 Jan. 15, 2004

Related U.S. Application Data

(62) Division of application No. 09/403,752, filed as application No. PCT/CA98/00394 on Apr. 30, 1998, now Pat. No. 6,593,132.

(60) Provisional application No. 60/063,715, filed on Oct. 29, 1997, provisional application No. 60/045,148, filed on Apr. 30, 1997.

(51) Int. Cl.
*C07K 14/00* (2006.01)

(52) U.S. Cl. .................................................. 530/350

(58) Field of Classification Search ................. 530/350
See application file for complete search history.

(56) References Cited

U.S. PATENT DOCUMENTS

| | | | |
|---|---|---|---|
| 4,736,866 | A | 4/1988 | Leder et al. |
| 4,816,397 | A | 3/1989 | Boss et al. |
| 4,816,567 | A | 3/1989 | Cabilly et al. |
| 4,869,903 | A | 9/1989 | Lifson et al. |
| 5,101,025 | A | 3/1992 | Piatak, Jr. et al. |
| 5,128,460 | A | 7/1992 | Piatak, Jr. et al. |
| 6,333,303 | B1 | 12/2001 | Borgford |

FOREIGN PATENT DOCUMENTS

| | | |
|---|---|---|
| EP | 145111 | 6/1985 |
| EP | 171496 | 2/1986 |
| EP | 173494 | 5/1986 |
| EP | 239400 | 9/1987 |
| EP | 466222 | 1/1992 |
| WO | WO 86/01533 | 3/1986 |
| WO | WO 90/10457 | 9/1990 |
| WO | WO92/06193 | 4/1992 |
| WO | WO94/18332 | 8/1994 |
| WO | WO97/41233 | 11/1997 |

OTHER PUBLICATIONS

Abad-Zapatero, C. et al., *Protein Sci.* 5:640-652 (1996).
Allured, V.S. et al., *Proc. Natl. Acad. Sci. USA* 83:1320-1324 (1986).
Amann et al., *Gene* 69:301-315 (1988).
Baldari. et al., *Embo J.* 6:229-234 (1987).
Bever Jr., C.T., Panitch, H.S., and Johnson, K.P. (1994) Neurology 44(4), 745-8.
Blackman, M.J. et al. (*Mol. Biochem. Parasitol.* 62:103-114 (1995 or 1993?).
Blaha, I. et al., *FEBS Lett.* 309:389-393 (1992).
Blum, J.S. et al., *J. Biol. Chem.* 266: 22091-22095 (1991).
Bonifacino, J.S., *Nature* 384: 405-406 (1996).
Brinster et al. *Proc. Natl. Acad. Sci. USA* 82:4438-4442 (1985).
Carvalho, K: et al., *Biochem. Biophys. Res. Comm.* 191:172-179 (1993).
Chang et al., *Nature* 275:615 (1978).
Chirgwin et al., *Biochemistry* 18, 5294-5299 (1979).
Cohen, P., Graves, H.C., Peehl, D.M., Kamarei, M., Giudice, L.C., and Rosenfeld, R.G. (1992) Journal of Clinal Endocrinology and Metabolism 75(4), 1046-53.
Cole et al., Monoclonal Antibodies in Cancer Therapy Allen R., Bliss, Inc., pp. 77-96 (1985).
Collier, R.J. & Kandel, J., *J. Biol. Chem.* 246:1496-1503 (1971).
Collier, R.J. et al., *J. Biol. Chem.* 257:5283-5285 (1982).
Columblatti, M. et al., *J. Biol. Chem.* 261:3030-3035 (1986).
Conover, C.A. and De Leon, D.D., *J. Biol. Chem.* 269(10), 7076-80 (1994).
Cook, J.P. et al., *Bioconjugate Chem.* 4, 440-447 (1993).
Cooper, J.A. and Bujard, H. (*Mol. Biochem. Parasitol.* 56:151-160 (1992).
Cullen et al. (*Bio/Technology* 5:369 (1987).
Cutfield, S.M. et al., *Biochemistry* 35:398-410 (1995).
Darke et al. (*J. Biol. Chem.* 254:2307-2312 (1988).
Demeure, M.J. et al., *World J. Surg.* 16:770-776 (1992).
DiIannit, 1990, J. Biol. Chem. 285: 17345-17354 (1990).
Emmanuel, F. et al., Anal. *Biochem.* 173: 134-141 (1988).
Endo, Y. & Tsurugi, K. J., *Biol. Chem.* 262:8128 (1987).
Fiani, M.L. et al., *Arch. Biochem. Biophys.* 307: 225-230 (1993).
Funmatsu et al., *Jap. J. Med. Sci. Biol.* 23:264-267 (1970).
Fusek, M. et al. (*FEBS Lett.* 327:108-112 (1993).
Garred, O. et al. .(*J. Biol. Chem.* 270:10817-10821 (1995).
Gluzman, Y. (1975) Cell, 23, 175-182).
Goldberg, D.E. et al. (*J. Exp. Med.* 173:961-969 (1991).
Gray, G.L. et al., *Proc. Natl. Acad. Sci. USA* 81:2645-2649 (1984).
Greenfield, L. et al., *Proc. Natl. Acad. Sci. USA* 80:6853-6857 (1983).

(Continued)

*Primary Examiner*—Karen Cochrane Carlson
(74) *Attorney, Agent, or Firm*—Bereskin & Parr; Micheline Gravelle

(57) ABSTRACT

The present invention provides a protein having an A chain of a ricin-like toxin, a B chain of a ricin-like toxin and a heterologous linker amino acid sequence, linking the A and B chains. The linker sequence contains a cleavage recognition site for a disease specific protease such as a cancer, fungal, viral or parasitic protease. The invention also relates to a nucleic acid molecule encoding the protein and to expression vectors incorporating the nucleic acid molecule. Also provided is a method of inhibiting or destroying mammalian cancer cells, cells infected with a virus, a fungus, or parasite; or parasites utilizing the nucleic acid molecules and proteins of the invention and pharmaceutical compositions for treating human cancer, viral infection, fungal infection, or parasitic infection.

28 Claims, 254 Drawing Sheets

OTHER PUBLICATIONS

Halling, K. et al. *Nucleic Acids Res.* 13:8019 (1985).
Hammer et al. *Nature* 315:680-683 (1985).
Hansen, G., Schuster, A., Zubrod, C., and Wahn, V. (1995) Respiration 62(3), 117-24.
Hinnen et al., *Proc. Natl. Acad. Sci. USA* 75:1929 (1978).
Hirowatari, Y. et al., *Arch. Virol.* 133:349-356 (1993).
Hirowatari, Y. et al., *Anal. Biochem.* 225:113-120 (1995).
Holmberg, K. and Myer, R., *Scand. J. Infect. Dis.* 18:179-192 (1986).
Honn, K.V. et al. (*Biochem. Pharmacol.* 34:235-241 (1985).
Huse et al., *Science* 246:1275-1281 (1989).
Itoh et al., *J. Bacteriology* 153:163 (1983).
Jewell, D.A. et al., *Biochemistry* 31:7862-7869 (1992).
Kaufman et al., *EMBO J.* 6:187-195 (1987).
Kohler and Milstein (*Nature* 256:495-497 (1975).
Kozbor et al., *Immunology Today* 4:7279 (1983).
Krane, S.M., *Ann. N.Y. Acad. Sci.* 732:1-10 (1994).
Kurjan and Herskowitz, *Cell* 30:933-943 (1982).
Lamb and Lord, *Eur. J. Biochem.* 14:265-270 (1985).
Leppla, S.H. et al. (Bacterial Protein Toxins zbl.bakt.suppl. 24:431-442 (1994).
Liu F. & Roizman, B. (*J. Virol.* 65:5149-5156 (1991).
Long, A.C. et al., *FEBS Lett.* 258:75-78 (1989).
Lord, J.M., *Eur. J. Biochem.* 146:411-416 (1985).
Lord, J.M., *Eur. J. Biochem.* 146:403-409 (1985).
Lord, J.M. et al., *FASAB Journal* 8:201-208 (1994).
Lucklow, V.A., and Summers, M.D., *Virology* 170:31-39 (1989).
Mackay, A.R. et al. *Lab. Invest.* 70:800-806 (1994).
May, M.J. et al. Embo. Journal, 8:301-308 at 302-303 (1989).
McCafferty et al., *Nature* 348:552-554 (1990).
McKerrow, J.H. et al., *J. Biol. Chem.* 260:3703-3707 (1985).
McPherson, R.A. et al. (*Mol. Biochem. Parasitol.* 62:233-242 (1993).
Merrifield, *J. Am. Chem. Assoc.* 85:2149-2154 (1964).
Messing, Meth in Enzymology 101:20-77, 1983.
Mikkelsen, T. et al. *J. Neurosurge*, 83:285-290 (1995).
Moore, D.H. et al. *Gynecol. Oncol.* 65:78-82 (1997).
Morrison et al., *Proc. Natl Acad. Sci.* U.S.A. 81:6851 (1985).
Muller, H.L., Oh, Y., Gargosky, S.E., Lehrnbecher, T., Hintz, R.L., and Rosenfeld, R.G. (1993) Journal of Clinical Endocrinology and Metabolism 77(5), 1113-9.
Nakano et al. (1995) J. of Neurosurgery 83(2), 298-307.
Nichols and Yanofsky, Meth in Enzymology 101:155, (1983).
Nwagwu, M. et al. (*Exp. Parasitol.* 75:399-414 (1992).
O'Dea, K.P. et al., *Mol. Biochem. Parasitol.* 72:111-119 (1995).
O'Hare et al. (*FEBS Lett.* 273:200-204 (1990).
Ogata, M. et al., *J. Biol. Chem.* 267:25396-25401 (1992).
Olsnes, S. & Phil, A. in Molecular action of toxins and viruses (eds. Cohen, P. & vanHeyningen, S.) 51-105 Elsevier Biomedical Press, Amsterdam, 1982).
Olson et al., *AIDS Res. and Human Retroviruses* 7:1025-1030 (1991).
Olsson et al., *Meth. Enzymol.*, 92:3-16 (1982).
Palmiter and Brinster *Cell* 41:343-345 (1985).
Palmiter et al. *Science* 222:809-814 (1983).
Panchal, R.G. et al., *Nature Biotechnology* 14:852-857 (1996).
Pastan et al., *Annals New York Academy of Sciences* 758:345-353 (1995).
Pastan, I. et al., *Annu. Rev. Biochem.* 61:331-354 (1992).
Peng, K-W, et al. *Human Gene Therapy*, 8:729-738 (1997).
Pettit, S.C. et al., *J. Biol. Chem.* 266:14539-14547 (1991).
Ray, T.L. and Payne, C.D. (*Infect. Immunol.* 58:508-514 (1990).
Remold, H.H. et al. (*Biochim. Biophys. Acta* 167:399-406 (1968).
Richardson, P.T. et al., *FEBS Lett.* 255:15-20 (1989).
Rosenthal, P.J. et al. (*J. Clin. Invest.* 91:1052-1056 (1993).
Ruchel, R. et al, *Zentralbl. Bakteriol. Mikrobiol Hyg. I Abt. Orig. A.* 255:537-548 (1983).
Russell et al., Gene 20: 231, (1982).
Rutenber, E. et al. *Proteins* 10:240-250 (1991).
Sandvig, K. et al., *Biochem. Soc. Trans.* 21:707-711 (1993).
Sandvig, K. & van Deurs, B., *FEBS Lett.* 346: 99-102 (1994).
Scarborough, P.E. et al., *Protein Sci.* 2:264-276 (1993).
Schreiber, B, et al., *Diagn. Microbiol. Infect. Dis.* 3:1-5 (1985).
Schultz et al., *Gene* 54:113-123 (1987).
Schwartz, M.K., *Clin. Chim. Acta* 237:67-78 (1995).
Seed, B., *Nature* 329:840 (1987).
Shi, Y.E. et al., *Cancer Res.* 53:1409-1415 (1993).
Simmons et al., *Biol. Chem.* 261:7912 (1986).
Sinkar et al., *J. Biosci* (Bangalore) 11:47-58 (1987).
Sloane, B.F. et al. (*Proc. Natl. Acad. Sci. USA* 83:2483-2487 (1986).
Spiess, E. et al., *J. Histochem. Cytochem.* 42:917-929 (1994).
Spooner et al., *Mol. Immunol.* 31:117-125, (1994).
Takeda et al., *Nature* 314:452 (1985), Cabilly et al.
Teng et al., *Proc. Natl. Acad. Sci.* U.S.A., 80:7308-7312 (1983).
Thompson, E.W. et al., *Breast Cancer Res. Treatment* 31:357-370 (1994).
Vasil, M.L. et al., *Infect. Immunol.* 16:353-361 (1977).
Vieira and Messing, *Gene* 19:259-268 (1982).
Vitetta et al., *Science* 238:1098-1104(1987).
Vitetta & Thorpe, *Seminars in Cell Biology* 2:47-58 (1991).
Vitetta et al., *Immunology Today* 14:252-259 (1993).
Ward et al., *Nature* 341:544-546 (1989).
Weidner, J.R. et al. (*Arch. Biochem. Biophys.* 286:402-408 (1991).
Welch, A.R. et al. (*Arch. Biochem. Biophys.* 324:59-64 (1995).
Welch, A.R. (*Proc. Natl. Acad. Sci. USA* 88:10792-10796 (1991).
Wellner, R.B. et al. *J. Toxicol. Toxin Reviews*, 14(4), 483-522 (1995).
Westby et al., *Bioconjugate Chem.* 3:377-382 (1992).
Weston et al., *Mol. Biol.* 244:410-422 (1994).
Wiertz, E.J. et al., *Nature* 384: 432-438 (1996).
Woessner, J.F., *Ann. N.Y. Acad. Sci.* 732:11-21 (1994).
Young, T.N. et al. *Gynecol. Oncol.* 62:89-99 (1996).

FIGURE 1-1

Complete Sequence of Baculovirus Transfer Vector, pVL1393

```
ID   PVL1393    preliminary; circular DNA; SYN;
9632 BP.
XX
AC   IG1137;
XX
DT   01-FEB-1993 (Rel. 7, Created)
DT   01-JUL-1995 (Rel. 12, Last updated, Version
1)
XX
DE   E. coli plasmid vector pVL1393 - complete.
XX
KW   cloning vector.
XX
OS   Cloning vector
OC   Artificial sequences; Cloning vehicles.
XX
RN   [1]
RC   p2Bac from baculovirus
RC   p2Blue from p2Bac
RC   pBlueBac from AcNPV
RC   pBlueBac2 from AcNPV
RC   pBlueBacIII from AcNPV
RC   pBlueBacHisA from AcNPV
RC   pBlueBacHisB from AcNPV
RC   pBlueBacHisC from AcNPV
RC   pVL1392, pVL1393 from pAc360
RA   ;
RT   ;
RL   The Digest 5:2-2(1992).
XX
CC   NM (pVL1393)
CC   CM (yes)
CC   NA (ds-DNA)
CC   TP (circular)
CC   ST ()
CC   TY (plasmid)
CC   SP (British
Biotechnology)(Invitrogen)
CC   HO (E.coli NM522)(E.coli
INValphaF')(insect)
CC   CP ()
CC   FN (expression)(transfer)
CC   SE ()
CC   PA (pAC360)
CC   BR (pVL1392)
CC   OF ()
CC   OR ()
XX
FH   Key              Location/Qualifiers
FH
```

FIGURE 1-2

```
FT   misc_feature      0..0
FT                     /note="1. pAc360, ori/amp/AcMNPV
polyhedrin gene
FT                     -> pVL1393 9632bp"
FT   transposon        0..0
FT                     /note="TRN AcMNPV"
FT   misc_binding      868..868
FT                     /note="SIT SacII"
FT   misc_binding      1395..1395
FT                     /note="SIT ApaI"
FT   misc_binding      1901..1901
FT                     /note="SIT XhoI"
FT   promoter          0..0
FT                     /note="PRO AcMNPV polyhedrin gene"
FT   misc_binding      0..0
FT                     /note="MCS
FT                     BamHI-SmaI-XbaI-EcoRI-NotI-XmaIII-PstI-
BglII"
FT   rep_origin        0..0
FT                     /note="ORI E. coli pMB1 (ColE1 and
pBR322)"
FT   CDS               complement(0..0)
FT                     /note="ANT E. coli beta-lactamase gene
(bla)
FT                     ampicillin resistance gene (apr/amp)"
XX
SQ   Sequence 9632 BP; 2602 A; 2122 C; 2176 G; 2732 T; 0
other;
     aagctttact cgtaaagcga gttgaaggat catatttagt tgcgtttatg
     agataagatt gaaagcacgt gtaaaatgtt tcccgcgcgt tggcacaact
     atttacaatg cggccaagtt ataaaagatt ctaatctgat atgttttaaa
     acacctttgc ggcccgagtt gtttgcgtac gtgactagcg aagaagatgt
     gtggaccgca gaacagatag taaaacaaaa ccctagtatt ggagcaataa
     tcgatttaac caacacgtct aaatattatg atggtgtgca ttttttgcgg
     gcgggcctgt tatacaaaaa aattcaagta cctggccaga ctttgccgcc
     tgaaagcata gttcaagaat ttattgacac ggtaaaagaa tttacagaaa
     agtgtcccgg catgttggtg ggcgtgcact gcacacacgg tattaatcgc
     accggttaca tggtgtgcag atatttaatg cacaccctgg gtattgcgcc
     gcaggaagcc atagatagat tcgaaaaagc cagaggtcac aaaattgaaa
     gacaaaatta cgttcaagat ttattaattt aattaatatt atttgcattc
     tttaacaaat actttatcct attttcaaat tgttgcgctt cttccagcga
     accaaaacta tgcttcgctt gctccgttta gcttgtagcc gatcagtggc
     gttgttccaa tcgacggtag gattaggccg gatattctcc accacaatgt
     tggcaacgtt gatgttacgt ttatgctttt ggttttccac gtacgtcttt
     tggccggtaa tagccgtaaa cgtagtgccg tcgcgcgtca cgcacaacac
     cggatgtttg cgcttgtccg cggggtattg aaccgcgcga tccgacaaat
     ccaccacttt ggcaactaaa tcggtgacct gcgcgtcttt tttctgcatt
     atttcgtctt tcttttgcat ggtttcctgg aagccggtgt acatgcggtt
     tagatcagtc atgacgcgcg tgacctgcaa atctttggcc tcgatctgct
     tgtccttgat ggcaacgatg cgttcaataa actcttgttt tttaacaagt
     tcctcggttt tttgcgccac caccgcttgc agcgcgtttg tgtgctcggt
     gaatgtcgca atcagcttag tcaccaactg tttgctctcc tcctcccgtt
     gtttgatcgc gggatcgtac ttgccggtgc agagcacttg aggaattact
     tcttctaaaa gccattcttg taattctatg gcgtaaggca atttggactt
```

FIGURE 1-3 cataatcagc tgaatcacgc cggatttagt aatgagcact gtatgcggct
gcaaatacag cgggtcgccc cttttcacga cgctgttaga ggtagggccc
ccatttgga tggtctgctc aaataacgat ttgtatttat tgtctacatg
aacacgtata gctttatcac aaactgtata ttttaaactg ttagcgacgt
ccttggccac gaaccggacc tgttggtcgc gctctagcac gtaccgcagg
ttgaacgtat cttctccaaa tttaaattct ccaattttaa cgcgagccat
tttgatacac gtgtgtcgat tttgcaacaa ctattgtttt ttaacgcaaa
ctaaacttat tgtggtaagc aataattaaa tatgggggaa catgcgccgc
tacaacactc gtcgttatga acgcagacgg cgccggtctc ggcgcaagcg
gctaaaacgt gttgcgcgtt caacgcggca aacatcgcaa aagccaatag
tacagttttg atttgcatat taacggcgat tttttaaatt atcttattta
ataaatagtt atgacgccta caactccccg cccgcgttga ctcgctgcac
ctcgagcagt tcgttgacgc cttcctccgt gtggccgaac acgtcgagcg
ggtggtcgat gaccagcggc gtgccgcacg cgacgcacaa gtatctgtac
accgaatgat cgtcgggcga aggcacgtcg gcctccaagt ggcaatattg
gcaaattcga aaatatatac agttgggttg tttgcgcata tctatcgtgg
cgttgggcat gtacgtccga acgttgattt gcatgcaagc cgaaattaaa
tcattgcgat tagtgcgatt aaaacgttgt acatcctcgc ttttaatcat
gccgtcgatt aaatcgcgca atcgagtcaa gtgatcaaag tgtggaataa
tgttttcttt gtattcccga gtcaagcgca gcgcgtattt taacaaacta
gccatcttgt aagttagttt catttaatgc aactttatcc aataatatat
tatgtatcgc acgtcaagaa ttaacaatgc gcccgttgtc gcatctcaac
acgactatga tagagatcaa ataaagcgcg aattaaatag cttgcgacgc
aacgtgcacg atctgtgcac gcgttccggc acgagctttg attgtaataa
gtttttacga agcgatgaca tgacccccgt agtgacaacg atcacgccca
aaagaactgc cgactacaaa attaccgagt atgtcggtga cgttaaaact
attaagccat ccaatcgacc gttagtcgaa tcaggaccgc tggtgcgaga
agccgcgaag tatggcgaat gcatcgtata acgtgtggag tccgctcatt
agagcgtcat gtttagacaa gaaagctaca tatttaattg atcccgatga
ttttattgat aaattgaccc taactccata cacggtattc tacaatggcg
gggttttggt caaaatttcc ggactgcgat tgtacatgct gttaacggct
ccgcccacta ttaatgaaat taaaaattcc aattttaaaa aacgcagcaa
gagaaacatt tgtatgaaag aatgcgtaga aggaaagaaa aatgtcgtcg
acatgctgaa caacaagatt aatatgcctc cgtgtataaa aaaaatattg
aacgatttga aagaaaacaa tgtaccgcgc ggcggtatgt acaggaagag
gtttatacta aactgttaca ttgcaaacgt ggtttcgtgt gccaagtgtg
aaaaccgatg tttaatcaag gctctgacgc atttctacaa ccacgactcc
aagtgtgtgg gtgaagtcat gcatctttta atcaaatccc aagatgtgta
taaaccacca aactgccaaa aaatgaaaac tgtcgacaag ctctgtccgt
ttgctggcaa ctgcaagggt ctcaatccta tttgtaatta ttgaataata
aaacaattat aaatgctaaa tttgtttttt attaacgata caaaccaaac
gcaacaagaa catttgtagt attatctata attgaaaacg cgtagttata
atcgctgagg taatatttaa aatcattttc aaatgattca cagttaattt
gcgacaatat aattttattt tcacataaac tagacgcctt gtcgtcttct
tcttcgtatt ccttctcttt ttcatttttc tcctcataaa aattaacata
gttattatcg tatccatata tgtatctatc gtatagagta aatttttgt
tgtcataaat atatatgtct tttttaatgg ggtgtatagt accgctgcgc
atagtttttc tgtaatttac aacagtgcta ttttctggta gttcttcgga
gtgtgttgct ttaattatta aatttatata atcaatgaat ttgggatcgt
cggttttgta caatatgttg ccggcatagt
acgcagcttc ttctagttca attacaccat tttttagcag caccggatta
acataacttt ccaaaatgtt gtacgaaccg ttaaacaaaa acagttcacc
tccctttct atactattgt ctgcgagcag ttgtttgttg ttaaaaataa
cagccattgt aatgagacgc acaaactaat atcacaaact ggaaatgtct

FIGURE 1-4 ctgtcccgat ttatttgaaa cactacaaat taaaggcgag ctttcgtacc
aacttgttag caatattatt agacagctgt gtgaagcgct caacgatttg
cacaagcaca atttcataca caacgacata aaactcgaaa atgtcttata
tttcgaagca cttgatcgcg tgtatgtttg cgattacgga ttgtgcaaac
acgaaaactc acttagcgtg cacgacggca cgttggagta ttttagtccg
gaaaaaattc gacacacaac tatgcacgtt tcgtttgact ggtacgcggc
gtgttaacat acaagttgct aacgtaatca tggtcatagc tgtttcctgt
gtgaaattgt tatccgctca caattccaca caacatacga gccggaagca
taaagtgtaa agcctggggt gcctaatgag tgagctaact cacattaatt
gcgttgcgct cactgcccgc tttccagtcg ggaaacctgt cgtgccagct
gcattaatga atcggccaac gcgcggggag aggcggtttg cgtattgggc
gctcttccgc ttcctcgctc actgactcgc tgcgctcggt cgttcggctg
cggcgagcgg tatcagctca ctcaaaggcg gtaatacggt tatccacaga
atcaggggat aacgcaggaa agaacatgtg agcaaaaggc cagcaaaagg
ccaggaaccg taaaaaggcc gcgttgctgg cgtttttcca taggctccgc
ccccctgacg agcatcacaa aaatcgacgc tcaagtcaga ggtggcgaaa
cccgacagga ctataaagat accaggcgtt tccccctgga agctccctcg
tgcgctctcc tgttccgacc ctgccgctta ccggatacct gtccgccttt
ctcccttcgg gaagcgtggc gctttctcat agctcacgct gtaggtatct
cagttcggtg taggtcgttc gctccaagct gggctgtgtg cacgaacccc
ccgttcagcc cgaccgctgc gccttatccg gtaactatcg tcttgagtcc
aacccggtaa
gacacgactt atcgccactg gcagcagcca ctggtaacag gattagcaga
gcgaggtatg taggcggtgc tacagagttc ttgaagtggt ggcctaacta
cggctacact agaaggacag tatttggtat ctgcgctctg ctgaagccag
ttaccttcgg aaaaagagtt ggtagctctt gatccggcaa acaaaccacc
gctggtagcg gtggtttttt tgtttgcaag cagcagatta cgcgcagaaa
aaaaggatct caagaagatc ctttgatctt ttctacgggg tctgacgctc
agtggaacga aaactcacgt taagggattt tggtcatgag attatcaaaa
aggatcttca cctagatcct tttaaattaa aaatgaagtt ttaaatcaat
ctaaagtata tatgagtaaa cttggtctga cagttaccaa tgcttaatca
gtgaggcacc tatctcagcg atctgtctat ttcgttcatc catagttgcc
tgactccccg tcgtgtagat aactacgata cgggagggct taccatctgg
ccccagtgct gcaatgatac cgcgagaccc acgctcaccg gctccagatt
tatcagcaat aaaccagcca gccggaaggg ccgagcgcag aagtggtcct
gcaactttat ccgcctccat ccagtctatt aattgttgcc gggaagctag
agtaagtagt tcgccagtta atagtttgcg caacgttgtt gccattgcta
caggcatcgt ggtgtcacgc tcgtcgtttg gtatggcttc attcagctcc
ggttcccaac gatcaaggcg agttacatga tcccccatgt tgtgcaaaaa
agcggttagc tccttcggtc ctccgatcgt tgtcagaagt aagttggccg
cagtgttatc actcatggtt atggcagcac tgcataattc tcttactgtc
atgccatccg taagatgctt ttctgtgact ggtgagtact caaccaagtc
attctgagaa tagtgtatgc ggcgaccgag ttgctcttgc ccggcgtcaa
tacgggataa taccgcgcca catagcagaa ctttaaaagt gctcatcatt
ggaaaacgtt cttcggggcg aaaactctca aggatcttac cgctgttgag
atccagttcg atgtaaccca ctcgtgcacc caactgatct tcagcatctt
ttactttcac cagcgtttct gggtgagcaa aaacaggaag gcaaaatgcc
gcaaaaaagg gaataagggc gacacggaaa tgttgaatac tcatactctt
cctttttcaa tattattgaa gcatttatca gggttattgt ctcatgagcg
gatacatatt tgaatgtatt tagaaaaata aacaaatagg ggttccgcgc
acatttcccc gaaaagtgcc acctgacgtc taagaaacca ttattatcat
gacattaacc tataaaaata ggcgtatcac gaggcccttt cgtctcgcgc
gtttcggtga tgacggtgaa aacctctgac acatgcagct cccggagacg
gtcacagctt gtctgtaagc ggatgccggg agcagacaag cccgtcaggg

FIGURE 1-5 atcaatatat agttgctgat atcatggaga taattaaaat gataaccatc
tcgcaaataa ataagtattt tactgttttc gtaacagttt tgtaataaaa
aaacctataa atattccgga ttattcatac cgtcccacca tcgggcgcgg
atcccgggta ccttctagaa ttccggagcg gccgctgcag atctgatcct
ttcctgggac ccggcaagaa ccaaaaactc actctcttca aggaaatccg
taatgttaaa cccgacacga tgaagcttgt cgttggatgg aaaggaaaag
agttctacag ggaaacttgg acccgcttca tggaagacag cttccccatt
gttaacgacc aagaagtgat ggatgttttc cttgttgtca acatgcgtcc
cactagaccc aaccgttgtt acaaattcct ggcccaacac gctctgcgtt
gcgaccccga ctatgtacct catgacgtga ttaggatcgt cgagccttca
tgggtgggca gcaacaacga gtaccgcatc agcctggcta agaagggcgg
cggctgccca ataatgaacc ttcactctga gtacaccaac tcgttcgaac
agttcatcga tcgtgtcatc tgggagaact tctacaagcc catcgtttac
atcggtaccg actctgctga agaggaggaa attctccttg aagtttccct
ggtgttcaaa gtaaaggagt ttgcaccaga cgcacctctg ttcactggtc
cggcgtatta aaacacgata cattgttatt agtacattta ttaagcgcta
gattctgtgc gttgttgatt tacagacaat tgttgtacgt attttaataa
ttcattaaat ttataatctt tagggtggta tgttagagcg aaaatcaaat
gattttcagc gtctttatat ctgaatttaa atattaaatc ctcaatagat
ttgtaaaata ggtttcgatt agtttcaaac aagggttgtt tttccgaacc
gatggctgga ctatctaatg gattttcgct caacgccaca aaacttgcca
aatcttgtag cagcaatcta gctttgtcga tattcgtttg tgtttttgttt
tgtaataaag gttcgacgtc gttcaaaata ttatgcgctt ttgtatttct
ttcatcactg tcgttagtgt acaattgact cgacgtaaac acgttaaata
aagcttggac atatttaaca tcgggcgtgt tagctttatt aggccgatta
tcgtcgtcgt cccaaccctc gtcgttagaa gttgcttccg aagacgattt
tgccatagcc acacgacgcc tattaattgt gtcggctaac acgtccgcga
tcaaatttgt agttgagctt tttggaatta tttctgattg cgggcgtttt
tgggcgggtt tcaatctaac tgtgcccgat tttaattcag acaacacgtt
agaaagcgat ggtgcaggcg gtggtaacat ttcagacggc aaatctacta
atggcggcgg tggtggagct gatgataaat ctaccatcgg tggaggcgca
ggcggggctg gcggcggagg cggaggcgga ggtggtggcg gtgatgcaga
cggcggttta ggctcaaatg tctctttagg caacacagtc ggcacctcaa
ctattgtact ggtttcgggc gccgtttttg gtttgaccgg tctgagacga
gtgcgatttt tttcgtttct aatagcttcc aacaattgtt gtctgtcgtc
taaaggtgca gcgggttgag gttccgtcgg cattggtgga gcgggcggca
attcagacat cgatggtggt ggtggtggtg gaggcgctgg aatgttaggc
acgggagaag gtggtggcgg cggtgccgcc ggtataattt gttctggttt
agtttgttcg cgcacgattg tgggcaccgg cgcaggcgcc gctggctgca
caacggaagg tcgtctgctt cgaggcagcg cttggggtgg tggcaattca
atattataat tggaatacaa atcgtaaaaa tctgctataa gcattgtaat
ttcgctatcg tttaccgtgc cgatatttaa caaccgctca atgtaagcaa
ttgtattgta aagagattgt ctcaagctcg ccgcacgccg ataacaagcc
ttttcatttt tactacagca ttgtagtggc gagacacttc gctgtcgtcg
acgtacatgt atgctttgtt gtcaaaaacg tcgttggcaa gctttaaaat
atttaaaaga acatctctgt tcagcaccac tgtgttgtcg taaatgttgt
ttttgataat ttgcgcttcc gcagtatcga cacgttcaaa aaattgatgc
gcatcaattt tgttgttcct attattgaat aaataagatt gtacagattc
atatctacga ttcgtcatgg ccaccacaaa tgctacgctg caaacgctgg
tacaatttta cgaaaactgc aaaaacgtca aaactcggta taaaataatc
aacgggcgct ttggcaaaat atctatttta tcgcacaagc ccactagcaa
attgtatttg cagaaaacaa tttcggcgca caattttaac gctgacgaaa
taaaagttca ccagttaatg agcgaccacc caaattttat aaaaatctat
tttaatcacg gttccatcaa caaccaagtg atcgtgatgg actacattga

FIGURE 1-6 cgcgtcagcg ggtgttggcg ggtgtcgggg ctggcttaac tatgcggcat
cagagcagat tgtactgaga gtgcaccata tgcggtgtga aataccgcac
agatgcgtaa ggagaaaata ccgcatcagg cgccattcgc cattcaggct
gcgcaactgt tgggaagggc gatcggtgcg ggcctcttcg ctattacgcc
agctggcgaa agggggatgt gctgcaaggc gattaagttg ggtaacgcca
gggttttccc agtcacgacg ttgtaaaacg acggccagtg cc

FIGURE 2D-1

```
            10        20        30        40        50
             |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTTTGCTTAAATCGAGAATGGTGCCAAATTTTAATGC
    AGCAGTGTCAAAAGAAACGAATTTAGCTCTTACCACGGTTTAAAATTACG
```

FIGURE 2D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 3D-1

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTCGTCCGAAGCCACAGCAATTTTTTGGACTTATGAATGC
    AGCAGTGTCAAAGCAGGCTTCGGTGTCGTTAAAAAACCTGAATACTTACG

951 TGATGTTTGTATGGATCCTGAGCCCATAGTGCGTATCGTAGGTCGAAATG
```

FIGURE 3D-2

ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
AGTTCTTACTACCTTGGTAAAATTTAAACATATCACCTAACCACAATCTA

1651 GTGAGGCGATCGGATCCGAGCCTTAAACAAATCATTCTTTACCCTCTCCA
CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
GAGAACGTCACACACACAGGACGGTACTTTTATCTACCGAATTTATTTTT

1801 GGACATTGTAAATTTTGTAACTGAAAGGACAGCAAGTTATATCGAATTCC
CCTGTAACATTTAAAACATTGACTTTCCTGTCGTTCAATATAGCTTAAGG

1851 TGCAG
ACGTC

FIGURE 4D-1

```
              10        20        30        40        50
               |         |         |         |         |
   1  GAATTCATGAAACCGGGAGGAAATACTATTGTAATATGGATGTATGCAGT
      CTTAAGTACTTTGGCCCTCCTTTATGATAACATTATACCTACATACGTCA

  51  GGCAACATGGCTTTGTTTTGGATCCACCTCAGGGTGGTCTTTCACATTAG
      CCGTTGTACCGAAACAAAACCTAGGTGGAGTCCCACCAGAAAGTGTAATC

 101  AGGATAACAACATATTCCCCAAACAATACCCAATTATAAACTTTACCACA
      TCCTATTGTTGTATAAGGGGTTTGTTATGGGTTAATATTTGAAATGGTGT

 151  GCGGGTGCCACTGTGCAAAGCTACACAAACTTTATCAGAGCTGTTCGCGG
      CGCCCACGGTGACACGTTTCGATGTGTTTGAAATAGTCTCGACAAGCGCC

 201  TCGTTTAACAACTGGAGCTGATGTGAGACATGATATACCAGTGTTGCCAA
      AGCAAATTGTTGACCTCGACTACACTCTGTACTATATGGTCACAACGGTT

 251  ACAGAGTTGGTTTGCCTATAAACCAACGGTTTATTTTAGTTGAACTCTCA
      TGTCTCAACCAAACGGATATTTGGTTGCCAAATAAAATCAACTTGAGAGT

 301  AATCATGCAGAGCTTTCTGTTACATTAGCGCTGGATGTCACCAATGCATA
      TTAGTACGTCTCGAAAGACAATGTAATCGCGACCTACAGTGGTTACGTAT

 351  TGTGGTCGGCTACCGTGCTGGAAATAGCGCATATTTCTTTCATCCTGACA
      ACACCAGCCGATGGCACGACCTTTATCGCGTATAAAGAAAGTAGGACTGT

 401  ATCAGGAAGATGCAGAAGCAATCACTCATCTTTTCACTGATGTTCAAAAT
      TAGTCCTTCTACGTCTTCGTTAGTGAGTAGAAAAGTGACTACAAGTTTTA

 451  CGATATACATTCGCCTTTGGTGGTAATTATGATAGACTTGAACAACTTGC
      GCTATATGTAAGCGGAAACCACCATTAATACTATCTGAACTTGTTGAACG

 501  TGGTAATCTGAGAGAAAATATCGAGTTGGGAAATGGTCCACTAGAGGAGG
      ACCATTAGACTCTCTTTTATAGCTCAACCCTTTACCAGGTGATCTCCTCC

 551  CTATCTCAGCGCTTTATTATTACAGTACTGGTGGCACTCAGCTTCCAACT
      GATAGAGTCGCGAAATAATAATGTCATGACCACCGTGAGTCGAAGGTTGA

 601  CTGGCTCGTTCCTTTATAATTTGCATCCAAATGATTTCAGAAGCAGCAAG
      GACCGAGCAAGGAAATATTAAACGTAGGTTTACTAAAGTCTTCGTCGTTC

 651  ATTCCAATATATTGAGGGAGAAATGCGCACGAGAATTAGGTACAACCGGA
      TAAGGTTATATAACTCCCTCTTTACGCGTGCTCTTAATCCATGTTGGCCT

 701  GATCTGCACCAGATCCTAGCGTAATTACACTTGAGAATAGTTGGGGGAGA
      CTAGACGTGGTCTAGGATCGCATTAATGTGAACTCTTATCAACCCCCTCT

 751  CTTTCCACTGCAATTCAAGAGTCTAACCAAGGAGCCTTTGCTAGTCCAAT
      GAAAGGTGACGTTAAGTTCTCAGATTGGTTCCTCGGAAACGATCAGGTTA

 801  TCAACTGCAAAGACGTAATGGTTCCAAATTCAGTGTGTACGATGTGAGTA
      AGTTGACGTTTCTGCATTACCAAGGTTTAAGTCACACATGCTACACTCAT

 851  TATTAATCCCTATCATAGCTCTCATGGTGTATAGATGCGCACCTCCACCA
      ATAATTAGGGATAGTATCGAGAGTACCACATATCTACGCGTGGAGGTGGT

 901  TCGTCACAGTTTTCTTTGCGTCCACTGGCATTGTGGCGAAGTTTTAATGC
      AGCAGTGTCAAAAGAAACGCAGGTGACCGTAACACCGCTTCAAAATTACG

 951  TGATGTTTGTATGGATCCTGAGCCCATAGTGCGTATCGTAGGTCGAAATG
```

FIGURE 4D-2

ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
AGTTCTTACTACCTTGGTAAAATTTAAACATATCACCTAACCACAATCTA

651 GTGAGGCGATCGGATCCGAGCCTTAAACAAATCATTCTTTACCCTCTCCA
CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
GAGAACGTCACACACACAGGACGGTACTTTTATCTACCGAATTTATTTTT

1801 GGACATTGTAAATTTTGTAACTGAAAGGACAGCAAGTTATATCGAATTCC
CCTGTAACATTTAAAACATTGACTTTCCTGTCGTTCAATATAGCTTAAGG

1851 TGCAG
ACGTC

FIGURE 5B

WT preproricin linker

```
primer MMP9-1
5'- GGGCAGCGAAATTTTAATGCTGAT        -3'
    *  **   *
TCTTTGCTTATAAGGCCAGTGGTGCCAAATTTTAAT
AGAAACGAATATTCCGGTCACCACGGTTTAAAATTA
     **   ****   ***
3'- AGCAGTGTCAAAAGAGGCGTTCCTTAACGT-5'
primer MMP9-1
```

PCR mutagenesis ligate with pBluescript SK pAP 219 linker
(MMP-9 variant)

```
TCTCCGCAAGGAATTGCAGGGCAGCGAAATTTTAAT
AGAGGCGTTCCTTAACGTCCCGTCGCTTTAAAATTA
```

FIGURE 5D-1

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTCCGCAAGGAATTGCAGGGCAGCGAAATTTTAATGC
    AGCAGTGTCAAAAGAGGCGTTCCTTAACGTCCCGTCGCTTTAAAATTACG
```

FIGURE 5D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 6D-1

```
              10        20        30        40        50
               |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTGATGTGGATGAAAGGGATGTGAGGGAATTTGCTTCTTT
    AGCAGTGTCAAACTACACCTACTTTCCCTACACTCCCTTAAACGAAGAAA

951 TTTAGCTGATGTTTGTATGGATCCTGAGCCCATAGTGCGTATCGTAGGTC
```

FIGURE 6D-2

```
     AAATCGACTACAAACATACCTAGGACTCGGGTATCACGCATAGCATCCAG

1001 GAAATGGTCTATGTGTTGATGTTAGGGATGGAAGATTCCACAACGGAAAC
     CTTTACCAGATACACAACTACAATCCCTACCTTCTAAGGTGTTGCCTTTG

1051 GCAATACAGTTGTGGCCATGCAAGTCTAATACAGATGCAAATCAGCTCTG
     CGTTATGTCAACACCGGTACGTTCAGATTATGTCTACGTTTAGTCGAGAC

1101 GACTTTGAAAAGAGACAATACTATTCGATCTAATGGAAAGTGTTTAACTA
     CTGAAACTTTTCTCTGTTATGATAAGCTAGATTACCTTTCACAAATTGAT

1151 CTTACGGGTACAGTCCGGGAGTCTATGTGATGATCTATGATTGCAATACT
     GAATGCCCATGTCAGGCCCTCAGATACACTACTAGATACTAACGTTATGA

1201 GCTGCAACTGATGCCACCCGCTGGCAAATATGGGATAATGGAACCATCAT
     CGACGTTGACTACGGTGGGCGACCGTTTATACCCTATTACCTTGGTAGTA

1251 AAATCCCAGATCTAGTCTAGTTTTAGCAGCGACATCAGGGAACAGTGGTA
     TTTAGGGTCTAGATCAGATCAAAATCGTCGCTGTAGTCCCTTGTCACCAT

1301 CCACACTTACAGTGCAAACCAACATTTATGCCGTTAGTCAAGGTTGGCTT
     GGTGTGAATGTCACGTTTGGTTGTAAATACGGCAATCAGTTCCAACCGAA

1351 CCTACTAATAATACACAACCTTTTGTTACAACCATTGTTGGGCTATATGG
     GGATGATTATTATGTGTTGGAAAACAATGTTGGTAACAACCCGATATACC

1401 TCTGTGCTTGCAAGCAAATAGTGGACAAGTATGGATAGAGGACTGTAGCA
     AGACACGAACGTTCGTTTATCACCTGTTCATACCTATCTCCTGACATCGT

1451 GTGAAAAGGCTGAACAACAGTGGGCTCTTTATGCAGATGGTTCAATACGT
     CACTTTTCCGACTTGTTGTCACCCGAGAAATACGTCTACCAAGTTATGCA

1501 CCTCAGCAAAACCGAGATAATTGCCTTACAAGTGATTCTAATATACGGGA
     GGAGTCGTTTTGGCTCTATTAACGGAATGTTCACTAAGATTATATGCCCT

1551 AACAGTTGTTAAGATCCTCTCTTGTGGCCCTGCATCCTCTGGCCAACGAT
     TTGTCAACAATTCTAGGAGAGAACACCGGGACGTAGGAGACCGGTTGCTA

1601 GGATGTTCAAGAATGATGGAACCATTTTAAATTTGTATAGTGGATTGGTG
     CCTACAAGTTCTTACTACCTTGGTAAAATTTAAACATATCACCTAACCAC

1651 TTAGATGTGAGGCGATCGGATCCGAGCCTTAAACAAATCATTCTTTACCC
     AATCTACACTCCGCTAGCCTAGGCTCGGAATTTGTTTAGTAAGAAATGGG

1701 TCTCCATGGTGACCCAAACCAAATATGGTTACCATTATTTTGATAGACAG
     AGAGGTACCACTGGGTTTGGTTTATACCAATGGTAATAAAACTATCTGTC

1751 ATTACTCTCTTGCAGTGTGTGTGTCCTGCCATGAAAATAGATGGCTTAAA
     TAATGAGAGAACGTCACACACACAGGACGGTACTTTTATCTACCGAATTT

1801 TAAAAAGGACATTGTAAATTTTGTAACTGAAAGGACAGCAAGTTATATCG
     ATTTTTCCTGTAACATTTAAAACATTGACTTTCCTGTCGTTCAATATAGC

1851 AATTCCTGCAG
     TTAAGGACGTC
```

FIGURE 7B

WT preproricin linker primer MAL-A1

5'- AATTATGATGAAGAGGATGCTGATGTTTGTATG -3'

********* ***

TCTTTGCTTATAAGGCCAGTGGTGCCAAATTTTAAT

AGAAACGAATATTCCGGTCACCACGGTTTAAAATTA

**** *   **

3'- GGTAGCAGTGTCAAAGTCCACCAAGTTAACGTC -5' primer MAL-A2

PCR mutagenesis ligate with pBluescript SK pAP 223 linker
(MAL-A variant)

CAGGTGGTTCAATTGCAGAATTATGATGAAGAGGAT

GTCCACCAAGTTAACGTCTTAATACTACTTCTCCTA

FIGURE 7D-1

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTCAGGTGGTTCAATTGCAGAATTATGATGAAGAGGATGC
    AGCAGTGTCAAAGTCCACCAAGTTAACGTCTTAATACTACTTCTCCTACG
```

FIGURE 7D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 8D-1

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTTGCCGATTTTCGGGGAATCGGAGGACAATGATGAAGC
    AGCAGTGTCAAAAACGGCTAAAAGCCCCTTAGCCTCCTGTTACTACTTCG
```

FIGURE 8D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 9D-1

```
         10        20        30        40        50
          |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTCAGGTGGTTACAGGGGAAGCGATATCAGTTACTATGGC
    AGCAGTGTCAAAGTCCACCAATGTCCCCTTCGCTATAGTCAATGATACCG
```

FIGURE 9D-2

```
 951 TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 10B

WT preproricin linker

```
                       primer MAL-D1
                        5'- CTGTCGTTCCCTACTAATGCTGATGTTTGT  -3'
                            *  **  *****  **
TCTTTGCTTATAAGGCCAGTGGTGCCAAATTTTAAT
AGAAACGAATATTCCGGTCACCACGGTTTAAAATTA
*    *** *  * ***
3'- GGTAGCAGTGTCAAACGAAACCTCTCTTGCAAG-5'
          primer MAL-D2
```

PCR mutagenesis ligate with pBluescript SK pAP 229 linker
(MAL-D variant)

```
GCTTTGGAGAGAACGTTCCTGTCGTTCCCTACTAAT
CGAAACCTCTCTTGCAAGGACAGCAAGGGATGATTA
```

FIGURE 10D-1

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTGCTTTGGAGAGAACGTTCCTGTCGTTCCCTACTAATGC
    AGCAGTGTCAAACGAAACCTCTCTTGCAAGGACAGCAAGGGATGATTACG
```

FIGURE 10D-2

```
 951 TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 11D-1

```
             10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTAAATTCCAAGATATGCTAAATAATTCACAGCATCAGGC
    AGCAGTGTCAAATTTAAGGTTCTATACGATTTATTAAGTGTCGTAGTCCG
```

FIGURE 11D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 12B

WT preproricin linker primer HSV1-A

5'- TCGTCGGCACATGTTAATGCTGATGTTTGT -3'

TCTTTGCTTATAAGGCCAGTGGTGCCAAATTTTAAT

AGAAACGAATATTCCGGTCACCACGGTTTAAAATTA

3'- AGCAGTGTCAAAAGACGCGAACATTTGCGT-5' primer HSV1-A

PCR mutagenesis ligate with pBluescript SK pAP 233 linker
(HSV1-A variant)

TCTGCGCTTGTAAACGCATCGTCGGCACATGTTAAT

AGACGCGAACATTTGCGTAGCAGCCGTGTACAATTA

FIGURE 12D-1

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTGCGCTTGTAAACGCATCGTCGGCACATGTTAATGC
    AGCAGTGTCAAAAGACGCGAACATTTGCGTAGCAGCCGTGTACAATTACG
```

FIGURE 12D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 13D-1

```
             10        20        30        40        50
              |         |         |         |         |
  1  GAATTCATGAAACCGGGAGGAAATACTATTGTAATATGGATGTATGCAGT
     CTTAAGTACTTTGGCCCTCCTTTATGATAACATTATACCTACATACGTCA

 51  GGCAACATGGCTTTGTTTTGGATCCACCTCAGGGTGGTCTTTCACATTAG
     CCGTTGTACCGAAACAAAACCTAGGTGGAGTCCCACCAGAAAGTGTAATC

101  AGGATAACAACATATTCCCCAAACAATACCCAATTATAAACTTTACCACA
     TCCTATTGTTGTATAAGGGGTTTGTTATGGGTTAATATTTGAAATGGTGT

151  GCGGGTGCCACTGTGCAAAGCTACACAAACTTTATCAGAGCTGTTCGCGG
     CGCCCACGGTGACACGTTTCGATGTGTTTGAAATAGTCTCGACAAGCGCC

201  TCGTTTAACAACTGGAGCTGATGTGAGACATGATATACCAGTGTTGCCAA
     AGCAAATTGTTGACCTCGACTACACTCTGTACTATATGGTCACAACGGTT

251  ACAGAGTTGGTTTGCCTATAAACCAACGGTTTATTTTAGTTGAACTCTCA
     TGTCTCAACCAAACGGATATTTGGTTGCCAAATAAAATCAACTTGAGAGT

301  AATCATGCAGAGCTTTCTGTTACATTAGCGCTGGATGTCACCAATGCATA
     TTAGTACGTCTCGAAAGACAATGTAATCGCGACCTACAGTGGTTACGTAT

351  TGTGGTCGGCTACCGTGCTGGAAATAGCGCATATTTCTTTCATCCTGACA
     ACACCAGCCGATGGCACGACCTTTATCGCGTATAAAGAAAGTAGGACTGT

401  ATCAGGAAGATGCAGAAGCAATCACTCATCTTTTCACTGATGTTCAAAAT
     TAGTCCTTCTACGTCTTCGTTAGTGAGTAGAAAAGTGACTACAAGTTTTA

451  CGATATACATTCGCCTTTGGTGGTAATTATGATAGACTTGAACAACTTGC
     GCTATATGTAAGCGGAAACCACCATTAATACTATCTGAACTTGTTGAACG

501  TGGTAATCTGAGAGAAAATATCGAGTTGGGAAATGGTCCACTAGAGGAGG
     ACCATTAGACTCTCTTTTATAGCTCAACCCTTTACCAGGTGATCTCCTCC

551  CTATCTCAGCGCTTTATTATTACAGTACTGGTGGCACTCAGCTTCCAACT
     GATAGAGTCGCGAAATAATAATGTCATGACCACCGTGAGTCGAAGGTTGA

601  CTGGCTCGTTCCTTTATAATTTGCATCCAAATGATTTCAGAAGCAGCAAG
     GACCGAGCAAGGAAATATTAAACGTAGGTTTACTAAAGTCTTCGTCGTTC

651  ATTCCAATATATTGAGGGAGAAATGCGCACGAGAATTAGGTACAACCGGA
     TAAGGTTATATAACTCCCTCTTTACGCGTGCTCTTAATCCATGTTGGCCT

701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTACGTATTTACAGGCATCGGAGAAATTTAAGAATGC
     AGCAGTGTCAAAAGATGCATAAATGTCCGTAGCCTCTTTAAATTCTTACG
```

FIGURE 13D-2

951 TGATGTTTGTATGGATCCTGAGCCCATAGTGCGTATCGTAGGTCGAAATG
ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
AGTTCTTACTACCTTGGTAAAATTTAAACATATCACCTAACCACAATCTA

1651 GTGAGGCGATCGGATCCGAGCCTTAAACAAATCATTCTTTACCCTCTCCA
CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
GAGAACGTCACACACACAGGACGGTACTTTTATCTACCGAATTTATTTTT

1801 GGACATTGTAAATTTTGTAACTGAAAGGACAGCAAGTTATATCGAATTCC
CCTGTAACATTTAAAACATTGACTTTCCTGTCGTTCAATATAGCTTAAGG

1851 TGCAG
ACGTC

FIGURE 14D-1

```
         10        20        30        40        50
          |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTCAGGATGTAAACGCAGTGGAGGCAAGTTCTAATGC
    AGCAGTGTCAAAAGAGTCCTACATTTGCGTCACCTCCGTTCAAGATTACG
```

FIGURE 14D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 15B

WT preproricin linker

```
                                    primer VZV-B1
                                     5'- TCGACGGGATATGGTAATGCTGATGTTTGT -3'
                                         ** ** ** *  **
-----------TCTTTGCTTATAAGGCCAGTGGTGCCAAATTTTAAT-----------
-----------AGAAACGAATATTCCGGTCACCACGGTTTAAAATTA-----------
               *  ** *  ** *
3'- AGCAGTGTCAAAAGACACATAAATGTCCGT-5'
            primer VZV-A2
```

PCR mutagenesis ligate with pBluescript SK pAP 239 linker
(VZV-B variant)

```
-----------TCTGTGTATTTACAGGCATCGACGGGATATGGTAAT-----------
-----------AGACACATAAATGTCCGTAGCTGCCCTATACCATTA-----------
```

FIGURE 15D-1

```
            10        20        30        40        50
             |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTGTGTATTTACAGGCATCGACGGGATATGGTAATGC
    AGCAGTGTCAAAAGACACATAAATGTCCGTAGCTGCCCTATACCATTACG
```

FIGURE 15D-2

951 TGATGTTTGTATGGATCCTGAGCCCATAGTGCGTATCGTAGGTCGAAATG
ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
AGTTCTTACTACCTTGGTAAAATTTAAACATATCACCTAACCACAATCTA

1651 GTGAGGCGATCGGATCCGAGCCTTAAACAAATCATTCTTTACCCTCTCCA
CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
GAGAACGTCACACACACAGGACGGTACTTTTATCTACCGAATTTATTTTT

1801 GGACATTGTAAATTTTGTAACTGAAAGGACAGCAAGTTATATCGAATTCC
CCTGTAACATTTAAAACATTGACTTTCCTGTCGTTCAATATAGCTTAAGG

1851 TGCAG
ACGTC

PCR Mutagenesis of Preproricin Gene to Create an EBV-A Variant Gene a) Cloning Strategy

FIGURE 16B

WT preproricin linker primer EBV-A1

```
                         5'- TCGGCGTCAGGTGTTAATGCTGATGTTTGT -3'
                             ** *  *  ** *
——————TCTTTGCTTATAAGGCCAGTGGTGCCAAATTTTAAT——————
——————AGAAACGAATATTCCGGTCACCACGGTTTAAAATTA——————
         **     *  ** *
3'- AGCAGTGTCAAAAGATTCGAACATGTCCGT-5'
```

primer EBV-A2

↓ PCR mutagenesis

↓ ligate with pBluescript SK pAP241 linker
(EBV-A variant)

```
——————TCTAAGCTTGTACAGGCATCGGCGTCAGGTGTTAAT——————
——————AGATTCGAACATGTCCGTAGCCGCAGTCCACAATTA——————
```

FIGURE 16D-1

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTAAGCTTGTACAGGCATCGGCGTCAGGTGTTAATGC
    AGCAGTGTCAAAAGATTCGAACATGTCCGTAGCCGCAGTCCACAATTACG
```

FIGURE 16D-2

951 TGATGTTTGTATGGATCCTGAGCCCATAGTGCGTATCGTAGGTCGAAATG
ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
AGTTCTTACTACCTTGGTAAAATTTAAACATATCACCTAACCACAATCTA

1651 GTGAGGCGATCGGATCCGAGCCTTAAACAAATCATTCTTTACCCTCTCCA
CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
GAGAACGTCACACACACAGGACGGTACTTTTATCTACCGAATTTATTTTT

1801 GGACATTGTAAATTTTGTAACTGAAAGGACAGCAAGTTATATCGAATTCC
CCTGTAACATTTAAAACATTGACTTTCCTGTCGTTCAATATAGCTTAAGG

1851 TGCAG
ACGTC

FIGURE 17B

WT preproricin linker

```
              primer EBV-B1
               5'- TCGGACGCACCTGATAATGCTGATGTTTGT -3'
                   **   ***  ** **
TCTTTGCTTATAAGGCCAGTGGTGCCAAATTTTAAT
AGAAACGAATATTCCGGTCACCACGGTTTAAAATTA
    * **  *   * *
3'- AGCAGTGTCAAAAGAAGCATAGATTTCCGT-5'
         primer EBV-B2
```

PCR mutagenesis ligate with pBluescript SK pAP 243 linker
(EBV-B variant)

```
TCTTCGTATCTAAAGGCATCGGACGCACCTGATAAT
AGAAGCATAGATTTCCGTAGCCTGCGTGGACTATTA
```

FIGURE 17D-1

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTTCGTATCTAAAGGCATCGGACGCACCTGATAATGC
    AGCAGTGTCAAAAGAAGCATAGATTTCCGTAGCCTGCGTGGACTATTACG
```

FIGURE 17D-2

```
 951 TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 18D-1

```
             10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTGGGGTTGTAAATGCATCGTGTAGACTTGCTAATGC
    AGCAGTGTCAAAAGACCCCAACATTTACGTAGCACATCTGAACGATTACG
```

FIGURE 18D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 19B

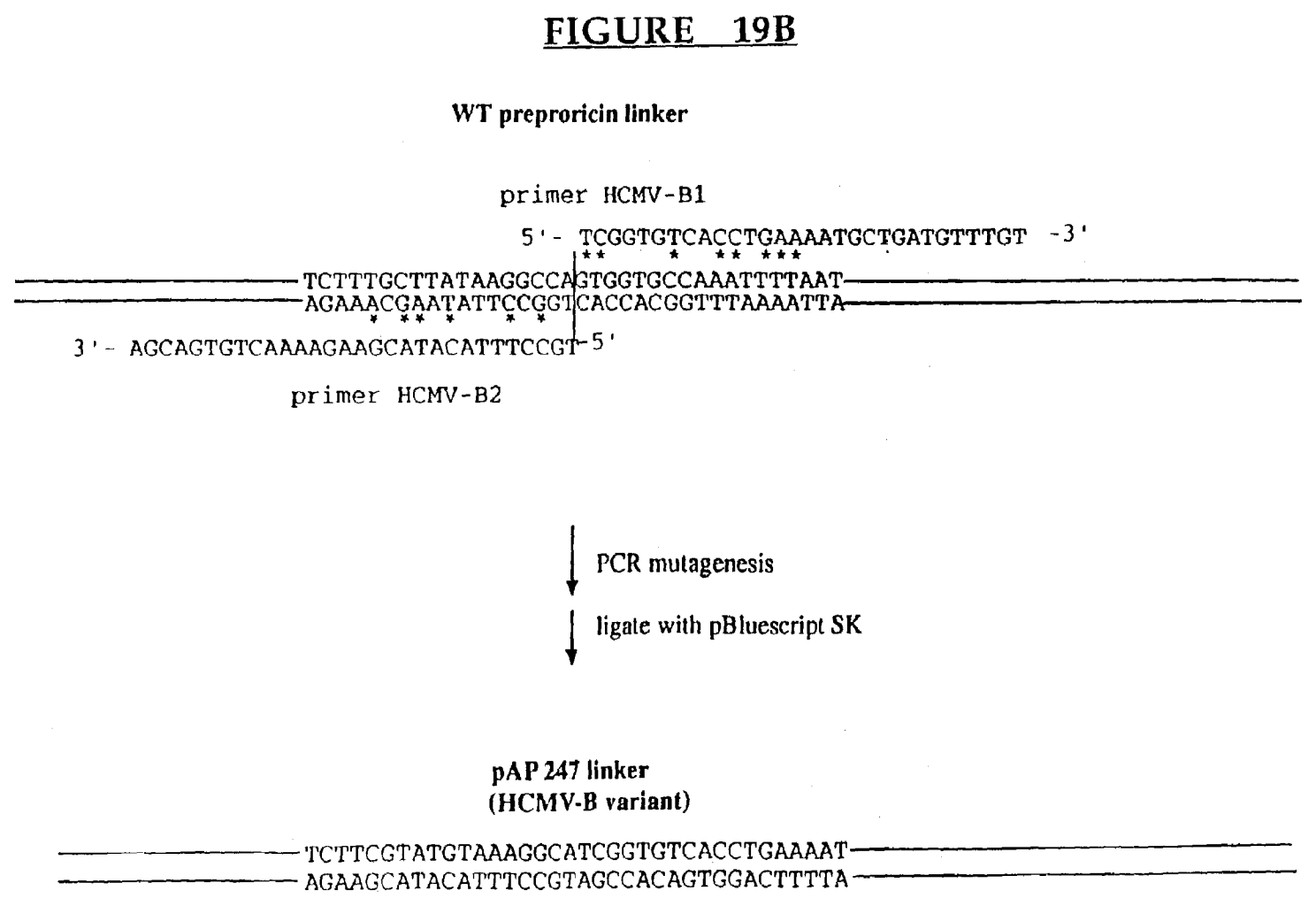

WT preproricin linker primer HCMV-B1

5'- TCGGTGTCACCTGAAAATGCTGATGTTTGT -3'

TCTTTGCTTATAAGGCCAGTGGTGCCAAATTTTAAT

AGAAACGAATATTCCGGTCACCACGGTTTAAAATTA

3'- AGCAGTGTCAAAAGAAGCATACATTTCCGT -5' primer HCMV-B2

PCR mutagenesis ligate with pBluescript SK pAP 247 linker
(HCMV-B variant)

TCTTCGTATGTAAAGGCATCGGTGTCACCTGAAAAT

AGAAGCATACATTTCCGTAGCCACAGTGGACTTTTA

FIGURE 19D-1

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTTCGTATGTAAAGGCATCGGTGTCACCTGAAAATGC
    AGCAGTGTCAAAAGAAGCATACATTTCCGTAGCCACAGTGGACTTTTACG
```

FIGURE 19D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 20D-1

```
         10        20        30        40        50
          |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTTCGATTTTAAATGCATCGGTGCCAAATTTTAATGC
    AGCAGTGTCAAAAGAAGCTAAAATTTACGTAGCCACGGTTTAAAATTACG
```

FIGURE 20D-2

```
 951 TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 21

Ricin linker (wild type):

A chain- S L L I R P V V P N F N -B chain pAP-213/pAP-214 linker (Cathepsin B):

A chain- S L L K S R M V P N F N -B chain pAP-215/pAP-216 linker (MMP-3):

A chain- R P K P Q Q F F G L M N -B chain pAP-217/pAP-218 linker (MMP-7):

A chain- S L R P L A L W R S F N -B chain pAP-219/pAP-220 linker (MMP-9):

A chain- S P Q G I A G Q R N F N -B chain pAP-221/pAP-222 linker (THERMOLYSIN-LIKE MMP):

A chain- D V D E R D V R G F A S F L -B chain pAP-241/pAP-242 linker (EBV-A):

A chain- S K L V Q A S A S G V N -B chain pAP-243/pAP-244 linker (EBV-B):

A chain- S S Y L K A S D A P D N -B chain

FIGURE 22B

WT preproricin linker primer ILTV-B1

5'- AATGAGGTAATTACTAATGCTGATGTTTGT -3'

TCTTTGCTTATAAGGCCAGTGGTGCCAAATTTTAAT

AGAAACGAATATTCCGGTCACCACGGTTTAAAATTA

3'- AGCAGTGTCAAAAGATTCATAGATGTCCGT -5' primer ILTV-B2

PCR mutagenesis ligate with pBluescript SK pAP 253 linker
(ILTV-B variant)

TCTAAGTATCTACAGGCAAATGAGGTAATTACTAAT

AGATTCATAGATGTCCGTTTACTCCATTAATGATTA

FIGURE 22D-1

```
             10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTAAGTATCTACAGGCAAATGAGGTAATTACTAATGC
    AGCAGTGTCAAAAGATTCATAGATGTCCGTTTACTCCATTAATGATTACG
```

FIGURE 22D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

pAP-144 template
primer Ricin-109Eco
primer HAV-A1
signal peptide
A chain
linker
B chain
primer HAV-A2
primer 1729C Xba
PCR mutagenesis
PCR mutagenesis
gel purify
EcoRI
gel purify
gel purify
XbaI
gel purify
HAV-A linker
A chain
B chain
Signal peptide
EcoRI
XbaI
pAP-257
pBluescript SK
EcoRI
XbaI
EcoRI/ XbaI
gel purify vector
triple ligation

FIGURE 23D-1

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTGAGCTTAGAACGCAATCGTTCTCAAATTGGAATGC
    AGCAGTGTCAAAAGACTCGAATCTTGCGTTAGCAAGAGTTTAACCTTACG
```

FIGURE 23D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

```
              10         20         30         40         50
               |          |          |          |          |
  1  GAATTCATGAAACCGGGAGGAAATACTATTGTAATATGGATGTATGCAGT
     CTTAAGTACTTTGGCCCTCCTTTATGATAACATTATACCTACATACGTCA

 51  GGCAACATGGCTTTGTTTTGGATCCACCTCAGGGTGGTCTTTCACATTAG
     CCGTTGTACCGAAACAAAACCTAGGTGGAGTCCCACCAGAAAGTGTAATC

101  AGGATAACAACATATTCCCCAAACAATACCCAATTATAAACTTTACCACA
     TCCTATTGTTGTATAAGGGGTTTGTTATGGGTTAATATTTGAAATGGTGT

151  GCGGGTGCCACTGTGCAAAGCTACACAAACTTTATCAGAGCTGTTCGCGG
     CGCCCACGGTGACACGTTTCGATGTGTTTGAAATAGTCTCGACAAGCGCC

201  TCGTTTAACAACTGGAGCTGATGTGAGACATGATATACCAGTGTTGCCAA
     AGCAAATTGTTGACCTCGACTACACTCTGTACTATATGGTCACAACGGTT

251  ACAGAGTTGGTTTGCCTATAAACCAACGGTTTATTTTAGTTGAACTCTCA
     TGTCTCAACCAAACGGATATTTGGTTGCCAAATAAAATCAACTTGAGAGT

301  AATCATGCAGAGCTTTCTGTTACATTAGCGCTGGATGTCACCAATGCATA
     TTAGTACGTCTCGAAAGACAATGTAATCGCGACCTACAGTGGTTACGTAT

351  TGTGGTCGGCTACCGTGCTGGAAATAGCGCATATTTCTTTCATCCTGACA
     ACACCAGCCGATGGCACGACCTTTATCGCGTATAAAGAAAGTAGGACTGT

401  ATCAGGAAGATGCAGAAGCAATCACTCATCTTTTCACTGATGTTCAAAAT
     TAGTCCTTCTACGTCTTCGTTAGTGAGTAGAAAAGTGACTACAAGTTTTA

451  CGATATACATTCGCCTTTGGTGGTAATTATGATAGACTTGAACAACTTGC
     GCTATATGTAAGCGGAAACCACCATTAATACTATCTGAACTTGTTGAACG

501  TGGTAATCTGAGAGAAAATATCGAGTTGGGAAATGGTCCACTAGAGGAGG
     ACCATTAGACTCTCTTTTATAGCTCAACCCTTTACCAGGTGATCTCCTCC

551  CTATCTCAGCGCTTTATTATTACAGTACTGGTGGCACTCAGCTTCCAACT
     GATAGAGTCGCGAAATAATAATGTCATGACCACCGTGAGTCGAAGGTTGA

601  CTGGCTCGTTCCTTTATAATTTGCATCCAAATGATTTCAGAAGCAGCAAG
     GACCGAGCAAGGAAATATTAAACGTAGGTTTACTAAAGTCTTCGTCGTTC

651  ATTCCAATATATTGAGGGAGAAATGCGCACGAGAATTAGGTACAACCGGA
     TAAGGTTATATAACTCCCTCTTTACGCGTGCTCTTAATCCATGTTGGCCT

701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTGAGCTTTGGTCGCAAGGGATCGATGATGATAATGC
     AGCAGTGTCAAAAGACTCGAAACCAGCGTTCCCTAGCTACTACTATTACG
```

FIGURE 24D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 25D-1

```
        10         20         30         40         50
         |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTAAGCCTGCAAAGTTCTTCAGGCTAAATTTTAATGC
    AGCAGTGTCAAAAGATTCGGACGTTTCAAGAAGTCCGATTTAAAATTACG
```

FIGURE 25D-2

```
951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 26

Ricin linker (wild type):

A chain- S L L I R P V V P N F N -B chain pAP-223/224 linker (MAL-A):

A chain- Q V V Q L Q N Y D E E D -B chain pAP-225/226 linker (MAL-B):

A chain- L P I F G E S E D N D E -B chain pAP-227/228 linker (MAL-C):

A chain- Q V V T G E A I S V T M -B chain pAP-229/230 linker (MAL-D):

A chain- A L E R T F L S F P T N -B chain pAP-231/pAP-232 linker (MAL-E):

A chain- K F Q D M L N I S Q H Q -B chain

FIGURE 27

Ricin linker (wild type):
A chain- S L L I R P V V P N F N -B chain pAP-245/246 linker (CMV-A):
A chain- S G V V N A S C R L A N -B chain pAP-247/248 linker (CMV-B):
A chain- S S Y V K A S V S P E N -B chain pAP-233/234 linker (HERPES SIMPLEX-1 A):
A chain- S A L V N A S S A H V N -B chain pAP-235/236 linker (HERPES SIMPLEX-1 B):
A chain- S T Y L Q A S E K F K N -B chain pAP-249/250 linker (HUMAN HERPES VIRUS-6):
A chain- S S I L N A S V P N F N -B chain pAP-237/pAP-238 linker (VZV-A):
A chain- S Q D V N A V E A S S N -B chain pAP-239/pAP-240 linker (VZV-B):
A chain- S V Y L Q A S T G Y G N -B chain pAP-253/pAP-254 linker (ILV):
A chain- S K Y L Q A N E V I T N -B chain pAP-255/pAP-256 linker (HAV-A):
A chain- S E L R T Q S F S N W N -B chain pAP-257/pAP-258 linker (HAV-B):
A chain- S E L W S Q G I D D D N -B chain

FIGURE 28

Ricin linker (wild type):

A chain- S L L I R P V V P N F N -B chain pAP-259/260 linker (CAP-A):

A chain- S K P A K F F R L N F N -B chain pAP-261/262 linker (CAP-B):

A chain- S K P I E F F R L N F N -B chain pAP-263/264 linker (CAP-C):

A chain- S K P A E F F A L N F N -B chain

PCR Mutagenesis of Preproricin Gene to Create A Variant Gene in Baculovirus Transfer Vector, pVL 1393 a) Cloning Strategy

PCR Mutagenesis of Preproricin Gene to Create An HCV-A Variant Gene in Baculovirus Transfer Vector, pVL 1393 a) Cloning Strategy

FIGURE 30B

Sequence of HCV-A Linker Region

WT preproricin linker

```
                          primer HCV-A1
                            5'- TCGACATGGGTTTTTAATGCTGATGTT     -3'
                                ** ********
-------------TCTTTGCTTATAAGGCCAGTGGTGCCAAATTTTAAT-------------
-------------AGAAACGAATATTCCGGTCACCACGGTTTAAAATTA-------------
             **    ****  ** *
3'- GGTAGCAGTGTCAAACTAAACCTCCATCACTGT-5'

                  5' primer HCV-A2
```

PCR mutagenesis ligate with pVL1393 pAP 262 linker
(HCV-A variant)

```
-------------GATTTGGAGGTAGTGACATCGACATGGGTTTTTAAT-------------
-------------CTAAACCTCCATCACTGTAGCTGTACCCAAAAATTA-------------
```

FIGURE 30C - 1

Sequence of pAP262 insert

```
             10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA
```

FIGURE 30C - 2

```
801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTGATTTGGAGGTAGTGACATCGACATGGGTTTTTAATGC
     AGCAGTGTCAAACTAAACCTCCATCACTGTAGCTGTACCCAAAAATTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA
```

FIGURE 30C-3

```
1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP262

FIGURE 30D

-Amino Acid Sequence Comparison of Mutant Preproricin Linker Region of HCV-A to Wild Type

| | |
|---|---|
| Wild type Ricin linker: | A chain- S L L I R P V V P N F N -B chain |
| pAP-262 linker:<br>(HCV-A linker) | A chain- D L E V V T S T W V F N -B chain |

PCR Mutagenesis of Preproricin Gene to Create An HCV-B Variant Gene in Baculovirus Transfer Vector, pVL 1393 a) Cloning Strategy

FIGURE 31B

Sequence of HCV-B Linker Region

WT preproricin linker

```
                     primer HCV-B1
                       5'- GCGTCACACCTTTTTAATGCTGATGTT     -3'
                            *  ********
-----------TCTTTGCTTATAAGGCCAGTGGTGCCAAATTTTAAT-----------
-----------AGAAACGAATATTCCGGTCACCACGGTTTAAAATTA-----------
            ** **  * *** **  ***
3'- GGTAGCAGTGTCAAACTACTCTACCTTCTCACA-5'
               5' primer HCV-B2
```

PCR mutagenesis ligate with pVL1393 pAP 264 linker
(HCV-B variant)

```
-----------GATGAGATGGAAGAGTGTGCGTCACACCTTTTTAAT-----------
-----------CTACTCTACCTTCTCACACGCAGTGTGGAAAAATTA-----------
```

FIGURE 31C-1

Sequence of pAP264 insert

```
             10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA
```

FIGURE 31C-2

```
 801 TCAACTGCAAAGACGTAATGGTTCCAAATTCAGTGTGTACGATGTGAGTA
     AGTTGACGTTTCTGCATTACCAAGGTTTAAGTCACACATGCTACACTCAT

 851 TATTAATCCCTATCATAGCTCTCATGGTGTATAGATGCGCACCTCCACCA
     ATAATTAGGGATAGTATCGAGAGTACCACATATCTACGCGTGGAGGTGGT

 901 TCGTCACAGTTTGATGAGATGGAAGAGTGTGCGTCACACCTTTTTAATGC
     AGCAGTGTCAAACTACTCTACCTTCTCACACGCAGTGTGGAAAAATTACG

 951 TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA
```

FIGURE 31C-3

```
1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP2-64

FIGURE 31D

-Amino Acid Sequence Comparison of Mutant Preproricin Linker Region of HCV-B to Wild Type

| | | |
|---|---|---|
| Wild type Ricin linker: | A chain- S L L I R P V V P N F N -B chain |
| pAP-264 linker: (HCV-B linker) | A chain- D E M E E C A S H L F N -B chain |

- PCR Mutagenesis of Preproricin Gene to Create An HCV-C Variant Gene in Baculovirus Transfer Vector, pVL 1393 a) Cloning Strategy

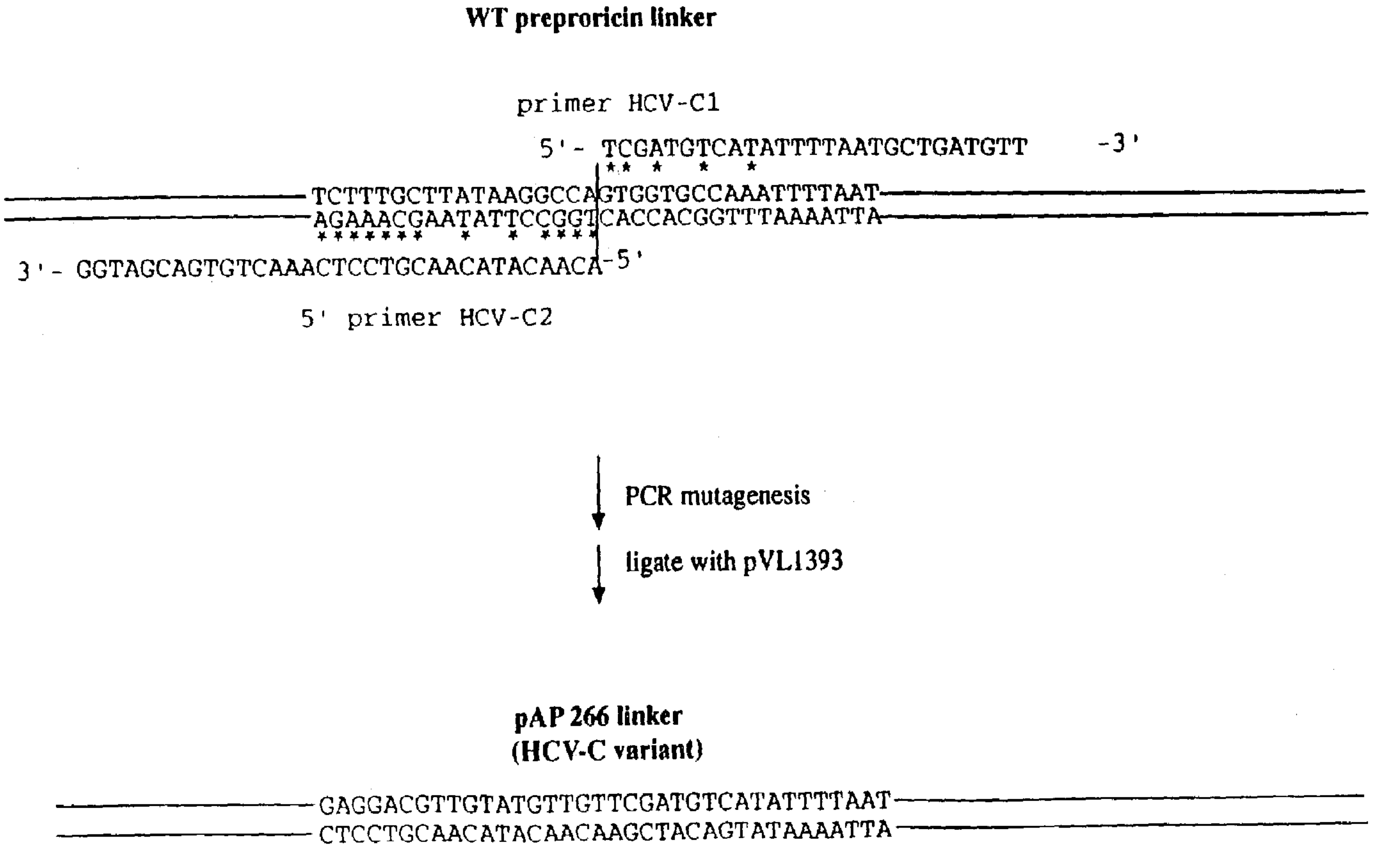

FIGURE 32B

Sequence of HCV-C Linker Region

WT preproricin linker

```
                              primer HCV-C1
                5'- TCGATGTCATATTTTAATGCTGATGTT           -3'
                    ** *   *     *            
        TCTTTGCTTATAAGGCCAGTGGTGCCAAATTTTAAT
        AGAAACGAATATTCCGGTCACCACGGTTTAAAATTA
        *  *  *     *  ****      
3'- GGTAGCAGTGTCAAACTCCTGCAACATACAACA -5'
                 5' primer HCV-C2
```

↓ PCR mutagenesis
↓ ligate with pVL1393 pAP 266 linker
(HCV-C variant)

```
—————GAGGACGTTGTATGTTGTTCGATGTCATATTTTAAT————
—————CTCCTGCAACATACAACAAGCTACAGTATAAAATTA————
```

FIGURE 32C-1

Sequence of pAP266 insert

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA
```

FIGURE 32C-2

```
801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTGAGGACGTTGTATGTTGTTCGATGTCATATTTTAATGC
     AGCAGTGTCAAACTCCTGCAACATACAACAAGCTACAGTATAAAATTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA
```

FIGURE 32C-3

```
1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP266

FIGURE 32D

-Amino Acid Sequence Comparison of Mutant Preproricin Linker Region of HCV-C to Wild Type

| | |
|---|---|
| Wild type Ricin linker: | A chain- S L L I R P V V P N F N -B chain |
| pAP-266 linker: (HCV-C linker) | A chain- E D V V C C S M S Y F N -B chain |

PCR Mutagenesis of Preproricin Gene to Create An HCV-D Variant Gene in Baculovirus Transfer Vector, pVL 1393 a) Cloning Strategy

FIGURE 33B

Sequence of HCV-D Linker Region

WT preproricin linker

```
                         primer HCV-D1
                           5'- GCGCCAATAACTGCTTATGCTGATGTTTGTATG -3'
                                * *****  * ** *
------------TCTTTGCTTATAAGGCCAGTGGTGCCAAATTTTAAT------------
------------AGAAACGAATATTCCGGTCACCACGGTTTAAAATTA------------
            ***** *** * ** *
3'- GGTAGCAGTGTCAAATTCCCCACCTCTAACGAT-5'
                5' primer HCV-D2
```

PCR mutagenesis ligate with pVL1393 pAP 268 linker
(HCV-D variant)

```
------------AAGGGGTGGAGATTGCTAGCGCCAATAACTGCTTAT------------
------------TTCCCCACCTCTAACGATCGCGGTTATTGACGAATA------------
```

FIGURE 33C-1

Sequence of pAP268 insert

```
              10        20        30        40        50
               |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA
```

FIGURE 33C-2

```
801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTAAGGGGTGGAGATTGCTAGCGCCAATAACTGCTTATGC
     AGCAGTGTCAAATTCCCCACCTCTAACGATCGCGGTTATTGACGAATACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA
```

FIGURE 33C-3

```
1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP268

FIGURE 33D

-Amino Acid Sequence Comparison of Mutant Preproricin Linker Region of HCV-D to Wild Type

| | |
|---|---|
| Wild type Ricin linker: | A chain- S L L I R P V V P N F N -B chain |
| pAP-268 linker:<br>(HCV-D linker) | A chain- K G W R L L A P I T A Y -B chain |

PCR Mutagenesis of Preproricin Gene to Create A Variant Gene in Baculovirus Transfer Vector, pVL 1393 a) Cloning Strategy

FIGURE 34B

Sequence of MMP-2 Linker Region

WT preprocin linker

```
                                     primer 270-3'
                                        5'- TGGGCTCCTAATTTTAATGCTGATGTTTGT -3'
                                           |**   **   *
-----------------TCTTTGCTTATAAGGCCA|GTGGTACCAAATTTTAAT-------------------
-----------------AGAAACGAATATTCCGGT|CACCATGGTTTAAAATTA-------------------
                            ***  **  ***
  3'-AGCAGTGTCAAAAGAAACGGGGACCCAAAT -5'
                 primer 270-5'
```

1) PCR mutagenesis

2) Ligate with pVL1393 pAP 270 linker
(MMP-2 variant)

```
-----------------TCTTTGCCCCTGGGTTTA|TGGGCTCCTAATTTTAAT------------------
-----------------AGAAACGGGGACCCAAAT|ACCCGAGGATTAAAATTA -----------------
```

FIGURE 34C-1

Sequence of pAP270 insert

```
            10        20        30        40        50
             |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 34C - 2

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTTTGCCCCTGGGTTTATGGGCTCCTAATTTTAATGC
     AGCAGTGTCAAAAGAAACGGGGACCCAAATACCCGAGGATTAAAATTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 34C-3

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP270

FIGURE 34D

Amino acid sequence Comparison of Mutant Preproricin Linker region of MMP-2 to Wild Type

| | |
|---|---|
| Wild type ricin linker: | A chain- S L L I R P V V P N F N -B chain |
| pAP-270 (MMP-2) linker: | A chain- S L P L G L W A P N F N -B chain |

PCR Mutagenesis of Preproricin Gene to Create A Variant Gene in Baculovirus Transfer Vector, pVL 1393 a) Cloning Strategy

FIGURE 35B

Sequence of Cathepsin B (Site 2) Linker Region

WT preprocin linker

```
                                  primer 272-3'
                                     5'- AGGATGCCAAATTTTAATGCTGATGTTTGT -3'
                                         |** * *
------------------TCTTTGCTTATAAGGCCA|GTGGTACCAAATTTTAAT--------------------
------------------AGAAACGAATATTCCGGT|CACCATGGTTTAAAATTA--------------------
                                *****
   3'-AGCAGTGTCAAAAGAAACGAATATCGATCT -5'
                  primer 272-5'
```

1) PCR mutagenesis

2) Ligate with pVL1393 pAP 272 linker
(Cathepsin B Site 2 variant)

```
------------------TCTTTGCTTATAGCTAGA|AGGATGCCTAATTTTAAT------------------
------------------AGAAACGAATATCGATCT|TCCTACGGATTAAAATTA ------------------
```

FIGURE 35C-1

Sequence of pAP272 insert

```
            10        20        30        40        50
             |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 35C-2

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTTTGCTTATAGCTAGAAGGATGCCTAATTTTAATGC
     AGCAGTGTCAAAAGAAAGGAATATCGATCTTCCTACGGATTAAAATTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 35C-3

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP272

FIGURE 35D

Amino acid sequence Comparison of Mutant Preproricin Linker region of Cathepsin B Site 2 to Wild Type

```
Wild type ricin linker:        A chain- S L L I R P V V P N F N -B chain

pAP-272(Cathepsin B 2)linker:  A chain- S L L I A R R M P N F N -B chain
```

PCR Mutagenesis of Preproricin Gene to Create A Variant Gene in Baculovirus Transfer Vector, pVL 1393 a) Cloning Strategy

FIGURE 36B

Sequence of Cathepsin L Linker Region

WT preprocin linker

```
                                        primer 274-3'
                                           5'- TCATGGGCTAATTTTAATGCTGATGTTTGT -3'
                                               |******** *
------------------TCTTTGCTTATAAGGCCA|GTGGTACCAAATTTTAAT--------------------
------------------AGAAACGAATATTCCGGT|CACCATGGTTTAAAATTA--------------------
                                 *** **
   3'-AGCAGTGTCAAAAGAAACGAATATAAGGCC -5'
                  primer 274-5'
```

1) PCR mutagenesis

2) Ligate with pVL1393 pAP 274 linker
(Cathepsin L variant)

```
------------------TCTTTGCTTATATTCCGG|TCATGGGCTAATTTTAAT-------------------
------------------AGAAACGAATATAAGGCC|AGTACCCGATTAAAATTA ------------------
```

FIGURE 36C-1

Sequence of pAP274 insert

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 36C-2

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTTTGCTTATATTCCGGTCATGGGCTAATTTTAATGC
     AGCAGTGTCAAAAGAAAGGAATATAAGGCCAGTACCCGATTAAAATTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 36C - 3

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP274

FIGURE 36D

Amino acid sequence Comparison of Mutant Preproricin Linker region of Cathepsin L to Wild Type

| | |
|---|---|
| Wild type ricin linker: | A chain- S L L I R P V V P N F N -B chain |
| pAP-274 (Cathepsin L)linker: | A chain- S L L I F R S W A N F N -B chain |

PCR Mutagenesis of Preproricin Gene to Create A Variant Gene in Baculovirus Transfer Vector, pVL 1393 a) Cloning Strategy

FIGURE 37B

Sequence of Cathepsin D Linker Region

WT preprocin linker

```
                          primer 276-3'
                             5'- ACTGTTATTGTTATCACCGCTGATGTTTGT -3'
                                |***  ****** * * **
------------------TCTTTGCTTATAAGGCCA|GTGGTACCAAATTTTAAT--------------------
------------------AGATAACGAATATTCCGG|CACCATGGTTTAAAATTA--------------------
                       ****  * * *** *
   3'-AGCAGTGTCAAAAGACCACAACAGTAGCGA -5'
                  primer 276-5'
```

1) PCR mutagenesis

2) Ligate with pVL1393 pAP 276 linker
(Cathepsin D variant)

```
------------------TCTGGTGTTGTCATCGCT|ACTGTTATTGTTATCACC  ------------------
------------------AGACCACAACAGTAGCGA|TGACAATAACAATAGTGG  -----------------
```

FIGURE 37C-1

Sequence of pAP276 insert

```
              10         20         30         40         50
               |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 37C-2

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTGGTGTTGTCATCGCTACTGTTATTGTTATCACCGC
     AGCAGTGTCAAAAGACCACAACAGTAGCGATGACAATAACAATAGTGGCG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 37C-3

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP276

FIGURE 37D

Amino acid sequence Comparison of Mutant Preproricin Linker region of Cathepsin D to Wild Type

| | |
|---|---|
| Wild type ricin linker: | A chain- S L L I R P V V P N F N -B chain |
| pAP-276 (Cathepsin D) linker: | A chain- S G V V I A T V I V I T -B chain |

PCR Mutagenesis of Preproricin Gene to Create A Variant Gene in Baculovirus Transfer Vector, pVL 1393 a) Cloning Strategy

FIGURE 38B

Sequence of MMP-1 (Interstitial collagenase) Linker Region

WT preprocin linker

```
                                          primer 278-3'
                                             5'- ATTTGGGGACAGTTTAATGCTGATGTTTGT -3'
                                                 * ****** * *
------------------TCTTTGCTTATAAGGCCA|GTGGTACCAAATTTTAAT-------------------
------------------AGAAACGAATATTCCGGT|CACCATGGTTTAAAATTA-------------------
                             ** *********
   3'-AGCAGTGTCAAAAGAAACCCAGGAGTTCCG -5'
                   primer 278-5'
```

1) PCR mutagenesis

2) Ligate with pVL1393 pAP 278 linker
(MMP-1 variant)

```
------------------TCTTTGGGTCCTCAAGGC|ATTTGGGGACAGTTTAAT------------------
------------------AGAAACCCAGGAGTTCCG|TAAACCCCTGTCAAATTA -----------------
```

FIGURE 38C-1

Sequence of pAP278 insert

```
         10        20        30        40        50
          |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 38C - 2

```
 701 GATCTGCACCAGATCCTAGCGTAATTACACTTGAGAATAGTTGGGGGAGA
     CTAGACGTGGTCTAGGATCGCATTAATGTGAACTCTTATCAACCCCCTCT

 751 CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

 801 TCAACTGCAAAGACGTAATGGTTCCAAATTCAGTGTGTACGATGTGAGTA
     AGTTGACGTTTCTGCATTACCAAGGTTTAAGTCACACATGCTACACTCAT

 851 TATTAATCCCTATCATAGCTCTCATGGTGTATAGATGCGCACCTCCACCA
     ATAATTAGGGATAGTATCGAGAGTACCACATATCTACGCGTGGAGGTGGT

 901 TCGTCACAGTTTTCTTTGGGTCCTCAAGGCATTTGGGGACAGTTTAATGC
     AGCAGTGTCAAAAGAAACGCAGGAGTTCCGTAAACCCCTGTCAAATTACG

 951 TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 38C-3

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
AGTTCTTACTACCTTGGTAAAATTTAAACATATCACCTAACCACAATCTA

1651 GTGAGGCGATCGGATCCGAGCCTTAAACAAATCATTCTTTACCCTCTCCA
CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
GAGAACGTCACACACACAGGACGGTACTTTTATCTACCGAATTTATTTTT

1801 GGACATTGTAAATTTTGTAACTGAAAGGACAGCAAGTTATATCGAATTCC
CCTGTAACATTTAAAACATTGACTTTCCTGTCGTTCAATATAGCTTAAGG

1851 TGCAG
ACGTC

Total number of bases is: 1855.

Sequence name: PAP278

FIGURE 38D

Figure 38. d) Amino acid sequence Comparison of Mutant Preproricin Linker region of MMP-1 (Interstitial collagenase) to Wild Type

| | |
|---|---|
| Wild type ricin linker: | A chain- S L L I R P V V P N F N -B chain |
| pAP-278 (MMP-1) linker: | A chain- S L G P Q G I W G Q F N -B chain |

PCR Mutagenesis of Preproricin Gene to Create A Variant Gene in Baculovirus Transfer Vector, pVL 1393 a) Cloning Strategy

FIGURE 39B

Sequence of Urokinase-Type Plasminogen Activator Linker Region

WT preprocin linker

```
                                          primer 280-3'
                                             5'- GTTGTCGGTGGCTCTGTAGCTGATGTTTGT -3'
                                                      *   ******* * ***
------------------TCTTTGCTTATAAGGCCA|GTGGTACCAAATTTTAAT-------------------
------------------AGAAACGAATATTCCGGT|CACCATGGTTTAAAATTA-------------------
                  ************* ***
   3'-AGCAGTGTCAAATTTTTTAGGGGACCTTCT -5'
                  primer 280-5'
```

1) PCR mutagenesis

2) Ligate with pVL1393 pAP 280 linker
(uPA variant)

```
------------------AAAAAATCCCCTGGAAGA|GTTGTCGGTGGCTCTGTA ------------------
------------------TTTTTTAGGGGACCTTCT|CAACAGCCACCGAGACAT -----------------
```

FIGURE 39C-1

Sequence of pAP280 insert

```
            10        20        30        40        50
             |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 39C-2

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTAAAAAATCCCCTGGAAGAGTTGTCGGTGGCTCTGTAGC
     AGCAGTGTCAAATTTTTTAGGGGACCTTCTCAACAGCCACCGAGACATCG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 39C - 3

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP280

FIGURE 39D

Figure 39. d) Amino acid sequence Comparison of Mutant Preproricin Linker region of Urokinase-Type Plasminogen Activator to Wild Type

| | |
|---|---|
| Wild type ricin linker: | A chain- S L L I R P V V P N F N -B chain |
| pAP-280 (uPA) linker: | A chain- K K S P G R V V G G S V-B chain |

PCR Mutagenesis of Preproricin Gene to Create A Variant Gene in Baculovirus Transfer Vector, pVL 1393 a) Cloning Strategy

FIGURE 40B

Sequence of MT-MMP Linker Region

WT preprocin linker

```
                          primer 282-3'
                             5'- GCTCCTGGTATTCTTGGCGCTGATGTTTGT -3'
                                  ********* * *  ***
------------------TCTTTGCTTATAAGGCCA|GTGGTACCAAATTTTAAT-------------------
------------------AGAAACGAATATTCCGGT|CACCATGGTTTAAAATTA-------------------
                  * ******** *******
   3'-AGCAGTGTCAAAGGGGTTCCTGAGGATCCC -5'
                  primer 282-5'
```

1) PCR mutagenesis

2) Ligate with pVL1393 pAP 282 linker
(MT-MMP variant)

```
------------------CCCCAAGGACTCCTAGGG|GCTCCTGGTATTCTTGGC -------------------
------------------GGGGTTCCTGAGGATCCC|CGAGGACCATAAGAACCG ------------------
```

FIGURE 40C-1

Sequence of pAP282 insert

```
         10         20         30         40         50
          |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 40C - 2

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTCCCCAAGGACTCCTAGGGGCTCCTGGTATTCTTGGCGC
     AGCAGTGTCAAAGGGGTTCCTGAGGATCCCCGAGGACCATAAGAACCGCG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 40C-3

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP282

FIGURE 40D

Amino acid sequence Comparison of Mutant Preproricin Linker region of MT-MMP to Wild Type

| | |
|---|---|
| Wild type ricin linker: | A chain- S L L I R P V V P N F N -B chain |
| pAP-282 (MT-MMP) linker: | A chain- P Q G L L G A P G I L G-B chain |

PCR Mutagenesis of Preproricin Gene to Create A Variant Gene in Baculovirus Transfer Vector, pVL 1393 a) Cloning Strategy

FIGURE 41B

Sequence of MMP-11 (Stromelysin-3) Linker Region

WT preprocin linker

```
                                                   primer 284-3'
                                                5'- ATGGGAAGAGGCCATGCTCGTTTAGTTCATGTCGAAGAGCCTCACACTGCTGATGTTTGTATGGAT-3
                                                    |
-----------------TCTTTGCTTATAAGGCCA|GTGGTACCAAATTTTAAT-------------------
-----------------AGAAACGAATATTCCGGT|CACCATGGTTTAAAATTA-------------------

3'-GGTGGTAGCAGTGTCAAAGTGCCGGGGCTCCCAAATTCTCACCCTAAAATACTTAGACTGCAG -5'
                  primer 284-5'
```

1) PCR mutagenesis

2) Ligate with pVL1393 pAP 284 linker
(MMP-11 variant)

```
---CACGGCCCCGAGGGTTTAAGAGTGGGATTTTATGAATCTGACGTC|ATGGGAAGAGGCCATGCTCGTTTAGTTCATGTCGAAGAGCCTCACACT---
---GTGCCGGGGCTCCCAAATTCTCACCCTAAAATACTTAGACTGCAG|TACCCTTCTCCGGTACGAGCAAATCAAGTACAGCAACTCGGAGTGTGA---
```

FIGURE 41C-1

Sequence of pAP284 insert

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 41C - 2

701 GATCTGCACCAGATCCTAGCGTAATTACACTTGAGAATAGTTGGGGGAGA
CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
AGTTGACGTTTCTGCATTACCAAGGTTTAAGTCACACATGCTACACTCAT

851 TATTAATCCCTATCATAGCTCTCATGGTGTATAGATGCGCACCTCCACCA
ATAATTAGGGATAGTATCGAGAGTACCACATATCTACGCGTGGAGGTGGT

901 TCGTCACAGTTT
AGCAGTGTCAAA

Linker Sequence:
CACGGCCCCGAGGGTTTAAGAGTGGGATTTTATGAATCTGACGTCATGGG
GTGCCGGGGCTCCCAAATTCTCACCCTAAAATACTTAGACTGCAGTACCC AAGAGGCCATGCTCGTTTAGTTCATGTCGAAGAGCCTCACACT
TTCTCCGGTACGAGCAAATCAAGTACAGCAACTCGGAGTGTGA

949 GC
CG

951 TGATGTTTGTATGGATCCTGAGCCCATAGTGCGTATCGTAGGTCGAAATG
ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

FIGURE 41C-3

```
1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 41D

Amino acid sequence Comparison of Mutant Preproricin Linker region of MMP-11 (Stromelysin-3) to Wild Type

Wild type ricin linker: A chain- S L L I R P V V P N F N -B chain pAP-284 (MMP-11) linker:
A chain- H G P E G L R V G F Y E S D V M G R G H A R L V H V E E P H T -B chain

PCR Mutagenesis of Preproricin Gene to Create A Variant Gene in Baculovirus Transfer Vector, pVL 1393 a) Cloning Strategy

FIGURE 42B

Sequence of MMP-13 = Collagenase-3 Linker Region

WT preprocin linker

```
                          primer 286-3'
                             5'- GGTCAACGAGGCATTGTCGCTGATGTTTGT -3'
                                     ****   *  ****   ***
------------------TCTTTGCTTATAAGGCCA|GTGGTACCAAATTTTAAT--------------------
------------------AGAAACGAATATTCCGGT|CACCATGGTTTAAAATTA--------------------
                  ******  ********* *
   3'-AGCAGTGTCAAACCTGGAGTCCCCGAACGA -5'
                  primer 286-5'
```

1) PCR mutagenesis

2) Ligate with pVL1393 pAP 286 linker
(MMP-13 variant)

```
------------------GGACCTCAGGGGCTTGCT|GGTCAACGAGGCATTGTC ------------------
------------------CCTGGAGTCCCCGAACGA|CCAGTTGCTCCGTAACAG ------------------
```

FIGURE 42C-1

Sequence of pAP286 insert

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
```

FIGURE 42C - 2

```
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTGGACCTCAGGGGCTTGCTGGTCAACGAGGCATTGTCGC
     AGCAGTGTCAAACCTGGAGTCCCCGAACGACCAGTTGCTCCGTAACAGCG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
```

FIGURE 42C-3

```
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 42D

Amino acid sequence Comparison of Mutant Preproricin Linker region of MMP-13 (Collagenase-3) to Wild Type

| | |
|---|---|
| Wild type ricin linker: | A chain- S L L I R P V V P N F N -B chain |
| pAP-286 (MMP-13) linker: | A chain- G P Q G L A G Q R G I V -B chain |

PCR Mutagenesis of Preproricin Gene to Create A Variant Gene in Baculovirus Transfer Vector, pVL 1393 a) Cloning Strategy

FIGURE 43B

Sequence of Tissue-type Plasminogen Activator (tPA) Linker Region

WT preprocin linker

```
                                  primer 288-3'
                                     5'- GGTCGTAAAGCTCTTGAAGCTGATGTTTGT -3'
                                             ******* ** *    *
------------------TCTTTGCTTATAAGGCCA|GTGGTACCAAATTTTAAT--------------------
------------------AGAAACGAATATTCCGGT|CACCATGGTTTAAAATTA--------------------
                  ******** *********
   3'-AGCAGTGTCAAACCGCCTAGACCCGTTTCC -5'
                  primer 288-5'
```

1) PCR mutagenesis

2) Ligate with pVL1393 pAP 288 linker
(tPA variant)

```
------------------ GGCGGATCTGGGCAAAGG|GGTCGTAAAGCTCTTGAA -------------------
------------------ CCGCCTAGACCCGTTTCC|CCAGCATTTCGAGAACTT ------------------
```

FIGURE 43C - 1

Sequence of pAP288 insert

```
            10        20        30        40        50
             |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
```

FIGURE 43C-2

CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
AGTTGACGTTTCTGCATTACCAAGGTTTAAGTCACACATGCTACACTCAT

851 TATTAATCCCTATCATAGCTCTCATGGTGTATAGATGCGCACCTCCACCA
ATAATTAGGGATAGTATCGAGAGTACCACATATCTACGCGTGGAGGTGGT

901 TCGTCACAGTTTGGCGGATCTGGGCAAAGGGGTCGTAAAGCTCTTGAAGC
AGCAGTGTCAAACCGCCTAGACCCGTTTCCCCAGCATTTCGAGAACTTCG

951 TGATGTTTGTATGGATCCTGAGCCCATAGTGCGTATCGTAGGTCGAAATG
ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT

FIGURE 43C-3

```
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP288

FIGURE 43D

Amino acid sequence Comparison of Mutant Preproricin Linker region of Tissue-type Plasminogen Activator (tPA) to Wild Type

| | |
|---|---|
| Wild type ricin linker: | A chain- S L L I R P V V P N F N -B chain |
| pAP-288 (tPA) linker: | A chain- G G S G Q R G R K A L E-B chain |

PCR Mutagenesis of Preproricin Gene to Create A Variant Gene in Baculovirus Transfer Vector, pVL 1393 a) Cloning Strategy

FIGURE 44B

Sequence of human Prostate-Specific Antigen (PSA) Linker Region

WT preprocin linker

```
                                             primer 290-3'
                                                5'- TCTTCCGATATTTTTAATGCTGATGTTTGT -3'
                                                     *********  *
------------------TCTTTGCTTATAAGGCCA|GTGGTACCAAATTTTAAT--------------------
------------------AGAAACGAATATTCCGGT|CACCATGGTTTAAAATTA--------------------
                                *********   *
   3'-AGCAGTGTCAAAAGAAACAGTCGAGAAGAG -5'
                  primer 290-5'
```

1) PCR mutagenesis

2) Ligate with pVL1393 pAP 290 linker
(PSA variant)

```
------------------TCTTTGTCAGCTCTTCTC|TCTTCCGATATTTTTAAT--------------------
------------------AGAAACAGTCGAGAAGAG|AGAAGGCTATAAAAATTA -------------------
```

FIGURE 44C-1

Sequence of pAP290 insert

```
             10         20         30         40         50
              |          |          |          |          |
  1  GAATTCATGAAACCGGGAGGAAATACTATTGTAATATGGATGTATGCAGT
     CTTAAGTACTTTGGCCCTCCTTTATGATAACATTATACCTACATACGTCA

 51  GGCAACATGGCTTTGTTTTGGATCCACCTCAGGGTGGTCTTTCACATTAG
     CCGTTGTACCGAAACAAAACCTAGGTGGAGTCCCACCAGAAAGTGTAATC

101  AGGATAACAACATATTCCCCAAACAATACCCAATTATAAACTTTACCACA
     TCCTATTGTTGTATAAGGGGTTTGTTATGGGTTAATATTTGAAATGGTGT

151  GCGGGTGCCACTGTGCAAAGCTACACAAACTTTATCAGAGCTGTTCGCGG
     CGCCCACGGTGACACGTTTCGATGTGTTTGAAATAGTCTCGACAAGCGCC

201  TCGTTTAACAACTGGAGCTGATGTGAGACATGATATACCAGTGTTGCCAA
     AGCAAATTGTTGACCTCGACTACACTCTGTACTATATGGTCACAACGGTT

251  ACAGAGTTGGTTTGCCTATAAACCAACGGTTTATTTTAGTTGAACTCTCA
     TGTCTCAACCAAACGGATATTTGGTTGCCAAATAAAATCAACTTGAGAGT

301  AATCATGCAGAGCTTTCTGTTACATTAGCGCTGGATGTCACCAATGCATA
     TTAGTACGTCTCGAAAGACAATGTAATCGCGACCTACAGTGGTTACGTAT

351  TGTGGTCGGCTACCGTGCTGGAAATAGCGCATATTTCTTTCATCCTGACA
     ACACCAGCCGATGGCACGACCTTTATCGCGTATAAAGAAAGTAGGACTGT

401  ATCAGGAAGATGCAGAAGCAATCACTCATCTTTTCACTGATGTTCAAAAT
     TAGTCCTTCTACGTCTTCGTTAGTGAGTAGAAAAGTGACTACAAGTTTTA

451  CGATATACATTCGCCTTTGGTGGTAATTATGATAGACTTGAACAACTTGC
     GCTATATGTAAGCGGAAACCACCATTAATACTATCTGAACTTGTTGAACG

501  TGGTAATCTGAGAGAAAATATCGAGTTGGGAAATGGTCCACTAGAGGAGG
     ACCATTAGACTCTCTTTTATAGCTCAACCCTTTACCAGGTGATCTCCTCC

551  CTATCTCAGCGCTTTATTATTACAGTACTGGTGGCACTCAGCTTCCAACT
     GATAGAGTCGCGAAATAATAATGTCATGACCACCGTGAGTCGAAGGTTGA

601  CTGGCTCGTTCCTTTATAATTTGCATCCAAATGATTTCAGAAGCAGCAAG
     GACCGAGCAAGGAAATATTAAACGTAGGTTTACTAAAGTCTTCGTCGTTC

651  ATTCCAATATATTGAGGGAGAAATGCGCACGAGAATTAGGTACAACCGGA
     TAAGGTTATATAACTCCCTCTTTACGCGTGCTCTTAATCCATGTTGGCCT

701  GATCTGCACCAGATCCTAGCGTAATTACACTTGAGAATAGTTGGGGGAGA
```

FIGURE 44C-2

```
     CTAGACGTGGTCTAGGATCGCATTAATGTGAACTCTTATCAACCCCCTCT

 751 CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

 801 TCAACTGCAAAGACGTAATGGTTCCAAATTCAGTGTGTACGATGTGAGTA
     AGTTGACGTTTCTGCATTACCAAGGTTTAAGTCACACATGCTACACTCAT

 851 TATTAATCCCTATCATAGCTCTCATGGTGTATAGATGCGCACCTCCACCA
     ATAATTAGGGATAGTATCGAGAGTACCACATATCTACGCGTGGAGGTGGT

 901 TCGTCACAGTTTTCTTTGTCAGCTCTTCTCTCTTCCGATATTTTTAATGC
     AGCAGTGTCAAAAGAAACAGTCGAGAAGAGAGAAGGCTATAAAAATTACG

 951 TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
```

FIGURE 44C-3

```
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP290

FIGURE 44D

Amino acid sequence Comparison of Mutant Preproricin Linker region of human Prostate-Specific Antigen (PSA) to Wild Type

| | |
|---|---|
| Wild type ricin linker: | A chain- S L L I R P V V P N F N -B chain |
| pAP-290 (PSA) linker: | A chain- S L S A L L S S D I F N -B chain |

PCR Mutagenesis of Preproricin Gene to Create A Variant Gene in Baculovirus Transfer Vector, pVL 1393 a) Cloning Strategy

FIGURE 45B

Sequence of Kallikrein (hK3) Linker Region

WT preprocin linker

```
                                     primer 292-3'
                                        5'- ATTATCGGTGGCTTTAATGCTGATGTTTGT -3'
                                             * **  *******
----------------TCTTTGCTTATAAGGCCA|GTGGTACCAAATTTTAAT------------------
----------------AGAAACGAATATTCCGGT|CACCATGGTTTAAAATTA------------------
                      *   * *****
   3'-AGCAGTGTCAAAAGAAACGGATCTAAATTT -5'
                primer 292-5'
```

1) PCR mutagenesis

2) Ligate with pVL1393 pAP 292 linker
(Kallikrein variant)

```
----------------TCTTTGCCTAGATTTAAA|ATTATCGGTGGCTTTAAT------------------
----------------AGAAACGGATCTAAATTT|TAATAGCCACCGAAATTA ------------------
```

FIGURE 45C-1

Sequence of pAP292 insert

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
```

FIGURE 45C-2

CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
AGTTGACGTTTCTGCATTACCAAGGTTTAAGTCACACATGCTACACTCAT

851 TATTAATCCCTATCATAGCTCTCATGGTGTATAGATGCGCACCTCCACCA
ATAATTAGGGATAGTATCGAGAGTACCACATATCTACGCGTGGAGGTGGT

901 TCGTCACAGTTTTCTTTGCCTAGATTTAAAATTATCGGTGGCTTTAATGC
AGCAGTGTCAAAAGAAACGGATCTAAATTTTAATAGCCACCGAAATTACG

951 TGATGTTTGTATGGATCCTGAGCCCATAGTGCGTATCGTAGGTCGAAATG
ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
TCCGACTTGTTGTCACCCGAGAAATACGTCTACCAAGTTATGCAGGAGTC

1501 CAAAACCGAGATAATTGCCTTACAAGTGATTCTAATATACGGGAAACAGT

FIGURE 45C-3

GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
AGTTCTTACTACCTTGGTAAAATTTAAACATATCACCTAACCACAATCTA

1651 GTGAGGCGATCGGATCCGAGCCTTAAACAAATCATTCTTTACCCTCTCCA
CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
GAGAACGTCACACACACAGGACGGTACTTTTATCTACCGAATTTATTTTT

1801 GGACATTGTAAATTTTGTAACTGAAAGGACAGCAAGTTATATCGAATTCC
CCTGTAACATTTAAAACATTGACTTTCCTGTCGTTCAATATAGCTTAAGG

1851 TGCAG
ACGTC

Total number of bases is: 1855.

Sequence name: PAP292

FIGURE 45D

Amino acid sequence Comparison of Mutant Preproricin Linker region of Kallikrein (hK3) to Wild Type

| | |
|---|---|
| Wild type ricin linker: | A chain- S L L I R P V V P N F N -B chain |
| pAP-292 (hK3) linker: | A chain- S L P R F K I I G G F N -B chain |

PCR Mutagenesis of Preproricin Gene to Create A Variant Gene in Baculovirus Transfer Vector, pVL 1393 a) Cloning Strategy

FIGURE 46B

Sequence of Neutrophil Elastase Linker Region

WT preprocin linker

```
                                         primer 294-3'
                                            5'- GTTCCTGGTAATTTTAATGCTGATGTTTGT -3'
                                                 **  ******
----------------TCTTTGCTTATAAGGCCA|GTGGTACCAAATTTTAAT------------------
----------------AGAAACGAATATTCCGGT|CACCATGGTTTAAAATTA------------------
                            ***  ***  *
   3'-AGCAGTGTCAAAAGAAACGAACCGTAACGA -5'
               primer 294-5'
```

1) PCR mutagenesis

2) Ligate with pVL1393 pAP 294 linker
(Neutrophil elastase variant)

```
----------------TCTTTGCTTGGCATTGCT|GTTCCTGGTAATTTTAAT------------------
----------------AGAAACGAACCGTAACGA|CAAGGACCATTAAAATTA ------------------
```

FIGURE 46C-1

Sequence of pAP294 insert

```
            10         20         30         40         50
             |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
```

FIGURE 46C-2

```
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTTTGCTTGGCATTGCTGTTCCTGGTAATTTTAATGC
     AGCAGTGTCAAAAGAAACGAACCGTAACGACAAGGACCATTAAAATTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
```

FIGURE 46C - 3

```
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP294

FIGURE 46D

Amino acid sequence Comparison of Mutant Preproricin Linker region of Neutrophil elastase to Wild Type Wild type ricin linker: A chain- S L L I R P V V P N F N -B chain pAP-294 (Neutrophil elastase) linker:
A chain- S L L G I A V P G N F N -B chain

PCR Mutagenesis of Preproricin Gene to Create A Variant Gene in Baculovirus Transfer Vector, pVL 1393 a) Cloning Strategy

FIGURE 47B

Sequence of Calpain Linker Region

WT preprocin linker

```
                         primer 296-3'
                            5'- ACTCCTAGAACCCCCCCAGCTGATGTTTGT -3'
                                ********    ********
-----------------TCTTTGCTTATAAGGCCA|GTGGTACCAAATTTTAAT-------------------
-----------------AGAAACGAATATTCCGGT|CACCATGGTTTAAAATTA-------------------
                 *    *** ** *****
   3'-AGCAGTGTCAAAAAAAAGTTTTTATAACAA -5'
                 primer 296-5'
```

1) PCR mutagenesis

2) Ligate with pVL1393 pAP 296 linker
(Calpain variant)

```
-----------------TTTTTCAAAAATATTGTT|ACTCCTAGAACCCCCCCA -------------------
-----------------AAAAAGTTTTTATAACAA|TGAGGATCTTGGGGGGGT
```

FIGURE 47C - 1

Sequence of pAP296 insert

```
             10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
```

FIGURE 47C-2

```
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTTTTTCAAAAATATTGTTACTCCTAGAACCCCCCCAGC
     AGCAGTGTCAAAAAAAAGTTTTTATAACAATGAGGATCTTGGGGGGGTCG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
```

FIGURE 47C - 3

```
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: PAP296

FIGURE 47D

Amino acid sequence Comparison of Mutant Preproricin Linker region of Calpain to Wild Type

| | |
|---|---|
| Wild type ricin linker: | A chain- S L L I R P V V P N F N -B chain |
| pAP-296 (Calpain) linker: | A chain- F F K N I V T P R T P P -B chain |

Cleavage of pAP 214 by Cathepsin B

A. Ricin standard

B. pAP 214

C. pAP 214 digested with 100 ng of Cathepsin B (18 hours)

D. pAP 214 digested with 618 ng of Cathepsin B (18 hours)

Cleavage of pAP 220 with MMP-9

A. pAP 220

B. pAP 220 digested with 200 ng of MMP-9 (16 hrs)

C. pAP 220 digested with 20 ng of MMP-9 (16hrs)

D. pAP 220 digested with 20 ng of MMP-9 (2hrs)

Activation of pAP 214

A. 41.7 pg of pAP 214 digested with Cathepsin B
B. 291 pg of pAP 214 digested with Cathpepsin B
C. 2.0 ng of pAP 214 digested with Cathepsin B
D. 14.2 ng of pAP 214 digested with Cathepsin B
E. 100 ng of pAP 214 digested with Cathepsin B
F. Negative control
G. Ricin A chain
H. 41.7 pg of pAP 214 variant
I. 291 pg of pAP 214 variant
J. 2.0 ng of pAP 214 variant
K. 14.2 ng of pAP 214 variant
L. 100ng of pAP 214 variant
M. RNA ladder

Activation of pAP 220

A. 48.5 pg of pAP 220 variant
B. 291 pg of pAP 220 variant
C. 2.0 ng of pAP 220 variant
D. 14.3 ng of pAP 220 variant
E. 100 ng of pAP 220 variant
F. Ricin A chain
G. Negative Control
H. 48.5 pg of pAP 220 variant digested with MMP-9
I. 291 pg of pAP 220 variant digested with MMP-9
J. 2.0 ng of pAP 220 variant digested with MMP-9
K. 14.3 ng of pAP 220 variant digested with MMP-9
L. 100 ng of pAP 220 variant digested with MMP-9
M. RNA ladder Cleavage of pAP-248 Protein by The Human Cytomegalovirus (HCMV) protease A. pAP-248 (0.279 ug)
B. pAP-248 protein (0.279 μg) digested with 0.25 μg of the HCMV protease
C. Ricin standard (20 ng)
D. Ricin standard (40 ng)

Activation of pAP-248 Protein

A. 90 ng of pAP-248 variant
B. 12.8 ng of pAP-248 variant
C. 1.8 ng of pAP-248 variant
D. 260 pg pAP-248 variant
E. 37 pg of pAP-248 variant
F. Negative control
G. Ricin A chain
H. 37 pg of pAP-248 digested with HCMV protease
I. 260 pg of pAP-248 digested with HCMV protease
J. 1.8 ng of pAP-248 digested with HCMV protease
K. 12.8 ng of pAP-248 digested with HCMV protease
L. 90 ng of pAP-248 digested with HCMV protease
M. RNA ladder Cleavage of pAP-256 protein by The Hepatits A Virus 3C (HAV 3C) Protease A. Ricin standard (0.250 ug)
B. pAP-256 protein (0.378 ug)
C. pAP-256 protein digested (0.302 ug) with 1.25 μg of the HAV 3C protease

Activation of pAP-256 Protein

A. 100 ng of pAP-256 variant
B. 14.2 ng of pAP-256 variant
C. 2.0 ng of pAP-256 variant
D. 291 pg of pAP-256 variant
E. 41.7 pg of pAP-256 variant
F. Negative control
G. Ricin A chain
H. 41.7 pg of pAP-256 digested with HAV 3C protease
I. 291 pg of pAP-256 digested with HAV 3C protease
J. 2.0 ng of pAP-256 digested with HAV 3C protease
K. 14.2 ng of pAP-256 digested with HAV 3C protease
L. 100 ng of pAP-256 digested with HAV 3C protease
M. RNA ladder

Cytotoxicity of Digested and Undigested pAP 214 with Cathepsin B to COS-1 Cells

| | Ricin | pAP 214 | pAP 214 + Cathepsin B |
|---|---|---|---|
| $IC_{50}$ (ng/ml) | 0.11 | 1.9 | 0.078 |
| Relative Toxicity | 1X | 17X | 0.7X |

Cytotoxicity of pAP220 Digested with MMP-9 Compared to Freshly Thawed pAP220 and Ricin on COS-1 Cells

| | Ricin | pAP 220 | pAP 220 + MMP-9 |
|---|---|---|---|
| $IC_{50}$ (ng/ml) | 0.31 | 6.7 | 0.13 |
| Relative Toxicity | 1X | 22X | 0.4X |

Cleavage of pAP-270 protein by The Matrix Metalloproteinase 2 (MMP-2)

A. pAP-270 (0.120 μg) undigested

B. pAP-270 (0.120 μg) digested with 0.250 μg MMP-2

C. Ricin Standard (0.05 μg)

Activation of pAP-270 protein

A. 100 ng of digested pAP-270
B. 14.2 ng of digested pAP-270
C. 2.0 ng of digested pAP-270
D. 290 pg of digested pAP-270
E. 46 ng of digested pAP-270
F. Ricin A chain
G. Negative control
H. 46 pg of pAP-270
I. 290 pg of pAP-270
J. 2.0 ng of pAP-270
K. 14.2 ng of pAP-270
L. 100 ng of pAP-270

Cleavage of pAP-288 protein by Plasminogen Tissue Activator (t-PA)

A. Ricin Standard (0.05μg)

B. pAP-288 (0.66 μg) undigested

C. pAP-288 (0.60 μg) digested with 0.18 μg of t-PA protease

Activation of pAP-288 protein

A. 200 ng of pAP-288
B. 28.4 ng of pAP-288
C. 4.0 ng of pAP-288
D. 482 pg of pAP-288
E. 83.4 pg of pAP-288
F. Ricin A chain
G. Negative control
H. 83.4 pg of pAP-288 digested with tissue Plasminogen Activator (t-PA)
I. 482 pg of pAP-288 digested with t-PA
J. 4.0 ng of pAP-288 digested with t-PA
K. 28.4 ng of pAP-288 digested with t-PA
L. 200 ng of pAP-288 digested with t-PA
M. RNA ladder

Cleavage of pAP 294 With Human Neutrophil Elastase

A. Ricin Standard ( 0.050 μg)

B. pAP 294 protein ( 0.171 μg) digested with 1.42 μg of Human Neutrophil Elastase C. pAP 294 protein ( 0.121 μg)

FIGURE 63

Activation of pAP 294 Protein

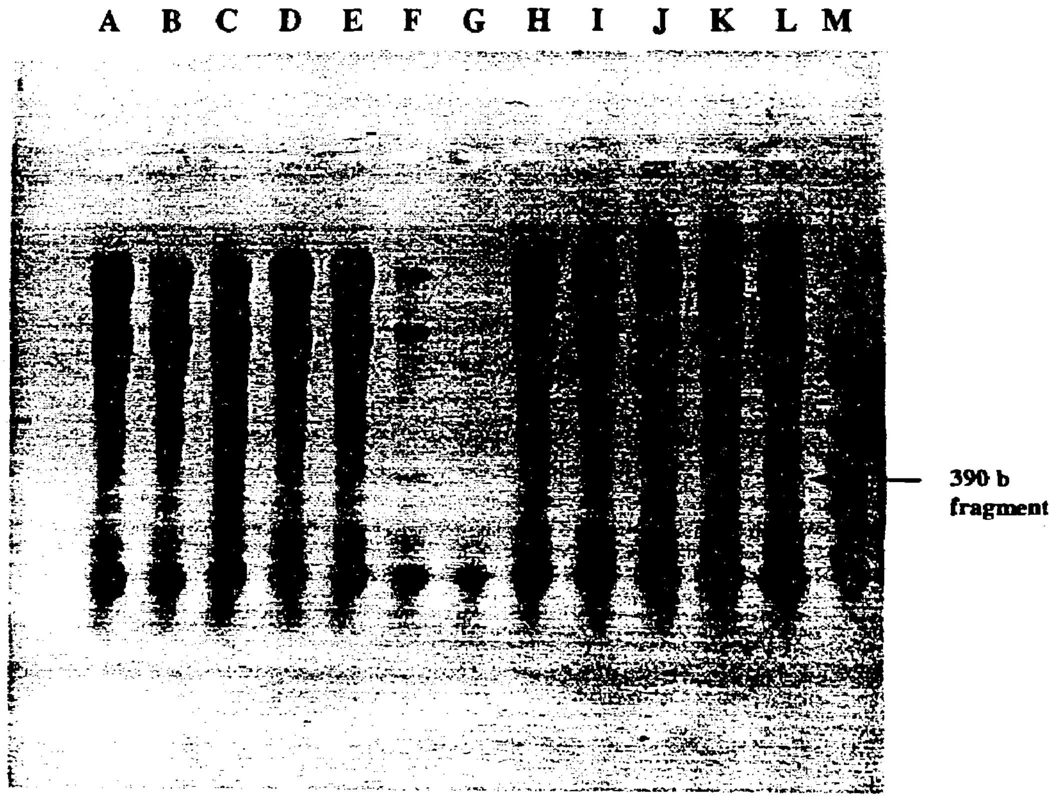

A. 60 ng of pAP 294
B. 8..57 ng of pAP 294
C. 1.22 ng of pAP 294
D. 175 pg of pAP 294
E. 25 pg of pAP 294
F. Ricin A chain
G. Negative Control
H. 360 ng of pAP 294 digested with Human Neutrophil Elastase
I. 51 ng of pAP 294 digested with Human Neutrophil Elastase
J. 7.3 ng of pAP 294 digested with Human Neutrophil Elastase
K. 1.0 ng of pAP 294 digested with Human Neutrophil Elastase
L. 150 pg of pAP 294 digested with Human Neutrophil Elastase
M. RNA ladder

Cleavage of pAP 296 with Calpain

A. Ricin Standard (0.05 μg)

B. pAP 296 (0.761 μg) undigested

C. pAP 296 (0.761 μg ) digested with 4.0 μg of Calpain

FIGURE 65

Activation of pAP 296 Protein

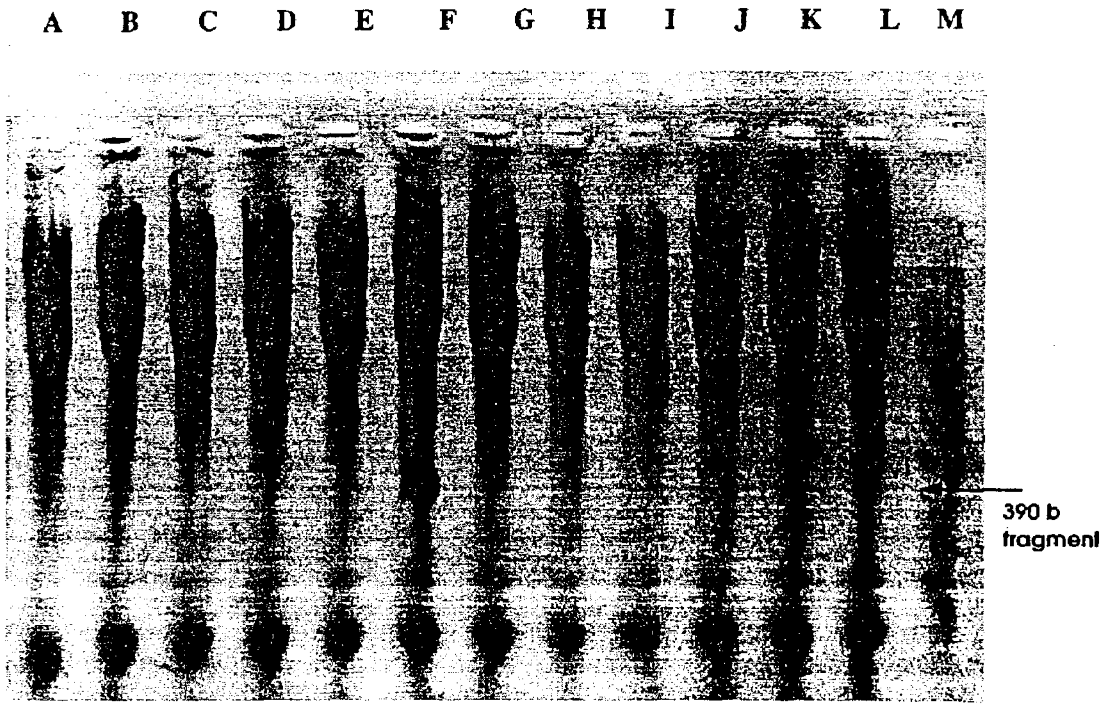

A. 100 ng of pAP 296 variant
B. 14.2 ng of pAP 296 variant
C. 2.0 ng of pAP 296 variant
D. 290 pg of pAP 296 variant
E. 46 pg of pAP 296 variant
F. Ricin A chain
G. Negative control
H. 46 pg of pAP 296 variant digested with Calpain
I. 290 pg of pAP 296 variant digested with Calpain
J. 2.0 ng of pAP 296 variant digested with Calpain
K. 14.2 ng of pAP 296 variant digested with Calpain
L. 100 ng of pAP 296 variant digested with Calpain
M. RNA ladder

Cleavage of pAP-222 Protein by The Matrix Metalloproteinase 2 (MMP-2)

A. Ricin Standard (0.250 ug)
B. pAP-222 Protein (0.250 ug)
C. pAP-222 protein ( 0.250 ug) digested with 0.28 ug of MMP-2

FIGURE 67
A B C D E F G H I J K L M
390 b fragment

Activation of pAP-222 Protein

A. 100 ng of pAP-222 variant
B. 14.2 ng of pAP-222 variant
C. 2.0 ng of pAP-222 variant
D. 291 pg of pAP-222 variant
E. 41.7 pg of pAP-222 variant
F. Ricin A chain
G. Ricin A chain
H. 41.7 pg of pAP-222 digested with MMP-2
I. 291 pg of pAP-222 digested with MMP-2
J. 2.0 ng of pAP-222 digested with MMP-2
K. 14.2 ng of pAP-222 digested with MMP-2
L. 100 ng of pAP-222 digested with MMP-2
M. RNA ladder

SEQUENCE LISTING

<160> NUMBER OF SEQ ID NOS: 142

<210> SEQ ID NO 1
<211> LENGTH: 9632
<212> TYPE: DNA
<213> ORGANISM: Artificial Sequence
<220> FEATURE:
<223> OTHER INFORMATION: Baculovirus transfer vector pVL1393

<400> SEQUENCE: 1
aagctttact cgtaaagcga gttgaaggat catatttagt tgcgtttatg agataagatt 60
gaaagcacgt gtaaaatgtt tcccgcgcgt tggcacaact atttacaatg cggccaagtt 120
ataaaagatt ctaatctgat atgttttaaa acacctttgc ggcccgagtt gtttgcgtac 180
gtgactagcg aagaagatgt gtggaccgca gaacagatag taaaacaaaa ccctagtatt 240

-continued

```
ggagcaataa tcgatttaac caacacgtct aaatattatg atggtgtgca tttttgcgg    300
gcgggcctgt tatacaaaaa aattcaagta cctggccaga ctttgccgcc tgaaagcata   360
gttcaagaat ttattgacac ggtaaaagaa tttacagaaa agtgtcccgg catgttggtg   420
ggcgtgcact gcacacacgg tattaatcgc accggttaca tggtgtgcag atatttaatg   480
cacaccctgg gtattgcgcc gcaggaagcc atagatagat tcgaaaaagc cagaggtcac   540
aaaattgaaa gacaaaatta cgttcaagat ttattaattt aattaatatt atttgcattc   600
tttaacaaat actttatcct attttcaaat tgttgcgctt cttccagcga accaaaacta   660
tgcttcgctt gctccgttta gcttgtagcc gatcagtggc gttgttccaa tcgacggtag   720
gattaggccg gatattctcc accacaatgt tggcaacgtt gatgttacgt ttatgctttt   780
ggttttccac gtacgtcttt tggccggtaa tagccgtaaa cgtagtgccg tcgcgcgtca   840
cgcacaacac cggatgtttg cgcttgtccg cggggtattg aaccgcgcga tccgacaaat   900
ccaccacttt ggcaactaaa tcggtgacct gcgcgtcttt tttctgcatt atttcgtctt   960
tcttttgcat ggtttcctgg aagccggtgt acatgcggtt tagatcagtc atgacgcgcg  1020
tgacctgcaa atctttggcc tcgatctgct tgtccttgat ggcaacgatg cgttcaataa  1080
actcttgttt tttaacaagt tcctcggttt tttgcgccac caccgcttgc agcgcgtttg  1140
tgtgctcggt gaatgtcgca atcagcttag tcaccaactg tttgctctcc tcctcccgtt  1200
gtttgatcgc gggatcgtac ttgccggtgc agagcacttg aggaattact tcttctaaaa  1260
gccattcttg taattctatg gcgtaaggca atttggactt cataatcagc tgaatcacgc  1320
cggatttagt aatgagcact gtatgcggct gcaaatacag cgggtcgccc cttttcacga  1380
cgctgttaga ggtagggccc ccattttgga tggtctgctc aaataacgat ttgtatttat  1440
tgtctacatg aacacgtata gctttatcac aaactgtata ttttaaactg ttagcgacgt  1500
ccttggccac gaaccggacc tgttggtcgc gctctagcac gtaccgcagg ttgaacgtat  1560
cttctccaaa tttaaattct ccaattttaa cgcgagccat tttgatacac gtgtgtcgat  1620
tttgcaacaa ctattgtttt ttaacgcaaa ctaaacttat tgtggtaagc aataattaaa  1680
tatgggggaa catgcgccgc tacaacactc gtcgttatga acgcagacgg cgccggtctc  1740
ggcgcaagcg gctaaaacgt gttgcgcgtt caacgcggca aacatcgcaa aagccaatag  1800
tacagttttg atttgcatat taacggcgat tttttaaatt atcttattta ataaatagtt  1860
atgacgccta caactccccg cccgcgttga ctcgctgcac ctcgagcagt tcgttgacgc  1920
cttcctccgt gtggccgaac acgtcgagcg ggtggtcgat gaccagcggc gtgccgcacg  1980
cgacgcacaa gtatctgtac accgaatgat cgtcgggcga aggcacgtcg gcctccaagt  2040
ggcaatattg gcaaattcga aaatatatac agttgggttg tttgcgcata tctatcgtgg  2100
cgttgggcat gtacgtccga acgttgattt gcatgcaagc cgaaattaaa tcattgcgat  2160
tagtgcgatt aaaacgttgt acatcctcgc ttttaatcat gccgtcgatt aaatcgcgca  2220
atcgagtcaa gtgatcaaag tgtggaataa tgttttcttt gtattcccga gtcaagcgca  2280
gcgcgtattt taacaaacta gccatcttgt aagttagttt catttaatgc aactttatcc  2340
aataatatat tatgtatcgc acgtcaagaa ttaacaatgc gcccgttgtc gcatctcaac  2400
acgactatga tagagatcaa ataaagcgcg aattaaatag cttgcgacgc aacgtgcacg  2460
atctgtgcac gcgttccggc acgagctttg attgtaataa gtttttacga agcgatgaca  2520
tgacccccgt agtgacaacg atcacgccca aaagaactgc cgactacaaa attaccgagt  2580
atgtcggtga cgttaaaact attaagccat ccaatcgacc gttagtcgaa tcaggaccgc  2640
```

-continued

```
tggtgcgaga agccgcgaag tatggcgaat gcatcgtata acgtgtggag tccgctcatt   2700
agagcgtcat gtttagacaa gaaagctaca tatttaattg atcccgatga ttttattgat   2760
aaattgaccc taactccata cacggtattc tacaatggcg gggttttggt caaaatttcc   2820
ggactgcgat tgtacatgct gttaacggct ccgcccacta ttaatgaaat taaaaattcc   2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga aagaaaacaa tgtaccgcgc ggcggtatgt acaggaagag gtttatacta   3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
atcaaatccc aagatgtgta taaaccacca aactgccaaa aaatgaaaac tgtcgacaag   3240
ctctgtccgt ttgctggcaa ctgcaagggt ctcaatccta tttgtaatta ttgaataata   3300
aaacaattat aaatgctaaa tttgtttttt attaacgata caaaccaaac gcaacaagaa   3360
catttgtagt attatctata attgaaaacg cgtagttata atcgctgagg taatatttaa   3420
aatcattttc aaatgattca cagttaattt gcgacaatat aattttattt tcacataaac   3480
tagacgcctt gtcgtcttct tcttcgtatt ccttctcttt ttcatttttc tcctcataaa   3540
aattaacata gttattatcg tatccatata tgtatctatc gtatagagta aatttttttgt   3600
tgtcataaat atatatgtct tttttaatgg ggtgtatagt accgctgcgc atagtttttc   3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat tttttagcag caccggatta acataacttt   3840
ccaaaatgtt gtacgaaccg ttaaacaaaa acagttcacc tcccttttct atactattgt   3900
ctgcgagcag ttgtttgttg ttaaaaataa cagccattgt aatgagacgc acaaactaat   3960
atcacaaact ggaaatgtct atcaatatat agttgctgat atcatggaga taattaaaat   4020
gataaccatc tcgcaaataa ataagtattt tactgttttc gtaacagttt tgtaataaaa   4080
aaacctataa atattccgga ttattcatac cgtcccacca tcgggcgcgg atcccgggta   4140
ccttctagaa ttccggagcg gccgctgcag atctgatcct ttcctgggac ccggcaagaa   4200
ccaaaaactc actctcttca aggaaatccg taatgttaaa cccgacacga tgaagcttgt   4260
cgttggatgg aaaggaaaag agttctacag ggaaacttgg acccgcttca tggaagacag   4320
cttccccatt gttaacgacc aagaagtgat ggatgttttc cttgttgtca acatgcgtcc   4380
cactagaccc aaccgttgtt acaaattcct ggcccaacac gctctgcgtt gcgaccccga   4440
ctatgtacct catgacgtga ttaggatcgt cgagccttca tgggtgggca gcaacaacga   4500
gtaccgcatc agcctggcta agaagggcgg cggctgccca ataatgaacc ttcactctga   4560
gtacaccaac tcgttcgaac agttcatcga tcgtgtcatc tgggagaact tctacaagcc   4620
catcgtttac atcggtaccg actctgctga agaggaggaa attctccttg aagtttccct   4680
ggtgttcaaa gtaaaggagt ttgcaccaga cgcacctctg ttcactggtc cggcgtatta   4740
aaacacgata cattgttatt agtacattta ttaagcgcta gattctgtgc gttgttgatt   4800
tacagacaat tgttgtacgt attttaataa ttcattaaat ttataatctt tagggtggta   4860
tgttagagcg aaaatcaaat gattttcagc gtctttatat ctgaatttaa atattaaatc   4920
ctcaatagat ttgtaaaata ggtttcgatt agtttcaaac aagggttgtt tttccgaacc   4980
```

-continued

```
gatggctgga ctatctaatg gattttcgct caacgccaca aaacttgcca aatcttgtag   5040
cagcaatcta gctttgtcga tattcgtttg tgttttgttt tgtaataaag gttcgacgtc   5100
gttcaaaata ttatgcgctt ttgtatttct ttcatcactg tcgttagtgt acaattgact   5160
cgacgtaaac acgttaaata aagcttggac atatttaaca tcgggcgtgt tagctttatt   5220
aggccgatta tcgtcgtcgt cccaaccctc gtcgttagaa gttgcttccg aagacgattt   5280
tgccatagcc acacgacgcc tattaattgt gtcggctaac acgtccgcga tcaaatttgt   5340
agttgagctt tttggaatta tttctgattg cgggcgtttt tgggcgggtt tcaatctaac   5400
tgtgcccgat tttaattcag acaacacgtt agaaagcgat ggtgcaggcg gtggtaacat   5460
ttcagacggc aaatctacta atggcggcgg tggtggagct gatgataaat ctaccatcgg   5520
tggaggcgca ggcggggctg gcggcggagg cggaggcgga ggtggtggcg gtgatgcaga   5580
cggcggttta ggctcaaatg tctctttagg caacacagtc ggcacctcaa ctattgtact   5640
ggtttcgggc gccgtttttg gtttgaccgg tctgagacga gtgcgatttt tttcgtttct   5700
aatagcttcc aacaattgtt gtctgtcgtc taaaggtgca gcgggttgag gttccgtcgg   5760
cattggtgga gcgggcggca attcagacat cgatggtggt ggtggtggtg gaggcgctgg   5820
aatgttaggc acgggagaag gtggtggcgg cggtgccgcc ggtataattt gttctggttt   5880
agtttgttcg cgcacgattg tgggcaccgg cgcaggcgcc gctggctgca caacggaagg   5940
tcgtctgctt cgaggcagcg cttggggtgg tggcaattca atattataat tggaatacaa   6000
atcgtaaaaa tctgctataa gcattgtaat ttcgctatcg tttaccgtgc cgatatttaa   6060
caaccgctca atgtaagcaa ttgtattgta aagagattgt ctcaagctcg ccgcacgccg   6120
ataacaagcc ttttcatttt tactacagca ttgtagtggc gagacacttc gctgtcgtcg   6180
acgtacatgt atgctttgtt gtcaaaaacg tcgttggcaa gctttaaaat atttaaaaga   6240
acatctctgt tcagcaccac tgtgttgtcg taaatgttgt ttttgataat ttgcgcttcc   6300
gcagtatcga cacgttcaaa aaattgatgc gcatcaattt tgttgttcct attattgaat   6360
aaataagatt gtacagattc atatctacga ttcgtcatgg ccaccacaaa tgctacgctg   6420
caaacgctgg tacaatttta cgaaaactgc aaaaacgtca aaactcggta taaaataatc   6480
aacgggcgct ttggcaaaat atctatttta tcgcacaagc ccactagcaa attgtatttg   6540
cagaaaacaa tttcggcgca caattttaac gctgacgaaa taaaagttca ccagttaatg   6600
agcgaccacc caaattttat aaaaatctat tttaatcacg gttccatcaa caaccaagtg   6660
atcgtgatgg actacattga ctgtcccgat ttatttgaaa cactacaaat taaaggcgag   6720
ctttcgtacc aacttgttag caatattatt agacagctgt gtgaagcgct caacgatttg   6780
cacaagcaca atttcataca caacgacata aaactcgaaa atgtcttata tttcgaagca   6840
cttgatcgcg tgtatgtttg cgattacgga ttgtgcaaac acgaaaactc acttagcgtg   6900
cacgacggca cgttggagta ttttagtccg gaaaaaattc gacacacaac tatgcacgtt   6960
tcgtttgact ggtacgcggc gtgttaacat acaagttgct aacgtaatca tggtcatagc   7020
tgtttcctgt gtgaaattgt tatccgctca caattccaca caacatacga gccggaagca   7080
taaagtgtaa agcctggggt gcctaatgag tgagctaact cacattaatt gcgttgcgct   7140
cactgcccgc tttccagtcg ggaaacctgt cgtgccagct gcattaatga atcggccaac   7200
gcgcggggag aggcggtttg cgtattgggc gctcttccgc ttcctcgctc actgactcgc   7260
tgcgctcggt cgttcggctg cggcgagcgg tatcagctca ctcaaaggcg gtaatacggt   7320
tatccacaga atcaggggat aacgcaggaa agaacatgtg agcaaaaggc cagcaaaagg   7380
```

-continued

```
ccaggaaccg taaaaaggcc gcgttgctgg cgtttttcca taggctccgc ccccctgacg   7440
agcatcacaa aaatcgacgc tcaagtcaga ggtggcgaaa cccgacagga ctataaagat   7500
accaggcgtt tccccctgga agctccctcg tgcgctctcc tgttccgacc ctgccgctta   7560
ccggatacct gtccgccttt ctcccttcgg gaagcgtggc gctttctcat agctcacgct   7620
gtaggtatct cagttcggtg taggtcgttc gctccaagct gggctgtgtg cacgaacccc   7680
ccgttcagcc cgaccgctgc gccttatccg gtaactatcg tcttgagtcc aacccggtaa   7740
gacacgactt atcgccactg gcagcagcca ctggtaacag gattagcaga gcgaggtatg   7800
taggcggtgc tacagagttc ttgaagtggt ggcctaacta cggctacact agaaggacag   7860
tatttggtat ctgcgctctg ctgaagccag ttaccttcgg aaaaagagtt ggtagctctt   7920
gatccggcaa acaaaccacc gctggtagcg gtggtttttt tgtttgcaag cagcagatta   7980
cgcgcagaaa aaaaggatct caagaagatc ctttgatctt ttctacgggg tctgacgctc   8040
agtggaacga aaactcacgt taagggattt tggtcatgag attatcaaaa aggatcttca   8100
cctagatcct tttaaattaa aaatgaagtt ttaaatcaat ctaaagtata tatgagtaaa   8160
cttggtctga cagttaccaa tgcttaatca gtgaggcacc tatctcagcg atctgtctat   8220
ttcgttcatc catagttgcc tgactccccg tcgtgtagat aactacgata cgggagggct   8280
taccatctgg ccccagtgct gcaatgatac cgcgagaccc acgctcaccg gctccagatt   8340
tatcagcaat aaaccagcca gccggaaggg ccgagcgcag aagtggtcct gcaactttat   8400
ccgcctccat ccagtctatt aattgttgcc gggaagctag agtaagtagt tcgccagtta   8460
atagtttgcg caacgttgtt gccattgcta caggcatcgt ggtgtcacgc tcgtcgtttg   8520
gtatggcttc attcagctcc ggttcccaac gatcaaggcg agttacatga tcccccatgt   8580
tgtgcaaaaa agcggttagc tccttcggtc ctccgatcgt tgtcagaagt aagttggccg   8640
cagtgttatc actcatggtt atggcagcac tgcataattc tcttactgtc atgccatccg   8700
taagatgctt ttctgtgact ggtgagtact caaccaagtc attctgagaa tagtgtatgc   8760
ggcgaccgag ttgctcttgc ccggcgtcaa tacgggataa taccgcgcca catagcagaa   8820
ctttaaaagt gctcatcatt ggaaaacgtt cttcggggcg aaaactctca aggatcttac   8880
cgctgttgag atccagttcg atgtaaccca ctcgtgcacc caactgatct tcagcatctt   8940
ttactttcac cagcgtttct gggtgagcaa aaacaggaag gcaaaatgcc gcaaaaaagg   9000
gaataagggc gacacggaaa tgttgaatac tcatactctt cctttttcaa tattattgaa   9060
gcatttatca gggttattgt ctcatgagcg gatacatatt tgaatgtatt tagaaaaata   9120
aacaaatagg ggttccgcgc acatttcccc gaaaagtgcc acctgacgtc taagaaacca   9180
ttattatcat gacattaacc tataaaaata ggcgtatcac gaggcccttt cgtctcgcgc   9240
gtttcggtga tgacggtgaa aacctctgac acatgcagct cccggagacg gtcacagctt   9300
gtctgtaagc ggatgccggg agcagacaag cccgtcaggg cgcgtcagcg ggtgttggcg   9360
ggtgtcgggg ctggcttaac tatgcggcat cagagcagat tgtactgaga gtgcaccata   9420
tgcggtgtga aataccgcac agatgcgtaa ggagaaaata ccgcatcagg cgccattcgc   9480
cattcaggct gcgcaactgt tgggaagggc gatcggtgcg ggcctcttcg ctattacgcc   9540
agctggcgaa agggggatgt gctgcaaggc gattaagttg ggtaacgcca gggttttccc   9600
agtcacgacg ttgtaaaacg acggccagtg cc                                 9632
```

<210> SEQ ID NO 2

-continued

<211> LENGTH: 36
<212> TYPE: DNA
<213> ORGANISM: Artificial Sequence
<220> FEATURE:
<223> OTHER INFORMATION: Cathepsin B linker regions of pAP-213

<400> SEQUENCE: 2
tctttgctta aatcgagaat ggtgccaaat tttaat 36

<210> SEQ ID NO 3
<211> LENGTH: 1855
<212> TYPE: DNA
<213> ORGANISM: Artificial Sequence
<220> FEATURE:
<223> OTHER INFORMATION: Cathepsin B linker regions of pAP-214

<400> SEQUENCE: 3
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttctctttgct taaatcgaga atggtgccaa attttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800

-continued ggacattgta aattttgtaa ctgaaaggac agcaagttat atcgaattcc tgcag 1855

<210> SEQ ID NO 4
<211> LENGTH: 36
<212> TYPE: DNA
<213> ORGANISM: Artificial Sequence
<220> FEATURE:
<223> OTHER INFORMATION: MMP-3 linker regions of pAP-215

<400> SEQUENCE: 4
cgtccgaagc cacagcaatt ttttggactt atgaat 36

<210> SEQ ID NO 5
<211> LENGTH: 1855
<212> TYPE: DNA
<213> ORGANISM: Artificial Sequence
<220> FEATURE:
<223> OTHER INFORMATION: pAP-216 insert

<400> SEQUENCE: 5
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttcgtccgaa gccacagcaa ttttttggac ttatgaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aacctttttgt tacaaccatt 1380 gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620

-continued

```
ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

```
<210> SEQ ID NO 6
<211> LENGTH: 36
<212> TYPE: DNA
<213> ORGANISM: Artificial Sequence
<220> FEATURE:
<223> OTHER INFORMATION: MMP-7 linker regions of pAP-217

<400> SEQUENCE: 6

tctttgcgtc cactggcatt gtggcgaagt tttaat                              36
```

```
<210> SEQ ID NO 7
<211> LENGTH: 1855
<212> TYPE: DNA
<213> ORGANISM: Artificial Sequence
<220> FEATURE:
<223> OTHER INFORMATION: pAP-218 insert

<400> SEQUENCE: 7

gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt ttctttgcg tccactggca ttgtggcgaa gttttaatgc tgatgtttgt     960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500
```

-continued caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 8
<211> LENGTH: 36
<212> TYPE: DNA
<213> ORGANISM: Artificial Sequence
<220> FEATURE:
<223> OTHER INFORMATION: MMP-9 linker regions of pAP-219

<400> SEQUENCE: 8
tctccgcaag gaattgcagg gcagcgaaat tttaat 36

<210> SEQ ID NO 9
<211> LENGTH: 1855
<212> TYPE: DNA
<213> ORGANISM: Artificial Sequence
<220> FEATURE:
<223> OTHER INFORMATION: pAP-220 insert

<400> SEQUENCE: 9
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctccgca aggaattgca gggcagcgaa attttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320

-continued

```
tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 10
<211> LENGTH: 42
<212> TYPE: DNA
<213> ORGANISM: Artificial Sequence
<220> FEATURE:
<223> OTHER INFORMATION: THERM-MMP linker regions of pAP-221

<400> SEQUENCE: 10

```
gatgtggatg aaagggatgt gagggaattt gcttcttttt ta                        42
```

<210> SEQ ID NO 11
<211> LENGTH: 1861
<212> TYPE: DNA
<213> ORGANISM: Artificial Sequence
<220> FEATURE:
<223> OTHER INFORMATION: pAP-222 insert

<400> SEQUENCE: 11

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt ttgatgtgga tgaaagggat gtgagggaat ttgcttcttt tttagctgat    960

gtttgtatgg atcctgagcc catagtgcgt atcgtaggtc gaaatggtct atgtgttgat   1020

gttagggatg gaagattcca caacggaaac gcaatacagt tgtggccatg caagtctaat   1080

acagatgcaa atcagctctg gactttgaaa agagacaata ctattcgatc taatggaaag   1140

tgtttaacta cttacgggta cagtccggga gtctatgtga tgatctatga ttgcaatact   1200
```

-continued gctgcaactg atgccacccg ctggcaaata tgggataatg gaaccatcat aaatcccaga 1260
tctagtctag ttttagcagc gacatcaggg aacagtggta ccacacttac agtgcaaacc 1320
aacatttatg ccgttagtca aggttggctt cctactaata atacacaacc ttttgttaca 1380
accattgttg ggctatatgg tctgtgcttg caagcaaata gtggacaagt atggatagag 1440
gactgtagca gtgaaaaggc tgaacaacag tgggctcttt atgcagatgg ttcaatacgt 1500
cctcagcaaa accgagataa ttgccttaca agtgattcta atatacggga aacagttgtt 1560
aagatcctct cttgtggccc tgcatcctct ggccaacgat ggatgttcaa gaatgatgga 1620
accattttaa atttgtatag tggattggtg ttagatgtga ggcgatcgga tccgagcctt 1680
aaacaaatca ttctttaccc tctccatggt gacccaaacc aaatatggtt accattattt 1740
tgatagacag attactctct tgcagtgtgt gtgtcctgcc atgaaaatag atggcttaaa 1800
taaaaaggac attgtaaatt ttgtaactga aaggacagca agttatatcg aattcctgca 1860
g 1861

<210> SEQ ID NO 12
<211> LENGTH: 36
<212> TYPE: DNA
<213> ORGANISM: Artificial Sequence
<220> FEATURE:
<223> OTHER INFORMATION: P.falciparum-A linker regions of pAP-223

<400> SEQUENCE: 12
caggtggttc aattgcagaa ttatgatgaa gaggat 36

<210> SEQ ID NO 13
<211> LENGTH: 1855
<212> TYPE: DNA
<213> ORGANISM: Artificial Sequence
<220> FEATURE:
<223> OTHER INFORMATION: pAP-224 insert

<400> SEQUENCE: 13
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttcaggtggt tcaattgcag aattatgatg aagaggatgc tgatgtttgt 960

-continued

```
atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 14
<211> LENGTH: 36
<212> TYPE: DNA
<213> ORGANISM: Artificial Sequence
<220> FEATURE:
<223> OTHER INFORMATION: P.falciparum-B linker regions of pAP-225

<400> SEQUENCE: 14

```
ttgccgattt tcggggaatc ggaggacaat gatgaa                               36
```

<210> SEQ ID NO 15
<211> LENGTH: 1855
<212> TYPE: DNA
<213> ORGANISM: Artificial Sequence
<220> FEATURE:
<223> OTHER INFORMATION: pAP-226 insert

<400> SEQUENCE: 15

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840
```

-continued

```
gatgtgagta tattaatccc tatcatagct ctcatggtgt atagatgcgc acctccacca    900

tcgtcacagt ttttgccgat tttcggggaa tcggaggaca atgatgaagc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 16
<211> LENGTH: 36
<212> TYPE: DNA
<213> ORGANISM: Artificial Sequence
<220> FEATURE:
<223> OTHER INFORMATION: P. falciparum-C linker regions of pAP-227

<400> SEQUENCE: 16

```
caggtggtta caggggaagc gatatcagtt actatg                               36
```

<210> SEQ ID NO 17
<211> LENGTH: 1855
<212> TYPE: DNA
<213> ORGANISM: Artificial Sequence
<220> FEATURE:
<223> OTHER INFORMATION: pAP-228 insert

<400> SEQUENCE: 17

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660
```

-continued

```
attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt ttcaggtggt tacaggggaa gcgatatcag ttactatggc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 18
<211> LENGTH: 36
<212> TYPE: DNA
<213> ORGANISM: Artificial Sequence
<220> FEATURE:
<223> OTHER INFORMATION: P. falciparum-D linker regions of pAP-229

<400> SEQUENCE: 18

```
gctttggaga gaacgttcct gtcgttccct actaat                                36
```

<210> SEQ ID NO 19
<211> LENGTH: 1855
<212> TYPE: DNA
<213> ORGANISM: Artificial Sequence
<220> FEATURE:
<223> OTHER INFORMATION: pAP-230 insert

<400> SEQUENCE: 19

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540
```

-continued ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttgctttgga gagaacgttc ctgtcgttcc ctactaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 20
<211> LENGTH: 36
<212> TYPE: DNA
<213> ORGANISM: Artificial Sequence
<220> FEATURE:
<223> OTHER INFORMATION: P. falciparum-E linker regions of pAP-231

<400> SEQUENCE: 20
aaattccaag atatgctaaa taattcacag catcag 36

<210> SEQ ID NO 21
<211> LENGTH: 1855
<212> TYPE: DNA
<213> ORGANISM: Artificial Sequence
<220> FEATURE:
<223> OTHER INFORMATION: pAP-232 insert

<400> SEQUENCE: 21
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360

-continued

```
taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt ttaaattcca agatatgcta aataattcac agcatcaggc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

```
<210> SEQ ID NO 22
<211> LENGTH: 36
<212> TYPE: DNA
<213> ORGANISM: Artificial Sequence
<220> FEATURE:
<223> OTHER INFORMATION: HSV-A linker regions of pAP-233

<400> SEQUENCE: 22

tctgcgcttg taaacgcatc gtcggcacat gttaat                               36


<210> SEQ ID NO 23
<211> LENGTH: 1855
<212> TYPE: DNA
<213> ORGANISM: Artificial Sequence
<220> FEATURE:
<223> OTHER INFORMATION: pAP-234 insert

<400> SEQUENCE: 23

gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240
```

-continued

```
gtgttgccaa acagagttgg tttgcctata aaccaacggt ttattttagt tgaactctca    300
aatcatgcag agctttctgt tacattagcg ctggatgtca ccaatgcata tgtggtcggc    360
taccgtgctg gaaatagcgc atatttcttt catcctgaca atcaggaaga tgcagaagca    420
atcactcatc ttttcactga tgttcaaaat cgatatacat tcgcctttgg tggtaattat    480
gatagacttg aacaacttgc tggtaatctg agagaaaata tcgagttggg aaatggtcca    540
ctagaggagg ctatctcagc gctttattat tacagtactg gtggcactca gcttccaact    600
ctggctcgtt cctttataat ttgcatccaa atgatttcag aagcagcaag attccaatat    660
attgagggag aaatgcgcac gagaattagg tacaaccgga gatctgcacc agatcctagc    720
gtaattacac ttgagaatag ttgggggaga ctttccactg caattcaaga gtctaaccaa    780
ggagcctttg ctagtccaat tcaactgcaa agacgtaatg gttccaaatt cagtgtgtac    840
gatgtgagta tattaatccc tatcatagct ctcatggtgt atagatgcgc acctccacca    900
tcgtcacagt tttctgcgct tgtaaacgca tcgtcggcac atgttaatgc tgatgtttgt    960
atggatcctg agcccatagt gcgtatcgta ggtcgaaatg gtctatgtgt tgatgttagg   1020
gatggaagat tccacaacgg aaacgcaata cagttgtggc catgcaagtc taatacagat   1080
gcaaatcagc tctggacttt gaaaagagac aatactattc gatctaatgg aaagtgttta   1140
actacttacg ggtacagtcc gggagtctat gtgatgatct atgattgcaa tactgctgca   1200
actgatgcca cccgctggca aatatgggat aatggaacca tcataaatcc cagatctagt   1260
ctagttttag cagcgacatc agggaacagt ggtaccacac ttacagtgca aaccaacatt   1320
tatgccgtta gtcaaggttg gcttcctact aataatacac aacctttgt tacaaccatt    1380
gttgggctat atggtctgtg cttgcaagca aatagtggac aagtatggat agaggactgt   1440
agcagtgaaa aggctgaaca acagtgggct ctttatgcag atggttcaat acgtcctcag   1500
caaaaccgag ataattgcct tacaagtgat tctaatatac gggaaacagt tgttaagatc   1560
ctctcttgtg gccctgcatc ctctggccaa cgatggatgt tcaagaatga tggaaccatt   1620
ttaaatttgt atagtggatt ggtgttagat gtgaggcgat cggatccgag ccttaaacaa   1680
atcattcttt accctctcca tggtgaccca aaccaaatat ggttaccatt attttgatag   1740
acagattact ctcttgcagt gtgtgtgtcc tgccatgaaa atagatggct taaataaaaa   1800
ggacattgta aattttgtaa ctgaaaggac agcaagttat atcgaattcc tgcag        1855
```

<210> SEQ ID NO 24
<211> LENGTH: 36
<212> TYPE: DNA
<213> ORGANISM: Artificial Sequence
<220> FEATURE:
<223> OTHER INFORMATION: HSV-B linker regions of pAP-235

<400> SEQUENCE: 24

```
tctacgtatt tacaggcatc ggagaaattt aagaat                                 36
```

<210> SEQ ID NO 25
<211> LENGTH: 1855
<212> TYPE: DNA
<213> ORGANISM: Artificial Sequence
<220> FEATURE:
<223> OTHER INFORMATION: pAP-236 insert

<400> SEQUENCE: 25

```
gaattcatga aaccgggagg aaatactatt gtaatatgga tgtatgcagt ggcaacatgg     60
```

-continued

```
ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttctacgta tttacaggca tcggagaaat ttaagaatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 26
<211> LENGTH: 36
<212> TYPE: DNA
<213> ORGANISM: Artificial Sequence
<220> FEATURE:
<223> OTHER INFORMATION: VZV-A linker regions of pAP-237

<400> SEQUENCE: 26

```
tctcaggatg taaacgcagt ggaggcaagt tctaat                                36
```

<210> SEQ ID NO 27
<211> LENGTH: 1855
<212> TYPE: DNA
<213> ORGANISM: Artificial Sequence
<220> FEATURE:
<223> OTHER INFORMATION: pAP-238 insert -continued

<400> SEQUENCE: 27
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctcagga tgtaaacgca gtggaggcaa gttctaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 28
<211> LENGTH: 36
<212> TYPE: DNA
<213> ORGANISM: Artificial Sequence
<220> FEATURE:
<223> OTHER INFORMATION: VZV-B linker regions of pAP-239

<400> SEQUENCE: 28
tctgtgtatt tacaggcatc gacgggatat ggtaat 36

<210> SEQ ID NO 29

-continued

<211> LENGTH: 1855
<212> TYPE: DNA
<213> ORGANISM: Artificial Sequence
<220> FEATURE:
<223> OTHER INFORMATION: pAP-240 insert

<400> SEQUENCE: 29
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctgtgta tttacaggca tcgacgggat atggtaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 30
<211> LENGTH: 36
<212> TYPE: DNA
<213> ORGANISM: Artificial Sequence
<220> FEATURE:
<223> OTHER INFORMATION: EBV-A linker regions of pAP-241

<400> SEQUENCE: 30

-continued tctaagcttg tacaggcatc ggcgtcaggt gttaat 36

<210> SEQ ID NO 31
<211> LENGTH: 1855
<212> TYPE: DNA
<213> ORGANISM: Artificial Sequence
<220> FEATURE:
<223> OTHER INFORMATION: pAP-242 insert

<400> SEQUENCE: 31
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttgtttcgca gaactatcca atagtgcaaa attttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 32
<211> LENGTH: 36
<212> TYPE: DNA

-continued

<213> ORGANISM: Artificial Sequence
<220> FEATURE:
<223> OTHER INFORMATION: EBV-B linker regions of pAP-243

<400> SEQUENCE: 32

```
tcttcgtatc taaaggcatc ggacgcacct gataat                              36
```

<210> SEQ ID NO 33
<211> LENGTH: 1855
<212> TYPE: DNA
<213> ORGANISM: Artificial Sequence
<220> FEATURE:
<223> OTHER INFORMATION: pAP-244 insert

<400> SEQUENCE: 33

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttcttcgta tctaaaggca tcggacgcac ctgataatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

-continued

<210> SEQ ID NO 34
<211> LENGTH: 36
<212> TYPE: DNA
<213> ORGANISM: Artificial Sequence
<220> FEATURE:
<223> OTHER INFORMATION: CMV-A linker regions of pAP-245

<400> SEQUENCE: 34
tctggggttg taaatgcatc gtgtagactt gctaat 36

<210> SEQ ID NO 35
<211> LENGTH: 1855
<212> TYPE: DNA
<213> ORGANISM: Artificial Sequence
<220> FEATURE:
<223> OTHER INFORMATION: pAP-246 insert

<400> SEQUENCE: 35
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctggggt tgtaaatgca tcgtgtagac ttgctaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680

-continued

```
atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855


<210> SEQ ID NO 36
<211> LENGTH: 36
<212> TYPE: DNA
<213> ORGANISM: Artificial Sequence
<220> FEATURE:
<223> OTHER INFORMATION: CMV-B linker regions of pAP-247

<400> SEQUENCE: 36

tcttcgtatg taaaggcatc ggtgtcacct gaaaat                                36


<210> SEQ ID NO 37
<211> LENGTH: 1855
<212> TYPE: DNA
<213> ORGANISM: Artificial Sequence
<220> FEATURE:
<223> OTHER INFORMATION: pPA-248 insert

<400> SEQUENCE: 37

gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttcttcgta tgtaaaggca tcggtgtcac ctgaaaatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560
```

-continued

```
ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

```
<210> SEQ ID NO 38
<211> LENGTH: 36
<212> TYPE: DNA
<213> ORGANISM: Artificial Sequence
<220> FEATURE:
<223> OTHER INFORMATION: HHV-6 linker regions of pAP-249

<400> SEQUENCE: 38

tcttcgattt taaatgcatc ggtgccaaat tttaat                              36
```

```
<210> SEQ ID NO 39
<211> LENGTH: 1855
<212> TYPE: DNA
<213> ORGANISM: Artificial Sequence
<220> FEATURE:
<223> OTHER INFORMATION: pAP-250 insert

<400> SEQUENCE: 39

gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttcttcgat tttaaatgca tcggtgccaa attttaatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380
```

-continued

```
gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 40
<211> LENGTH: 12
<212> TYPE: PRT
<213> ORGANISM: Artificial Sequence
<220> FEATURE:
<223> OTHER INFORMATION: Cancer protease-sensitive AA linkers in pAP-213 and pAP-214

<400> SEQUENCE: 40

```
Ser Leu Leu Lys Ser Arg Met Val Pro Asn Phe Asn
  1               5                  10
```

<210> SEQ ID NO 41
<211> LENGTH: 12
<212> TYPE: PRT
<213> ORGANISM: Artificial Sequence
<220> FEATURE:
<223> OTHER INFORMATION: Cancer protease-sensitive AA linkers in pAP-215 and pAP-216

<400> SEQUENCE: 41

```
Arg Pro Lys Pro Gln Gln Phe Phe Gly Leu Met Asn
  1               5                  10
```

<210> SEQ ID NO 42
<211> LENGTH: 12
<212> TYPE: PRT
<213> ORGANISM: Artificial Sequence
<220> FEATURE:
<223> OTHER INFORMATION: Cancer protease-sensitive AA linkers in pAP-217 and pAP-218

<400> SEQUENCE: 42

```
Ser Leu Arg Pro Leu Ala Leu Trp Arg Ser Phe Asn
  1               5                  10
```

<210> SEQ ID NO 43
<211> LENGTH: 12
<212> TYPE: PRT
<213> ORGANISM: Artificial Sequence
<220> FEATURE:
<223> OTHER INFORMATION: Cancer protease-sensitive AA linkers in pAP-219 and pAP-220

<400> SEQUENCE: 43

```
Ser Pro Gln Gly Ile Ala Gly Gln Arg Asn Phe Asn
  1               5                  10
```

<210> SEQ ID NO 44
<211> LENGTH: 14
<212> TYPE: PRT
<213> ORGANISM: Artificial Sequence
<220> FEATURE:
<223> OTHER INFORMATION: Cancer protease-sensitive AA linkers in aAP-221

-continued and pAP-222

<400> SEQUENCE: 44

Asp Val Asp Glu Arg Asp Val Arg Gly Phe Ala Ser Phe Leu
1 5 10

<210> SEQ ID NO 45
<211> LENGTH: 12
<212> TYPE: PRT
<213> ORGANISM: Artificial Sequence
<220> FEATURE:
<223> OTHER INFORMATION: Cancer protease-sensitive linkers pAP-241 and pAP-242

<400> SEQUENCE: 45

Ser Lys Leu Val Gln Ala Ser Ala Ser Gly Val Asn
1 5 10

<210> SEQ ID NO 46
<211> LENGTH: 12
<212> TYPE: PRT
<213> ORGANISM: Artificial Sequence
<220> FEATURE:
<223> OTHER INFORMATION: Cancer protease-sensitive linkers pAP243 and pAP-244

<400> SEQUENCE: 46

Ser Ser Tyr Leu Lys Ala Ser Asp Ala Pro Asp Asn
1 5 10

<210> SEQ ID NO 47
<211> LENGTH: 36
<212> TYPE: DNA
<213> ORGANISM: Artificial Sequence
<220> FEATURE:
<223> OTHER INFORMATION: ILV linker regions of pAP-253

<400> SEQUENCE: 47
tctaagtatc tacaggcaaa tgaggtaatt actaat 36

<210> SEQ ID NO 48
<211> LENGTH: 1855
<212> TYPE: DNA
<213> ORGANISM: Artificial Sequence
<220> FEATURE:
<223> OTHER INFORMATION: pAP-254 insert

<400> SEQUENCE: 48
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660

-continued

```
attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttctaagta tctacaggca aatgaggtaa ttactaatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag         1855
```

<210> SEQ ID NO 49
<211> LENGTH: 36
<212> TYPE: DNA
<213> ORGANISM: Artificial Sequence
<220> FEATURE:
<223> OTHER INFORMATION: HAV-A linker regions of pAP-257

<400> SEQUENCE: 49

```
tctgagctta gaacgcaatc gttctcaaat tggaat                                36
```

<210> SEQ ID NO 50
<211> LENGTH: 1855
<212> TYPE: DNA
<213> ORGANISM: Artificial Sequence
<220> FEATURE:
<223> OTHER INFORMATION: pAP-258 insert

<400> SEQUENCE: 50

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540
```

ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctgagct tagaacgcaa tcgttctcaa attggaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 51
<211> LENGTH: 36
<212> TYPE: DNA
<213> ORGANISM: Artificial Sequence
<220> FEATURE:
<223> OTHER INFORMATION: HAV-B linker regions of pAP-255

<400> SEQUENCE: 51
tctgagcttt ggtcgcaagg gatcgatgat gataat 36

<210> SEQ ID NO 52
<211> LENGTH: 1855
<212> TYPE: DNA
<213> ORGANISM: Artificial Sequence
<220> FEATURE:
<223> OTHER INFORMATION: pAP-256 insert

<400> SEQUENCE: 52
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360

-continued

```
taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttctgagct ttggtcgcaa gggatcgatg atgataatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 53
<211> LENGTH: 36
<212> TYPE: DNA
<213> ORGANISM: Artificial Sequence
<220> FEATURE:
<223> OTHER INFORMATION: CAN linker regions of pAP-259

<400> SEQUENCE: 53

```
tctaagcctg caaagttctt caggctaaat tttaat                                36
```

<210> SEQ ID NO 54
<211> LENGTH: 1855
<212> TYPE: DNA
<213> ORGANISM: Artificial Sequence
<220> FEATURE:
<223> OTHER INFORMATION: pAP-260 insert

<400> SEQUENCE: 54

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240
```

-continued gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctaagcc tgcaaagttc ttcaggctaa attttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aacctttgt tacaaccatt 1380 gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 55
<211> LENGTH: 12
<212> TYPE: PRT
<213> ORGANISM: Artificial Sequence
<220> FEATURE:
<223> OTHER INFORMATION: P.falciparum protease-sensitive linkers pAP-223
and pAP-224

<400> SEQUENCE: 55

Gln Val Val Gln Leu Gln Asn Tyr Asp Glu Glu Asp
1 5 10

<210> SEQ ID NO 56
<211> LENGTH: 12
<212> TYPE: PRT
<213> ORGANISM: Artificial Sequence
<220> FEATURE:
<223> OTHER INFORMATION: P.falciparum protease-sensitive linkers pAP-225
and pAP-226

<400> SEQUENCE: 56

```
Leu Pro Ile Phe Gly Glu Ser Glu Asp Asn Asp Glu
  1               5                   10


<210> SEQ ID NO 57
<211> LENGTH: 12
<212> TYPE: PRT
<213> ORGANISM: Artificial Sequence
<220> FEATURE:
<223> OTHER INFORMATION: P.falciparum protease-sensitive linker pAP-227
      and pAP-228

<400> SEQUENCE: 57

Gln Val Val Thr Gly Glu Ala Ile Ser Val Thr Met
  1               5                   10


<210> SEQ ID NO 58
<211> LENGTH: 12
<212> TYPE: PRT
<213> ORGANISM: Artificial Sequence
<220> FEATURE:
<223> OTHER INFORMATION: P.falciparum protease-sensitive linkers pAP-229
      and pAP-230

<400> SEQUENCE: 58

Ala Leu Glu Arg Thr Phe Leu Ser Phe Pro Thr Asn
  1               5                   10


<210> SEQ ID NO 59
<211> LENGTH: 12
<212> TYPE: PRT
<213> ORGANISM: Artificial Sequence
<220> FEATURE:
<223> OTHER INFORMATION: P.falciparum protease-sensitive linkers pAP-231
      and pAP-232

<400> SEQUENCE: 59

Lys Phe Gln Asp Met Leu Asn Ile Ser Gln His Gln
  1               5                   10


<210> SEQ ID NO 60
<211> LENGTH: 12
<212> TYPE: PRT
<213> ORGANISM: Artificial Sequence
<220> FEATURE:
<223> OTHER INFORMATION: Viral protease-sensitive linkers pAP-233 and
      pAP-234

<400> SEQUENCE: 60

Ser Ala Leu Val Asn Ala Ser Ser Ala His Val Asn
  1               5                   10


<210> SEQ ID NO 61
<211> LENGTH: 12
<212> TYPE: PRT
<213> ORGANISM: Artificial Sequence
<220> FEATURE:
<223> OTHER INFORMATION: Viral protease-sensitive linkers pAP-235 and
      pAP-236

<400> SEQUENCE: 61

Ser Thr Tyr Leu Gln Ala Ser Glu Lys Phe Lys Asn
  1               5                   10


<210> SEQ ID NO 62
<211> LENGTH: 12
<212> TYPE: PRT
<213> ORGANISM: Artificial Sequence
```

-continued

```
<220> FEATURE:
<223> OTHER INFORMATION: Viral protease-sensitive linkers pAP-249 and
      pAP-250

<400> SEQUENCE: 62

Ser Ser Ile Leu Asn Ala Ser Val Pro Asn Phe Asn
  1               5                   10


<210> SEQ ID NO 63
<211> LENGTH: 12
<212> TYPE: PRT
<213> ORGANISM: Artificial Sequence
<220> FEATURE:
<223> OTHER INFORMATION: Viral protease-sensitive linkers pAP-245 and
      pAP-246

<400> SEQUENCE: 63

Ser Gly Val Val Asn Ala Ser Cys Arg Leu Ala Asn
  1               5                   10


<210> SEQ ID NO 64
<211> LENGTH: 12
<212> TYPE: PRT
<213> ORGANISM: Artificial Sequence
<220> FEATURE:
<223> OTHER INFORMATION: Viral protease-sensitive linkers pAP-247 and
      pAP-248

<400> SEQUENCE: 64

Ser Ser Tyr Val Lys Ala Ser Val Ser Pro Glu Asn
  1               5                   10


<210> SEQ ID NO 65
<211> LENGTH: 12
<212> TYPE: PRT
<213> ORGANISM: Artificial Sequence
<220> FEATURE:
<223> OTHER INFORMATION: Viral protease-sensitive linkers pAP-237 and
      aAP-238

<400> SEQUENCE: 65

Ser Gln Asp Val Asn Ala Val Glu Ala Ser Ser Asn
  1               5                   10


<210> SEQ ID NO 66
<211> LENGTH: 12
<212> TYPE: PRT
<213> ORGANISM: Artificial Sequence
<220> FEATURE:
<223> OTHER INFORMATION: Viral protease-sensitive linkers pAP-239 and
      pAP-240

<400> SEQUENCE: 66

Ser Val Tyr Leu Gln Ala Ser Thr Gly Tyr Gly Asn
  1               5                   10


<210> SEQ ID NO 67
<211> LENGTH: 12
<212> TYPE: PRT
<213> ORGANISM: Artificial Sequence
<220> FEATURE:
<223> OTHER INFORMATION: Viral protease-sensitive linkers pAP-253 and
      pAP-254

<400> SEQUENCE: 67

Ser Lys Tyr Leu Gln Ala Asn Glu Val Ile Thr Asn
  1               5                   10
```

-continued

<210> SEQ ID NO 68
<211> LENGTH: 12
<212> TYPE: PRT
<213> ORGANISM: Artificial Sequence
<220> FEATURE:
<223> OTHER INFORMATION: Viral protease-sensitive linkers pAP-255 and
pAP-256

<400> SEQUENCE: 68

Ser Glu Leu Arg Thr Gln Ser Phe Ser Asn Trp Asn
1 5 10

<210> SEQ ID NO 69
<211> LENGTH: 12
<212> TYPE: PRT
<213> ORGANISM: Artificial Sequence
<220> FEATURE:
<223> OTHER INFORMATION: Viral protease-sensitive linkers pAP-257 and
pAP-258

<400> SEQUENCE: 69

Ser Glu Leu Trp Ser Gln Gly Ile Asp Asp Asp Asn
1 5 10

<210> SEQ ID NO 70
<211> LENGTH: 12
<212> TYPE: PRT
<213> ORGANISM: Artificial Sequence
<220> FEATURE:
<223> OTHER INFORMATION: Candida aspartic protease-sensitive linkers
pAP-259 and pAP-260

<400> SEQUENCE: 70

Ser Lys Pro Ala Lys Phe Phe Arg Leu Asn Phe Asn
1 5 10

<210> SEQ ID NO 71
<211> LENGTH: 12
<212> TYPE: PRT
<213> ORGANISM: Artificial Sequence
<220> FEATURE:
<223> OTHER INFORMATION: Candida aspartic protease-sensitive linkers
pAP-261 and pAP-

<400> SEQUENCE: 71

Ser Lys Pro Ile Glu Phe Phe Arg Leu Asn Phe Asn
1 5 10

<210> SEQ ID NO 72
<211> LENGTH: 12
<212> TYPE: PRT
<213> ORGANISM: Artificial Sequence
<220> FEATURE:
<223> OTHER INFORMATION: Candida aspartic protease-sensitive linkers
pAP-263 and pAP-264

<400> SEQUENCE: 72

Ser Lys Pro Ala Glu Phe Phe Ala Leu Asn Phe Asn
1 5 10

<210> SEQ ID NO 73
<211> LENGTH: 36
<212> TYPE: DNA
<213> ORGANISM: Artificial Sequence
<220> FEATURE:
<223> OTHER INFORMATION: HCV-A linker region of pAP-262

<400> SEQUENCE: 73

-continued

```
gatttggagg tagtgacatc gacatgggtt tttaat                              36


<210> SEQ ID NO 74
<211> LENGTH: 1855
<212> TYPE: DNA
<213> ORGANISM: Artificial Sequence
<220> FEATURE:
<223> OTHER INFORMATION: pAP-262 insert

<400> SEQUENCE: 74

gaattcatga aaccgggagg aaatactatt gtaatatgga tgtatgcagt ggcaacatgg      60

ctttgttttg gatccacctc agggtggtct ttcacattag aggataacaa catattcccc     120

aaacaatacc caattataaa ctttaccaca gcgggtgcca ctgtgcaaag ctacacaaac     180

tttatcagag ctgttcgcgg tcgtttaaca actggagctg atgtgagaca tgatatacca     240

gtgttgccaa acagagttgg tttgcctata aaccaacggt ttattttagt tgaactctca     300

aatcatgcag agctttctgt tacattagcg ctggatgtca ccaatgcata tgtggtcggc     360

taccgtgctg gaaatagcgc atatttcttt catcctgaca atcaggaaga tgcagaagca     420

atcactcatc ttttcactga tgttcaaaat cgatatacat tcgcctttgg tggtaattat     480

gatagacttg aacaacttgc tggtaatctg agagaaaata tcgagttggg aaatggtcca     540

ctagaggagg ctatctcagc gctttattat tacagtactg gtggcactca gcttccaact     600

ctggctcgtt cctttataat ttgcatccaa atgatttcag aagcagcaag attccaatat     660

attgagggag aaatgcgcac gagaattagg tacaaccgga gatctgcacc agatcctagc     720

gtaattacac ttgagaatag ttgggggaga ctttccactg caattcaaga gtctaaccaa     780

ggagcctttg ctagtccaat tcaactgcaa agacgtaatg gttccaaatt cagtgtgtac     840

gatgtgagta tattaatccc tatcatagct ctcatggtgt atagatgcgc acctccacca     900

tcgtcacagt ttgatttgga ggtagtgaca tcgacatggg tttttaatgc tgatgtttgt     960

atggatcctg agcccatagt gcgtatcgta ggtcgaaatg gtctatgtgt tgatgttagg    1020

gatggaagat tccacaacgg aaacgcaata cagttgtggc catgcaagtc taatacagat    1080

gcaaatcagc tctggacttt gaaaagagac aatactattc gatctaatgg aaagtgttta    1140

actacttacg ggtacagtcc gggagtctat gtgatgatct atgattgcaa tactgctgca    1200

actgatgcca cccgctggca aatatgggat aatggaacca tcataaatcc cagatctagt    1260

ctagttttag cagcgacatc agggaacagt ggtaccacac ttacagtgca aaccaacatt    1320

tatgccgtta gtcaaggttg gcttcctact aataatacac aacctttttgt tacaaccatt    1380

gttgggctat atggtctgtg cttgcaagca aatagtggac aagtatggat agaggactgt    1440

agcagtgaaa aggctgaaca acagtgggct ctttatgcag atggttcaat acgtcctcag    1500

caaaaccgag ataattgcct tacaagtgat tctaatatac gggaaacagt tgttaagatc    1560

ctctcttgtg gccctgcatc ctctggccaa cgatggatgt tcaagaatga tggaaccatt    1620

ttaaatttgt atagtggatt ggtgttagat gtgaggcgat cggatccgag ccttaaacaa    1680

atcattcttt accctctcca tggtgaccca aaccaaatat ggttaccatt attttgatag    1740

acagattact ctcttgcagt gtgtgtgtcc tgccatgaaa atagatggct taaataaaaa    1800

ggacattgta aattttgtaa ctgaaaggac agcaagttat atcgaattcc tgcag         1855


<210> SEQ ID NO 75
<211> LENGTH: 12
<212> TYPE: PRT
```

-continued

<213> ORGANISM: Artificial Sequence
<220> FEATURE:
<223> OTHER INFORMATION: Mutant Preproricin linker region for HCV-A, pAP-262

<400> SEQUENCE: 75

Asp Leu Glu Val Val Thr Ser Thr Trp Val Phe Asn
1 5 10

<210> SEQ ID NO 76
<211> LENGTH: 36
<212> TYPE: DNA
<213> ORGANISM: Artificial Sequence
<220> FEATURE:
<223> OTHER INFORMATION: HCV-B linker region of pAP-264

<400> SEQUENCE: 76
gatgagatgg aagagtgtgc gtcacacctt tttaat 36

<210> SEQ ID NO 77
<211> LENGTH: 1855
<212> TYPE: DNA
<213> ORGANISM: Artificial Sequence
<220> FEATURE:
<223> OTHER INFORMATION: pAP-264 insert

<400> SEQUENCE: 77
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttgatgagat ggaagagtgt gcgtcacacc tttttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440

-continued

```
agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

```
<210> SEQ ID NO 78
<211> LENGTH: 12
<212> TYPE: PRT
<213> ORGANISM: Artificial Sequence
<220> FEATURE:
<223> OTHER INFORMATION: Mutant preproricin linker region for HCV-B,
      pAP-264

<400> SEQUENCE: 78

Asp Glu Met Glu Glu Cys Ala Ser His Leu Phe Asn
  1               5                  10
```

```
<210> SEQ ID NO 79
<211> LENGTH: 36
<212> TYPE: DNA
<213> ORGANISM: Artificial Sequence
<220> FEATURE:
<223> OTHER INFORMATION: HCV-C linker region of pAP-266

<400> SEQUENCE: 79

gaggacgttg tatgttgttc gatgtcatat tttaat                               36
```

```
<210> SEQ ID NO 80
<211> LENGTH: 1855
<212> TYPE: DNA
<213> ORGANISM: Artificial Sequence
<220> FEATURE:
<223> OTHER INFORMATION: pAP-266 insert

<400> SEQUENCE: 80

gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840
```

-continued

```
gatgtgagta tattaatccc tatcatagct ctcatggtgt atagatgcgc acctccacca    900

tcgtcacagt ttgaggacgt tgtatgttgt tcgatgtcat attttaatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 81
<211> LENGTH: 12
<212> TYPE: PRT
<213> ORGANISM: Artificial Sequence
<220> FEATURE:
<223> OTHER INFORMATION: Mutant preproricin linker region for HCV-C, pAP-266

<400> SEQUENCE: 81

```
Glu Asp Val Val Cys Cys Ser Met Ser Tyr Phe Asn
  1               5                  10
```

<210> SEQ ID NO 82
<211> LENGTH: 36
<212> TYPE: DNA
<213> ORGANISM: Artificial Sequence
<220> FEATURE:
<223> OTHER INFORMATION: HCV-D linker region of pAP-268

<400> SEQUENCE: 82

```
aaggggtgga gattgctagc gccaataact gcttat                               36
```

<210> SEQ ID NO 83
<211> LENGTH: 1855
<212> TYPE: DNA
<213> ORGANISM: Artificial Sequence
<220> FEATURE:
<223> OTHER INFORMATION: pAP-268 insert

<400> SEQUENCE: 83

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300
```

-continued

```
aatcatgcag agctttctgt tacattagcg ctggatgtca ccaatgcata tgtggtcggc    360
taccgtgctg gaaatagcgc atatttcttt catcctgaca atcaggaaga tgcagaagca    420
atcactcatc ttttcactga tgttcaaaat cgatatacat tcgcctttgg tggtaattat    480
gatagacttg aacaacttgc tggtaatctg agagaaaata tcgagttggg aaatggtcca    540
ctagaggagg ctatctcagc gctttattat tacagtactg gtggcactca gcttccaact    600
ctggctcgtt cctttataat ttgcatccaa atgatttcag aagcagcaag attccaatat    660
attgagggag aaatgcgcac gagaattagg tacaaccgga gatctgcacc agatcctagc    720
gtaattacac ttgagaatag ttgggggaga ctttccactg caattcaaga gtctaaccaa    780
ggagcctttg ctagtccaat tcaactgcaa agacgtaatg gttccaaatt cagtgtgtac    840
gatgtgagta tattaatccc tatcatagct ctcatggtgt atagatgcgc acctccacca    900
tcgtcacagt ttaaggggtg gagattgcta gcgccaataa ctgcttatgc tgatgtttgt    960
atggatcctg agcccatagt gcgtatcgta ggtcgaaatg gtctatgtgt tgatgttagg   1020
gatggaagat tccacaacgg aaacgcaata cagttgtggc catgcaagtc taatacagat   1080
gcaaatcagc tctggacttt gaaaagagac aatactattc gatctaatgg aaagtgttta   1140
actacttacg ggtacagtcc gggagtctat gtgatgatct atgattgcaa tactgctgca   1200
actgatgcca cccgctggca aatatgggat aatggaacca tcataaatcc cagatctagt   1260
ctagttttag cagcgacatc agggaacagt ggtaccacac ttacagtgca aaccaacatt   1320
tatgccgtta gtcaaggttg gcttcctact aataatacac aaccttttgt tacaaccatt   1380
gttgggctat atggtctgtg cttgcaagca aatagtggac aagtatggat agaggactgt   1440
agcagtgaaa aggctgaaca acagtgggct ctttatgcag atggttcaat acgtcctcag   1500
caaaaccgag ataattgcct tacaagtgat tctaatatac gggaaacagt tgttaagatc   1560
ctctcttgtg gccctgcatc ctctggccaa cgatggatgt tcaagaatga tggaaccatt   1620
ttaaatttgt atagtggatt ggtgttagat gtgaggcgat cggatccgag ccttaaacaa   1680
atcattcttt accctctcca tggtgaccca aaccaaatat ggttaccatt attttgatag   1740
acagattact ctcttgcagt gtgtgtgtcc tgccatgaaa atagatggct taaataaaaa   1800
ggacattgta aattttgtaa ctgaaaggac agcaagttat atcgaattcc tgcag        1855
```

<210> SEQ ID NO 84
<211> LENGTH: 12
<212> TYPE: PRT
<213> ORGANISM: Artificial Sequence
<220> FEATURE:
<223> OTHER INFORMATION: Mutant preproricin linker region for HCV-D, pAP-268

<400> SEQUENCE: 84

```
Lys Gly Trp Arg Leu Leu Ala Pro Ile Thr Ala Tyr
  1               5                  10
```

<210> SEQ ID NO 85
<211> LENGTH: 36
<212> TYPE: DNA
<213> ORGANISM: Artificial Sequence
<220> FEATURE:
<223> OTHER INFORMATION: MMP-2 linker region of pAP-270

<400> SEQUENCE: 85

```
tctttgcccc tgggtttatg ggctcctaat tttaat                               36
```

-continued

<210> SEQ ID NO 86
<211> LENGTH: 1855
<212> TYPE: DNA
<213> ORGANISM: Artificial Sequence
<220> FEATURE:
<223> OTHER INFORMATION: pAP-270 insert

<400> SEQUENCE: 86
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctttgcc cctgggttta tgggctccta attttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aacctttgt tacaaccatt 1380 gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 87
<211> LENGTH: 12
<212> TYPE: PRT
<213> ORGANISM: Artificial Sequence
<220> FEATURE:
<223> OTHER INFORMATION: Mutant preproricin linker region for MMP-2, -continued pAP-270

<400> SEQUENCE: 87

Ser Leu Pro Leu Gly Leu Trp Ala Pro Asn Phe Asn
1 5 10

<210> SEQ ID NO 88
<211> LENGTH: 36
<212> TYPE: DNA
<213> ORGANISM: Artificial Sequence
<220> FEATURE:
<223> OTHER INFORMATION: Cathepsin B (Site 2) linker region of pAP-272

<400> SEQUENCE: 88
tctttgctta tagctagaag gatgcctaat tttaat 36

<210> SEQ ID NO 89
<211> LENGTH: 1855
<212> TYPE: DNA
<213> ORGANISM: Artificial Sequence
<220> FEATURE:
<223> OTHER INFORMATION: pAP-272 insert

<400> SEQUENCE: 89
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttctttgct tatagctaga aggatgccta attttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aacctttgt tacaaccatt 1380 gttgggctat atggtctgtg cttgcaagca aatagtggac aagtatggat agaggactgt 1440
agcagtgaaa aggctgaaca acagtgggct ctttatgcag atggttcaat acgtcctcag 1500

-continued caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 90
<211> LENGTH: 12
<212> TYPE: PRT
<213> ORGANISM: Artificial Sequence
<220> FEATURE:
<223> OTHER INFORMATION: Mutant preproricin linker region for Cathepsin B (site 2), p

<400> SEQUENCE: 90

Ser Leu Leu Ile Ala Arg Arg Met Pro Asn Phe Asn
1 5 10

<210> SEQ ID NO 91
<211> LENGTH: 36
<212> TYPE: DNA
<213> ORGANISM: Artificial Sequence
<220> FEATURE:
<223> OTHER INFORMATION: Cathepsin L linker region of pAP-274

<400> SEQUENCE: 91
tctttgctta tattccggtc atgggctaat tttaat 36

<210> SEQ ID NO 92
<211> LENGTH: 1855
<212> TYPE: DNA
<213> ORGANISM: Artificial Sequence
<220> FEATURE:
<223> OTHER INFORMATION: pAP-274 insert

<400> SEQUENCE: 92
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctttgct tatattccgg tcatgggcta attttaatgc tgatgtttgt 960

-continued

```
atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 93
<211> LENGTH: 12
<212> TYPE: PRT
<213> ORGANISM: Artificial Sequence
<220> FEATURE:
<223> OTHER INFORMATION: Mutant preproricin linker region of Cathepsin L, pAP-274

<400> SEQUENCE: 93

```
Ser Leu Leu Ile Phe Arg Ser Trp Ala Asn Phe Asn
  1               5                  10
```

<210> SEQ ID NO 94
<211> LENGTH: 36
<212> TYPE: DNA
<213> ORGANISM: Artificial Sequence
<220> FEATURE:
<223> OTHER INFORMATION: Cathepsin D linker region of pAP-276

<400> SEQUENCE: 94

```
tctggtgttg tcatcgctac tgttattgtt atcacc                              36
```

<210> SEQ ID NO 95
<211> LENGTH: 1855
<212> TYPE: DNA
<213> ORGANISM: Artificial Sequence
<220> FEATURE:
<223> OTHER INFORMATION: pAP-276 insert

<400> SEQUENCE: 95

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360
```

-continued

```
taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttctggtgt tgtcatcgct actgttattg ttatcaccgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag         1855
```

<210> SEQ ID NO 96
<211> LENGTH: 12
<212> TYPE: PRT
<213> ORGANISM: Artificial Sequence
<220> FEATURE:
<223> OTHER INFORMATION: Mutant preproricin linker region for Cathepsin D, pAP-276

<400> SEQUENCE: 96

```
Ser Gly Val Val Ile Ala Thr Val Ile Val Ile Thr
  1               5                  10
```

<210> SEQ ID NO 97
<211> LENGTH: 36
<212> TYPE: DNA
<213> ORGANISM: Artificial Sequence
<220> FEATURE:
<223> OTHER INFORMATION: MMP-1 linker region of pAP-278

<400> SEQUENCE: 97

```
tctttgggtc ctcaaggcat ttggggacag tttaat                               36
```

<210> SEQ ID NO 98
<211> LENGTH: 1855

-continued

<212> TYPE: DNA
<213> ORGANISM: Artificial Sequence
<220> FEATURE:
<223> OTHER INFORMATION: pAP-278 insert

<400> SEQUENCE: 98
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttctttggg tcctcaaggc atttggggac agtttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 99
<211> LENGTH: 12
<212> TYPE: PRT
<213> ORGANISM: Artificial Sequence
<220> FEATURE:
<223> OTHER INFORMATION: Mutant preproricin linker region for MMP-1,
pAP-278

<400> SEQUENCE: 99

-continued

Ser Leu Gly Pro Gln Gly Ile Trp Gly Gln Phe Asn
1 5 10

<210> SEQ ID NO 100
<211> LENGTH: 36
<212> TYPE: DNA
<213> ORGANISM: Artificial Sequence
<220> FEATURE:
<223> OTHER INFORMATION: Urokinase-Type Plasminogen Activator linder region of pAP-280

<400> SEQUENCE: 100
aaaaaatccc ctggaagagt tgtcggtggc tctgta 36

<210> SEQ ID NO 101
<211> LENGTH: 1855
<212> TYPE: DNA
<213> ORGANISM: Artificial Sequence
<220> FEATURE:
<223> OTHER INFORMATION: pAP-280 insert

<400> SEQUENCE: 101
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttaaaaaatc ccctggaaga gttgtcggtg gctctgtagc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560

-continued

```
ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 102
<211> LENGTH: 12
<212> TYPE: PRT
<213> ORGANISM: Artificial Sequence
<220> FEATURE:
<223> OTHER INFORMATION: Mutant preproricin linker region for
      Urokinase-Type Plasmino

<400> SEQUENCE: 102

```
Lys Lys Ser Pro Gly Arg Val Val Gly Gly Ser Val
  1               5                  10
```

<210> SEQ ID NO 103
<211> LENGTH: 36
<212> TYPE: DNA
<213> ORGANISM: Artificial Sequence
<220> FEATURE:
<223> OTHER INFORMATION: MT-MMP linker region of pAP-282

<400> SEQUENCE: 103

```
ccccaaggac tcctaggggc tcctggtatt cttggc                               36
```

<210> SEQ ID NO 104
<211> LENGTH: 1855
<212> TYPE: DNA
<213> ORGANISM: Artificial Sequence
<220> FEATURE:
<223> OTHER INFORMATION: pAP-282 insert

<400> SEQUENCE: 104

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt ttccccaagg actcctaggg gctcctggta ttcttggcgc tgatgtttgt    960

atggatcctg agcccatagt gcgtatcgta ggtcgaaatg gtctatgtgt tgatgttagg   1020
```

-continued

```
gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aacctttgt tacaaccatt    1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 105
<211> LENGTH: 12
<212> TYPE: PRT
<213> ORGANISM: Artificial Sequence
<220> FEATURE:
<223> OTHER INFORMATION: Mutant preproricin linker region for MT-MMP, PAP-282

<400> SEQUENCE: 105

```
Pro Gln Gly Leu Leu Gly Ala Pro Gly Ile Leu Gly
  1               5                  10
```

<210> SEQ ID NO 106
<211> LENGTH: 93
<212> TYPE: DNA
<213> ORGANISM: Artificial Sequence
<220> FEATURE:
<223> OTHER INFORMATION: MMP-11 linker region of pAP-284

<400> SEQUENCE: 106

```
cacggccccg agggtttaag agtgggattt tatgaatctg acgtcatggg aagaggccat     60

gctcgtttag ttcatgtcga agagcctcac act                                  93
```

<210> SEQ ID NO 107
<211> LENGTH: 1912
<212> TYPE: DNA
<213> ORGANISM: Artificial Sequence
<220> FEATURE:
<223> OTHER INFORMATION: pAP-284 insert

<400> SEQUENCE: 107

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360
```

-continued

```
taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt ttcacggccc cgagggttta agagtgggat tttatgaatc tgacgtcatg    960

ggaagaggcc atgctcgttt agttcatgtc gaagagcctc acactgctga tgtttgtatg   1020

gatcctgagc ccatagtgcg tatcgtaggt cgaaatggtc tatgtgttga tgttagggat   1080

ggaagattcc acaacggaaa cgcaatacag ttgtggccat gcaagtctaa tacagatgca   1140

aatcagctct ggactttgaa aagagacaat actattcgat ctaatggaaa gtgtttaact   1200

acttacgggt acagtccggg agtctatgtg atgatctatg attgcaatac tgctgcaact   1260

gatgccaccc gctggcaaat atgggataat ggaaccatca taaatcccag atctagtcta   1320

gttttagcag cgacatcagg gaacagtggt accacactta cagtgcaaac caacatttat   1380

gccgttagtc aaggttggct tcctactaat aatacacaac cttttgttac aaccattgtt   1440

gggctatatg gtctgtgctt gcaagcaaat agtggacaag tatggataga ggactgtagc   1500

agtgaaaagg ctgaacaaca gtgggctctt tatgcagatg gttcaatacg tcctcagcaa   1560

aaccgagata attgccttac aagtgattct aatatacggg aaacagttgt taagatcctc   1620

tcttgtggcc ctgcatcctc tggccaacga tggatgttca agaatgatgg aaccatttta   1680

aatttgtata gtggattggt gttagatgtg aggcgatcgg atccgagcct taaacaaatc   1740

attctttacc ctctccatgg tgacccaaac caaatatggt taccattatt ttgatagaca   1800

gattactctc ttgcagtgtg tgtgtcctgc catgaaaata gatggcttaa ataaaaagga   1860

cattgtaaat tttgtaactg aaaggacagc aagttatatc gaattcctgc ag           1912
```

```
<210> SEQ ID NO 108
<211> LENGTH: 31
<212> TYPE: PRT
<213> ORGANISM: Artificial Sequence
<220> FEATURE:
<223> OTHER INFORMATION: Mutant preproricin linker region for MMP-11,
      pAP-284

<400> SEQUENCE: 108

His Gly Pro Glu Gly Leu Arg Val Gly Phe Tyr Glu Ser Asp Val Met
  1               5                  10                  15

Gly Arg Gly His Ala Arg Leu Val His Val Glu Glu Pro His Thr
             20                  25                  30


<210> SEQ ID NO 109
<211> LENGTH: 36
<212> TYPE: DNA
<213> ORGANISM: Artificial Sequence
<220> FEATURE:
<223> OTHER INFORMATION: MMP-13 linker region of pAP-286

<400> SEQUENCE: 109
```

-continued

```
ggacctcagg ggcttgctgg tcaacgaggc attgtc                          36


<210> SEQ ID NO 110
<211> LENGTH: 1855
<212> TYPE: DNA
<213> ORGANISM: Artificial Sequence
<220> FEATURE:
<223> OTHER INFORMATION: pAP-286 insert

<400> SEQUENCE: 110

gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt ttggacctca ggggcttgct ggtcaacgag gcattgtcgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855


<210> SEQ ID NO 111
<211> LENGTH: 12
<212> TYPE: PRT
<213> ORGANISM: Artificial Sequence
```

-continued

<220> FEATURE:
<223> OTHER INFORMATION: Mutant preproricin linker region for MMP-13,
pAP-286

<400> SEQUENCE: 111

Gly Pro Gln Gly Leu Ala Gly Gln Arg Gly Ile Val
1 5 10

<210> SEQ ID NO 112
<211> LENGTH: 36
<212> TYPE: DNA
<213> ORGANISM: Artificial Sequence
<220> FEATURE:
<223> OTHER INFORMATION: Tissue-type Plasminogen Activator linker region
of pAP-288

<400> SEQUENCE: 112
ggcggatctg ggcaaagggg tcgtaaagct cttgaa 36

<210> SEQ ID NO 113
<211> LENGTH: 1855
<212> TYPE: DNA
<213> ORGANISM: Artificial Sequence
<220> FEATURE:
<223> OTHER INFORMATION: pAP-288 insert

<400> SEQUENCE: 113
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttggcggatc tgggcaaagg ggtcgtaaag ctcttgaagc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aacctttgt tacaaccatt 1380 gttgggctat atggtctgtg cttgcaagca aatagtggac aagtatggat agaggactgt 1440

-continued

```
agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

<210> SEQ ID NO 114
<211> LENGTH: 12
<212> TYPE: PRT
<213> ORGANISM: Artificial Sequence
<220> FEATURE:
<223> OTHER INFORMATION: Mutant preproricin linker region for Tissue-type Plasminogen

<400> SEQUENCE: 114

```
Gly Gly Ser Gly Gln Arg Gly Arg Lys Ala Leu Glu
  1               5                  10
```

<210> SEQ ID NO 115
<211> LENGTH: 36
<212> TYPE: DNA
<213> ORGANISM: Artificial Sequence
<220> FEATURE:
<223> OTHER INFORMATION: Human Prostate-Specific Antigen linker region of pAP-290

<400> SEQUENCE: 115

```
tctttgtcag ctcttctctc ttccgatatt tttaat                                36
```

<210> SEQ ID NO 116
<211> LENGTH: 1855
<212> TYPE: DNA
<213> ORGANISM: Artificial Sequence
<220> FEATURE:
<223> OTHER INFORMATION: pAP-290 insert

<400> SEQUENCE: 116

```
gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgatatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840
```

gatgtgagta tattaatccc tatcatagct ctcatggtgt atagatgcgc acctccacca 900
tcgtcacagt tttctttgtc agctcttctc tcttccgata tttttaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtggatt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 117
<211> LENGTH: 12
<212> TYPE: PRT
<213> ORGANISM: Artificial Sequence
<220> FEATURE:
<223> OTHER INFORMATION: Mutant preproricin linker region-human
Prostate-Specific Ant

<400> SEQUENCE: 117

Ser Leu Ser Ala Leu Leu Ser Ser Asp Ile Phe Asn
1 5 10

<210> SEQ ID NO 118
<211> LENGTH: 36
<212> TYPE: DNA
<213> ORGANISM: Artificial Sequence
<220> FEATURE:
<223> OTHER INFORMATION: Kallikrein linker region of pAP-292

<400> SEQUENCE: 118
tctttgccta gatttaaaat tatcggtggc tttaat 36

<210> SEQ ID NO 119
<211> LENGTH: 1855
<212> TYPE: DNA
<213> ORGANISM: Artificial Sequence
<220> FEATURE:
<223> OTHER INFORMATION: pAP-292 insert

<400> SEQUENCE: 119
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240

-continued

```
gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgc acctccacca    900

tcgtcacagt tttctttgcc tagatttaaa attatcggtg gctttaatgc tgatgtttgt    960

atggatcctg agcccatagt gcgtatcgta ggtcgaaatg gtctatgtgt tgatgttagg   1020

gatggaagat tccacaacgg aaacgcaata cagttgtggc catgcaagtc taatacagat   1080

gcaaatcagc tctggacttt gaaaagagac aatactattc gatctaatgg aaagtgttta   1140

actacttacg ggtacagtcc gggagtctat gtgatgatct atgattgcaa tactgctgca   1200

actgatgcca cccgctggca aatatgggat aatggaacca tcataaatcc cagatctagt   1260

ctagttttag cagcgacatc agggaacagt ggtaccacac ttacagtgca aaccaacatt   1320

tatgccgtta gtcaaggttg gcttcctact aataatacac aaccttttgt tacaaccatt   1380

gttgggctat atggtctgtg cttgcaagca aatagtggac aagtatggat agaggactgt   1440

agcagtgaaa aggctgaaca acagtgggct ctttatgcag atggttcaat acgtcctcag   1500

caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855
```

```
<210> SEQ ID NO 120
<211> LENGTH: 12
<212> TYPE: PRT
<213> ORGANISM: Artificial Sequence
<220> FEATURE:
<223> OTHER INFORMATION: Mutant Preproricin linker region for
      Kallikrein, pap-292

<400> SEQUENCE: 120

Ser Leu Pro Arg Phe Lys Ile Ile Gly Gly Phe Asn
  1               5                  10


<210> SEQ ID NO 121
<211> LENGTH: 36
<212> TYPE: DNA
<213> ORGANISM: Artificial Sequence
<220> FEATURE:
<223> OTHER INFORMATION: Neutrophil elastase linker region of pAP-294

<400> SEQUENCE: 121

tctttgcttg gcattgctgt tcctggtaat tttaat                                36
```

<210> SEQ ID NO 122
<211> LENGTH: 1855
<212> TYPE: DNA
<213> ORGANISM: Artificial Sequence
<220> FEATURE:
<223> OTHER INFORMATION: pAP-294 insert

<400> SEQUENCE: 122

```
gaattcatga aaccgggagg aaatactatt gtaatatgga tgtatgcagt ggcaacatgg      60
ctttgttttg gatccacctc agggtggtct ttcacattag aggataacaa catattcccc     120
aaacaatacc caattataaa ctttaccaca gcgggtgcca ctgtgcaaag ctacacaaac     180
tttatcagag ctgttcgcgg tcgtttaaca actggagctg atgtgagaca tgatatacca     240
gtgttgccaa acagagttgg tttgcctata aaccaacggt ttattttagt tgaactctca     300
aatcatgcag agctttctgt tacattagcg ctggatgtca ccaatgcata tgtggtcggc     360
taccgtgctg aaatagcgc atatttcttt catcctgaca atcaggaaga tgcagaagca     420
atcactcatc ttttcactga tgttcaaaat cgatatacat tcgcctttgg tggtaattat     480
gatagacttg aacaacttgc tggtaatctg agagaaaata tcgagttggg aaatggtcca     540
ctagaggagg ctatctcagc gctttattat tacagtactg gtggcactca gcttccaact     600
ctggctcgtt cctttataat ttgcatccaa atgatttcag aagcagcaag attccaatat     660
attgagggag aaatgcgcac gagaattagg tacaaccgga gatctgcacc agatcctagc     720
gtaattacac ttgagaatag ttgggggaga ctttccactg caattcaaga gtctaaccaa     780
ggagcctttg ctagtccaat tcaactgcaa agacgtaatg gttccaaatt cagtgtgtac     840
gatgtgagta tattaatccc tatcatagct ctcatggtgt atagatgcgc acctccacca     900
tcgtcacagt tttctttgct tggcattgct gttcctggta attttaatgc tgatgtttgt     960
atggatcctg agcccatagt gcgtatcgta ggtcgaaatg gtctatgtgt tgatgttagg    1020
gatggaagat tccacaacgg aaacgcaata cagttgtggc catgcaagtc taatacagat    1080
gcaaatcagc tctggacttt gaaaagagac aatactattc gatctaatgg aaagtgttta    1140
actacttacg ggtacagtcc gggagtctat gtgatgatct atgattgcaa tactgctgca    1200
actgatgcca cccgctggca aatatgggat aatggaacca tcataaatcc cagatctagt    1260
ctagttttag cagcgacatc agggaacagt ggtaccacac ttacagtgca aaccaacatt    1320
tatgccgtta gtcaaggttg gcttcctact aataatacac aaccttttgt tacaaccatt    1380
gttgggctat atggtctgtg cttgcaagca aatagtggac aagtatggat agaggactgt    1440
agcagtgaaa aggctgaaca acagtgggct ctttatgcag atggttcaat acgtcctcag    1500
caaaaccgag ataattgcct tacaagtgat tctaatatac gggaaacagt tgttaagatc    1560
ctctcttgtg gccctgcatc ctctggccaa cgatggatgt tcaagaatga tggaaccatt    1620
ttaaatttgt atagtggatt ggtgttagat gtgaggcgat cggatccgag ccttaaacaa    1680
atcattcttt accctctcca tggtgaccca aaccaaatat ggttaccatt attttgatag    1740
acagattact ctcttgcagt gtgtgtgtcc tgccatgaaa atagatggct taaataaaaa    1800
ggacattgta aattttgtaa ctgaaaggac agcaagttat atcgaattcc tgcag         1855
```

<210> SEQ ID NO 123
<211> LENGTH: 12
<212> TYPE: PRT
<213> ORGANISM: Artificial Sequence
<220> FEATURE:

<223> OTHER INFORMATION: Mutant preproricin linker region for neutrophil elastase, pA

<400> SEQUENCE: 123

Ser Leu Leu Gly Ile Ala Val Pro Gly Asn Phe Asn
1 5 10

<210> SEQ ID NO 124
<211> LENGTH: 36
<212> TYPE: DNA
<213> ORGANISM: Artificial Sequence
<220> FEATURE:
<223> OTHER INFORMATION: Calpain linker region of pAP-296

<400> SEQUENCE: 124
tttttcaaaa atattgttac tcctagaacc ccccca 36

<210> SEQ ID NO 125
<211> LENGTH: 1855
<212> TYPE: DNA
<213> ORGANISM: Artificial Sequence
<220> FEATURE:
<223> OTHER INFORMATION: pAP-296 insert
<400> SEQUENCE: 125
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgatatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttttttcaa aaatattgtt actcctagaa cccccccagc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500

-continued

```
caaaaccgag ataattgcct tacaagtgat tctaatatac gggaaacagt tgttaagatc   1560

ctctcttgtg gccctgcatc ctctggccaa cgatggatgt tcaagaatga tggaaccatt   1620

ttaaatttgt atagtggatt ggtgttagat gtgaggcgat cggatccgag ccttaaacaa   1680

atcattcttt accctctcca tggtgaccca aaccaaatat ggttaccatt attttgatag   1740

acagattact ctcttgcagt gtgtgtgtcc tgccatgaaa atagatggct taaataaaaa   1800

ggacattgta aattttgtaa ctgaaaggac agcaagttat atcgaattcc tgcag        1855


<210> SEQ ID NO 126
<211> LENGTH: 12
<212> TYPE: PRT
<213> ORGANISM: Artificial Sequence
<220> FEATURE:
<223> OTHER INFORMATION: Mutant preproricin linker region for calpain,
      pAP-296

<400> SEQUENCE: 126

Phe Phe Lys Asn Ile Val Thr Pro Arg Thr Pro Pro
  1               5                  10


<210> SEQ ID NO 127
<211> LENGTH: 12
<212> TYPE: PRT
<213> ORGANISM: Artificial Sequence
<220> FEATURE:
<223> OTHER INFORMATION: Wild type linker region

<400> SEQUENCE: 127

Ser Leu Leu Ile Arg Pro Val Val Pro Asn Phe Asn
  1               5                  10


<210> SEQ ID NO 128
<211> LENGTH: 20
<212> TYPE: DNA
<213> ORGANISM: Artificial Sequence
<220> FEATURE:
<223> OTHER INFORMATION: Oligonucleotide primers

<400> SEQUENCE: 128

aattaaccct cactaaaggg                                                  20


<210> SEQ ID NO 129
<211> LENGTH: 22
<212> TYPE: DNA
<213> ORGANISM: Artificial Sequence
<220> FEATURE:
<223> OTHER INFORMATION: T7 primer

<400> SEQUENCE: 129

gtaatacgac tcactatagg gc                                               22


<210> SEQ ID NO 130
<211> LENGTH: 33
<212> TYPE: DNA
<213> ORGANISM: Artificial Sequence
<220> FEATURE:
<223> OTHER INFORMATION: Oligonucleotide primer-Ricin-109

<400> SEQUENCE: 130

ggagatgaaa ccgggaggaa atactattgt aat                                   33


<210> SEQ ID NO 131
<211> LENGTH: 31
```

-continued

<212> TYPE: DNA
<213> ORGANISM: Artificial Sequence
<220> FEATURE:
<223> OTHER INFORMATION: Oligonucleotid primer-Ricin-99Eco

<400> SEQUENCE: 131
gcggaattcc gggaggaaat actattgtaa t 31

<210> SEQ ID NO 132
<211> LENGTH: 18
<212> TYPE: DNA
<213> ORGANISM: Artificial Sequence
<220> FEATURE:
<223> OTHER INFORMATION: Oligonucleotide primer-Ricin267

<400> SEQUENCE: 132
acggtttatt ttagttga 18

<210> SEQ ID NO 133
<211> LENGTH: 18
<212> TYPE: DNA
<213> ORGANISM: Artificial Sequence
<220> FEATURE:
<223> OTHER INFORMATION: Oligonucleotide primer-Ricin486

<400> SEQUENCE: 133
acttgctggt aatctgag 18

<210> SEQ ID NO 134
<211> LENGTH: 18
<212> TYPE: DNA
<213> ORGANISM: Artificial Sequence
<220> FEATURE:
<223> OTHER INFORMATION: Oligonucleotide primer-Ricin725

<400> SEQUENCE: 134
agaatagttg ggggagac 18

<210> SEQ ID NO 135
<211> LENGTH: 18
<212> TYPE: DNA
<213> ORGANISM: Artificial Sequence
<220> FEATURE:
<223> OTHER INFORMATION: Oligonucleotide primer-Ricin 937

<400> SEQUENCE: 135
aatgctgatg tttgtatg 18

<210> SEQ ID NO 136
<211> LENGTH: 18
<212> TYPE: DNA
<213> ORGANISM: Artificial Sequence
<220> FEATURE:
<223> OTHER INFORMATION: Oligonucleotide primer-Ricin 1151

<400> SEQUENCE: 136
cgggagtcta tgtgatga 18

<210> SEQ ID NO 137
<211> LENGTH: 18
<212> TYPE: DNA
<213> ORGANISM: Artificial Sequence
<220> FEATURE:
<223> OTHER INFORMATION: Oligonucleotide primer-Ricin 1399

<400> SEQUENCE: 137

-continued

```
gcaaatagtg gacaagta                                                  18


<210> SEQ ID NO 138
<211> LENGTH: 18
<212> TYPE: DNA
<213> ORGANISM: Artificial Sequence
<220> FEATURE:
<223> OTHER INFORMATION: Oligonucleotide primer-Ricin 1627

<400> SEQUENCE: 138

ggattggtgt tagatgtg                                                  18


<210> SEQ ID NO 139
<211> LENGTH: 19
<212> TYPE: DNA
<213> ORGANISM: Artificial Sequence
<220> FEATURE:
<223> OTHER INFORMATION: Oligonucleotide primer-Ricin 1729C

<400> SEQUENCE: 139

ataacttgct gtcctttca                                                 19


<210> SEQ ID NO 140
<211> LENGTH: 27
<212> TYPE: DNA
<213> ORGANISM: Artificial Sequence
<220> FEATURE:
<223> OTHER INFORMATION: Oligonucleotide primer-Ricin 1729C Xba

<400> SEQUENCE: 140

cgctctagat aacttgctgt cctttca                                        27


<210> SEQ ID NO 141
<211> LENGTH: 43
<212> TYPE: DNA
<213> ORGANISM: Artificial Sequence
<220> FEATURE:
<223> OTHER INFORMATION: Ricin109-Eco Oligonucleotide

<400> SEQUENCE: 141

ggaggaatcc ggagatgaaa ccgggaggaa atactattgt aat                      43


<210> SEQ ID NO 142
<211> LENGTH: 33
<212> TYPE: DNA
<213> ORGANISM: Artificial Sequence
<220> FEATURE:
<223> OTHER INFORMATION: Ricin1729-PstI

<400> SEQUENCE: 142

gtaggcgctg cagataactt gctgtccttt cag                                 33
```

RICIN-LIKE TOXIN VARIANTS FOR TREATMENT OF CANCER, VIRAL OR PARASITIC INFECTIONS

This application is a divisional of U.S. patent application Ser. No. 09/403,752, filed on Oct. 29, 1999, now U.S. Pat. No. 6,593,132, which is a national stage application of PCT/CA98/00395, filed Apr. 30, 1998, which claims benefit from U.S. provisional application Ser. No. 60/045,148 filed on Apr. 30, 1997 and U.S. provisional application Ser. No. 60/063,715 filed on Oct. 29, 1997, all of which are incorporated herein by reference.

FIELD OF THE INVENTION

The invention relates to proteins useful as therapeutics against cancer, viral infections, parasitic and fungal infections. The proteins contain A and B chains of a ricin-like toxin linked by a linker sequence that is specifically cleaved and activated by proteases specific to disease-associated pathogens or cells.

BACKGROUND OF THE INVENTION

Bacteria and plants are known to produce cytotoxic proteins which may consist of one, two or several polypeptides or subunits. Those proteins having a single subunit may be loosely classified as Type I proteins. Many of the cytotoxins which have evolved two subunit structures are referred to as type II proteins (Saelinger, C. B. in Trafficking of Bacterial Toxins (eds. Saelinger, C. B.) 1-13 (CRC Press Inc., Boca Raton, Fla., 1990). One subunit, the A chain, possesses the toxic activity whereas the second subunit, the B chain, binds cell surfaces and mediates entry of the toxin into a target cell. A subset of these toxins kill target cells by inhibiting protein biosynthesis. For example, bacterial toxins such as diphtheria toxin or *Pseudomonas* exotoxin inhibit protein synthesis by inactivating elongation factor 2. Plant toxins such as ricin, abrin, and bacterial toxin Shiga toxin, inhibit protein synthesis by directly inactivating the ribosomes (Olsnes, S. & Phil, A. in Molecular action of toxins and viruses (eds. Cohen, P. & vanHeyningen, S.) 51-105 Elsevier Biomedical Press, Amsterdam, 1982).

Ricin, derived from the seeds of *Ricinus communis* (castor oil plant), may be the most potent of the plant toxins. It is estimated that a single ricin A chain is able to inactivate ribosomes at a rate of 1500 ribosomes/minute. Consequently, a single molecule of ricin is enough to kill a cell (Olsnes, S. & Phil, A. in Molecular action of toxins and viruses (eds. Cohen, P. & vanHeyningen, S.) (Elsevier Biomedical Press, Amsterdam, 1982). The ricin toxin is a glycosylated heterodimer consisting of A and B chains with molecular masses of 30,625 Da and 31,431 Da linked by a disulphide bond. The A chain of ricin has an N-glycosidase activity and catalyzes the excision of a specific adenine residue from the 28S rRNA of eukaryotic ribosomes (Endo, Y. & Tsurugi, K. J., *Biol. Chem.* 262:8128 (1987)). The B chain of ricin, although not toxic in itself, promotes the toxicity of the A chain by binding to galactose residues on the surface of eukaryotic cells and stimulating receptor-mediated endocytosis of the toxin molecule (Simmons et al., Biol. Chem. 261:7912 (1986)). Once the toxin molecule consisting of the A and B chains is internalized into the cell via clathrin-dependent or independent mechanisms, the greater reduction potential within the cell induces a release of the active A chain, eliciting its inhibitory effect on protein synthesis and its cytotoxicity (Emmanuel, F. et al., Anal. *Biochem.* 173: 134-141 (1988); Blum, J. S. et al., *J. Biol. Chem.* 266: 22091-22095 (1991); Fiani, M. L. et al., *Arch. Biochem. Biophys.* 307: 225-230 (1993)). Empirical evidence suggests that activated toxin (e.g. ricin, shiga toxin and others) in the endosomes is transcytosed through the trans-Golgi network to the endoplasmic reticulum by retrograde transport before the A chain is translocated into the cytoplasm to elicit its action (Sandvig, K. & van Deurs, B., *FEBS Lett.* 346: 99-102 (1994).

Protein toxins are initially produced in an inactive, precursor form. Ricin is initially produced as a single polypeptide (preproricin) with a 35 amino acid N-terminal presequence and 12 amino acid linker between the A and B chains. The pre-sequence is removed during translocation of the ricin precursor into the endoplasmic reticulum (Lord, J. M., *Eur. J. Biochem.* 146:403-409 (1985) and Lord, J. M., *Eur. J. Biochem.* 146:411-416 (1985)). The proricin is then translocated into specialized organelles called protein bodies where a plant protease cleaves the protein at a linker region between the A and B chains (Lord, J. M. et al., *FASAB Journal* 8:201-208 (1994)). The two chains, however, remain covalently attached by an interchain disulfide bond (cysteine 259 in the A chain to cysteine 4 in the B chain) and mature disulfide linked ricin is stored in protein bodies inside the plant cells. The A chain is inactive in proricin (O'Hare, M. et al., *FEBS Lett.* 273:200-204 (1990)) and it is inactive in the disulfide-linked mature ricin (Richardson, P. T. et al., *FEBS Lett.* 255:15-20 (1989)). The ribosomes of the castor bean plant are themselves susceptible to inactivation by ricin A chain; however, as there is no cell surface galactose to permit B chain recognition the A chain cannot re-enter the cell. The exact mechanism of A chain release and activation in target cell cytoplasm is not known (Lord, J. M. et al., *FASAB Journal* 8:201-208 (1994)). However, it is known that for activation to take place the disulfide bond between the A and B chains must be reduced and, hence, the linkage between subunits broken.

Diphtheria toxin is produced by *Corynebacterium diphtheriae* as a 535 amino acid polypeptide with a molecular weight of approximately 58 kD (Greenfield, L. et al., *Proc. Natl. Acad. Sci. USA* 80:6853-6857 (1983); Pastan, I. et al., *Annu. Rev. Biochem.* 61:331-354 (1992); Collier, R J. & Kandel, J., *J. Biol. Chem.* 246:1496-1503 (1971)). It is secreted as a single-chain polypeptide consisting of 2 functional domains. Similar to proricin, the N-terminal domain (A-chain) contains the cytotoxic moiety whereas the C-terminal domain (B-chain) is responsible for binding to the cells and facilitates toxin endocytosis. Conversely, the mechanism of cytotoxicity for diphtheria toxin is based on ADP-ribosylation of EF-2 thereby blocking protein synthesis and producing cell death. The 2 functional domains in diphtheria toxin are linked by an arginine-rich peptide sequence as well as a disulphide bond. Once the diphtheria toxin is internalized into the cell, the arginine-rich peptide linker is cleaved by trypsin-like enzymes and the disulphide bond (Cys 186-201) is reduced. The cytotoxic domain is subsequently translocated into the cytosol substantially as described above for ricin and elicits ribosomal inhibition and cytotoxicity.

*Pseudomonas* exotoxin is also a 66 kD single-chain toxin protein secreted by *Pseudomonas aeruginosa* with a similar mechanism of cytotoxicity to that of diphtheria toxin (Pastan, I. et al., *Annu. Rev. Biochem.* 61:331-354 (1992); Ogata, M. et al., *J. Biol. Chem.* 267:25396-25401 (1992); Vagil, M. L. et al., *Infect. Immunol.* 16:353-361 (1977)). *Pseudomonas* exotoxin consists of 3 conjoint functional domains. The first domain Ia (amino acids 1-252) is responsible for cell binding and toxin endocytosis, a second domain II (amino acids 253-364) is responsible for toxin translocation from the endocytic vesicle to the cytosol, and a third domain III (amino acids 400-613) is responsible for protein synthesis inhibition and cytotoxicity. After *Pseudomonas* exotoxin enters the cell, the liberation of the cytotoxic domain is effected by both proteolytic cleavage of a polypeptide sequence in the second domain (near Arg 279) and the reduction of the disulphide bond (Cys 265-287) in the endocytic vesicles. In essence, the overall pathway to cytotoxicity is analogous to diphtheria toxin with the exception that the toxin translocation domain in *Pseudomonas* exotoxin is structurally distinct.

Other toxins possessing distinct functional domains for cytotoxicity and cell binding/toxin translocation include abrin, modeccin and volkensin (Sandvig, K. et al., *Biochem. Soc. Trans*. 21:707-711 (1993)). Some toxins such as Shiga toxin and cholera toxin also have multiple polypeptide chains responsible for receptor binding and endocytosis.

The ricin gene has been cloned and sequenced, and the X-ray crystal structures of the A and B chains have been described (Rutenber, E. et al. *Proteins* 10:240-250 (1991); Weston et al., *Mol. Bio*. 244:410-422, 1994; Lamb and Lord, *Eur. J. Biochem*. 14:265 (1985); Halling, K. et al. *Nucleic Acids Res*. 13:8019 (1985)). Similarly, the genes for diptheria toxin and *Pseudomonas* exotoxin have been cloned and sequenced, and the 3-dimensional structures of the toxin proteins have been elucidated and described (Columblatti, M. et al., *J. Biol. Chem*. 261:3030-3035 (1986); Allured, V. S. et al., *Proc. Natl. Acad. Sci. USA* 83:1320-1324 (1986); Gray, G. L. et al., *Proc. Natl. Acad. Sci. USA* 81:2645-2649 (1984); Greenfield, L. et al., *Proc. Natl. Acad. Sci. USA* 80:6853-6857 (1983); Collier, R J. et al., *J. Biol. Chem*. 257:5283-5285 (1982)).

The potential of bacterial and plant toxins for inhibiting mammalian retroviruses, particularly acquired immunodeficiency syndrome (AIDS), has been investigated. Bacterial toxins such as *Pseudomonas* exotoxin-A and subunit A of diphtheria toxin; dual chain ribosomal inhibitory plant toxins such as ricin, and single chain ribosomal inhibitory proteins such as trichosanthin and pokeweed antiviral protein have been used for the elimination of HIV infected cells (Olson et al., *AIDS Res. and Human Retroviruses* 7:1025-1030 (1991)). The high toxicity of these toxins for mammalian cells, combined with a lack of specificity of action poses a major problem to the development of pharmaceuticals incorporating the toxins, such as immunotoxins.

Due to their extreme toxicity there has been much interest in making ricin-based immunotoxins as therapeutic agents for specifically destroying or inhibiting infected or tumourous cells or tissues (Vitetta et al., *Science* 238:1098-1104 (1987)). An immunotoxin is a conjugate of a specific cell binding component, such as a monoclonal antibody or growth factor and the toxin in which the two protein components are covalently linked. Generally, the components are chemically coupled. However, the linkage may also be a peptide or disulfide bond. The antibody directs the toxin to cell types presenting a specific antigen thereby providing a specificity of action not possible with the natural toxin. Immunotoxins have been made both with the entire ricin molecule (i.e. both chains) and with the ricin A chain alone (Spooner et al., *Mol. Immunol*. 31:117-125, (1994)).

Immunotoxins made with the ricin dimer (IT-Rs) are more potent toxins than those made with only the A chain (IT-As). The increased toxicity of IT-Rs is thought to be attributed to the dual role of the B chains in binding to the cell surface and in translocating the A chain to the cytosolic compartment of the target cell (Vitetta et al., *Science* 238:1098-1104 (1987); Vitetta & Thorpe, *Seminars in Cell Biology* 2:47-58 (1991)). However, the presence of the B chain in these conjugates also promotes the entry of the immunotoxin into nontarget cells. Even small amounts of B chain may override the specificity of the cell-binding component as the B chain will bind nonspecifically to galactose associated with N-linked carbohydrates, which is present on most cells. IT-As are more specific and safer to use than IT-Rs. However, in the absence of the B chain the A chain has greatly reduced toxicity. Due to the reduced potency of IT-As as compared to IT-Rs, large doses of IT-As must be administered to patients. The large doses frequently cause immune responses and production of neutralizing antibodies in patients (Vitetta et al., *Science* 238:1098-1104 (1987)). IT-As and IT-Rs both suffer from reduced toxicity as the A chain is not released from the conjugate into the target cell cytoplasm.

A number of immunotoxins have been designed to recognize antigens on the surfaces of tumour cells and cells of the immune system (Pastan et al., *Annals New York Academy of Sciences* 758:345-353 (1995)). A major problem with the use of such immunotoxins is that the antibody component is its only targeting mechanism and the target antigen is often found on non-target cells (Vitetta et al., *Immunology Today* 14:252-259 (1993)). Also, the preparation of a suitable specific cell binding component may be problematic. For example, antigens specific for the target cell may not be available and many potential target cells and infective organisms can alter their antigenic make up rapidly to avoid immune recognition. In view of the extreme toxicity of proteins such as ricin, the lack of specificity of the immunotoxins may severely limit their usefulness as therapeutics for the treatment of cancer and infectious diseases.

The insertion of intramolecular protease cleavage sites between the cytotoxic and cell-binding components of a toxin can mimic the way that the natural toxin is activated. European patent application no. 466,222 describes the use of maize-derived pro-proteins which can be converted into active form by cleavage with extracellular blood enzymes such as factor Xa, thrombin or collagenase. Garred, O. et al. (*J. Biol. Chem*. 270:10817-10821 (1995)) documented the use of a ubiquitous calcium-dependent serine protease, furin, to activate shiga toxin by cleavage of the trypsin-sensitive linkage between the cytotoxic A-chain and the pentamer of cell-binding B-units. Westby et al. (*Bioconjugate Chem*. 3:375-381 (1992)) documented fusion proteins which have a specific cell binding component and proricin with a protease sensitive cleavage site specific for factor Xa within the linker sequence. O'Hare et al. (*FEBS Lett*. 273:200-204 (1990)) also described a recombinant fusion protein of RTA and staphylococcal protein A joined by a trypsin-sensitive cleavage site. In view of the ubiquitous nature of the extracellular proteases utilized in these approaches, such artificial activation of the toxin precursor or immunotoxin does not confer a mechanism for intracellular toxin activation and the problems of target specificity and adverse immunological reactions to the cell-binding component of the immunotoxin remain.

In a variation of the approach of insertion of intramolecular protease cleavage sites on proteins which combine a binding chain and a toxic chain, Leppla, S. H. et al. (Bacterial Protein Toxins zbl.bakt.suppl. 24:431-442 (1994)) suggest the replacement of the native cleavage site of the protective antigen (PA) produced by *Bacillus anthracis* with a cleavage site that is recognized by cells that contain a particular protease. PA, recognizes, binds, and thereby assists in the internalization of lethal factor (LF) and edema toxin (ET). also produced by *Bacillus anthracis*. However, this approach is wholly dependent on the availability of LF, or ET and PA all being localized to cells wherein the modified PA can be activated by the specific protease. It does not confer a mechanism for intracellular toxin activation and presents a problem of ensuring sufficient quantities of toxin for internalization in target cells.

The in vitro activation of a *Staphylococcus*-derived pore-forming toxin, α-hemolysin by extracellular tumour-associated proteases has been documented (Panchel, R. G. et al., *Nature Biotechnology* 14:852-857 (1996)). Artificial activation of α-hemolysin in vitro by said proteases was reported but the actual activity and utility of α-hemolysin in the destruction of target cells were not demonstrated.

Hemolysin does not inhibit protein synthesis but is a heptameric transmembrane pore which acts as a channel to allow leakage of molecules up to 3 kD thereby disrupting the ionic balances of the living cell. The α-hemolysin activation domain is likely located on the outside of the target cell (for activation by extracellular proteases). The triggering mechanism in the disclosed hemolysin precursor does not involve the intracellular proteolytic cleavage of 2 functionally distinct domains. Also, the proteases used for the α-hemolysin activation are ubiquitously secreted extracellular proteases and toxin activation would not be confined to activation in the vicinity of diseased cells. Such widespread activation of the toxin does not confer target specificity and limits the usefulness of said α-hemolysin toxin as therapeutics due to systemic toxicity.

A variety of proteases specifically associated with malignancy, viral infections and parasitic infections have been identified and described. For example, cathepsin is a family of serine, cysteine or aspartic endopeptidases and exopeptidases which has been implicated to play a primary role in cancer metastasis (Schwartz, M. K., *Clin. Chim. Acta* 237: 67-78 (1995); Spiess, E. et al., *J. Histochem. Cytochem*. 42:917-929 (1994); Scarborough, P. E. et al., *Protein Sci*. 2:264-276 (1993); Sloane, B. F. et al., *Proc. Natl. Acad. Sci. USA* 83:2483-2487 (1986); Mikkelsen, T. et al., *J. Neurosurge* 83:285-290 (1995)). Matrix metalloproteinases (MMPs or matrixins) are zinc-dependent proteinases consisting of collagenases, matrilysin, stromelysins, gelatinases and macrophage elastase (Krane, S. M., *Ann. N.Y. Acad. Sci*. 732:1-10 (1994); Woessner, J. F., *Ann. N.Y. Acad. Sci*. 732:11-21 (1994); Carvalho, K. et al., *Biochem. Biophys. Res. Comm*. 191:172-179 (1993); Nakano, A. et al. *J. of Neurosurge*, 83:298-307 (1995); Peng, K-W, et al. *Human Gene Therapy*, 8:729-738 (1997); More, D. H. et al. *Gynaecologic Oncology*, 65:78-82 (1997)). These proteases are involved in pathological matrix remodeling. Under normal physiological conditions, regulation of matrixin activity is effected at the level of gene expression. Enzymatic activity is also controlled stringently by tissue inhibitors of metalloproteinases (TIMPs) (Murphy, G. et al., *Ann. N.Y. Acad. Sci*. 732:31-41 (1994)). The expression of MMP genes is reported to be activated in inflammatory disorders (e.g. rheumatoid arthritis) and malignancy.

In malaria, parasitic serine and aspartic proteases are involved in host erythrocyte invasion by the *Plasmodium* parasite and in hemoglobin catabolism by intraerythrocytic malaria (O'Dea, K. P. et al., *Mol. Biochem. Parasitol*. 72:111-119 (1995); Blackman, M. J. et al., *Mol. Biochem. Parasitol*. 62:103-114 (1993); Cooper, J. A. et al., *Mol. Biochem. Parasitol*. 56:151-160 (1992); Goldberg, D. E. et al., *J. Exp. Med*. 173:961-969 (1991)). *Schistosoma mansoni* is also a pathogenic parasite which causes schistosomiasis or bilharzia. Elastinolytic proteinases have been associated specifically with the virulence of this particular parasite (McKerrow, J. H. et al., *J. Biol. Chem*. 260:3703-3707 (1985)).

Welch, A. R. et al. (*Proc. Natl. Acad. Sci. USA* 88:10797-10800 (1991)) has described a series of viral proteases which are specifically associated with human cytomegalovirus, human herpesviruses, Epstein-Barr virus, varicella zoster virus-I. and infectious laryngotracheitis virus. These proteases possess similar substrate specificity and play an integral role in viral scaffold protein restructuring in capsid assembly and virus maturation. Other viral proteases serving similar functions have also been documented for human T-cell leukemia virus (Blaha, I. et al., *FEBS Lett*. 309:389-393 (1992); Pettit, S. C. et al., *J. Biol. Chem*. 266:14539-14547 (1991)), hepatitis viruses (Hirowatari, Y. et al., *Anal. Biochem*. 225:113-120 (1995); Hirowatari, Y. et al., *Arch. Virol*. 133:349-356 (1993); Jewell, D. A. et al., *Biochemistry* 31:7862-7869 (1992)), poliomyelitis virus (Weidner, J. R. et al., *Arch. Biochem. Biophys*. 286:402-408 (1991)), and human rhinovirus (Long, A. C. et al., *FEBS Lett*. 258:75-78 (1989)).

*Candida* yeasts are dimorphic fungi which are responsible for a majority of opportunistic infections in AIDS patients (Holmberg, K. and Myer, R., *Scand. J. Infect. Dis*. 18:179-192 (1986)). Aspartic proteinases have been associated specifically with numerous virulent strains of *Candida* including *Candida albican, Candida tropicalis*, and *Candida parapsilosis* (Abad-Zapatero, C. et al., *Protein Sci*. 5:640-652 (1996); Cutfield, S. M. et al., *Biochemistry* 35:398-410 (1995); Ruchel, R. et al, *Zentralbl. Bakteriol. Mikrobiol Hyg. I Abt. Orig. A*. 255:537-548 (1983); Remold, H. et al., *Biochim. Biophys. Acta* 167:399-406 (1968)), and the levels of these enzymes have been correlated with the lethality of the strain (Schreiber, B, et al., *Diagn. Microbiol. Infect. Dis*. 3:1-5 (1985)).

SUMMARY OF THE INVENTION

The invention relates to novel recombinant toxic proteins which are specifically toxic to diseased cells but do not depend for their specificity of action on a specific cell binding component. The recombinant proteins of the invention have an A chain of a ricin-like toxin linked to a B chain by a synthetic linker sequence which may be cleaved specifically by a protease localized in cells or tissues affected by a specific disease to liberate the toxic A chain thereby selectively inhibiting or destroying the diseased cells or tissues. The term diseased cells as used herein, includes cells affected by cancer, or infected by fungi, or viruses, including retroviruses, or parasites.

Toxin targeting using the recombinant toxic proteins of the invention takes advantage of the fact that many DNA viruses exploit host cellular transport mechanisms to escape immunological destruction. This is achieved by enhancing the retrograde translocation of host major histocompatibility complex (MHC) type I molecules from the endoplasmic reticulum into the cytoplasm (Bonifacino, J. S., *Nature* 384: 405-406 (1996); Wiertz, E. J. et al., *Nature* 384: 432-438 (1996)). The facilitation of retrograde transport in diseased cells by the virus can enhance the transcytosis and cytotoxicity of a recombinant toxic protein of the present invention thereby further reducing non-specific cytotoxicity and improving the overall safety of the product.

The recombinant toxic proteins of the present invention may be used to treat diseases including various forms of cancer such as T- and B-cell lymphoproliferative diseases, ovarian cancer, pancreatic cancer, head and neck cancer, squamous cell carcinoma, gastrointestinal cancer, breast cancer, prostate cancer, non small cell lung cancer, malaria, and diverse viral disease states associated with infection with human cytomegalovirus, hepatitis virus, herpes virus, human rhinovirus, infectious laryngotracheitis virus, poliomyelitis virus, or varicella zoster virus.

In one aspect, the present invention provides a purified and isolated nucleic acid having a nucleotide sequence encoding an A chain of a ricin-like toxin, a B chain of a ricin-like toxin and a heterologous linker amino acid sequence, linking the A and B chains. The linker sequence is not a native linker sequence of a ricin-like toxin, but rather a synthetic heterologous linker sequence containing a cleavage recognition site for a disease-specific protease. The A and or the B chain may be those of ricin.

In an embodiment, of the invention the cleavage recognition site is the cleavage recognition site for a cancer-associated protease. In particular embodiments, the linker amino acid sequence comprises SLLKSRMVPNFN (SEQ ID NO: 40) or SLLIARRMPNFN (SEQ ID NO: 90) cleaved by cathepsin B; SKLVQASASGVN (SEQ ID NO: 45) or SSYLKASDAPDN (SEQ ID NO: 46) cleaved by an Epstein-Barr virus protease; RPKPQQFFGLMN (SEQ ID NO: 41) cleaved by MMP-3 (stromelysin); SLRPLALWRSFN (SEQ ID NO: 42) cleaved by MMP-7 (matrilysin); SPQGIAGQRNFN (SEQ ID NO: 43) cleaved by MMP-9; DVDERDVRGFASFL (SEQ ID NO: 44) cleaved by a thermolysin-like MMP; SLPLGLWAPNFN (SEQ ID NO: 87) cleaved by matrix metalloproteinase 2(MMP-2); SLLIFRSWANFN (SEQ ID NO: 93) cleaved by cathespin L; SGVVIATVIVIT (SEQ ID NO: 96) cleaved by cathespin D; SLGPQGIWGQFN (SEQ ID NO: 99) cleaved by matrix metalloproteinase 1(MMP-1); KKSPGRVVGGSV (SEQ ID NO: 102) cleaved by urokinase-type plasminogen activator; PQGLLGAPGILG (SEQ ID NO: 105) cleaved by membrane type 1 matrixmetalloproteinase (MT-MMP); HGPEGLRVGFYESDVMGRGHARLVHVEEPHT (SEQ ID NO: 108) cleaved by stromelysin 3 (or MMP-11), thermolysin, fibroblast collagenase and stromelysin-1; GPQGLAGQRGIV (SEQ ID NO: 111) cleaved by matrix metalloproteinase 13 (collagenase-3); GGSGQRGRKALE (SEQ ID NO: 114) cleaved by tissue-type plasminogen activator(tPA); SLSALLSSDIFN (SEQ ID NO: 117) cleaved by human prostate-specific antigen; SLPRFKIIGGFN (SEQ ID NO: 120) cleaved by kallikrein (hK3); SLLGIAVPGNFN (SEQ ID NO: 123) cleaved by neutrophil elastase; and FFKNIVTPRTPP (SEQ ID NO: 126) cleaved by calpain (calcium activated neutral protease). The nucleic acid sequences for ricin A and B chains with each of the linker sequences are shown in FIGS. 2D, 35C, 3D, 4D, 5D, 6D, 16D, 17D, 34C, 36C, 37C, 38C, 39C, 40C, 41C, 42C, 43C, 44C, 45C, 46C and 47C, respectively.

In another embodiment, the cleavage recognition site is the cleavage recognition site for a protease associated with the malaria parasite, *Plasmodium falciparum*. In particular embodiments, the linker amino acid sequence comprises QVVQLQNYDEED (SEQ ID NO: 55); LPIFGESEDNDE (SEQ ID NO: 56); QVVTGEAISVTM (SEQ ID NO: 57); ALERTFLSFPTN (SEQ ID NO: 58) or KFQDMLNISQHQ (SEQ ID NO: 59). The nucleic nucleotide sequences for ricin A and B chains with each of the linker sequences are shown in FIGS. 7D, 8D, 9D, 10D, and 11D.

In a another embodiment, the cleavage recognition site is the cleavage recognition site for a viral protease. The linker sequences preferably comprise the sequence Y-X-Y-A-Z wherein X is valine or leucine, Y is a polar amino acid, and Z is serine, asparagine or valine. In particular embodiments, the linker amino acid sequence comprises SGVVNASCRLAN (SEQ ID NO: 63) or SSYVKASVSPEN (SEQ ID NO: 64) cleaved by a human cytomegalovirus protease; SALVNASSAHVN (SEQ ID NO: 60) or STYLQASEKFKN (SEQ ID NO: 61) cleaved by a herpes simplex 1 virus protease; SSILNASVPNFN (SEQ ID NO: 62) cleaved by a human herpes virus 6 protease; SQDVNAVEASSN (SEQ ID NO: 65) or SVYLQASTGYGN (SEQ ID NO: 66) cleaved by a varicella zoster virus protease; or SKYLQANEVITN (SEQ ID NO: 67) cleaved by an infectious laryngotracheitis virus protease. The nucleic nucleotide sequences for ricin A and B chains with each of the linker sequences are shown in FIGS. 12D, 13D, 14D, 15D, 18D, 19D, 20D, and 22D.

In another embodiment, the cleavage recognition site is the cleavage recognition site for a hepatitis A viral protease. In particular embodiments, the linker amino acid sequence comprises SELRTQSFSNWN (SEQ ID NO: 68) or SELWSQGIDDDN (SEQ ID NO: 69) cleaved by a hepatitis A virus protease. The nucleic nucleotide sequences for ricin A and B chains with each of the linker sequences are shown in FIGS. 23D or 24D.

In another embodiment, the cleavage recognition site is the cleavage recognition site for a hepatitis C viral protease. In particular embodiments, the linker amino acid sequence comprises DLEVVTSTWVFN (SEQ ID NO: 75), DEMEECASHLFN (SEQ ID NO: 78), EDVVCCSMSYFN (SEQ ID NO: 81) or KGWRLLAPITAY (SEQ ID NO: 84) cleaved by a hepatitis C virus protease. The nucleic nucleotide sequences for ricin A and B chains with each of the linker sequences are shown in FIGS. 30C, 31C, 32C and 33C.

In another embodiment, the cleavage recognition site is the cleavage recognition site for a *Candida* fungal protease. In particular embodiments, the linker amino acid sequence is SKPAKFFRLNFN (SEQ ID NO: 70), SKPIEFFRLNFN (SEQ ID NO: 71) or SKPAEFFALNFN (SEQ ID NO: 72) cleaved by *Candida* aspartic protease. The nucleic nucleotide sequences for ricin A and B chains with the first linker sequence are shown in FIGS. 25D.

The present invention also provides a plasmid incorporating the nucleic acid of the invention. In an embodiment, the plasmid has the restriction map as shown in FIG. 2A, 3A, 4A, 5A, 6A, 7A, 8A, 9A, 10A, 11A, 12A, 13A, 14A, 15A, 16A, 17A, 18A, 19A, 22A, 23A, 24A, or 25A.

In another embodiment, the present invention provides a baculovirus transfer vector incorporating the nucleic acid of the invention. In particular embodiments, the invention provides a baculovirus transfer vector having the DNA sequence as shown in FIG. 1.

In a further embodiment, the present invention provides a baculovirus transfer vector incorporating the nucleic acid of the invention. In particular embodiments, the invention provides a baculovirus transfer vector having the restriction map as shown in FIG. 2C, 3C, 4C, 5C, 6C, 7C, 8C, 9C, 10C, 11C, 12C, 13C, 14C, 15C, 16C, 17C, 18C, 19C, 20C, 21C, 22C, 23C, 24C, 25C, 30A, 31A, 32A, 33A, 34A, 35A, 36A, 37A, 38A, 39A, 40A, 41A, 42A, 43A, 44A, 45A, 46A, or 47A, or having the DNA sequence as shown in FIG. 1.

In a further aspect, the present invention provides a recombinant protein comprising an A chain of a ricin-like toxin, a B chain of a ricin-like toxin and a heterologous linker amino acid sequence, linking the A and B chains, wherein the linker sequence contains a cleavage recognition site for a disease-specific protease (e.g. a cancer, viral, parasitic, or fungal protease). The A and/or the B chain may be those of ricin. In an embodiment, the cleavage recognition site is the cleavage recognition site for a cancer, viral or parasitic protease substantially as described above. In a particular embodiment, the cancer is T-cell or B-cell lymphoproliferative disease. In another particular embodiment, the virus is human cytomegalovirus, Epstein-Barr virus, hepatitis virus, herpes virus, human rhinovirus, infectious laryngotracheitis virus, poliomyelitis virus, or varicella zoster virus. In a further particular embodiment, the parasite is *Plasmodium falciparum.*

In a further aspect, the invention provides a pharmaceutical composition for treating a fungal infection, such as *Candida*, in a mammal comprising the recombinant protein of the invention and a pharmaceutically acceptable carrier, diluent or excipient.

In yet another aspect, the invention provides a method of inhibiting or destroying cells affected by a disease, which cells are associated with a disease specific protease, including cancer or infection with a virus, fungus, or a parasite each of which has a specific protease, comprising the steps of preparing a recombinant protein of the invention having a heterologous linker sequence which contains a cleavage recognition site for the disease-specific protease and administering the recombinant protein to the cells. In an embodiment, the cancer is T-cell or B-cell lymphoproliferative disease, ovarian cancer, pancreatic cancer, head and neck cancer, squamous cell carcinoma, gastrointestinal cancer, breast cancer, prostate cancer, non small cell lung cancer. In another embodiment, the virus is human cytomegalovirus, Epstein-Barr virus, hepatitis virus, herpes virus, human rhinovirus, human T-cell leukemia virus, infectious laryngotracheitis virus, poliomyelitis virus, or varicella zoster virus. In another embodiment, the parasite is *Plasmodium falciparum.*

The present invention also relates to a method of treating a mammal with disease wherein cells affected by the disease are associated with a disease specific protease, including cancer or infection with a virus, fungus, or a parasite each of which has a specific protease by administering an effective amount of one or more recombinant proteins of the invention to said mammal.

Still further, a process is provided for preparing a pharmaceutical for treating a mammal with disease wherein cells affected by the disease are associated with a disease specific protease, including cancer or infection with a virus, fungus, or a parasite each of which has a specific protease comprising the steps of preparing a purified and isolated nucleic acid having a nucleotide sequence encoding an A chain of a ricin-like toxin, a B chain of a ricin-like toxin and a heterologous linker amino acid sequence, linking the A and B chains, wherein the linker sequence contains a cleavage recognition site for the disease-specific protease; introducing the nucleic acid into a host cell; expressing the nucleic acid in the host cell to obtain a recombinant protein comprising an A chain of a ricin-like toxin, a B chain of a ricin-like toxin and a heterologous linker amino acid sequence, linking the A and B chains wherein the linker sequence contains the cleavage recognition site for the disease-specific protease; and suspending the protein in a pharmaceutically acceptable carrier, diluent or excipient.

In an embodiment, a process is provided for preparing a pharmaceutical for treating a mammal with disease wherein cells affected by the disease are associated with a disease specific protease, including cancer or infection with a virus, fungus, or a parasite each of which has a specific protease comprising the steps of identifying a cleavage recognition site for the protease; preparing a recombinant protein comprising an A chain of a ricin-like toxin, a B chain of a ricin-like toxin and a heterologous linker amino acid sequence, linking the A and B chains wherein the linker sequence contains the cleavage recognition site for the protease and suspending the protein in a pharmaceutically acceptable carrier, diluent or excipient.

In a further aspect, the invention provides a pharmaceutical composition for treating for treating a mammal with disease wherein cells affected by the disease are associated with a disease specific protease, including cancer or infection with a virus, fungus, or a parasite comprising the recombinant protein of the invention and a pharmaceutically acceptable carrier, diluent or excipient.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 1 shows the DNA sequence of the baculovirus transfer vector, pVL1393 (SEQ ID NO: 1);

FIG. 2D shows the DNA sequence of the pAP-214 insert containing ricin and the Cathepsin B linker (SEQ ID NO: 3);

FIG. 3D shows the DNA sequence of the pAP-216 insert containing ricin and the MMP-3 linker (SEQ ID NO: 5);

FIG. 4D shows the DNA sequence of the pAP-218 insert containing ricin and the MMP-7 linker (SEQ ID NO: 7);

FIG. 5B shows the nucleotide sequence of the MMP-9 linker regions of pAP-219 (SEQ ID NO: 8);

FIG. 5D shows the DNA sequence of the pAP-220 insert containing ricin and the MMP-9 linker (SEQ ID NO: 9);

FIG. 6D shows the DNA sequence of the pAP-222 insert containing ricin and the thermolysin-like MMP linker (SEQ ID NO: 11);

FIG. 7B shows the nucleotide sequence of the *Plasmodium falciparum*-A linker regions of pAP-223 (SEQ ID NO: 12);

FIG. 7D shows the DNA sequence of the pAP-224 insert containing ricin and the *Plasmodium falciparum*-A linker (SEQ ID NO: 13);

FIG. 8D shows the DNA sequence of the pAP-226 insert containing ricin and the *Plasmodium falciparum*-B linker (SEQ ID NO: 15);

FIG. 9D shows the DNA sequence of the pAP-228 insert containing ricin and the *Plasmodium falciparum*-C linker (SEQ ID NO: 17);

FIG. 10B shows the nucleotide sequence of the *Plasmodium falciparum*-D linker regions of pAP-229 (SEQ ID NO: 18);

FIG. 10D shows the DNA sequence of the pAP-230 insert containing ricin and the *Plasmodium falciparum*-D linker (SEQ ID NO: 19);

FIG. 11D shows the DNA sequence of the pAP-232 insert containing ricin and the *Plasmodium falciparum*-E linker (SEQ ID NO: 21);

FIG. 12B shows the nucleotide sequence of the HSV-A linker regions of pAP-233 (SEQ ID NO: 22);

FIG. 12D shows the DNA sequence of the pAP-234 insert containing ricin and the HSV-A linker (SEQ ID NO: 23);

FIG. 13D shows the DNA sequence of the pAP-236 insert containing ricin and the HSV-B linker (SEQ ID NO: 25);

FIG. 14D shows the DNA sequence of the pAP-238 insert containing ricin and the VZV-A linker (SEQ ID NO: 27);

FIG. 15B shows the nucleotide sequence of the VZV-B linker regions of pAP-239 (SEQ ID NO: 28);

FIG. 15D shows the DNA sequence of the pAP-240 insert containing ricin and the VZV-B linker (SEQ ID NO: 29);

FIG. 16B shows the nucleotide sequence of the EBV-A linker regions of pAP-241 (SEQ ID NO: 30);

FIG. 16D shows the DNA sequence of the pAP-242 insert containing ricin and the EBV-A linker (SEQ ID NO: 31);

FIG. 17B shows the nucleotide sequence of the EBV-B linker regions of pAP-243 (SEQ ID NO: 32);

FIG. 17D shows the DNA sequence of the pAP-244 insert containing ricin and the EBV-B linker (SEQ ID NO: 33);

FIG. 18D shows the DNA sequence of the pAP-246 insert containing ricin and the CMV-A linker (SEQ ID NO: 35);

FIG. 19B shows the nucleotide sequence of the CMV-B linker regions of pAP-247 (SEQ ID NO: 36);

FIG. 19D shows the DNA sequence of the pAP-248 insert containing ricin and the CMV-B linker (SEQ ID NO: 37);

FIG. 20D shows the DNA sequence of the pAP-250 insert containing ricin and the HHV-6 linker (SEQ ID NO: 39);

FIG. 21 shows the amino acid sequences of the wild type ricin linker and cancer protease-sensitive amino acid linkers contained in pAP-213 to pAP-222 and linkers pAP-241 to pAP-244 (SEQ ID NOS: 127 & 40-46);

FIG. 22B shows the nucleotide sequence of the ILV linker regions of pAP-253 (SEQ ID NO: 47);

FIG. 22D shows the DNA sequence of the pAP-254 insert containing ricin and the ILV linker (SEQ ID NO: 48);

FIG. 23D shows the DNA sequence of the pAP-258 insert containing ricin and the HAV-A linker (SEQ ID NO: 50);

FIG. 24D shows the DNA sequence of the pAP-256 insert containing ricin and the HAV-B linker (SEQ ID NO: 52);

FIG. 25D shows the DNA sequence of the pAP-260 insert containing ricin and the CAN linker (SEQ ID NO: 54);

FIG. 26 shows the amino acid sequences of the wild type ricin linker and *Plasmodium falciparum* protease-sensitive amino acid linkers contained in linkers pAP-223 to pAP-232 (SEQ ID NOS: 127 & 55-59);

FIG. 27 shows the amino acid sequences of the wild type ricin linker and the viral protease-sensitive amino acid linkers contained in pAP-233 to pAP-240, pAP-245-pAP-248, pAP-253 to pAP-258 (SEQ ID NOS: 127, 63-64, 60-62, 65-69);

FIG. 28 shows the amino acid sequences of the wild type ricin linker and the *Candida* aspartic protease-sensitive amino acid linker contained in pAP-259 to pAP-264 (SEQ ID NOS: 127, 70-72);

FIG. 30B shows the nucleotide sequence of the HCV-A linker region of pAP-262 (SEQ ID NO: 73);

FIG. 30C shows the DNA sequence of the pAP-262 insert (SEQ ID NO: 74);

FIG. 30D shows the amino acid sequence comparison of mutant preproricin linker region HCV-A to wild type (SEQ ID NOS: 127, 75);

FIG. 31B shows the nucleotide sequence of the HCV-B linker region of pAP-264 (SEQ ID NO: 76);

FIG. 31C shows the DNA sequence of the pAP-264 insert (SEQ ID NO: 77);

FIG. 31D shows the amino acid sequence comparison of mutant preproricin linker region HCV-B to wild type (SEQ ID NOS: 127, 78);

FIG. 32B shows the nucleotide sequence of the HCV-C linker region of pAP-266 (SEQ ID NO: 79);

FIG. 32C shows the DNA sequence of the pAP-266 insert (SEQ ID NO: 80);

FIG. 32D shows the amino acid sequence comparison of mutant preproricin linker region HCV-C to wild type (SEQ ID NOS: 127, 81);

FIG. 33B shows the nucleotide sequence of the HCV-D linker region of pAP-268 (SEQ ID NO: 82);

FIG. 33C shows the DNA sequence of the pAP-268 insert (SEQ ID NO: 83);

FIG. 33D shows the amino acid sequence comparison of mutant preproricin linker region HCV-D to wild type (SEQ ID NOS: 127, 84);

FIG. 34B shows the nucleotide sequence of the MMP-2 linker region of pAP-270 (SEQ ID NO: 85);

FIG. 34C shows the DNA sequence of the pAP-270 insert (SEQ ID NO: 86);

FIG. 34D shows the amino acid sequence comparison of mutant preproricin linker region of MMP-2 to wild type (SEQ ID NOS: 127, 87);

FIG. 35B shows the nucleotide sequence of the Cathepsin B (Site 2) linker region of pAP-272 (SEQ ID NO: 88);

FIG. 35C shows the DNA sequence of the pAP-272 insert (SEQ ID NO: 89);

FIG. 35D shows the amino acid sequence comparison of mutant preproricin linker region of Cathepsin B (Site 2) to wild type (SEQ ID NO: 90);

Figure 36A:
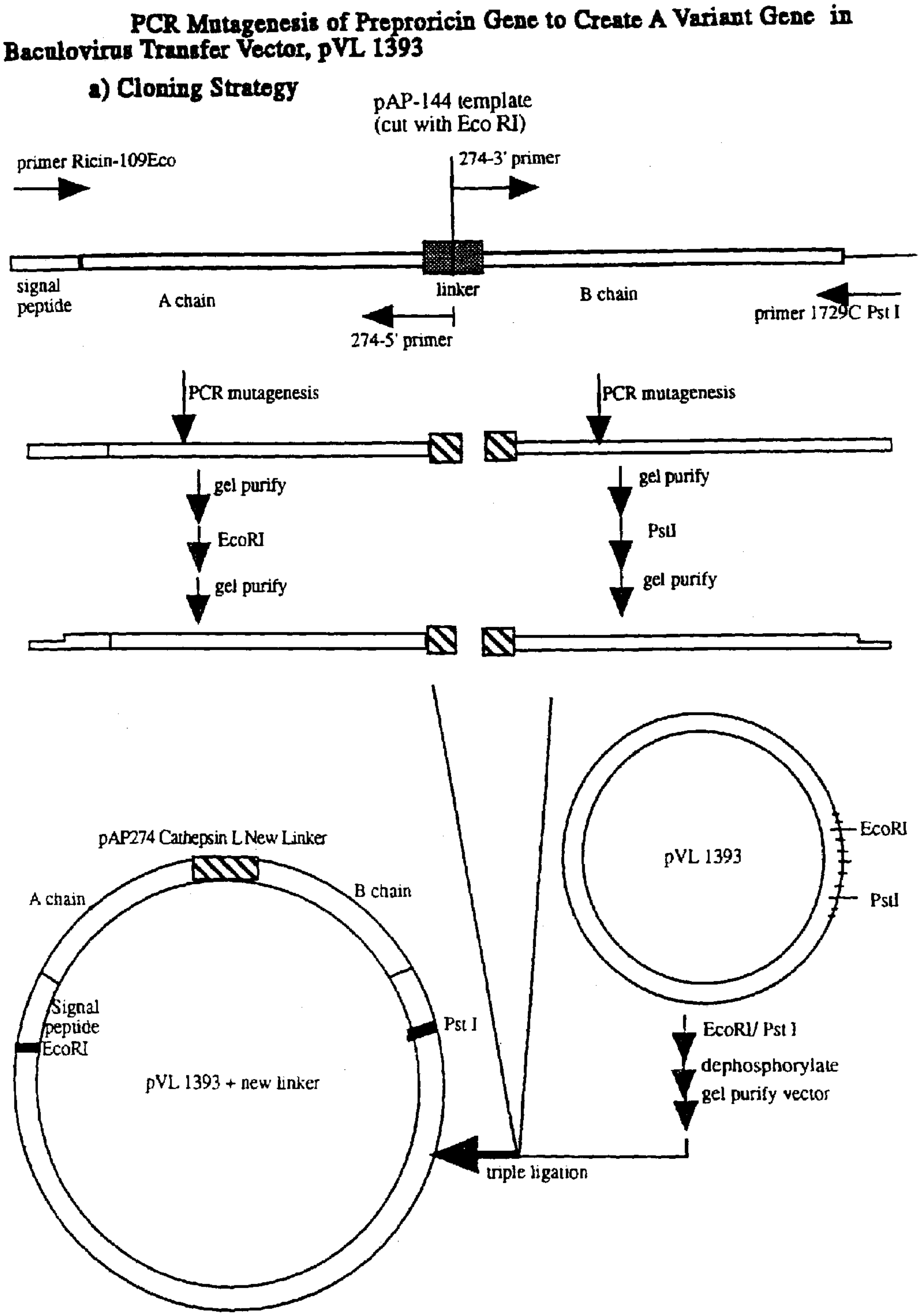
Figure 37A:
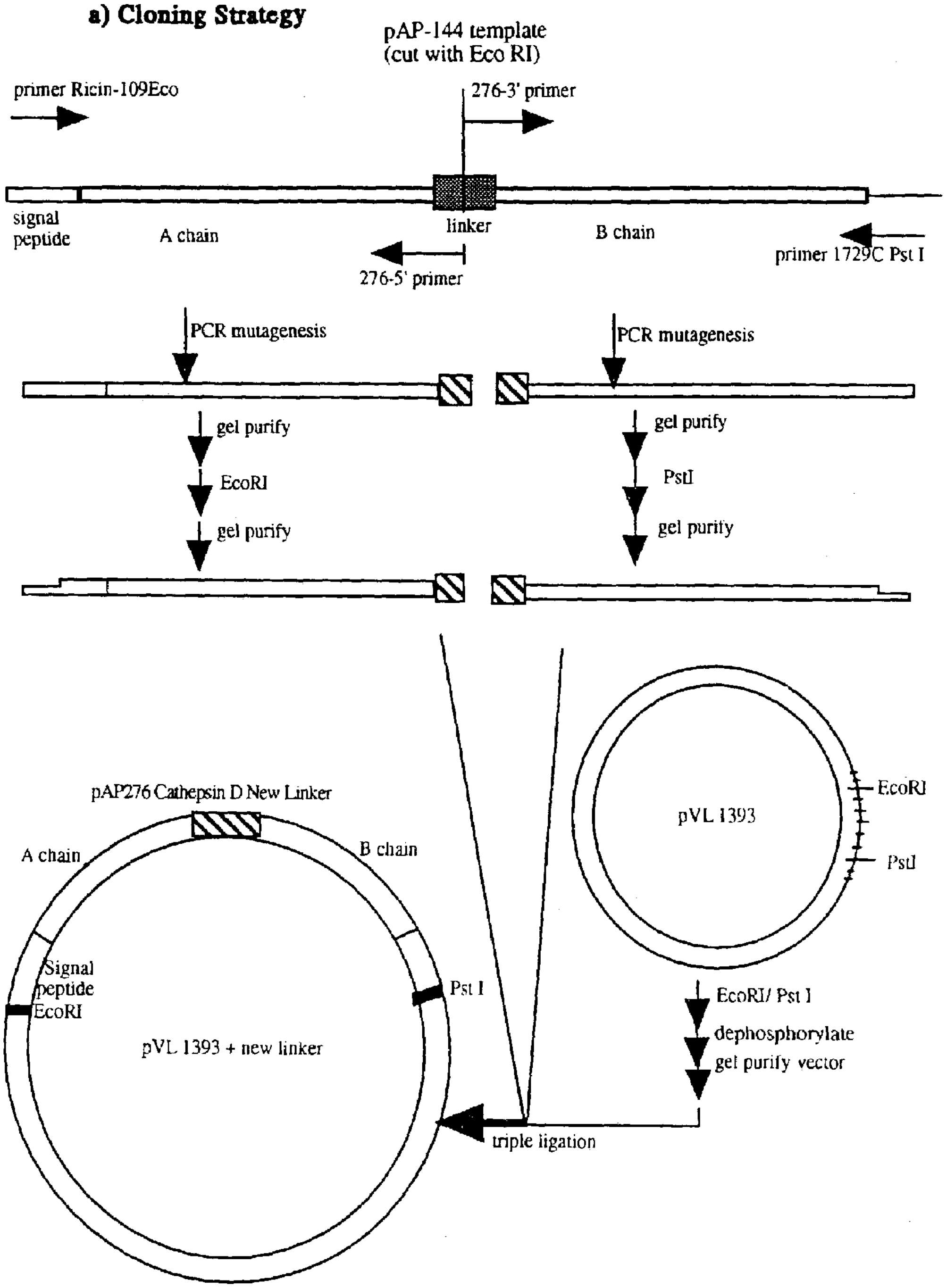
Figure 38A:
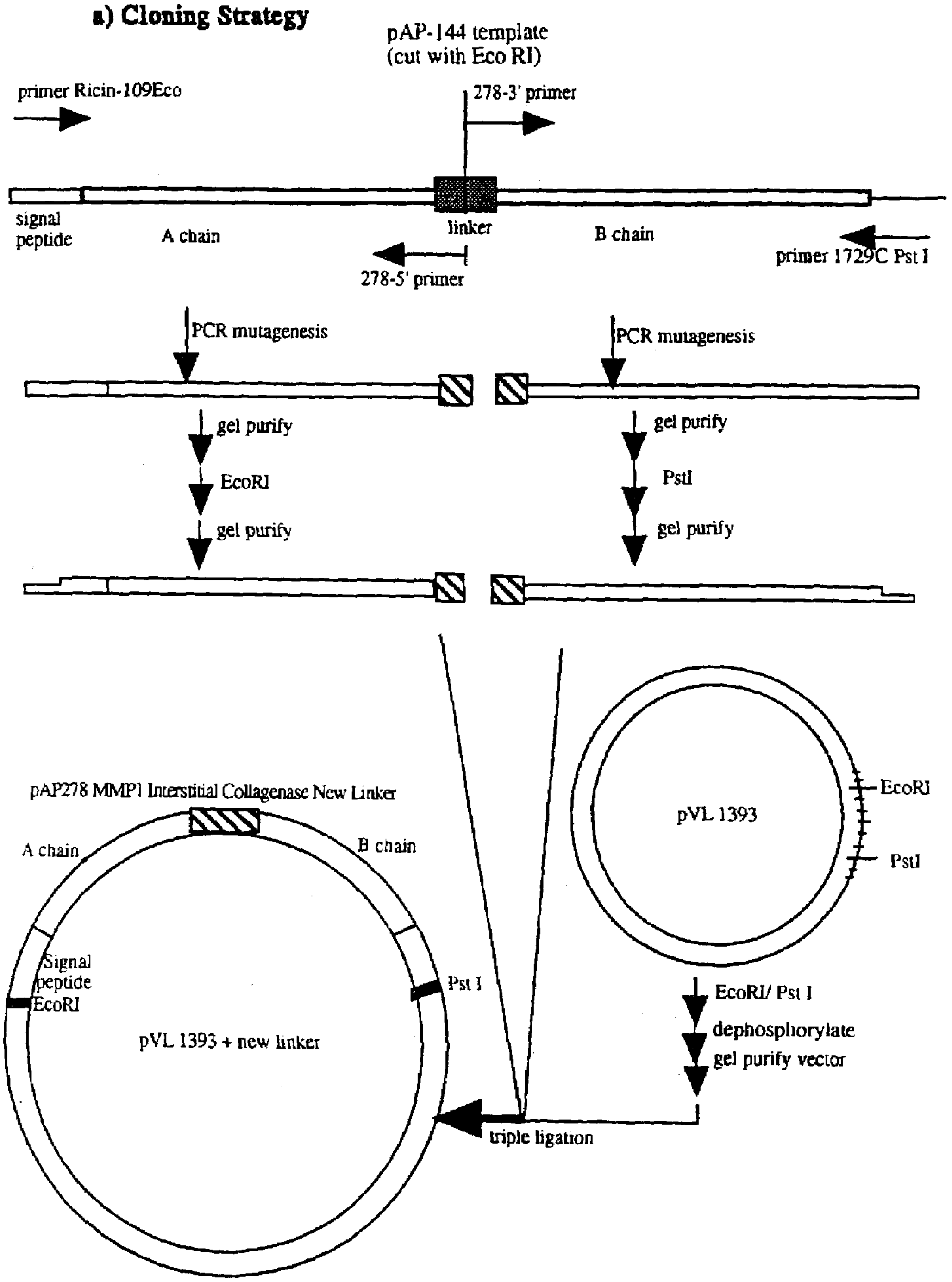
Figure 39A:
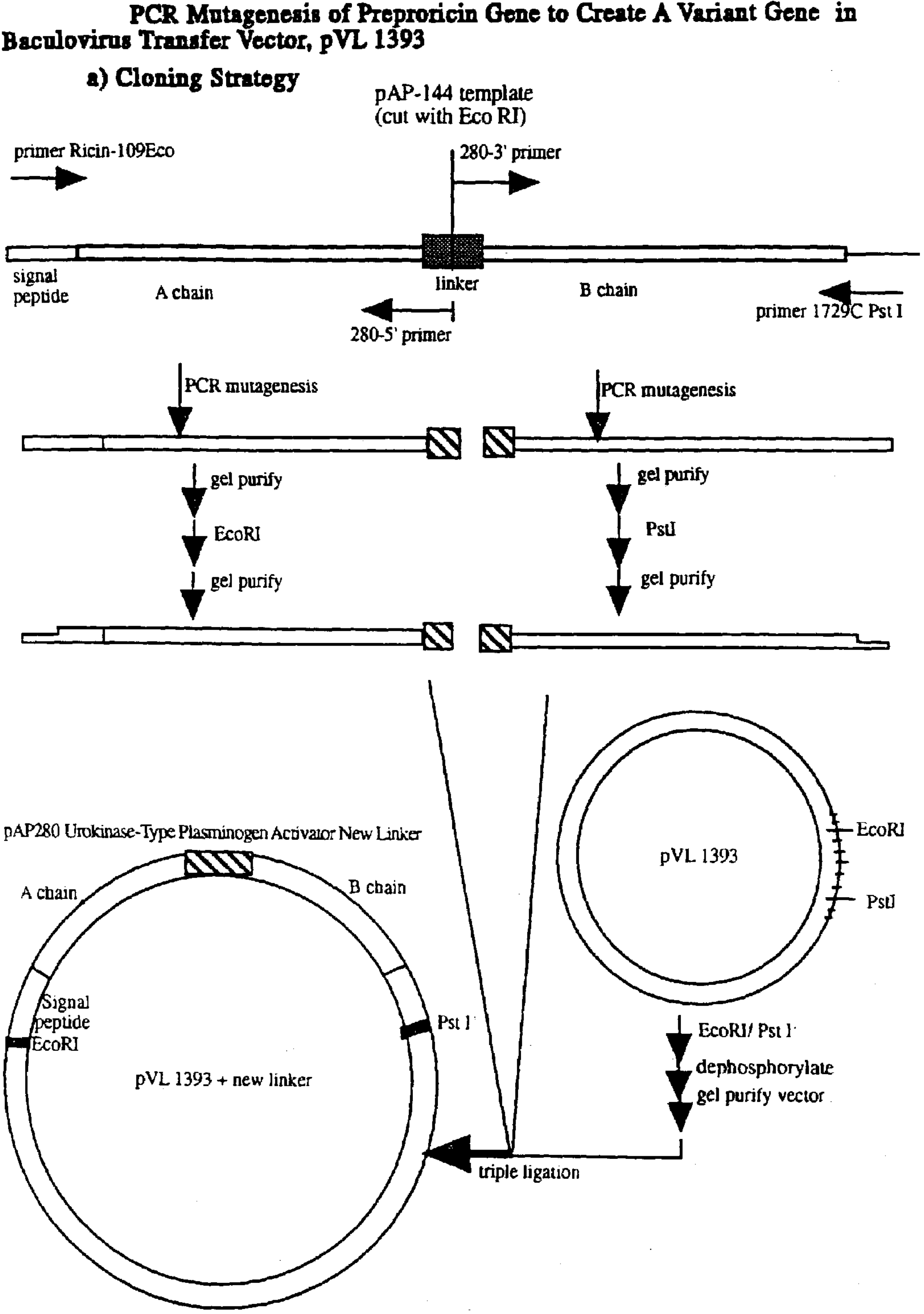
Figure 40A:
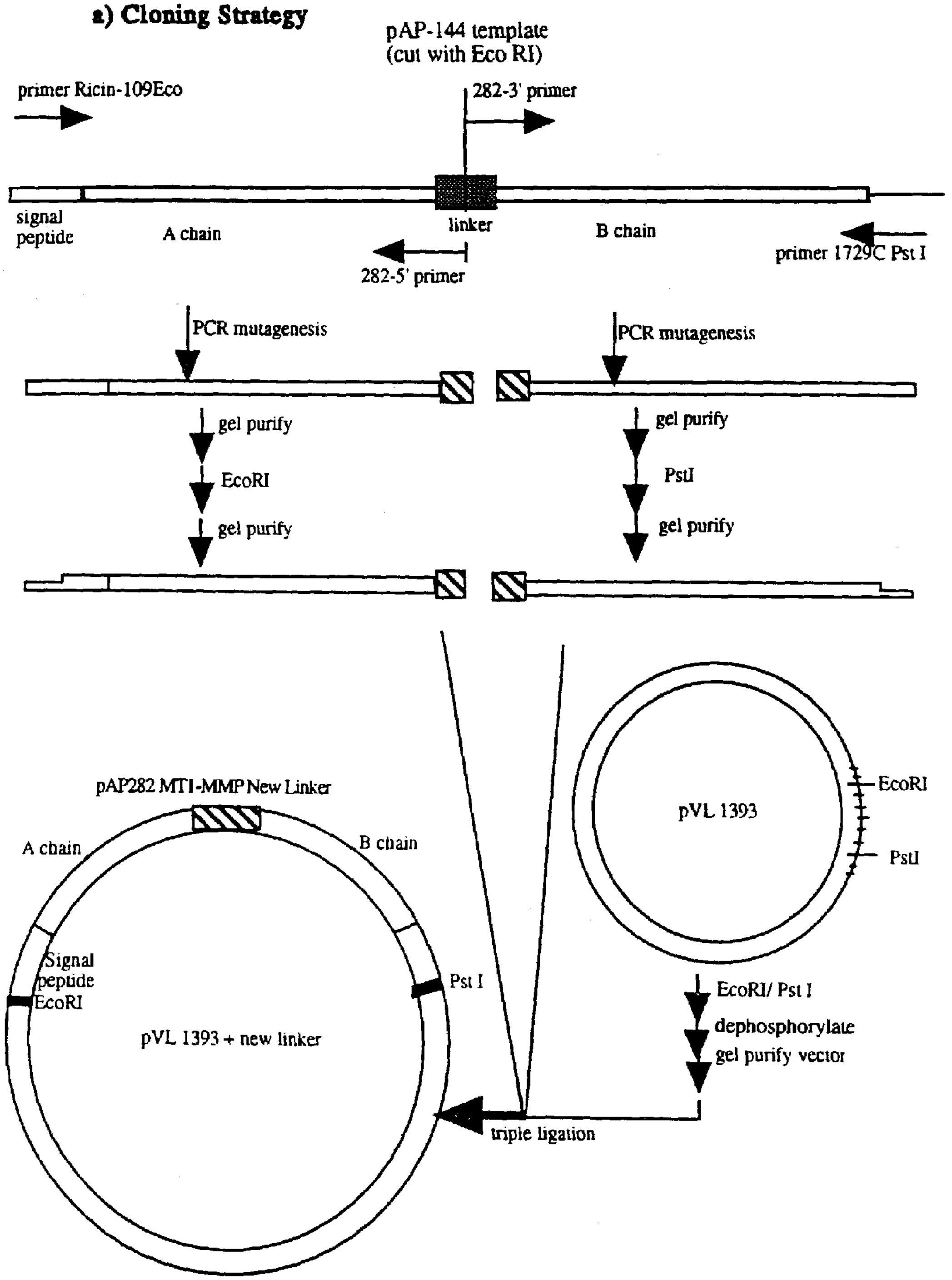
Figure 41A:
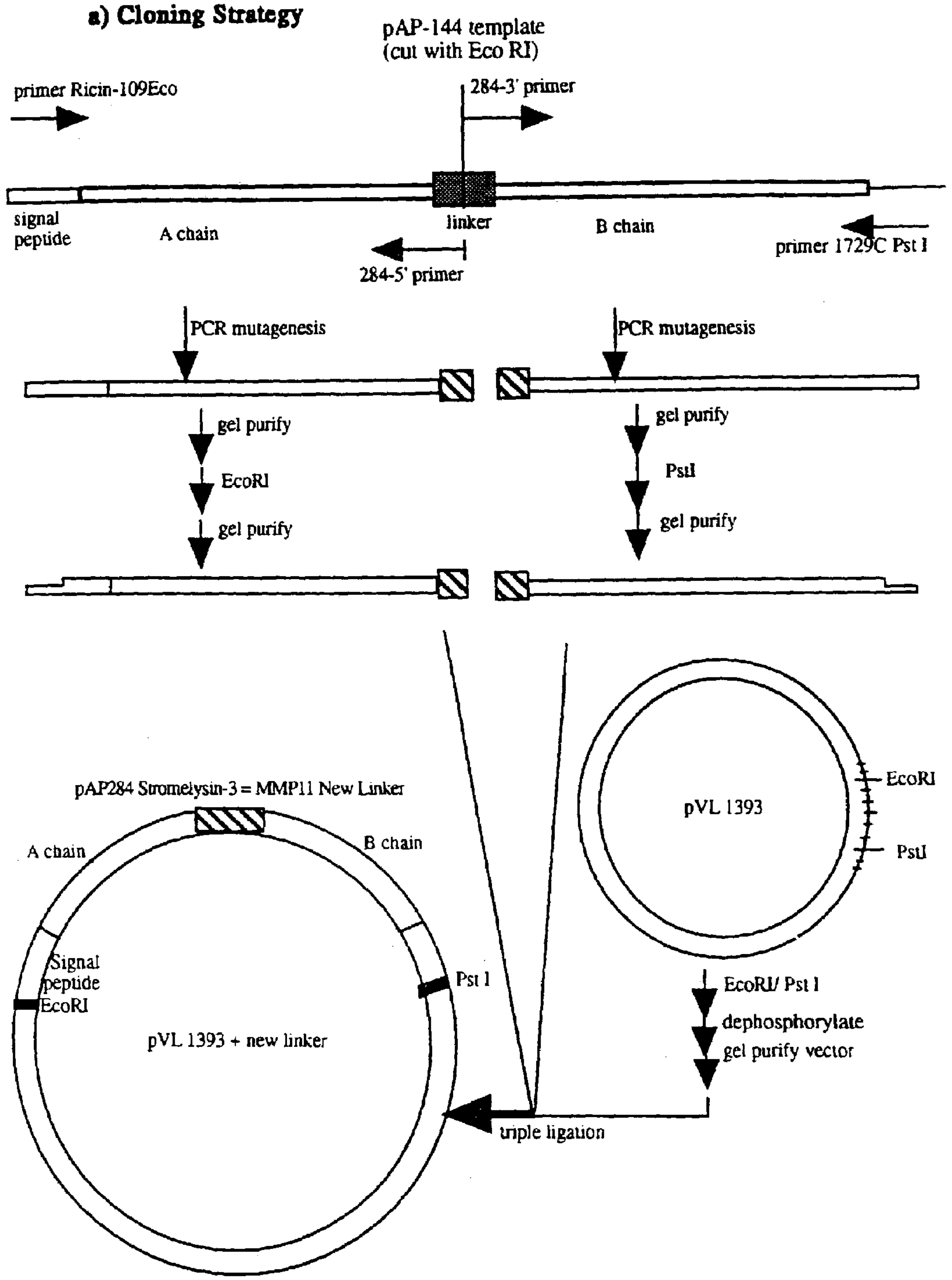
Figure 42A:
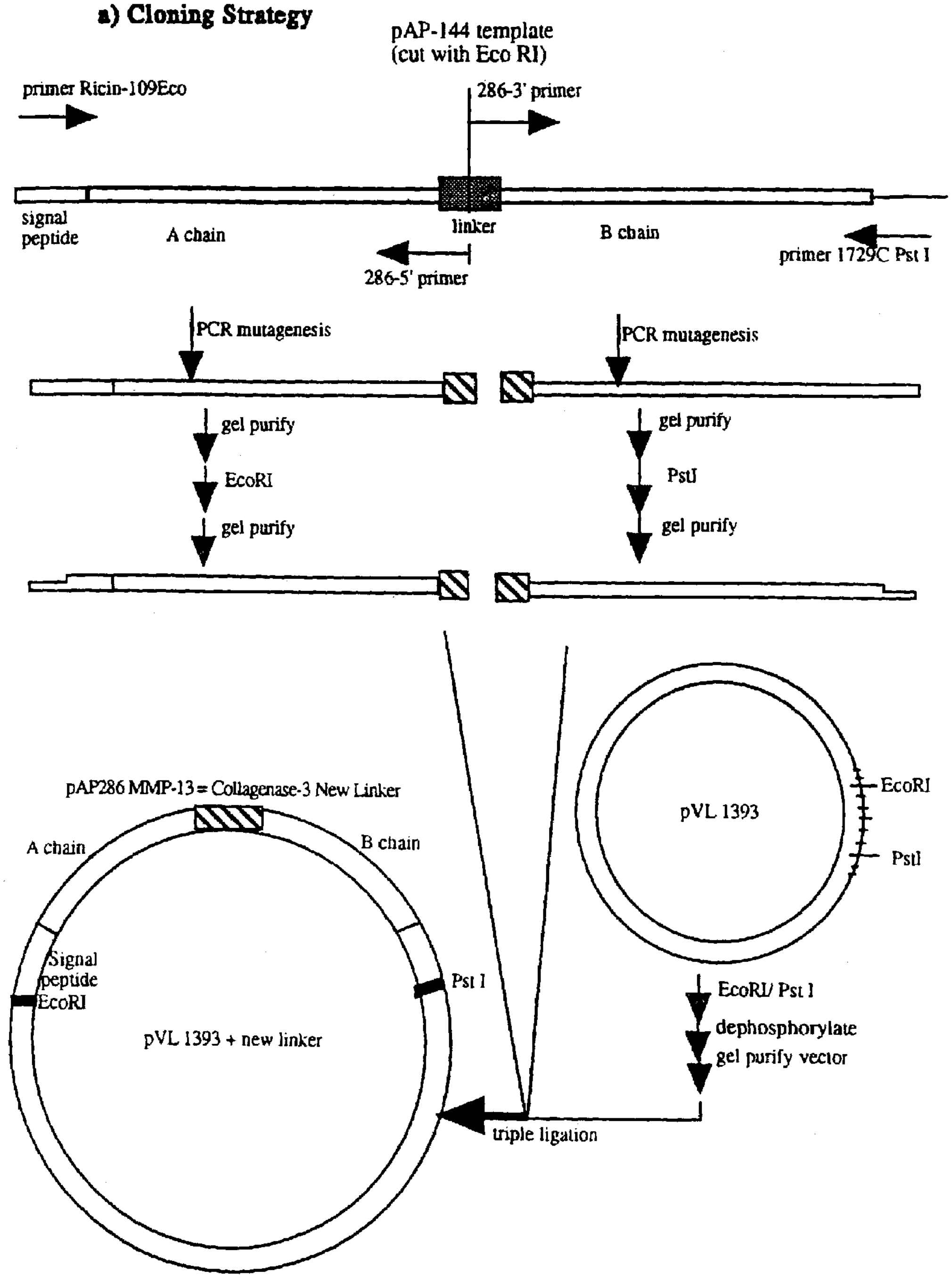
Figure 43A:
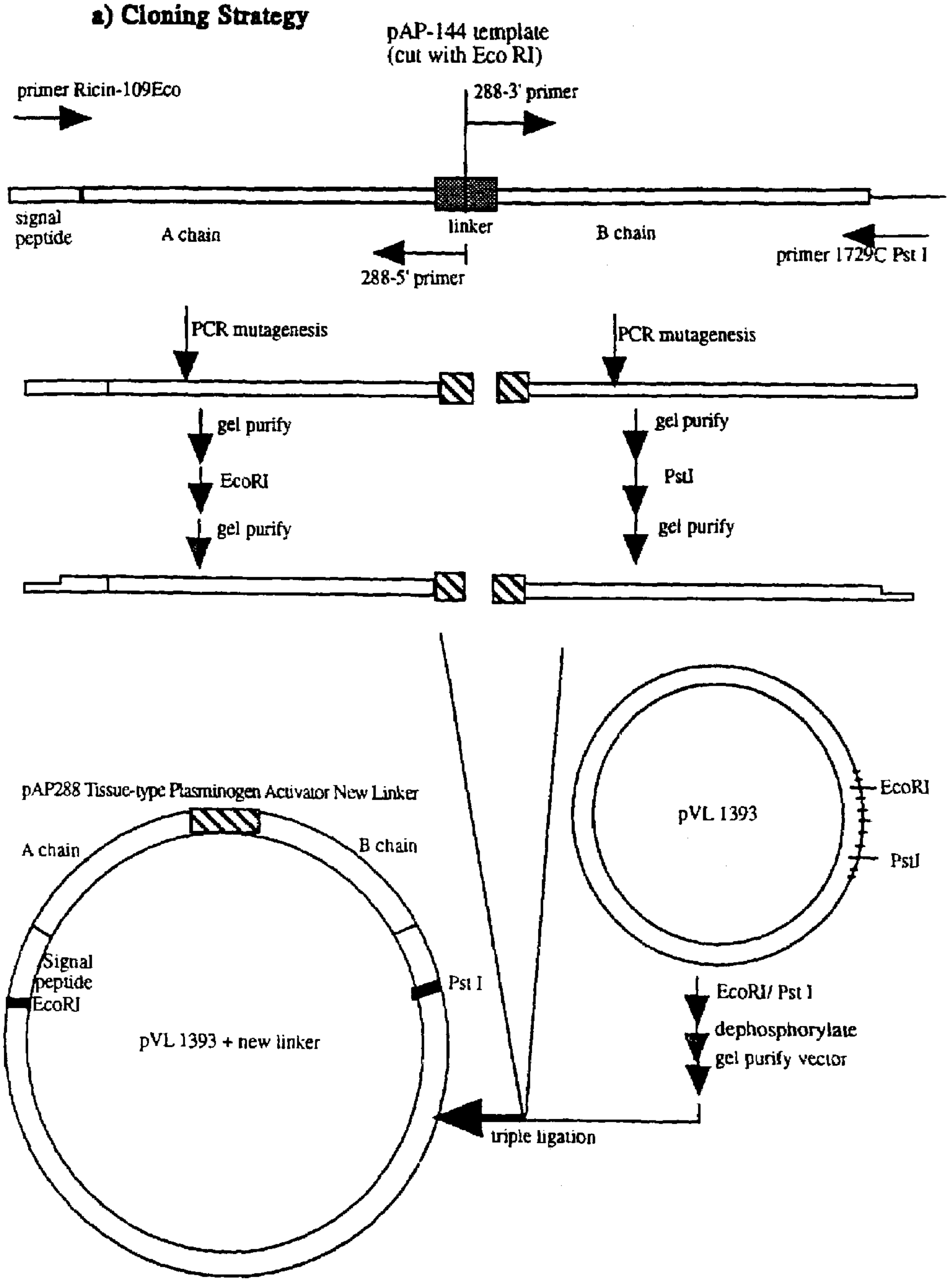
Figure 44A:
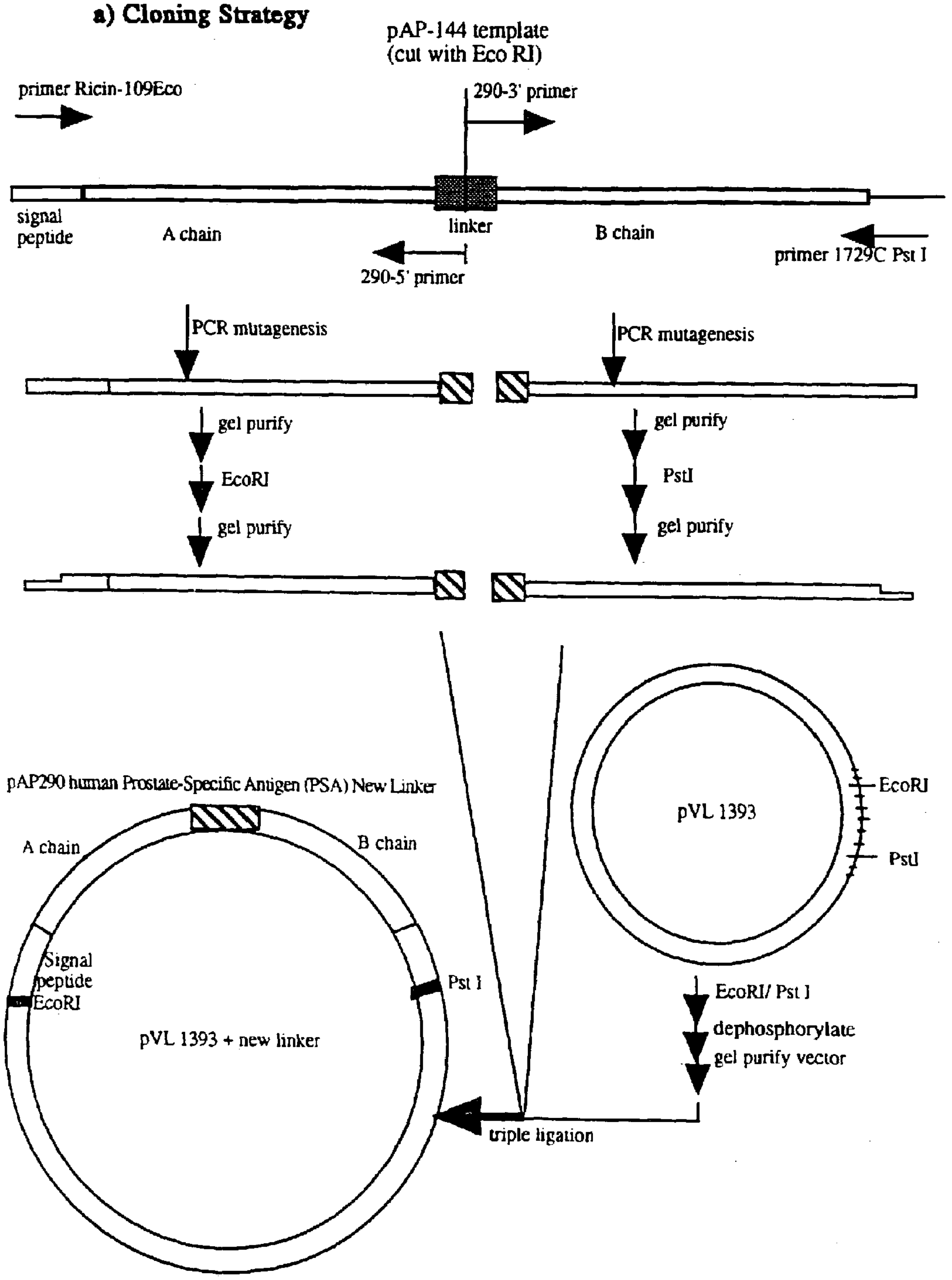
Figure 45A:
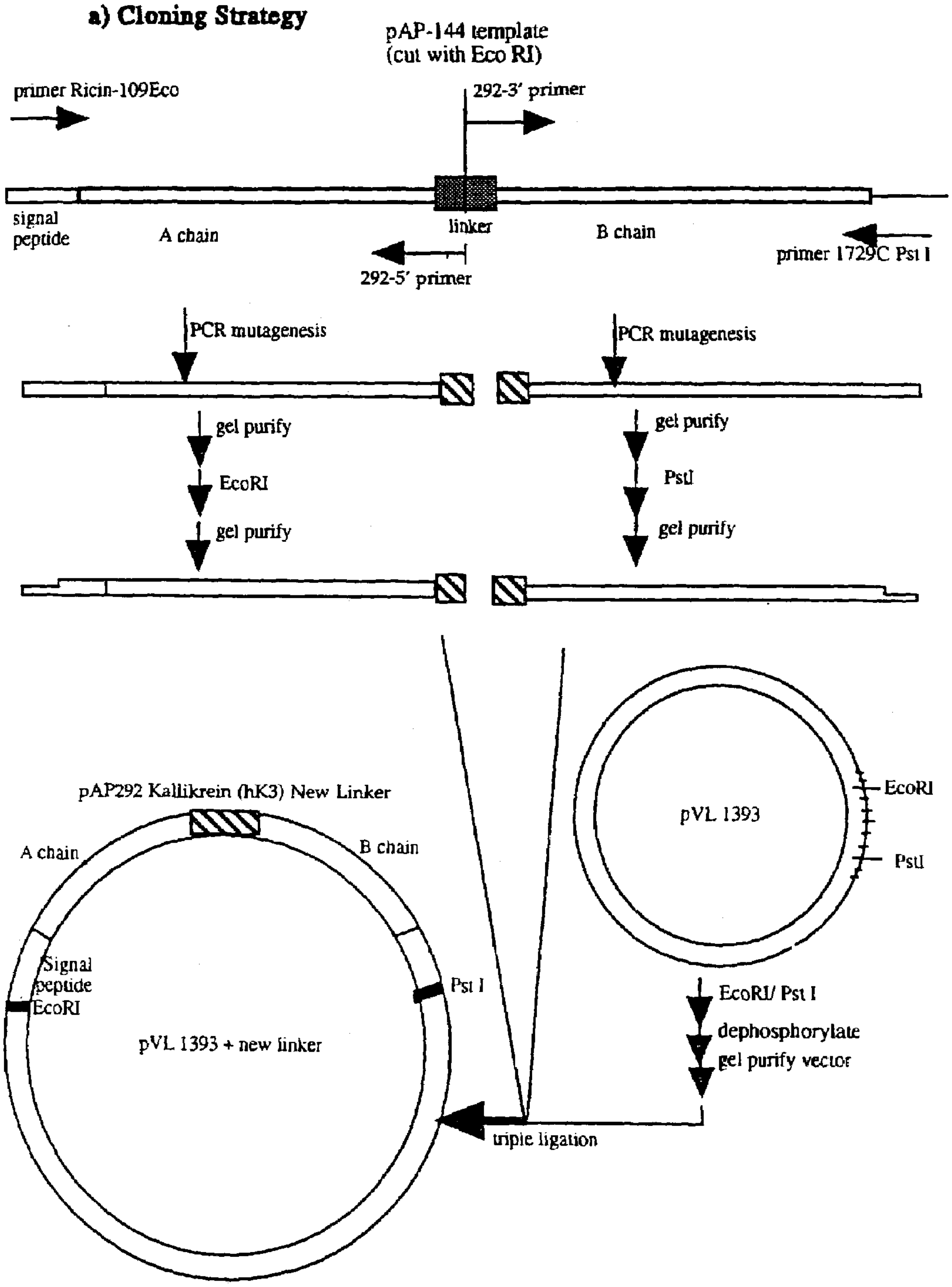
Figure 46A:
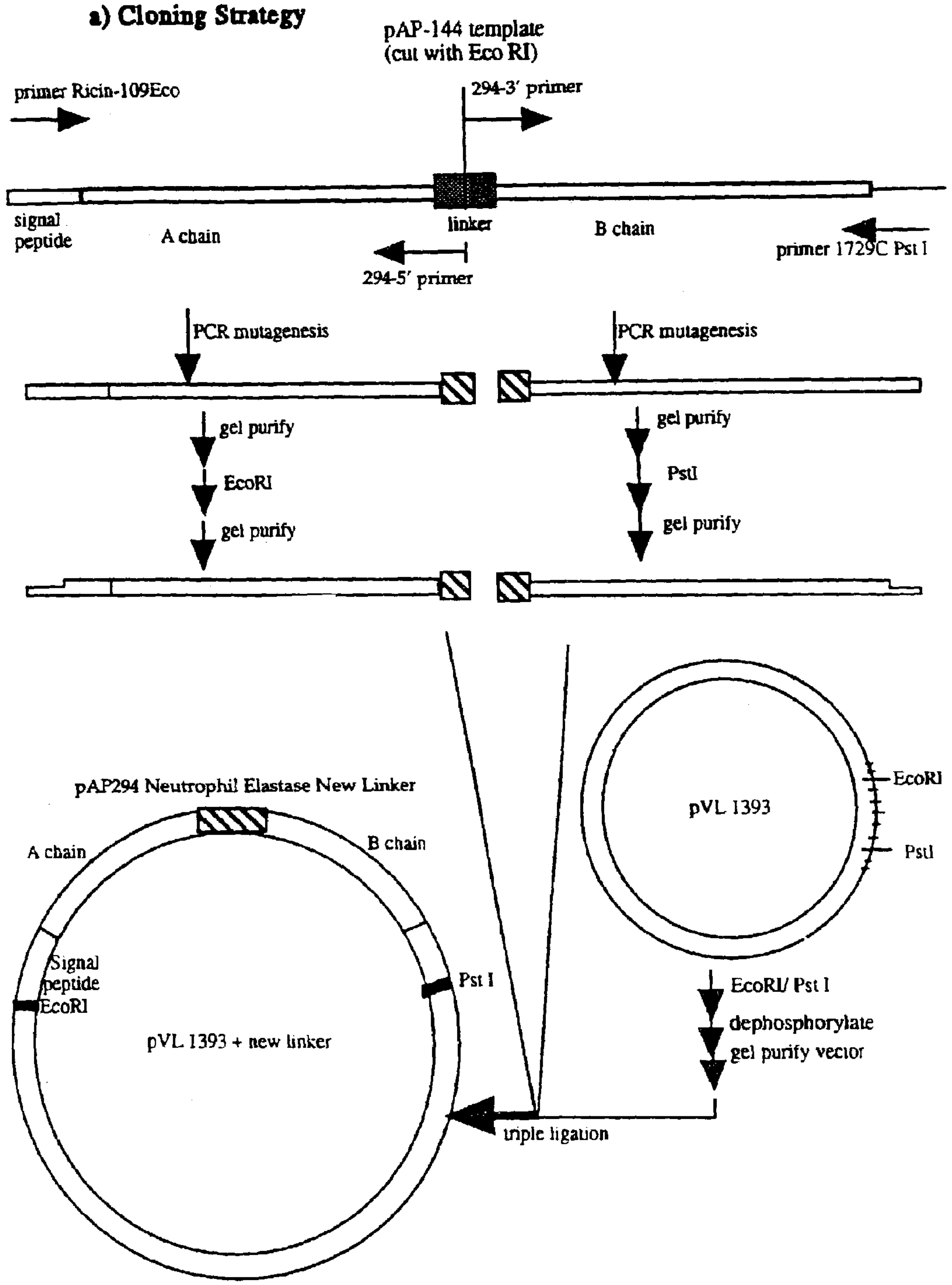
Figure 47A:
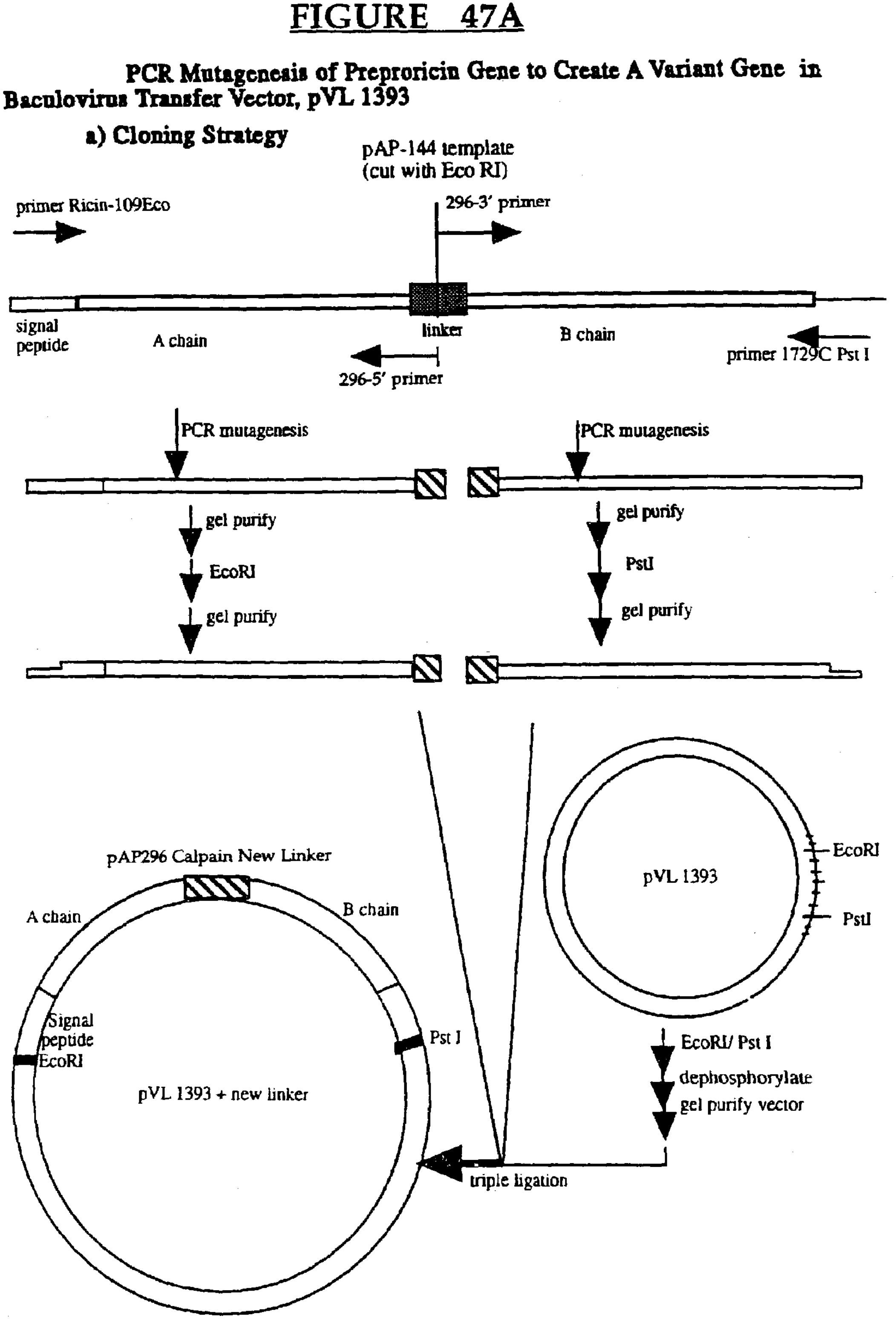
Figure 48:
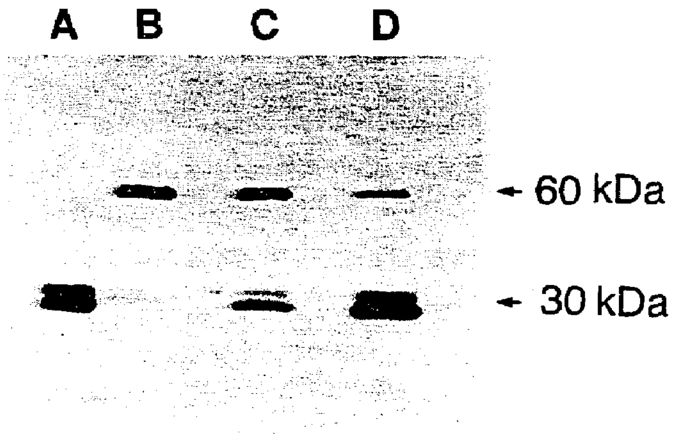
Figure 49:
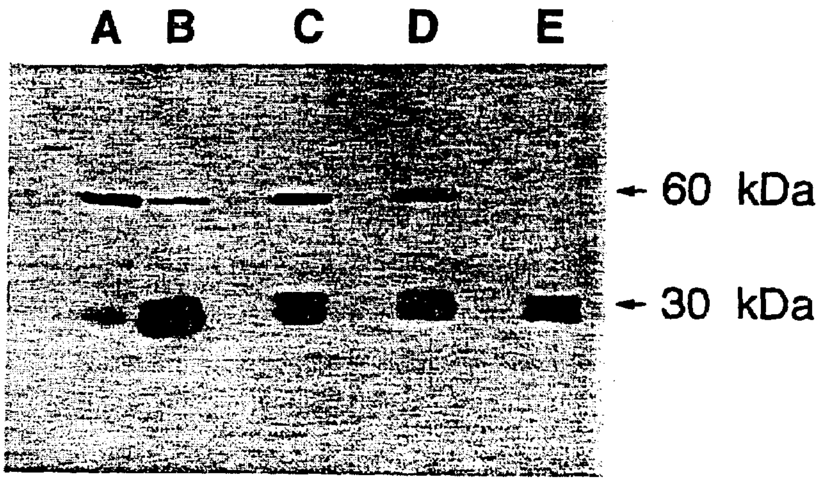
Figure 50:
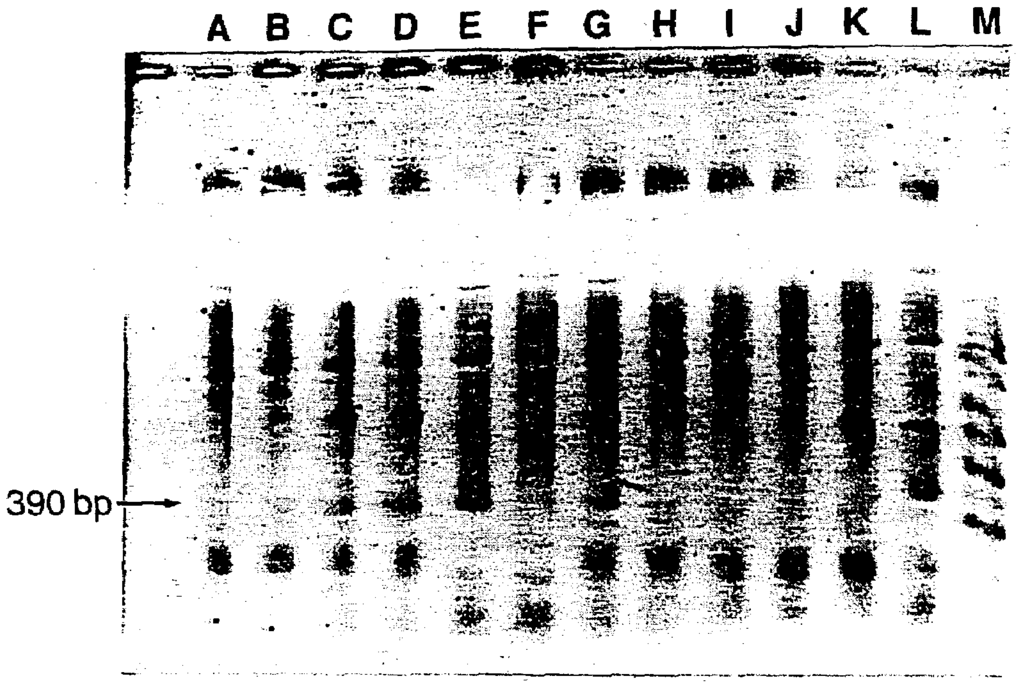

FIG. 36A summarizes the cloning strategy used to generate the pAP-274 construct;

FIG. 36B shows the nucleotide sequence of the Cathepsin L linker region of pAP-274 (SEQ ID NO: 91);

FIG. 36C shows the DNA sequence of the pAP-274 insert (SEQ ID NO: 92);

FIG. 36D shows the amino acid sequence comparison of mutant preproricin linker region of Cathepsin L to wild type (SEQ ID NOS: 127, 93);

FIG. 37A summarizes the cloning strategy used to generate the pAP-276 construct;

FIG. 37B shows the nucleotide sequence of the Cathepsin D linker region of pAP-276 (SEQ ID NO: 94);

FIG. 37C shows the DNA sequence of the pAP-276 insert (SEQ ID NO: 95);

FIG. 37D shows the amino acid sequence comparison of mutant preproricin linker region of Cathepsin D to wild type (SEQ ID NOS: 127, 96);

FIG. 38A summarizes the cloning strategy used to generate the pAP-278 construct;

FIG. 38B shows the nucleotide sequence of the MMP-1 linker region of pAP-278 (SEQ ID NO: 97);

FIG. 38C shows the DNA sequence of the pAP-278 insert (SEQ ID NO: 98);

FIG. 38D shows the amino acid sequence comparison of mutant preproricin linker region of MMP-1 to wild type (SEQ ID NOS: 127, 99);

FIG. 39A summarizes the cloning strategy used to generate the pAP-280 construct;

FIG. 39B shows the nucleotide sequence of the Urokinase Type Plasminogen Activator linker region of pAP-280 (SEQ ID NO: 100);

FIG. 39C shows the DNA sequence of the pAP-280 insert (SEQ ID NO: 101);

FIG. 39D shows the amino acid sequence comparison of mutant preproricin linker region of Urokinase-Type Plasminogen Activator to wild type (SEQ ID NO: 102);

FIG. 40A summarizes the cloning strategy used to generate the pAP-282 construct;

FIG. 40B shows the nucleotide sequence of the MT-MMP linker region of pAP-282 (SEQ ID NO: 103);

FIG. 40C shows the DNA sequence of the pAP-282 insert (SEQ ID NO: 104);

FIG. 40D shows the amino acid sequence comparison of mutant preproricin linker region of MT-MMP to wild type (SEQ ID NOS: 127, 105);

FIG. 41A summarizes the cloning strategy used to generate the pAP-284 construct;

FIG. 41B shows the nucleotide sequence of the MMP-11 linker region of pAP-284 (SEQ ID NO: 106);

FIG. 41C shows the DNA sequence of the pAP-284 insert (SEQ ID NO: 107);

FIG. 41D shows the amino acid sequence comparison of mutant preproricin linker region of MMP-11 into wild type (SEQ ID NOS: 127, 108);

FIG. 42A summarizes the cloning strategy used to generate the pAP-286 construct;

FIG. 42B shows the nucleotide sequence of the MMP-13 linker region of pAP-286 (SEQ ID NO: 109);

FIG. 42C shows the DNA sequence of the pAP-286 insert (SEQ ID NO: 110);

FIG. 42D shows the amino acid sequence comparison of mutant preproricin linker region of MMP-13 to wild type (SEQ ID NOS: 127, 111);

FIG. 43A summarizes the cloning strategy used to generate the pAP-288 construct;

FIG. 43B shows the nucleotide sequence of the Tissue type Plasminogen Activator linker region of pAP-288 (SEQ ID NO: 112);

FIG. 43C shows the DNA sequence of the pAP-288 insert (SEQ ID NO: 113);

FIG. 43D shows the amino acid sequence comparison of mutant preproricin linker region of Tissue-type Plasminogen Activator to wild type (SEQ ID NOS: 127, 114);

FIG. 44A summarizes the cloning strategy used to generate the pAP-290 construct;

FIG. 44B shows the nucleotide sequence of the human Prostate-Specific Antigen linker region of pAP-290 (SEQ ID NO: 115);

FIG. 44C shows the DNA sequence of the pAP-290 insert (SEQ ID NO: 116);

FIG. 44D shows the amino acid sequence comparison of mutant preproricin linker region of the human Prostate-Specific Antigen to wild type (SEQ ID NOS: 127, 117);

FIG. 45A summarizes the cloning strategy used to generate the pAP-292 construct;

FIG. 45B shows the nucleotide sequence of the kallikrein linker region of pAP-292 (SEQ ID NO: 118);

FIG. 45C shows the DNA sequence of the pAP-292 insert (SEQ ID NO: 119);

FIG. 45D shows the amino acid sequence comparison of mutant preproricin linker region of the kallikrein to wild type (SEQ ID NOS: 127, 120);

FIG. 46A summarizes the cloning strategy used to generate the pAP-294 construct;

FIG. 46B shows the nucleotide sequence of the neutrophil elastase linker region of pAP-294 (SEQ ID NO: 121);

FIG. 46C shows the DNA sequence of the pAP-294 insert (SEQ ID NO: 122);

FIG. 46D shows the amino acid sequence comparison of mutant preproricin linker region of neutrophil elastase to wild type (SEQ ID NOS: 127, 123);

FIG. 47A summarizes the cloning strategy used to generate the pAP-296 construct;

FIG. 47B shows the nucleotide sequence of the calpain linker region of pAP-296 (SEQ ID NO: 124);

FIG. 47C shows the DNA sequence of the pAP-296 insert (SEQ ID NO: 125);

FIG. 47D shows the amino acid sequence comparison of mutant preproricin linker region of calpain to wild type (SEQ ID NOS: 127, 126);

FIG. 48 is a blot showing cleavage of pAP-214 by Cathepsin B;

FIG. 49 is a blot showing cleavage of pAP-220 with MMP-9;

FIG. 50 is a blot showing activation of pAP-214; and

Figure 51:
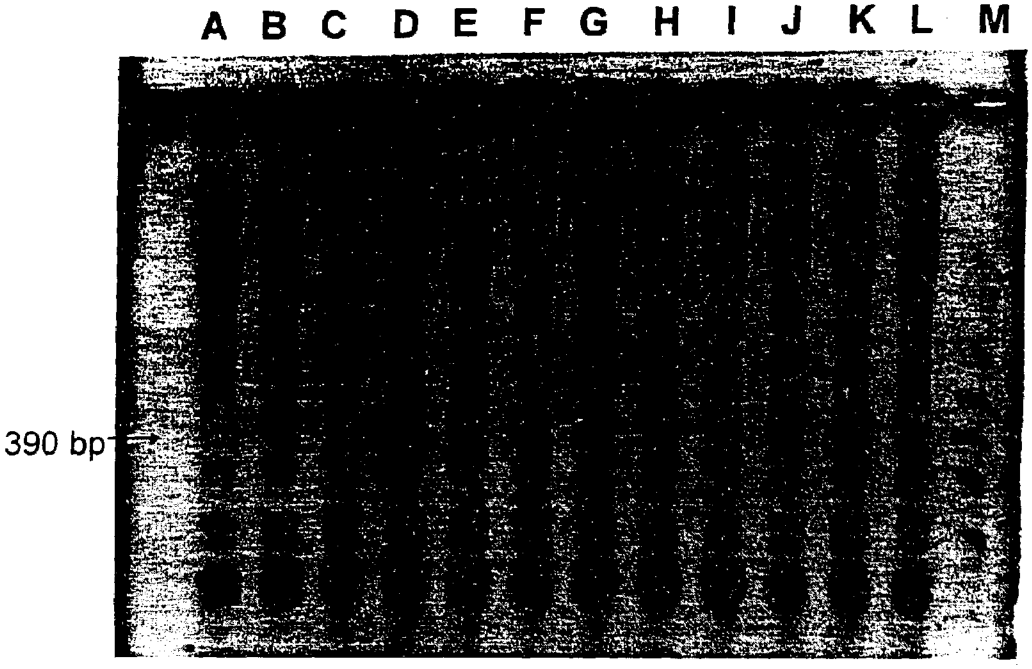

FIG. 51 is a blot showing activation of pAP-220.

Figure 52:
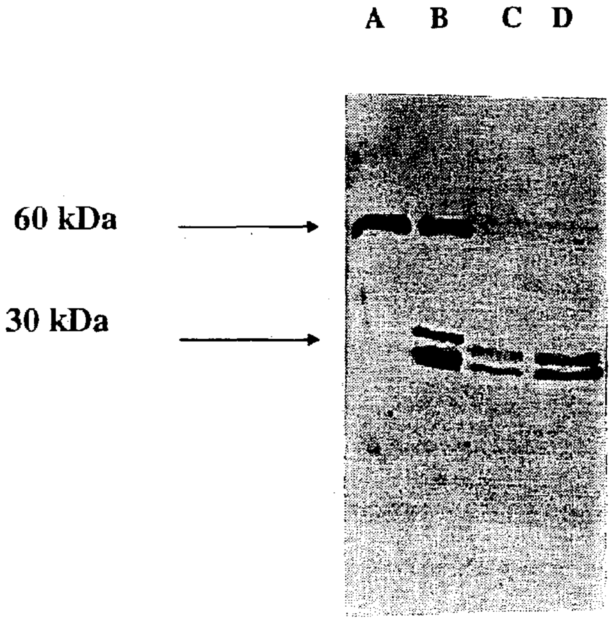

FIG. 52 is a blot showing cleavage of pAP-248 with Human Cytomegalovirus (HCMV).

Figure 53:
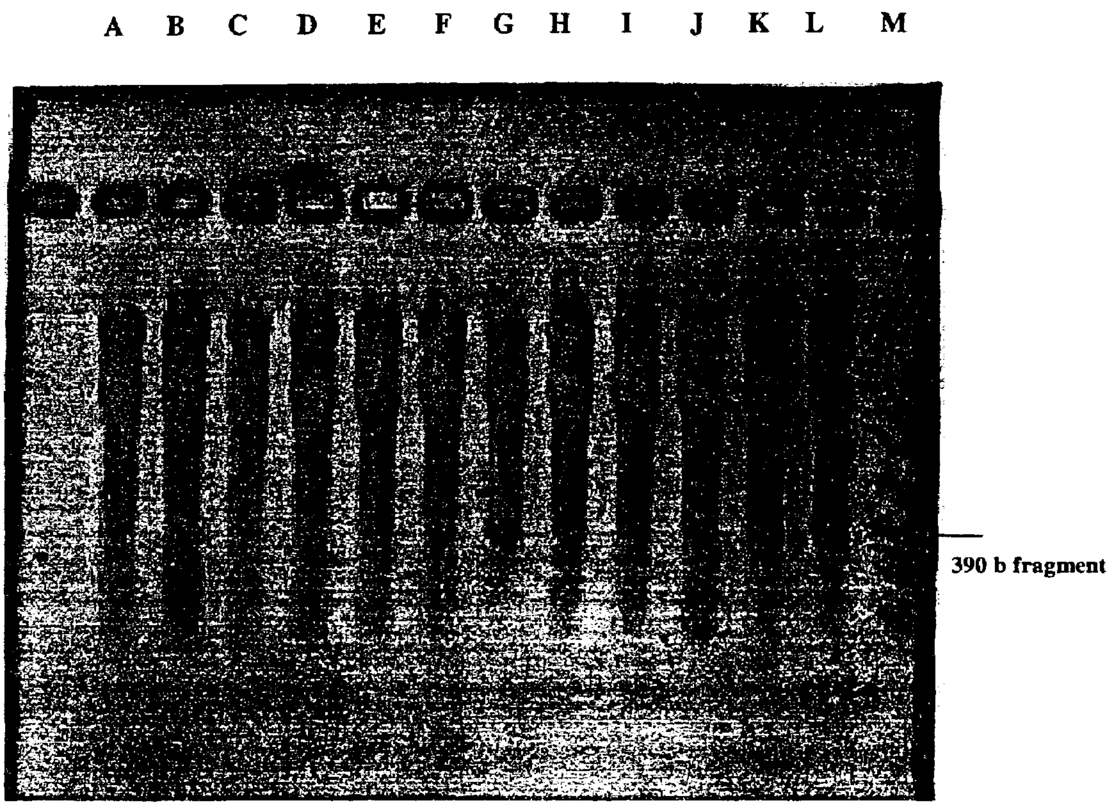

FIG. 53 is a blot showing activation of pAP-248.

Figure 54:
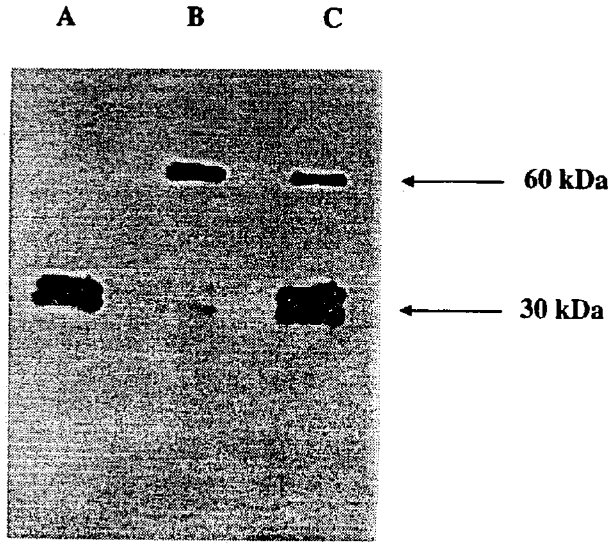

FIG. 54 is a blot showing cleavage of pAP-256 by HAV 3C.

Figure 55:
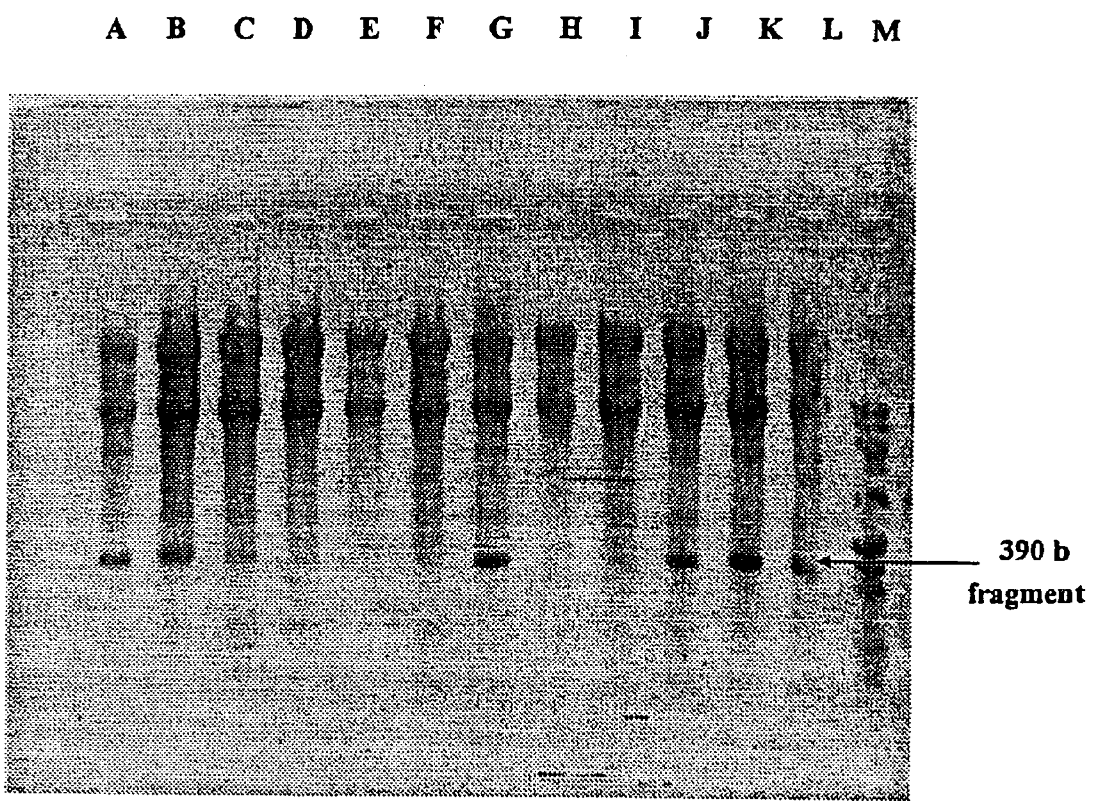

FIG. 55 is a blot showing activation of pAP-256.

Figure 56:
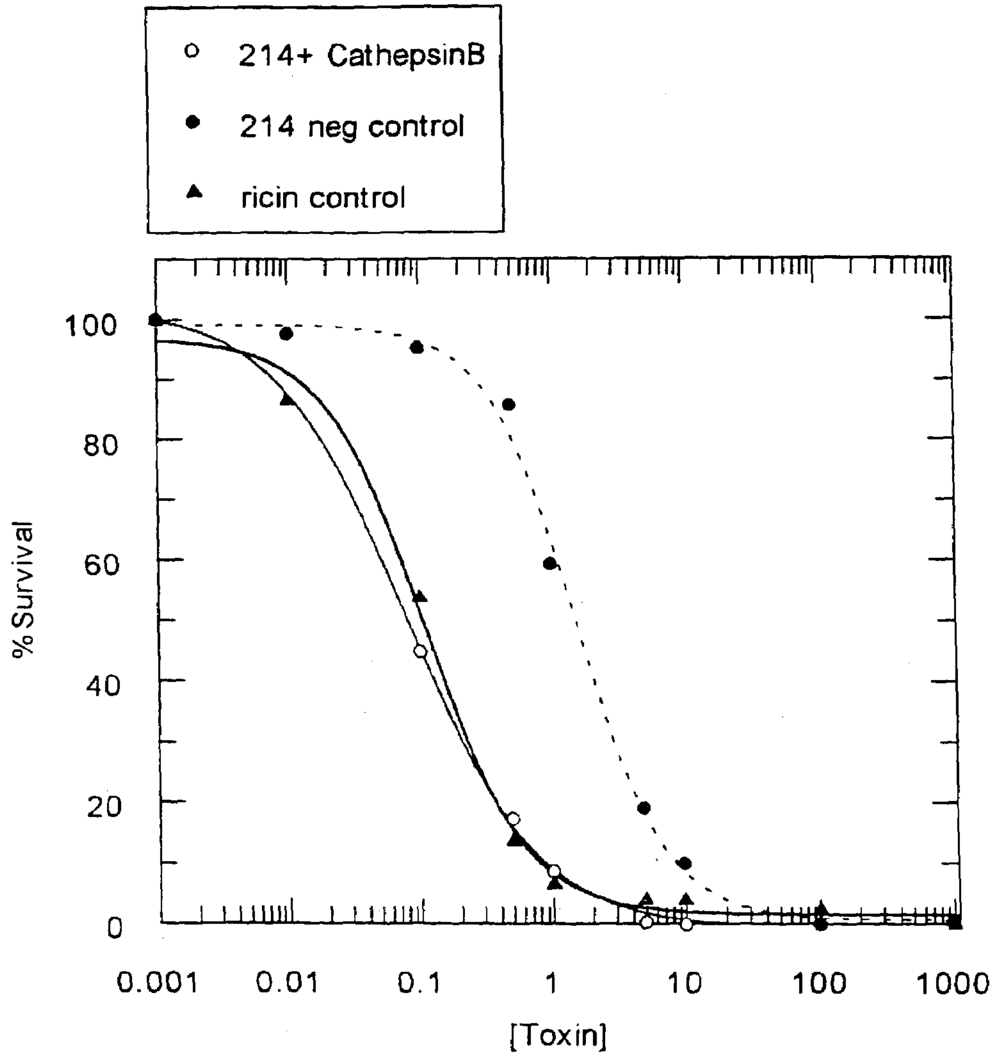

FIG. 56 is a semi-logithmic graph illustrating the cytotoxicity to COS-1 cells of undigested pAP-214 and pAP-214 digestedwith Cathepsin B.

Figure 57:
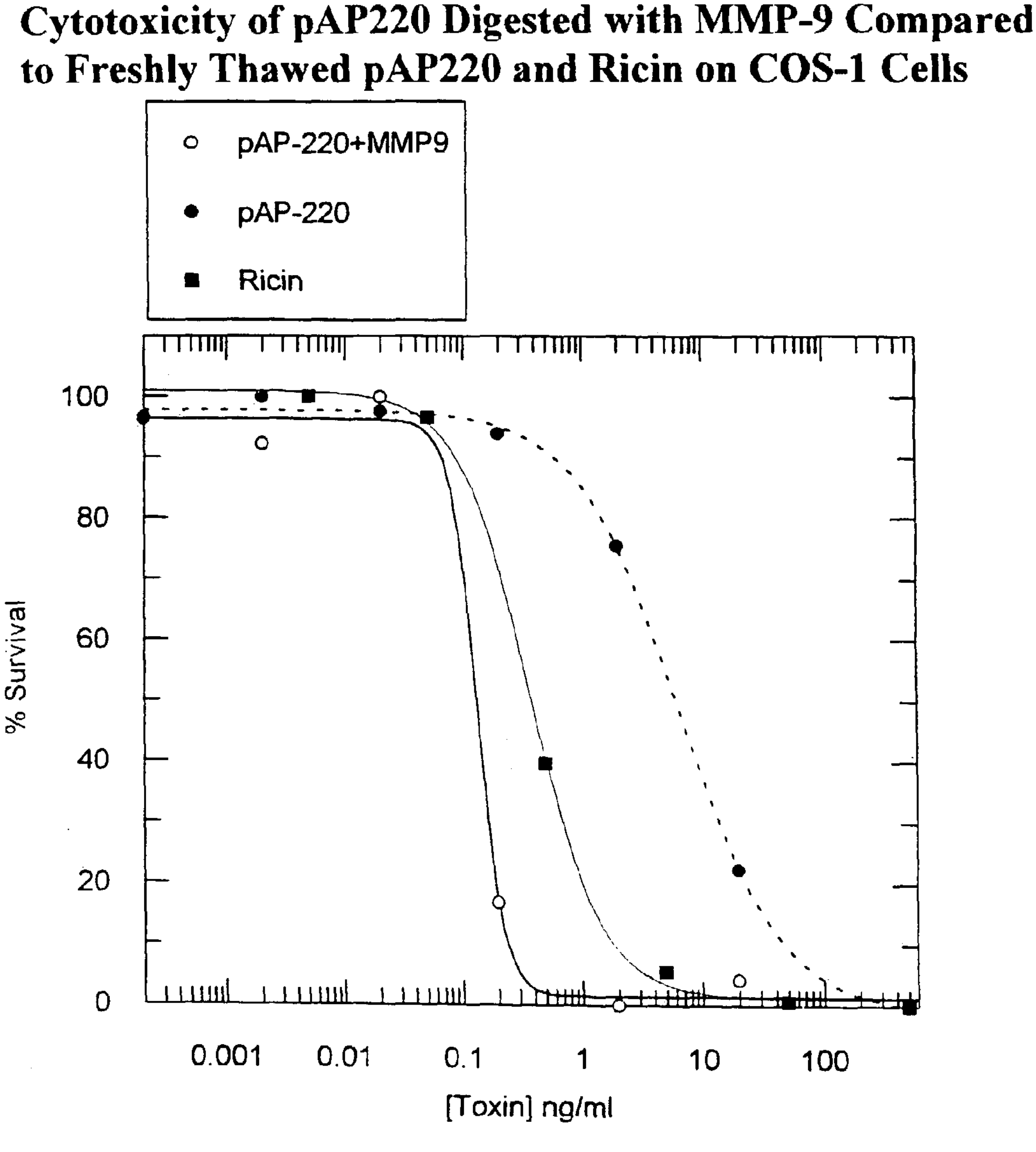

FIG. 57 is a semi-logithmic graph illustrating the cytotoxicity of pAP-220 digested with MMP-9 compared to freshly thawed pAP-220 and ricin on COS-1 cells.

Figure 58:
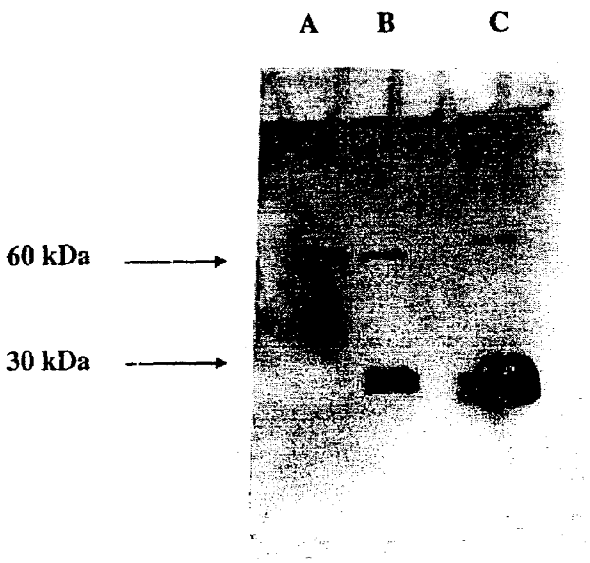

FIG. 58 is a blot showing cleavage of pAP-270 with MMP-2.

Figure 59:
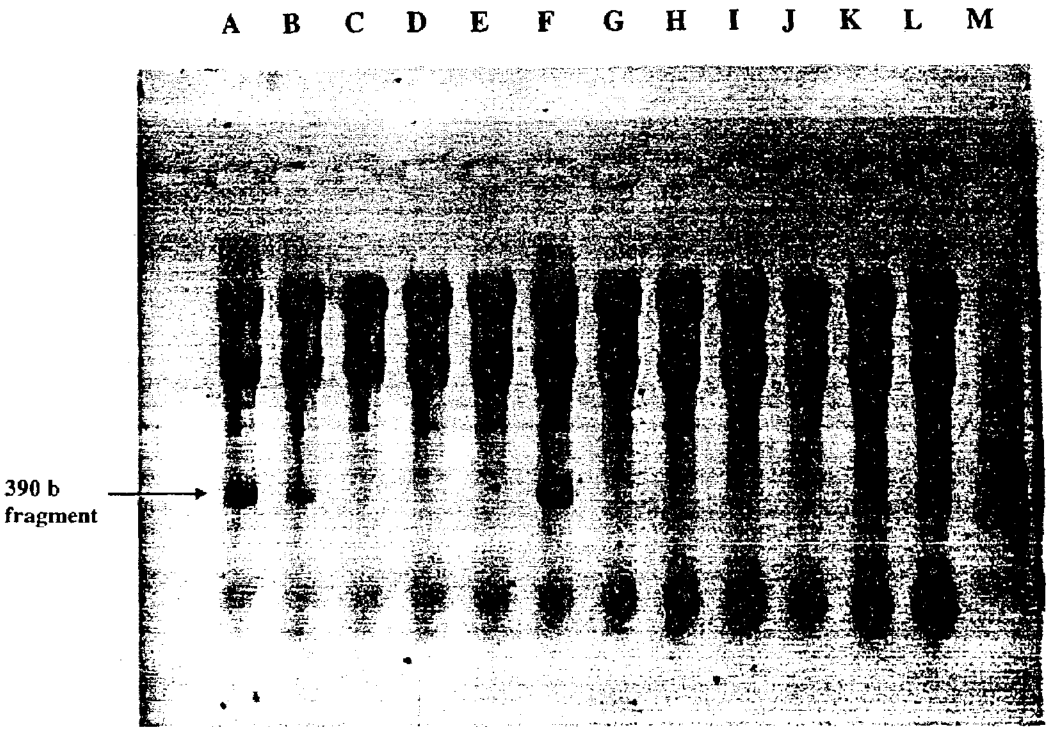

FIG. 59 is a blot showing activation of pAP-270.

Figure 60:
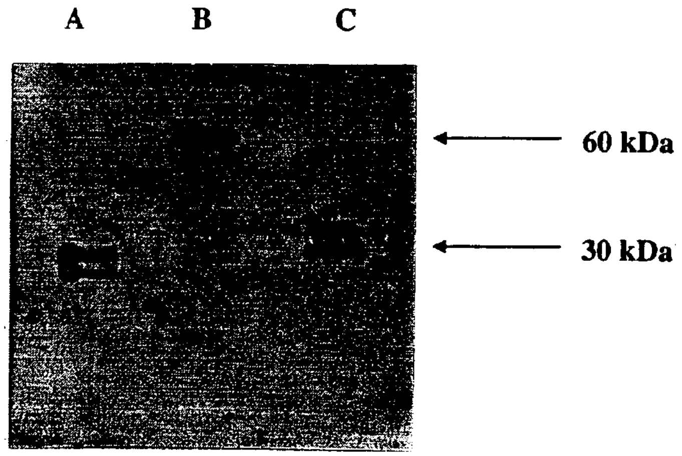

FIG. 60 is a blot showing cleavage of pAP-288 by t-PA.

Figure 61:
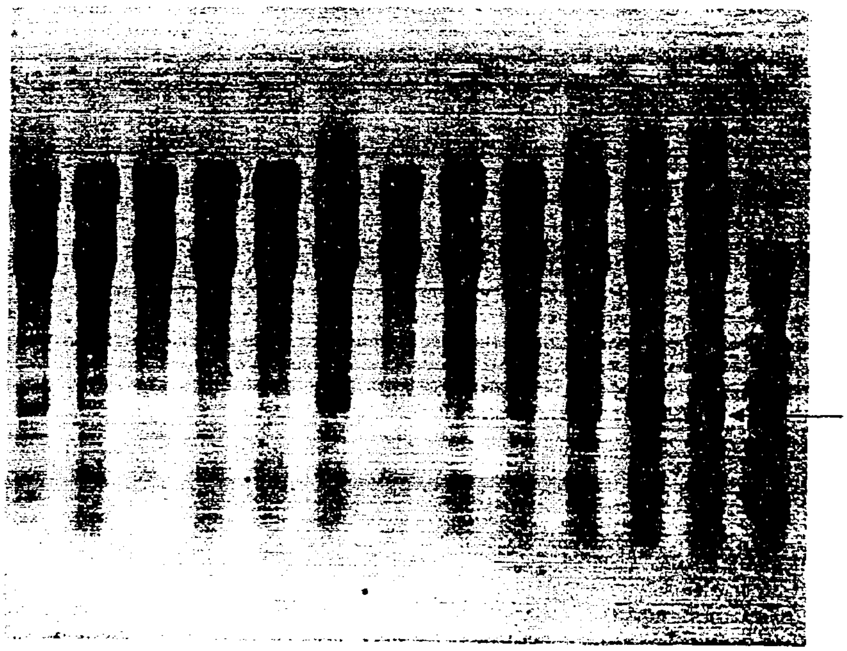

FIG. 61 is a blot showing activation of pAP-288.

Figure 62:
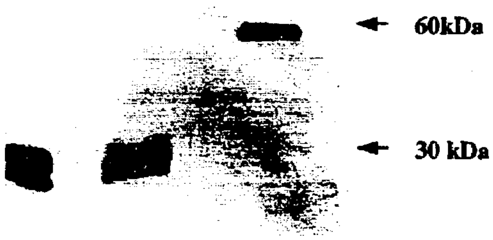

FIG. 62 is a blot showing cleavage of pAP-294 with human neutrophil elastase.

FIG. 63 is a blot showing activation of pAP-294.

Figure 64:
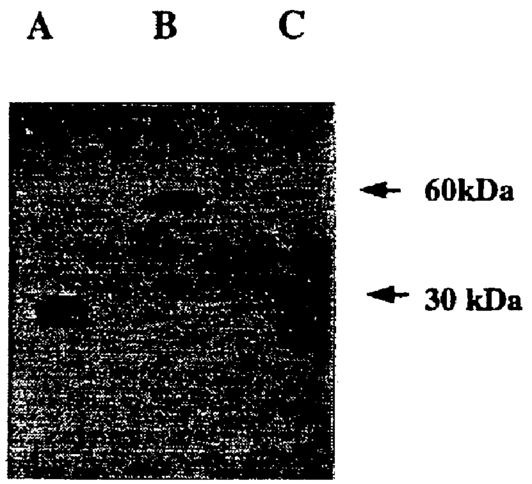

FIG. 64 is a blot showing cleavage of pAP-296 with calpain.

FIG. 65 is a blot showing activation of pAP-296.

Figure 66:
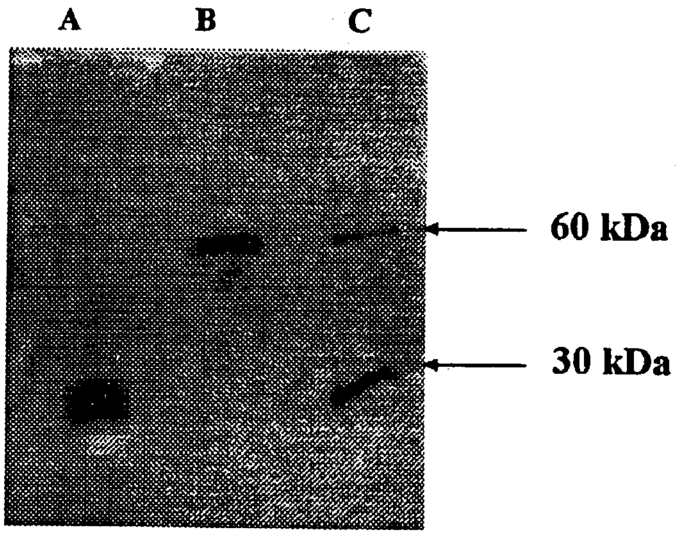

FIG. 66 is a blot showing cleavage of pAP-222 with MMP-2.

Figure 67:

FIG. 67 is a blot showing activation of pAP-222.

DETAILED DESCRIPTION OF THE INVENTION

Nucleic Acid Molecules of the Invention

As mentioned above, the present invention relates to novel nucleic acid molecules comprising a nucleotide sequence encoding an A chain of a ricin-like toxin, a B chain of a ricin-like toxin and a heterologous linker amino acid sequence, linking the A and B chains. The heterologous linker sequence contains a cleavage recognition site for a disease-specific protease (e.g. a viral protease, parasitic protease, cancer-associated protease, or a fungal protease).

The term "isolated and purified" as used herein refers to a nucleic acid substantially free of cellular material or culture medium when produced by recombinant DNA techniques, or chemical precursors, or other chemicals when chemically synthesized. An "isolated and purified" nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

The term "linker sequence" as used herein refers to an internal amino acid sequence within the protein encoded by the nucleic acid molecule of the invention which contains residues linking the A and B chain so as to render the A chain incapable of exerting its toxic effect, for example catalytically inhibiting translation of a eukaryotic ribosome. By heterologous is meant that the linker sequence is not a sequence native to the A or B chain of a ricin-like toxin or precursor thereof. However, preferably, the linker sequence may be of a similar length to the linker sequence of a ricin-like toxin and should not interfere with the role of the B chain in cell binding and transport into the cytoplasm. When the linker sequence is cleaved the A chain becomes active or toxic.

The nucleic acid molecule of the invention is cloned by subjecting a preproricin cDNA clone to site-directed mutagenesis in order to generate a series of variants differing only in the sequence between the A and B chains (linker region). Oligonucleotides, corresponding to the extreme 5' and 3' ends of the preproricin gene are synthesized and used to PCR amplify the gene. Using the cDNA sequence for preproricin (Lamb et al., *Eur. J. Biochem.* 145:266-270 (1985)), several oligonucleotide primers are designed to flank the start and stop codons of the preproricin open reading frame.

The preproricin cDNA is amplified using the upstream primer Ricin-99 or Ricin-109 and the downstream primer Ricin1729C with Vent DNA polymerase (New England Biolabs) using standard procedures (Sambrook et al., Molecular Cloning: A Laboratory Manual, Second Edition, (Cold Spring Harbor Laboratory Press, 1989)). The purified PCR fragment encoding the preproricin cDNA is then ligated into an Eco RI-digested pBluescript II SK plasmid (Stratagene), and is used to transform competent XL1-Blue cells (Stratagene). The cloned PCR product containing the putative preproricin gene is confirmed by DNA sequencing of the entire cDNA clone. The sequences and location of oligonucleotide primers used for sequencing are shown in Table 1.

The preproricin cDNA clone is subjected to site directed mutagenesis in order to generate a series of variants differing only in the sequence between the A and B chains (linker region). The wild-type preproricin linker region is replaced with the heterogenous linker sequences that are cleaved by the various disease-specific proteases as shown in FIGS. 21, 26, 27, 28, and Part D of FIGS. 30-47. Linker identification as used herein in connection with the sequences provided in these figures have been assigned the sequence ID numbers as discussed below.

The linker regions of the variants encode a cleavage recognition sequence for a disease-specific protease associated with for example, cancer, viruses, parasites, or fungi. The mutagenesis and cloning strategy used to generate the disease-specific protease-sensitive linker variants are summarized in Part A of FIGS. 2-20, and Part A of FIGS. 22-25. The first step involves a DNA amplification using a set of mutagenic primers in combination with the two flanking primers Richin-99Eco or Ricin-109Eco and Ricin1729C Pst I. Restriction digested PCR fragments are gel purified and then ligated with PBluescript SK which has been digested with Eco RI and Pst I. Ligation reactions are used to transform competent XL1-Blue cells (Stratagene). Recombinant clones are identified by restriction digests of plasmid miniprep DNA and the mutant linker sequences are confirmed by DNA sequencing. With respect to the nucleotide sequences and amino acid sequences prepared as a result of the implementation of this strategy the following sequences have been assigned the sequence ID numbers as indicated.

SEQ ID NO. 1 is used herein in connection with the DNA sequence of the baculovirus transfer vector, pVL1393.

The nucleotide sequence of Cathepsin B linker regions of pAP-213 are referred to herein as SEQ ID NO. 2.

The nucleotide sequence of Cathepsin B linker regions of pAP-214 are referred to herein as SEQ ID NO. 3.

The nucleotide sequence of MMP-3 linker regions of pAP-215 are referred to herein as SEQ ID NO. 4.

The DNA sequence of the pAP-216 insert containing ricin and the MMP-3 linker are referred to herein as SEQ ID NO. 5.

The nucleotide sequence of MMP-7 linker regions of pAP-217 are referred to herein as SEQ ID NO. 6.

The DNA sequence of the pAP-218 insert containing ricin and the MMP-7 linker are referred to herein as SEQ ID NO. 7.

The nucleotide sequence of MMP-9 linker regions of pAP-219 are referred to herein as SEQ ID NO. 8.

The DNA sequence of the pAP-220 insert containing ricin and the MMP-9 are referred to herein as SEQ ID NO. 9.

The nucleotide sequence of thermolysin-like MMP linker regions of pAP-221 are referred to herein as SEQ ID NO. 10.

The DNA sequence of of pAP-222 insert containing ricin and the thermolysin-like MMP linker are referred to herein as SEQ ID NO. 11.

The nucleotide sequence of *Plasmodium falciparum*-A linker regions of pAP-223 are referred to herein as SEQ ID NO. 12.

The DNA sequence of the pAP-224 insert containing ricin and the *Plasmodium falciparum*-A linker are referred to herein as SEQ ID NO. 13.

The nucleotide sequence of *Plasmodium falciparum*-B linker regions of pAP-225 are referred to herein as SEQ ID NO. 14.

The DNA sequence of the pAP-226 insert containing ricin and the *Plasmodium falciparum*-B linker are referred to herein as SEQ ID NO. 15.

The nucleotide sequence of *Plasmodium falciparum*-C linker regions of pAP-227 are referred to herein as SEQ ID NO. 16.

The DNA sequence of the pAP-228 insert containing ricin and the *Plasmodium falciparum*-C linker are referred to herein as SEQ ID NO. 17.

The nucleotide sequence of the the *Plasmodium falciparum*-D linker regions of pAP-229 is referred to herein as SEQ ID NO. 18.

The DNA sequence of the pAP-230 insert containing ricin and the *Plasmodium falciparum*-D linker is referred to herein as SEQ ID NO. 19.

The nucleotide sequence of the *Plasmodium falciparum*-E linker regions of pAP-231 is referred to herein as SEQ ID NO. 20.

The DNA sequence of the pAP-232 insert containing ricin and the *Plasmodium falciparum*-E linker is referred to herein as SEQ ID NO. 21.

The nucleotide sequence of the HSV-A linker regions of pAP-233 is referred to herein as SEQ ID NO. 22.

The DNA sequence of the pAP-234 insert containing ricin and the HSV-A linker is referred to herein as SEQ ID NO. 23.

The nucleotide sequence of the HSV-B linker regions of pAP-235 is referred to herein as SEQ ID NO. 24.

The DNA sequence of the pAP-236 insert containing ricin and the HSV-B linker is referred to herein as SEQ ID NO. 25.

The nucleotide sequence of the VZV-A linker regions of pAP-237 are referred to herein as SEQ ID NO. 26.

The DNA sequence of the pAP-238 insert containing ricin and the VZV-A linker are referred to herein as SEQ ID NO. 27.

The nucleotide sequence of the VZV-B linker regions of PAP-239 is referred to herein as SEQ ID NO. 28.

The DNA sequence of the pAP-240 insert containing ricin and the VZV-B linker is referred to herein as SEQ ID NO. 29.

The nucleotide sequence of the EBV-A linker regions of pAP-241 is referred to herein as SEQ ID NO. 30.

The DNA sequence of the pAP-242 insert containing ricin and the EBV-A linker is referred to herein as SEQ ID NO. 31.

The nucleotide sequence of the EBV-B linker regions of pAP-243 is referred to herein as SEQ ID NO. 32.

The DNA sequence of the pAP-244 insert containing ricin and the EBV-B linker is referred to herein as SEQ ID NO. 33.

The nucleotide sequence of the CMV-A linker regions of pAP-245 is referred to herein as SEQ ID NO. 34.

The DNA sequence of the pAP-246 insert containing ricin and the CMV-A linker is referred to herein as SEQ ID NO. 35.

The nucleotide sequence of the CMV-B linker regions of pAP-247 is referred to herein as SEQ ID NO. 36.

The DNA sequence of the pAP-248 insert containing ricin and the CMV-B linker is referred to herein as SEQ ID NO. 37.

The nucleotide sequence of the HHV-6 linker regions of pAP-249 is referred to herein as SEQ ID NO. 38.

The DNA sequence of the pAP-250 insert containing ricin and the HHV-6 linker is referred to herein as SEQ ID NO. 39.

The amino acid sequences of the cancer protease-sensitive amino acid linkers contained in the following pAP proteins have the sequence ID numbers as indicated: pAP-213 and pAP-214 (SEQ ID NO. 40); pAP-215 and pAP-216 (SEQ ID NO. 41); pAP-217 and pAP-218; (SEQ ID NO. 42); pAP-219 and pAP-220 (SEQ ID NO. 43); and pAP-221 and pAP-222 (SEQ ID NO. 44).

The amino acid sequences of the following cancer protease-sensitive linkers are referred to herein with the corresponding sequence ID numbers: pAP-241 and pAP-242 (SEQ ID NO. 45); and pAP-243 and pAP-244 (SEQ ID NO. 46).

The nucleotide sequence of the ILV linker regions of pAP-253 is referred to herein as SEQ ID NO. 47.

The DNA sequence of the pAP-254 insert containing ricin and the ILV linker is referred to herein as SEQ ID NO. 48.

The nucleotide sequence of the HAV-A linker regions of pAP-257 is referred to herein as SEQ ID NO. 49.

The DNA sequence of the pAP-258 insert containing ricin and HAV-A linker is referred to herein as SEQ ID NO. 50.

The nucleotide sequence of the HAV-B linker regions of pAP-255 is referred to herein as SEQ ID NO. 51.

The DNA sequence of the pAP-256 insert containing ricin and the HAV-B linker is referred to herein as SEQ ID NO. 52.

The nucleotide sequence of the CAN linker regions of pAP-259 is referred to herein as SEQ ID NO. 53.

The DNA sequence of the pAP-260 insert containing ricin and the CAN linker is referred to herein as SEQ ID NO. 54.

The amino acid sequences of *Plasmodium falciparum* protease-sensitive linkers are referred to herein by the sequence ID numbers as follows: pAP-223 and pAP-224 (SEQ ID NO 55); pAP-225 and pAP-226 (SEQ ID NO 56); pAP-227 and pAP-228 (SEQ ID NO 57); pAP-229 and pAP-230 (SEQ ID NO 58); and pAP-231 and pAP-232 (SEQ ID NO 59) (see FIG. 26).

The amino acid sequences of the viral protease-sensitive linkers which follow are referred to herein by the sequence ID numbers indicated: pAP-233 and pAP 234 (SEQ ID NO 60); pAP-235 and pAP-236 (SEQ ID NO 61); and pAP-249 and pAP-250 (SEQ ID NO 62) (see FIG. 27).

The amino acid sequences of the viral protease-sensitive linkers which follow are referred to herein by the sequence ID numbers indicated: pAP-245 and pAP-246 (SEQ ID NO 63); and pAP-247 and pAP-248 (SEQ ID NO 64) (see FIG. 27).

The amino acid sequences of the viral protease-sensitive linkers which follow are referred to herein by the sequence ID numbers indicated: pAP-237 and pAP-238 (SEQ ID NO 65); and pAP-239 and pAP-240 (SEQ ID NO 66); pAP-253 and pAP-254 (SEQ ID NO 67); pAP-255 and pAP-256 (SEQ ID NO 68); and pAP-257 and pAP-258 (SEQ ID NO 69) (see FIG. 27).

The amino acid sequences of the *Candida* aspartic protease-sensitive linkers are referred to herein by the sequence ID numbers indicated: pAP-259 and pAP-260 (SEQ ID NO 70); pAP-261 and pAP-262 (SEQ ID NO 71); and pAP-263 and pAP-264 (SEQ ID NO 72).

Figure 2A:
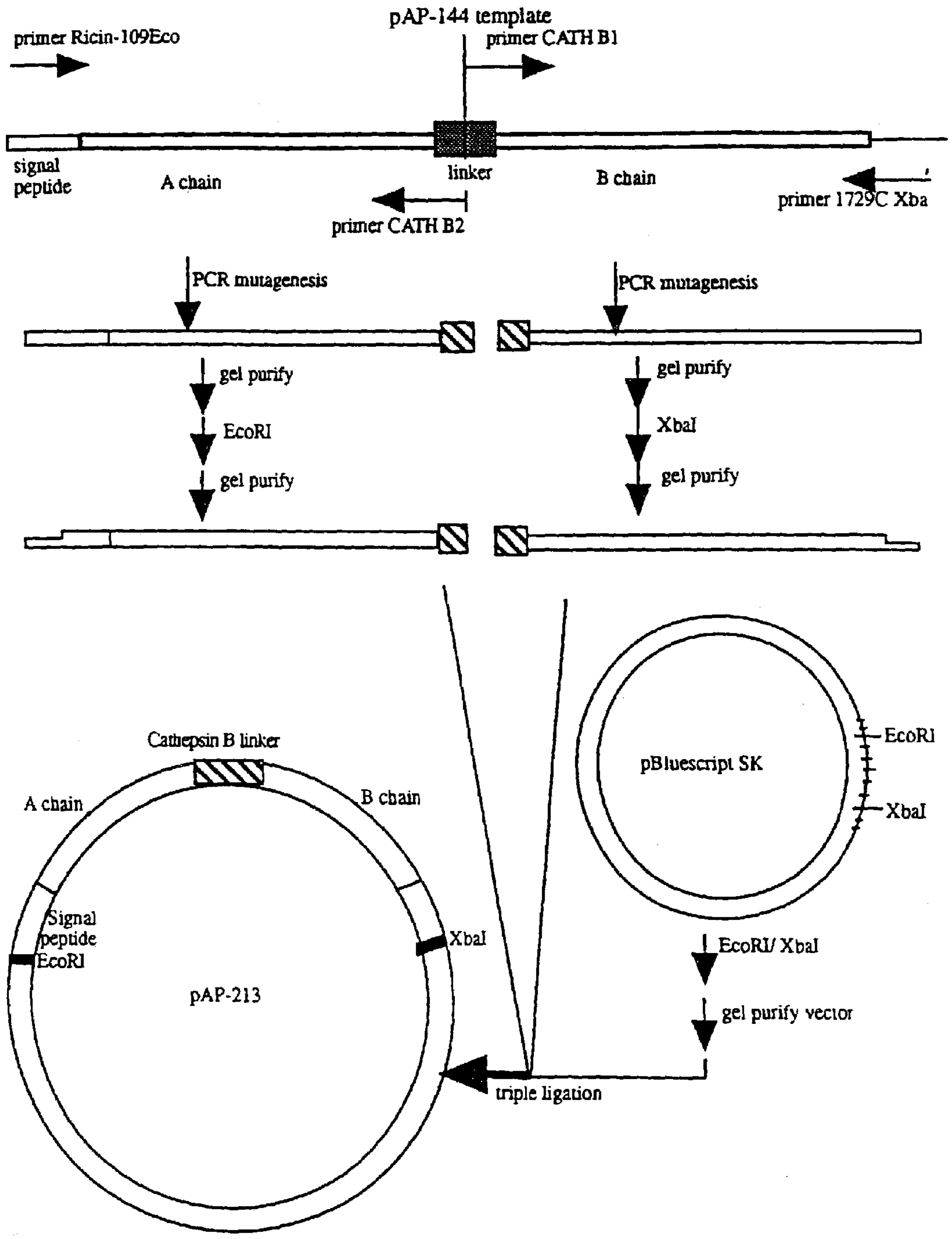
FIG. 2A summarizes the cloning strategy used to generate the pAP-213 construct
Figure 2B:
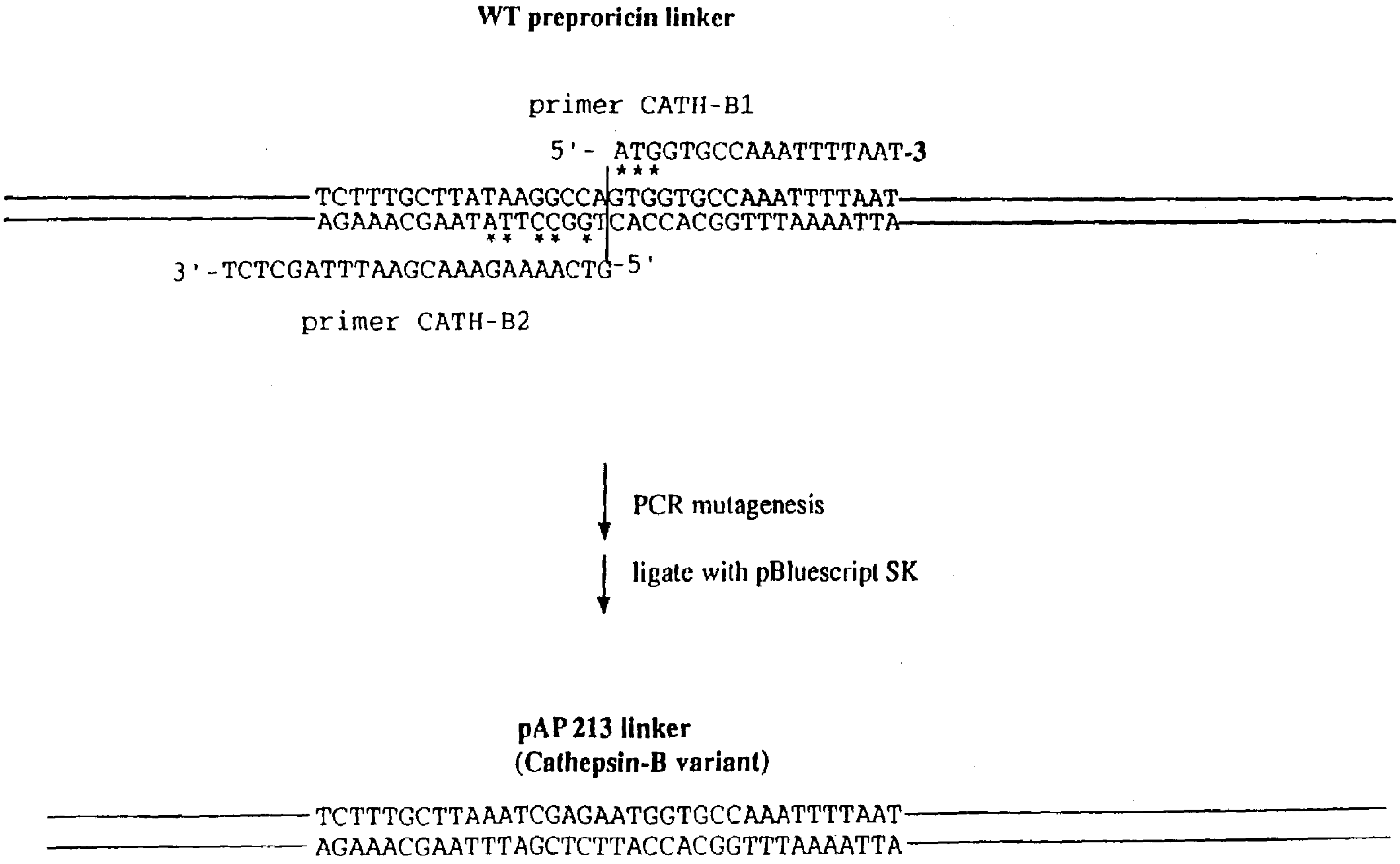
FIG. 2B shows the nucleotide sequence of the Cathepsin B linker regions of pAP-213 (SEQ ID NO:2)
Figure 2C:
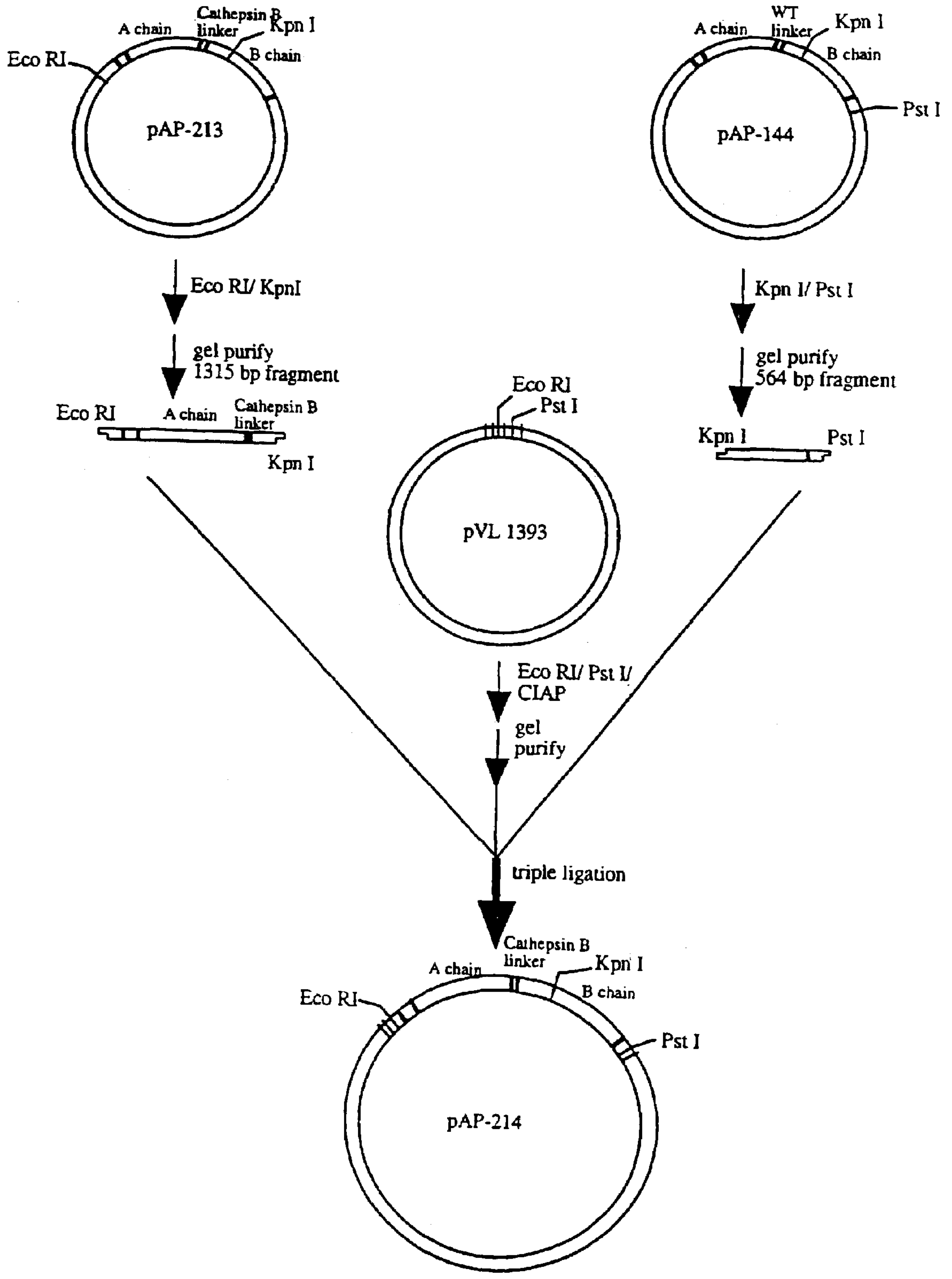
FIG. 2C shows the subcloning of the Cathepsin B linker variant into a baculovirus transfer vector.
Figure 3A:
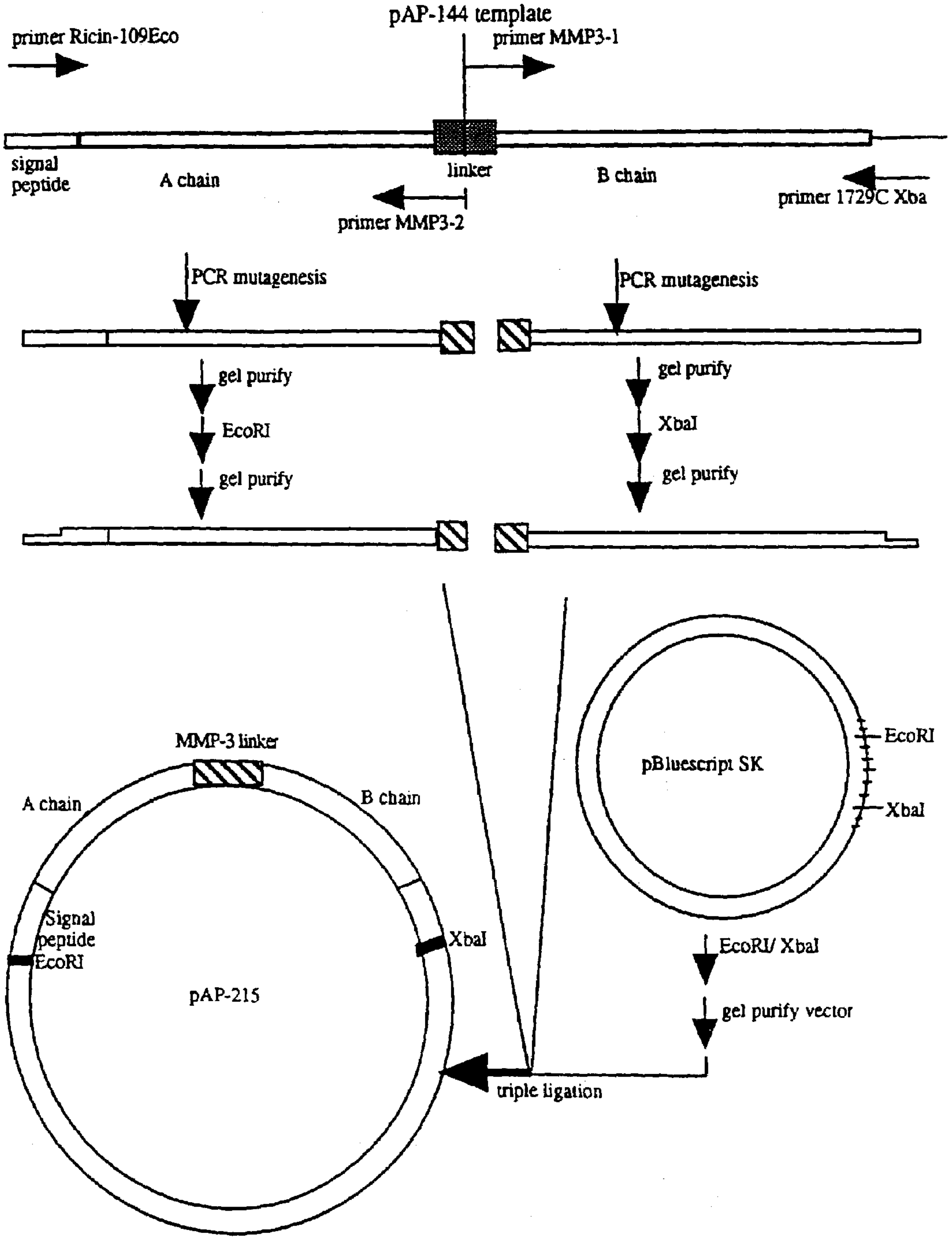
FIG. 3A summarizes the cloning strategy used to generate the pAP-215 construct.
Figure 3B:
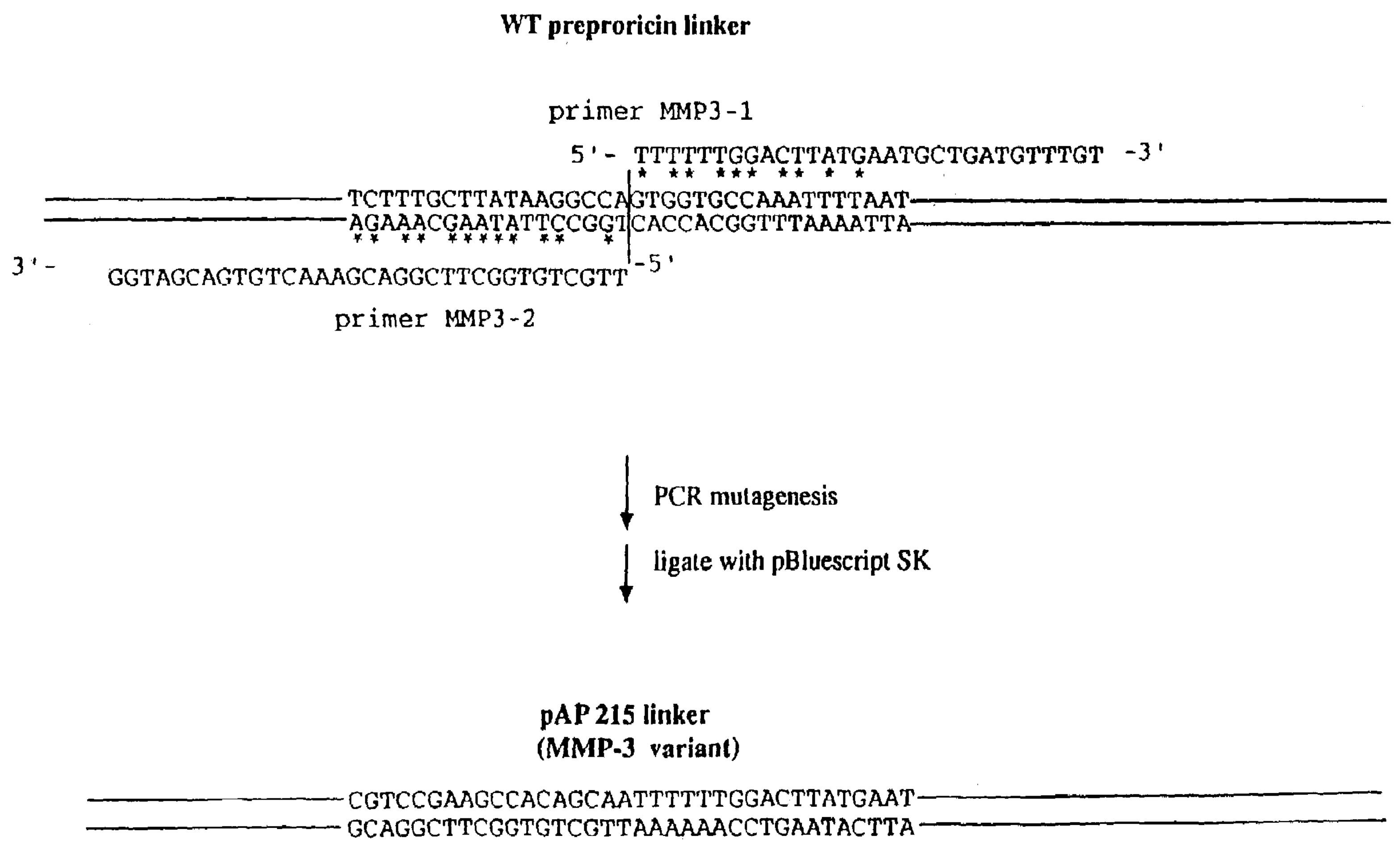
FIG. 3B shows the nucleotide sequence of the MMP-3 linker regions of pAP-215 (SEQ ID NO: 4)
Figure 3C:
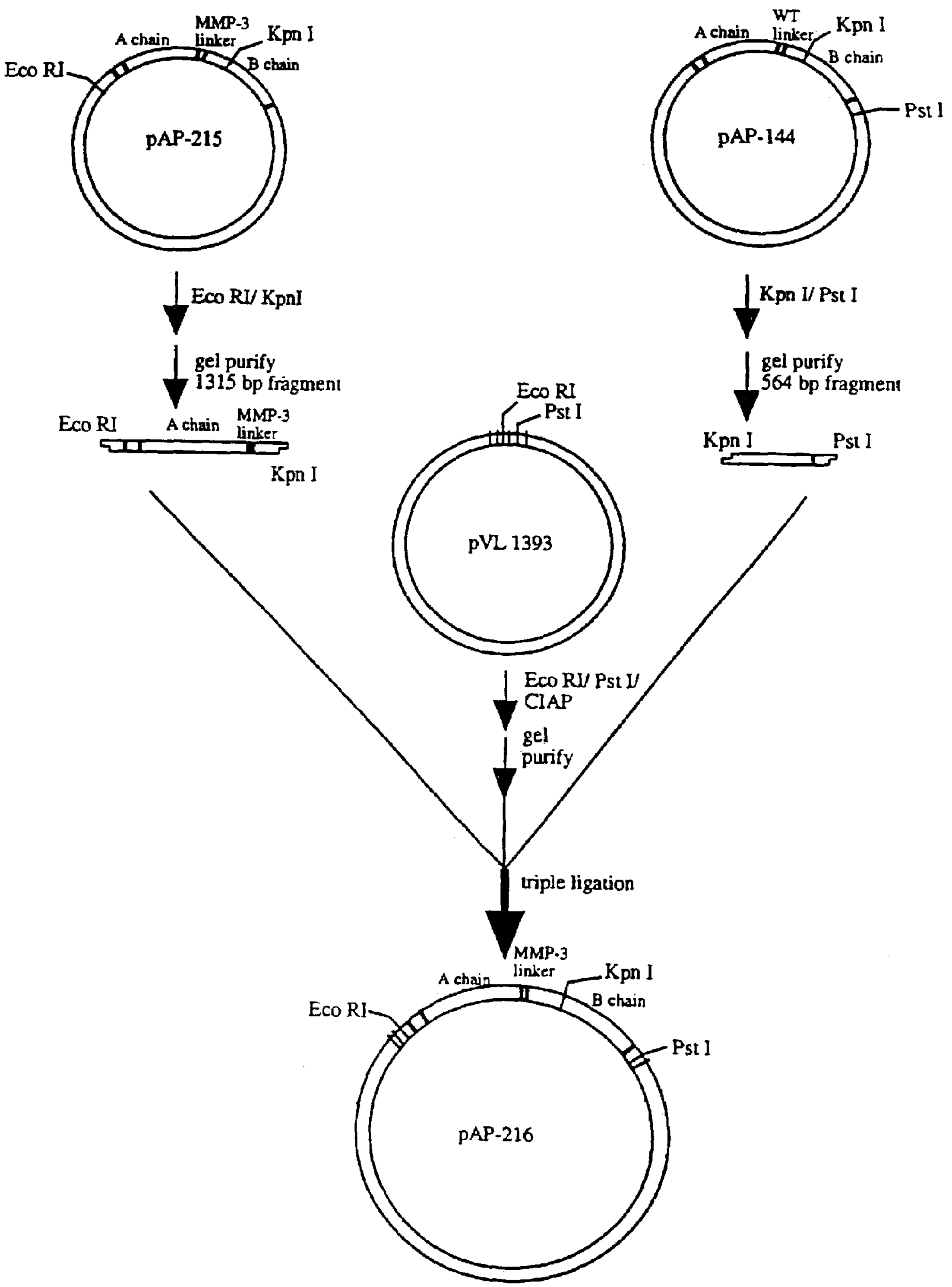
FIG. 3C shows the subcloning of the MMP-3 linker variant into a baculovirus transfer vector.
Figure 4A:
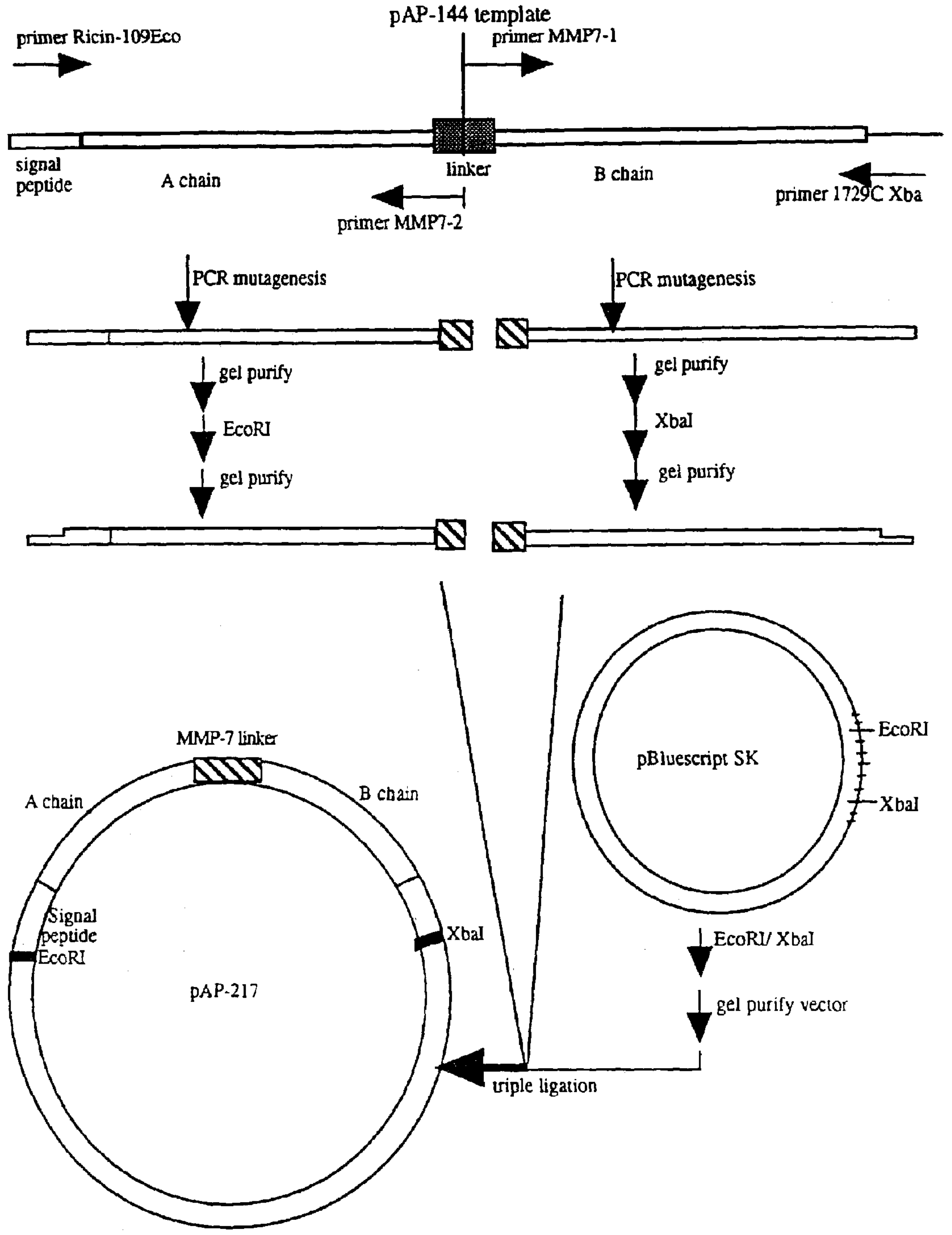
FIG. 4A summarizes the cloning strategy used to generate the pAP-217 construct.
Figure 4B:
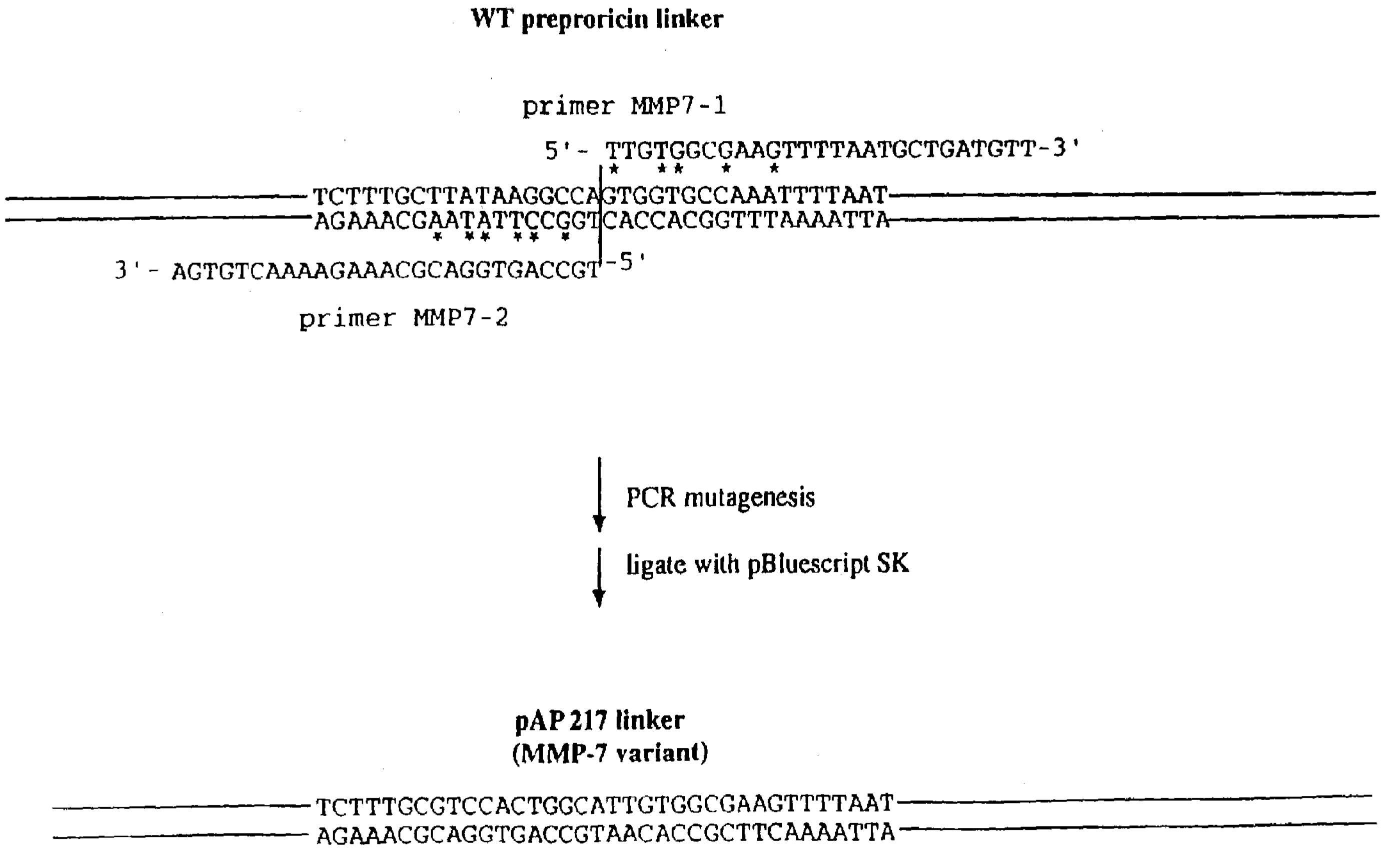
FIG. 4B shows the nucleotide sequence of the MMP-7 linker regions of pAP-217 (SEQ ID NO: 6)
Figure 4C:
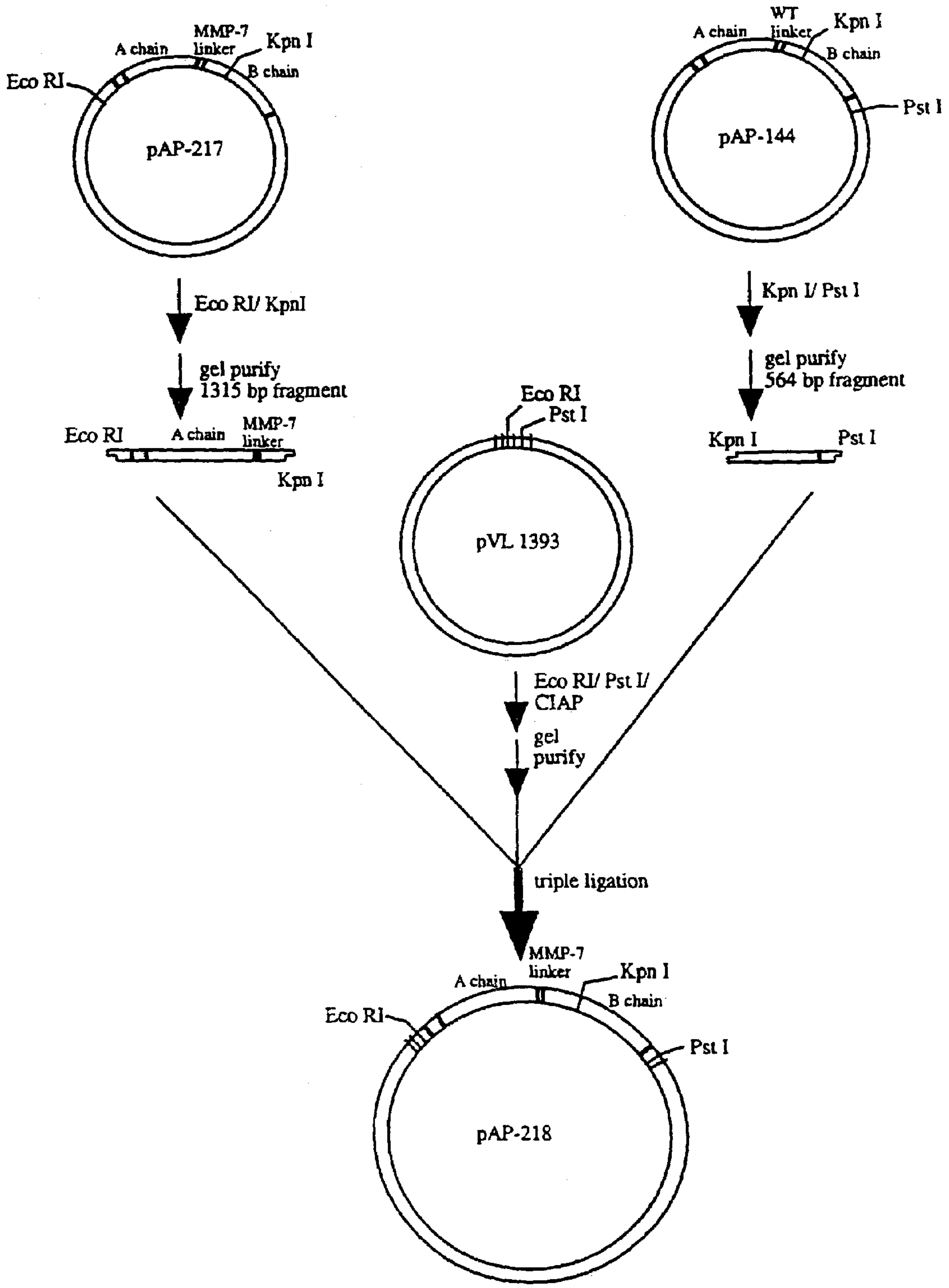
FIG. 4C shows the subcloning of the MMP-7 linker variant into a baculovirus transfer vector.
Figure 5A:
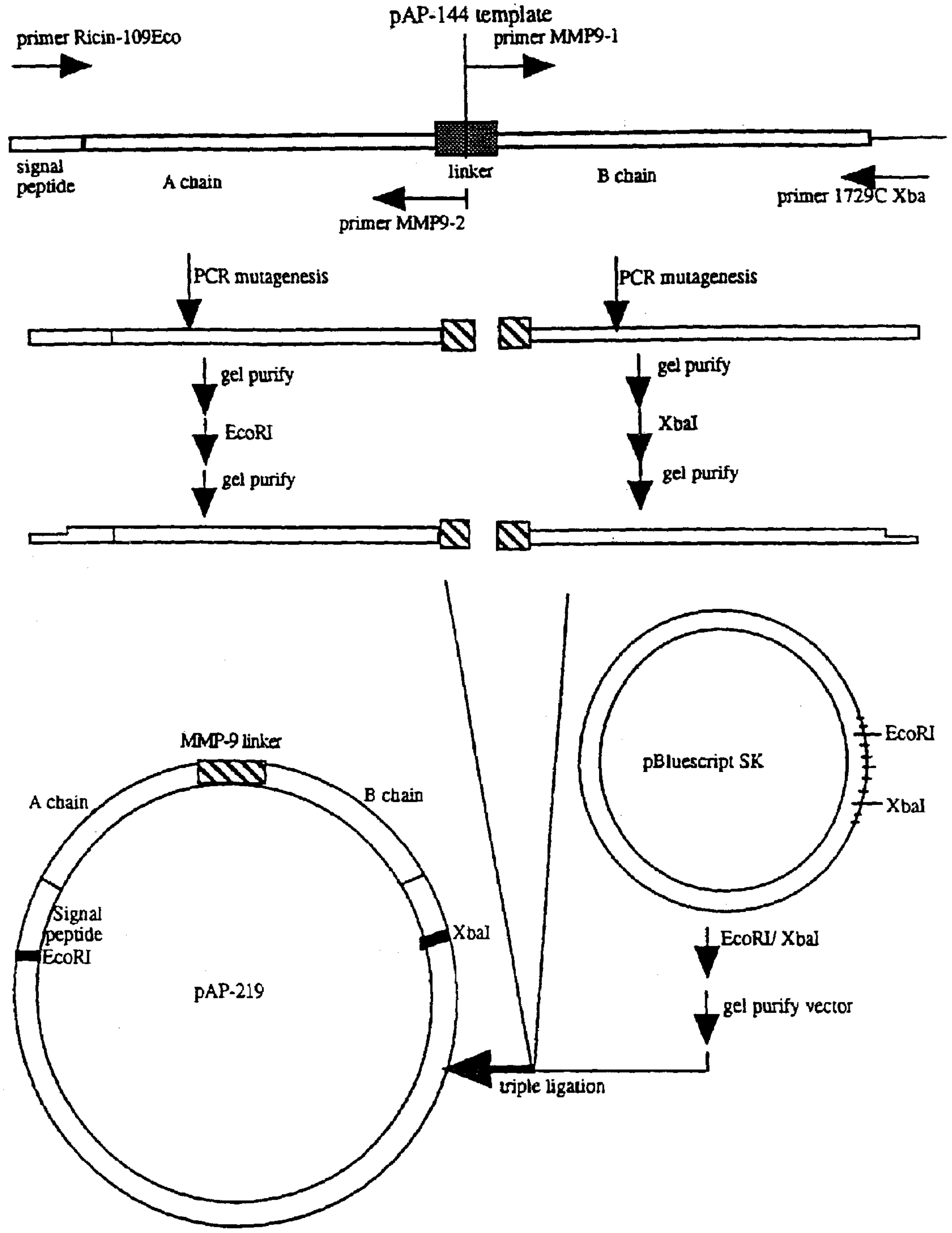
FIG. 5A summarizes the cloning strategy used to generate the pAP-219 construct.
Figure 5C:
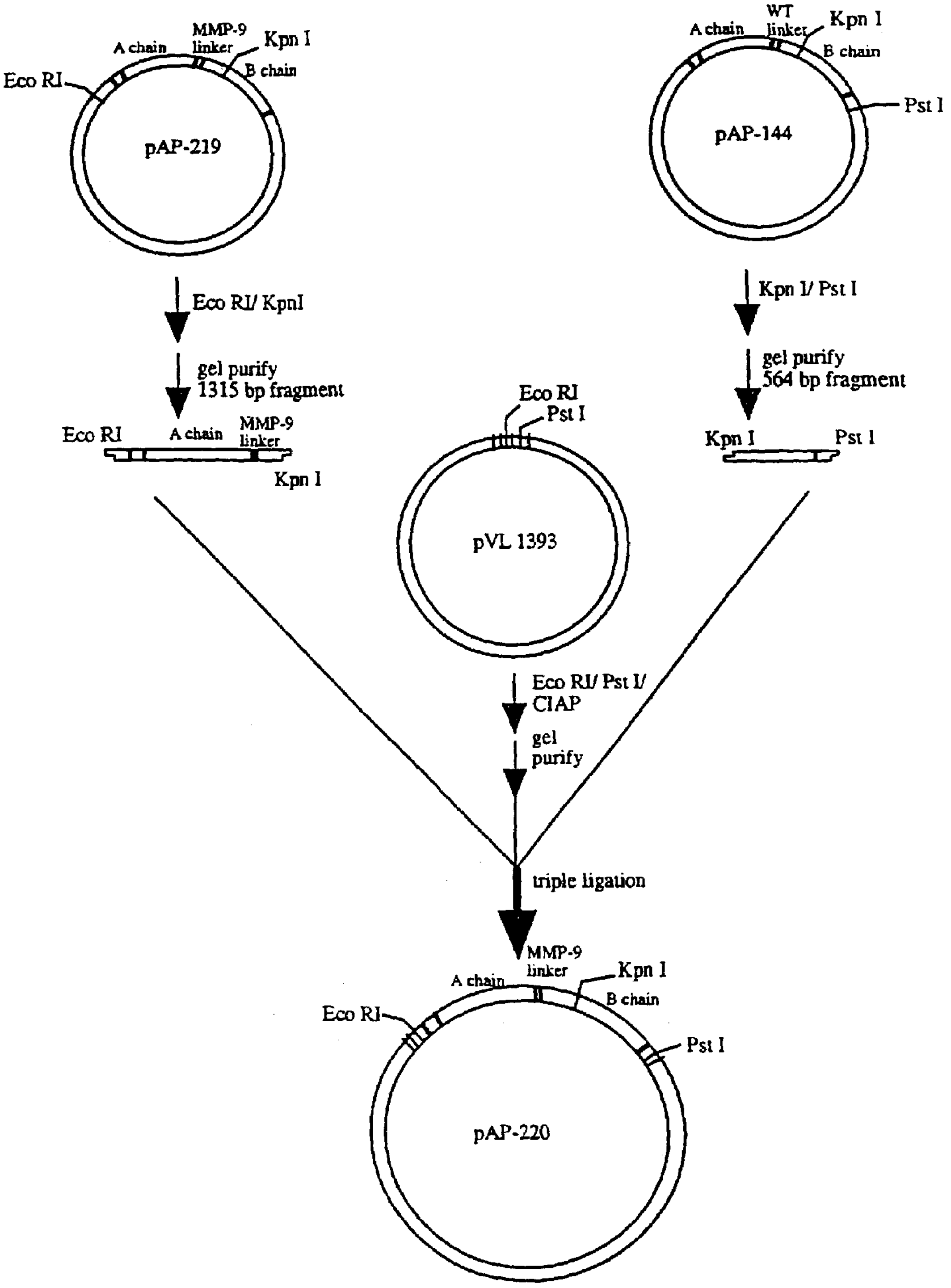
FIG. 5C shows the subcloning of the MMP-9 linker variant into a baculovirus transfer vector.
Figure 6A:
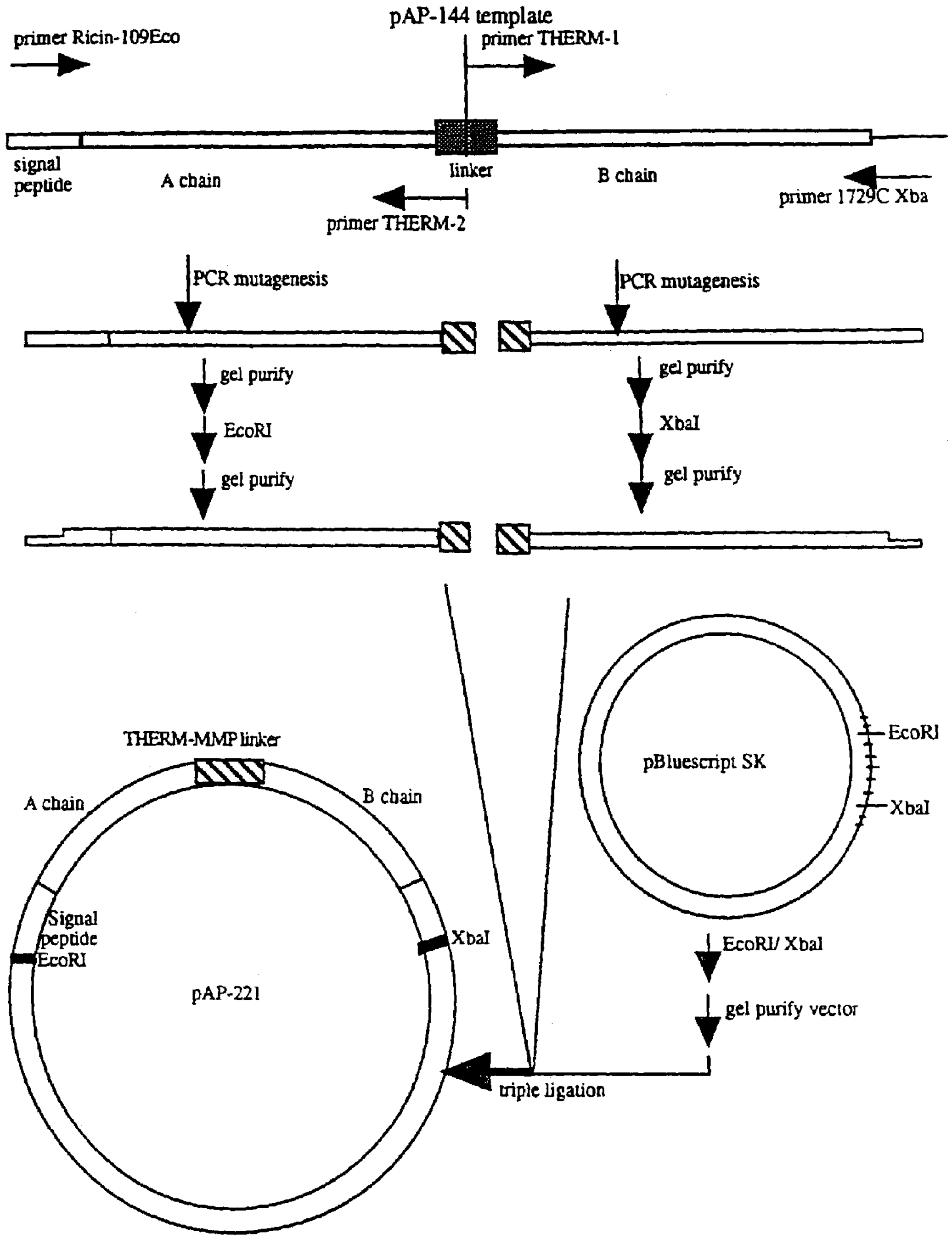
FIG. 6A summarizes the cloning strategy used to generate the pAP-221 construct.
Figure 6B:
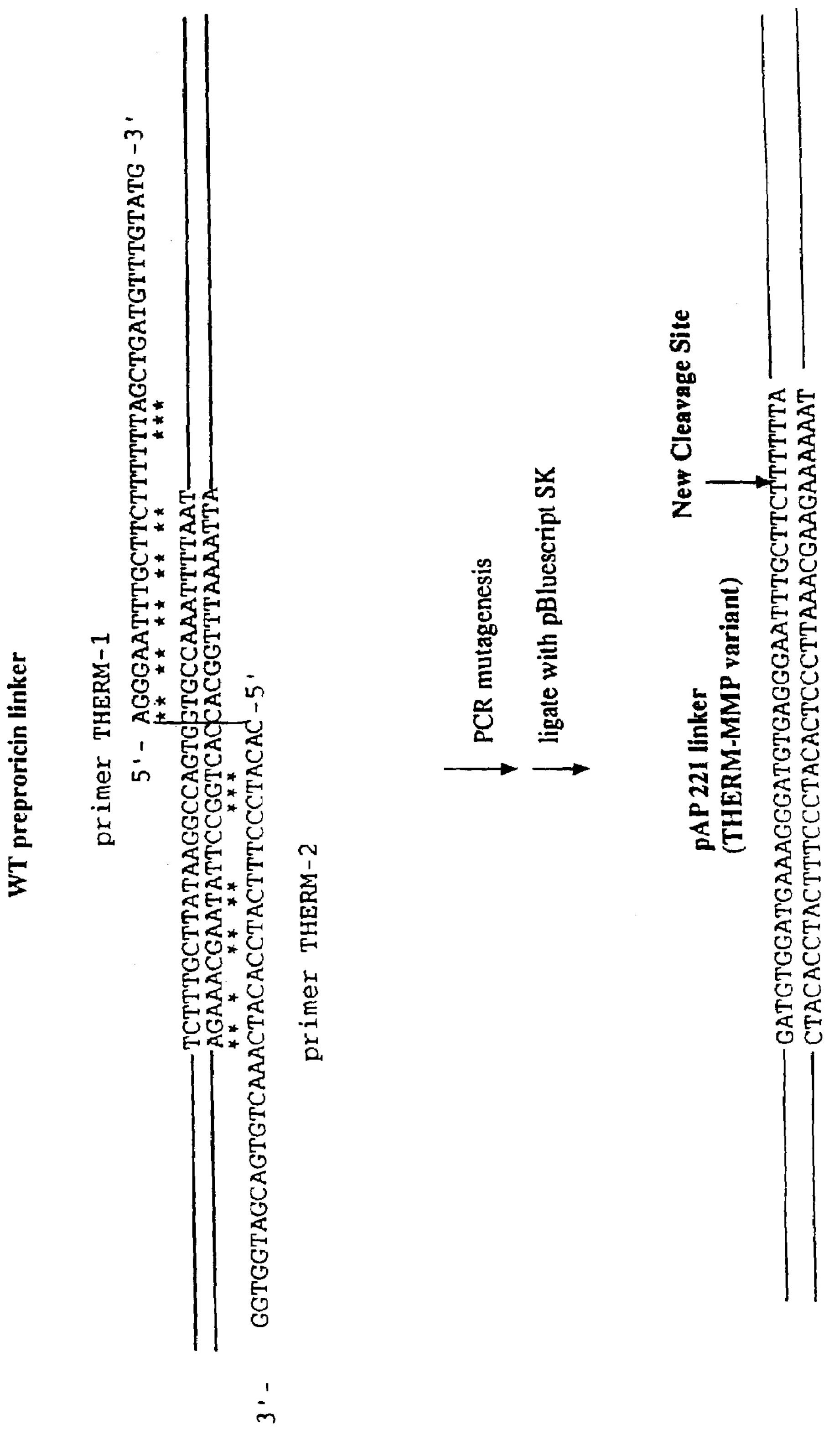
FIG. 6B shows the nucleotide sequence of the thermolysin-like MMP linker regions of pAP-221 (SEQ ID NO: 10)
Figure 6C:
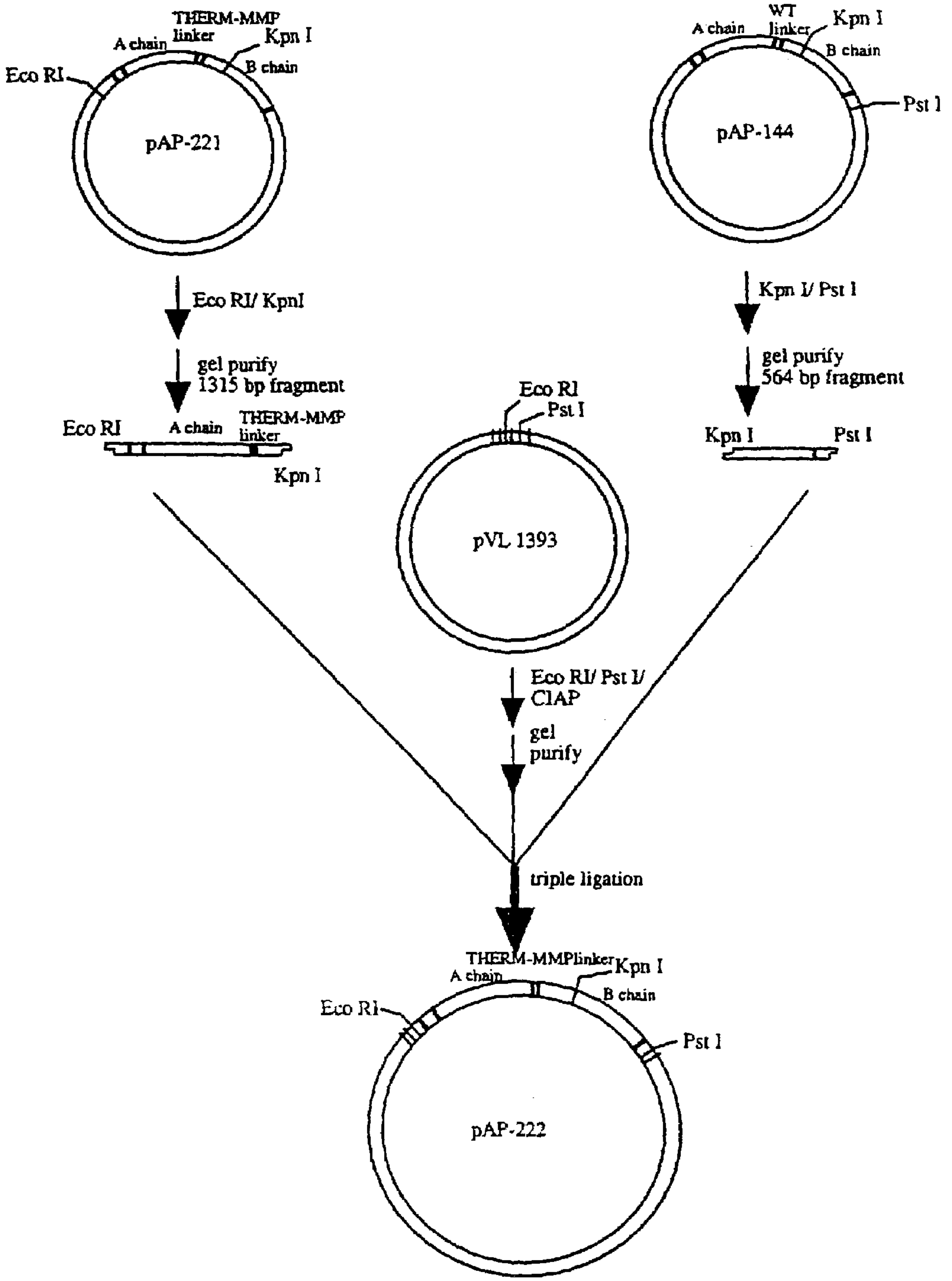
FIG. 6C shows the subcloning of the thermolysin-like MMP linker variant into a baculovirus transfer vector.
Figure 7A:
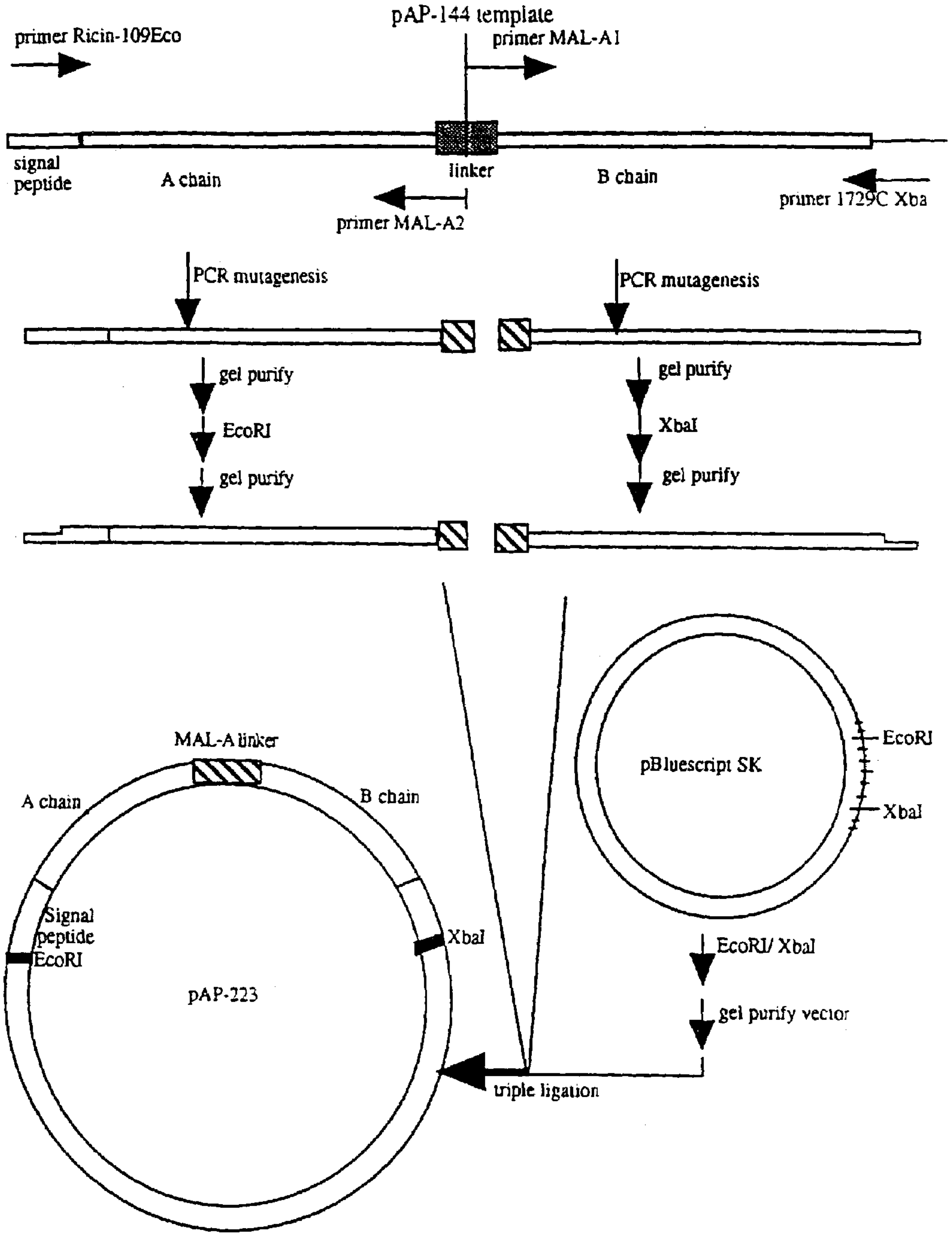
FIG. 7A summarizes the cloning strategy used to generate the pAP-223 construct.
Figure 7C:
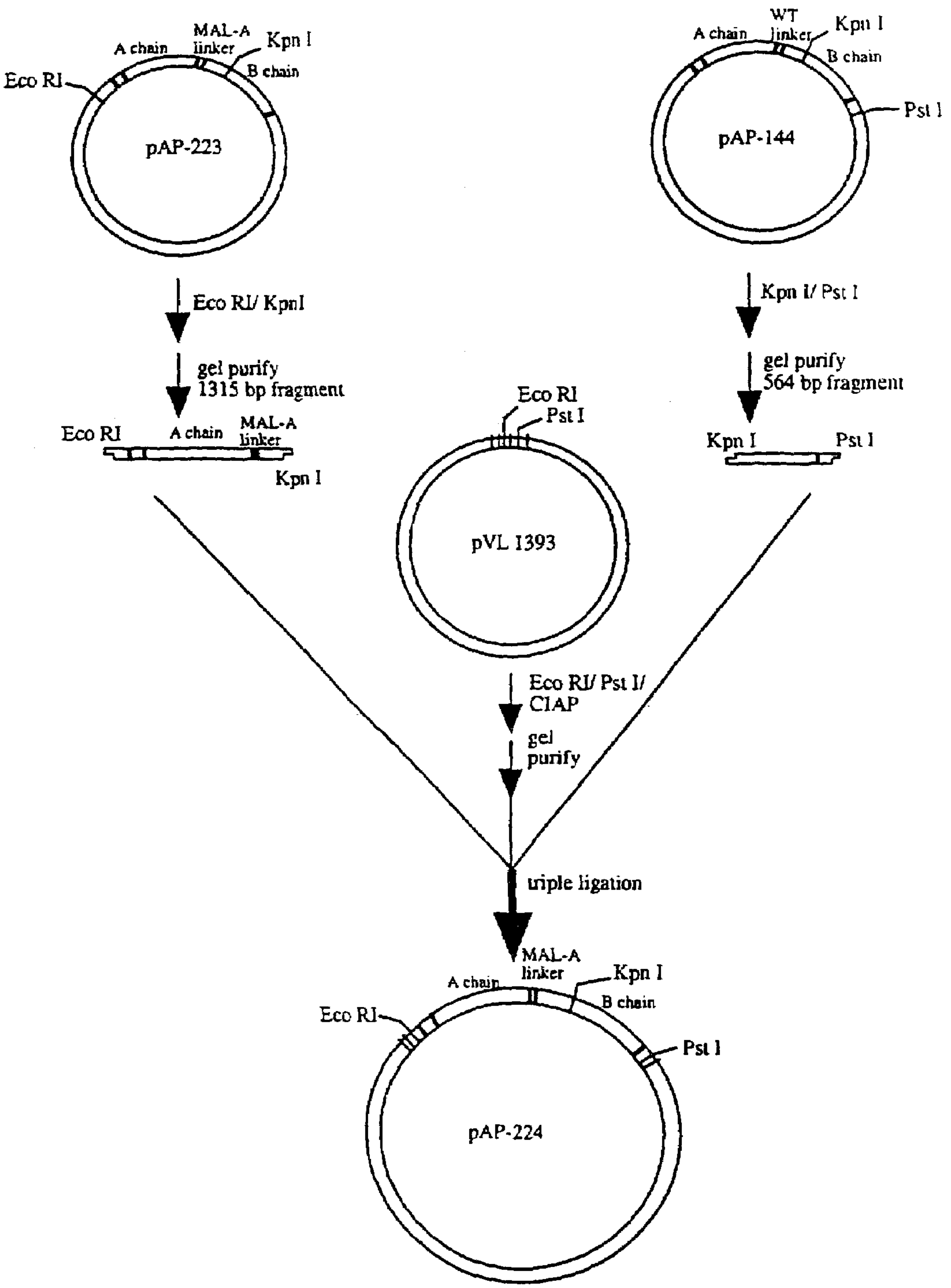
FIG. 7C shows the subcloning of the *Plasmodium falciparum*-A linker variant into a baculovirus transfer vector.
Figure 8A:
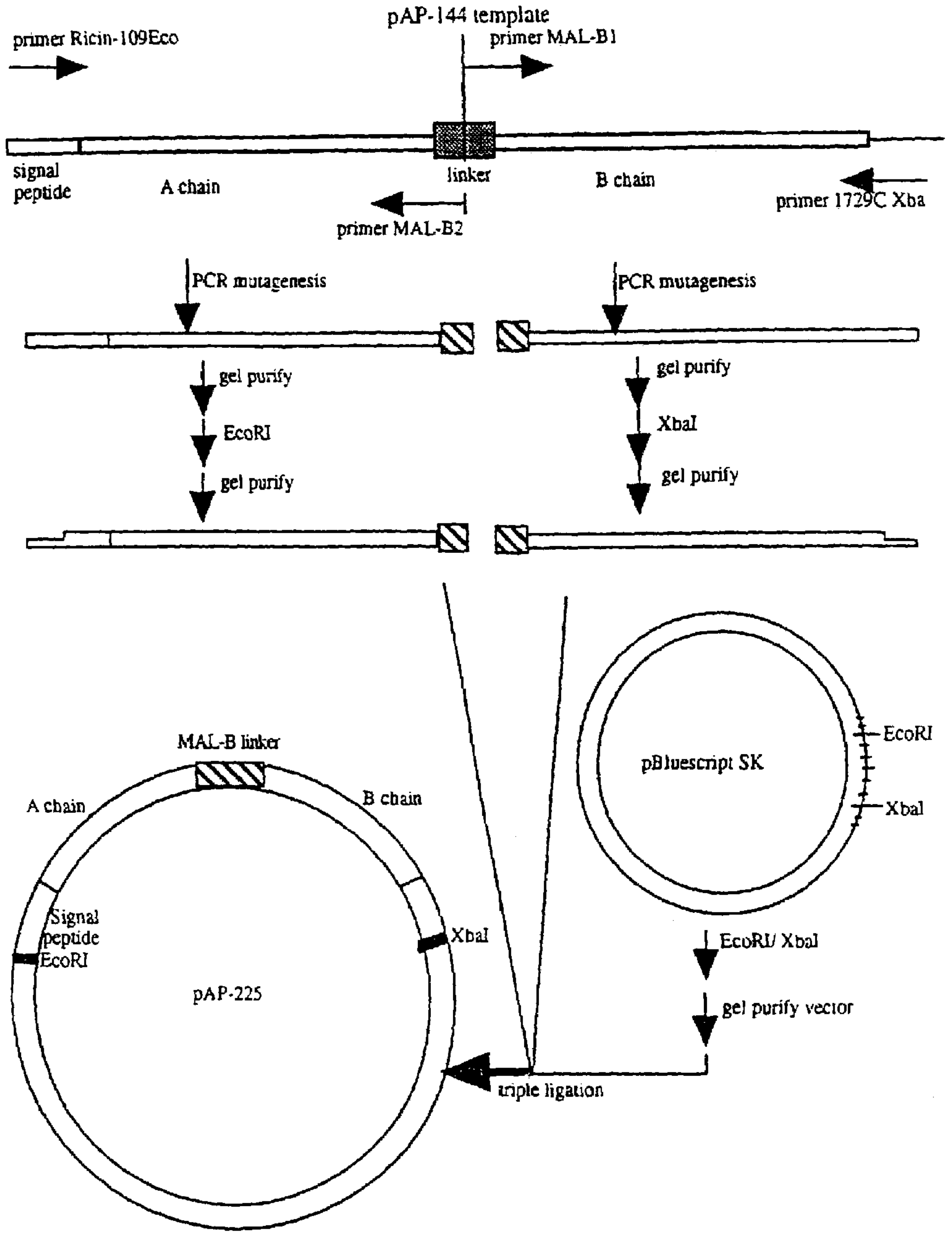
FIG. 8A summarizes the cloning strategy used to generate the pAP-225 construct.
Figure 8B:
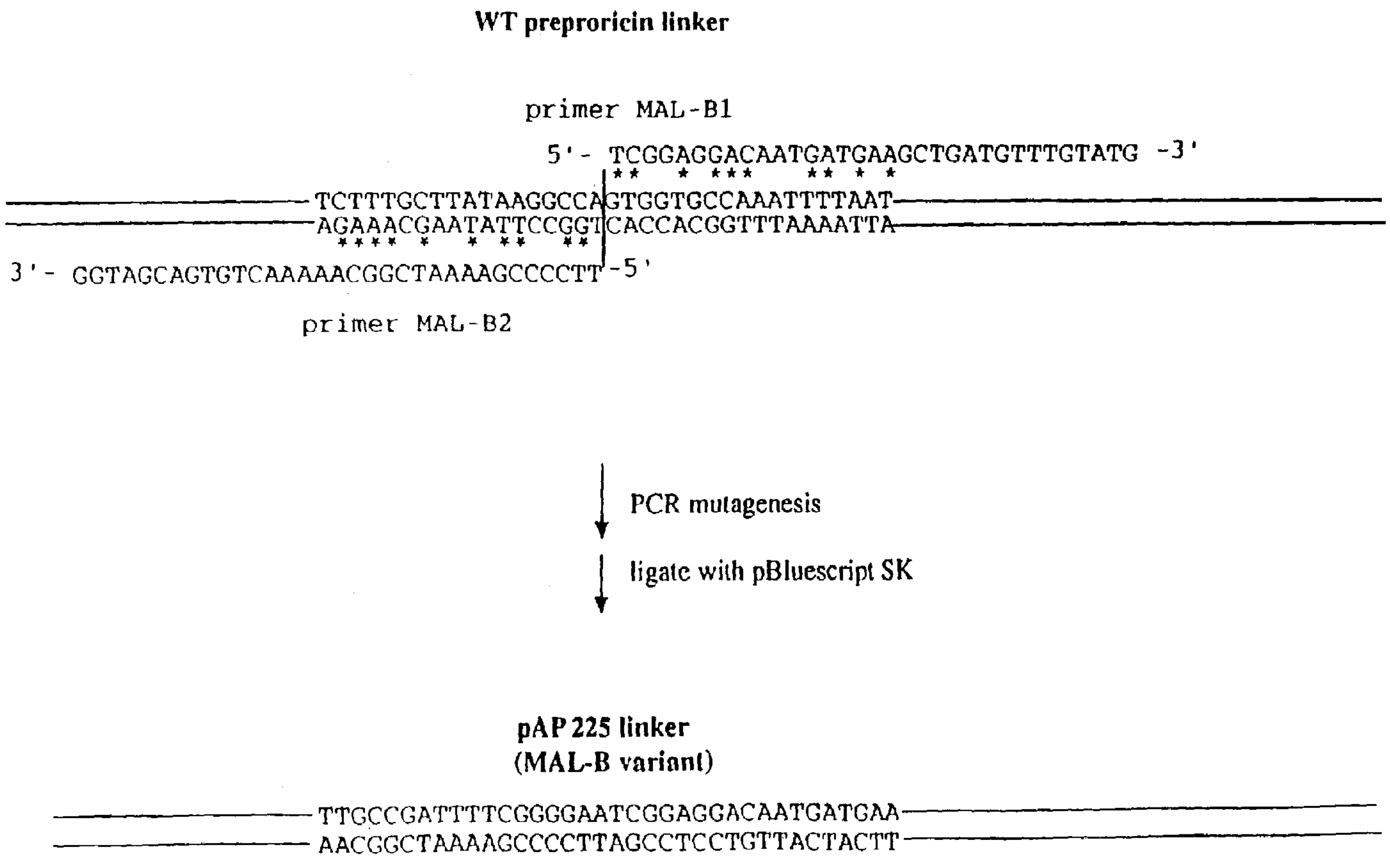
FIG. 8B shows the nucleotide sequence of the *Plasmodium falciparum*-B linker regions of pAP-225 (SEQ ID NO: 14)
Figure 8C:
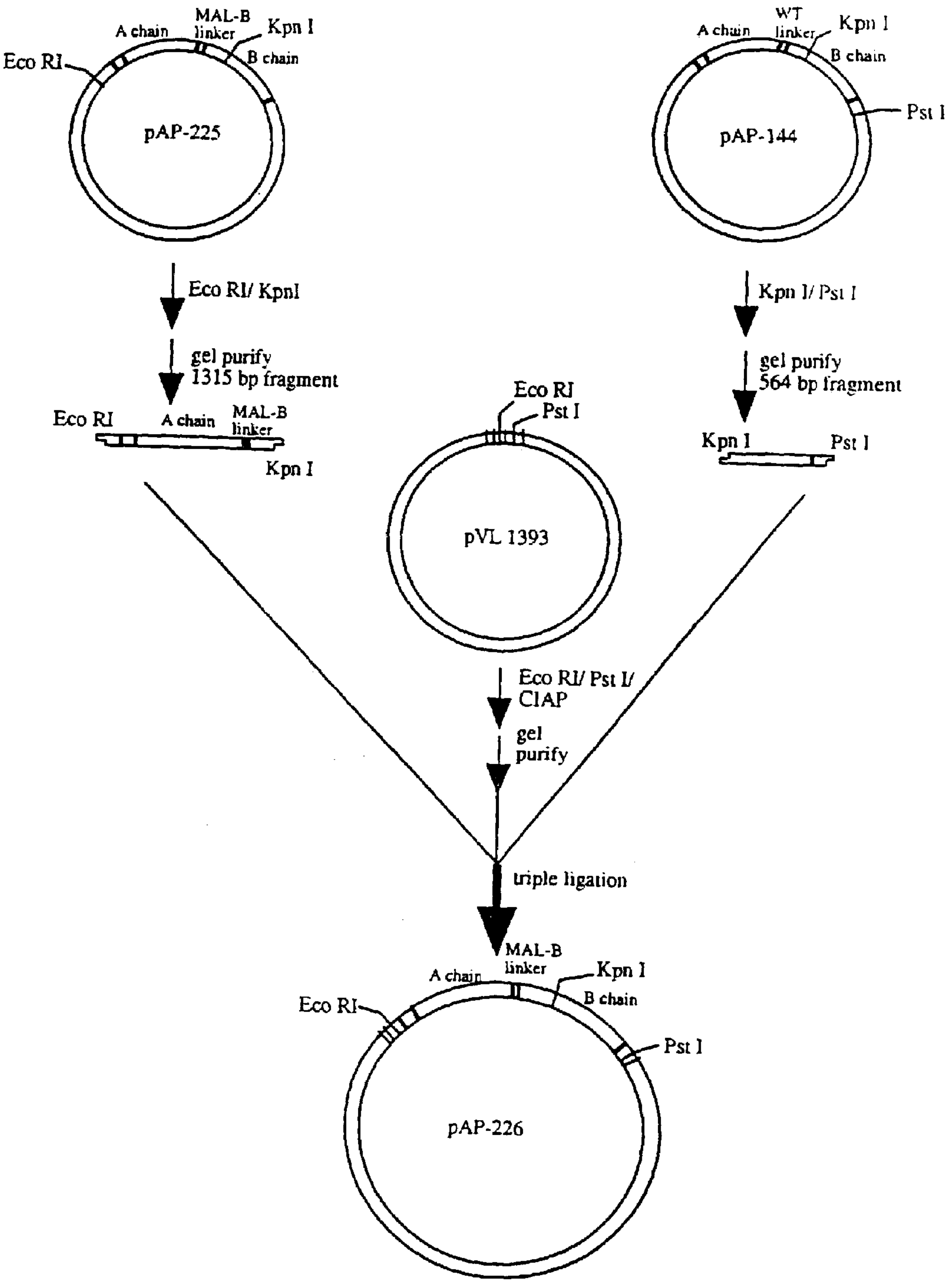
FIG. 8C shows the subcloning of the *Plasmodium falciparum*-B tinker variant into a baculovirus transfer vector.
Figure 9A:
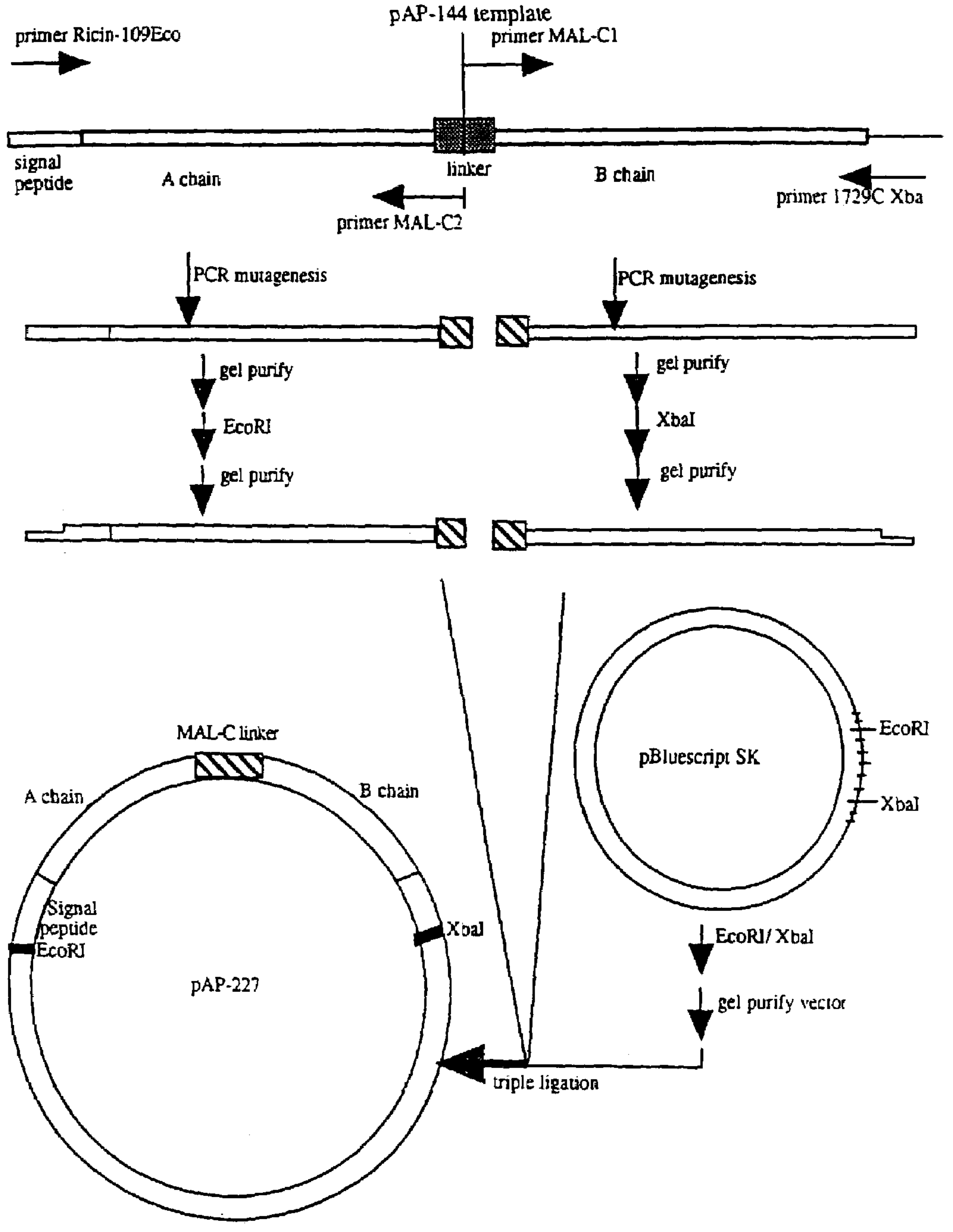
FIG. 9A summarizes the cloning strategy used to generate the pAP-227 construct.
Figure 9B:
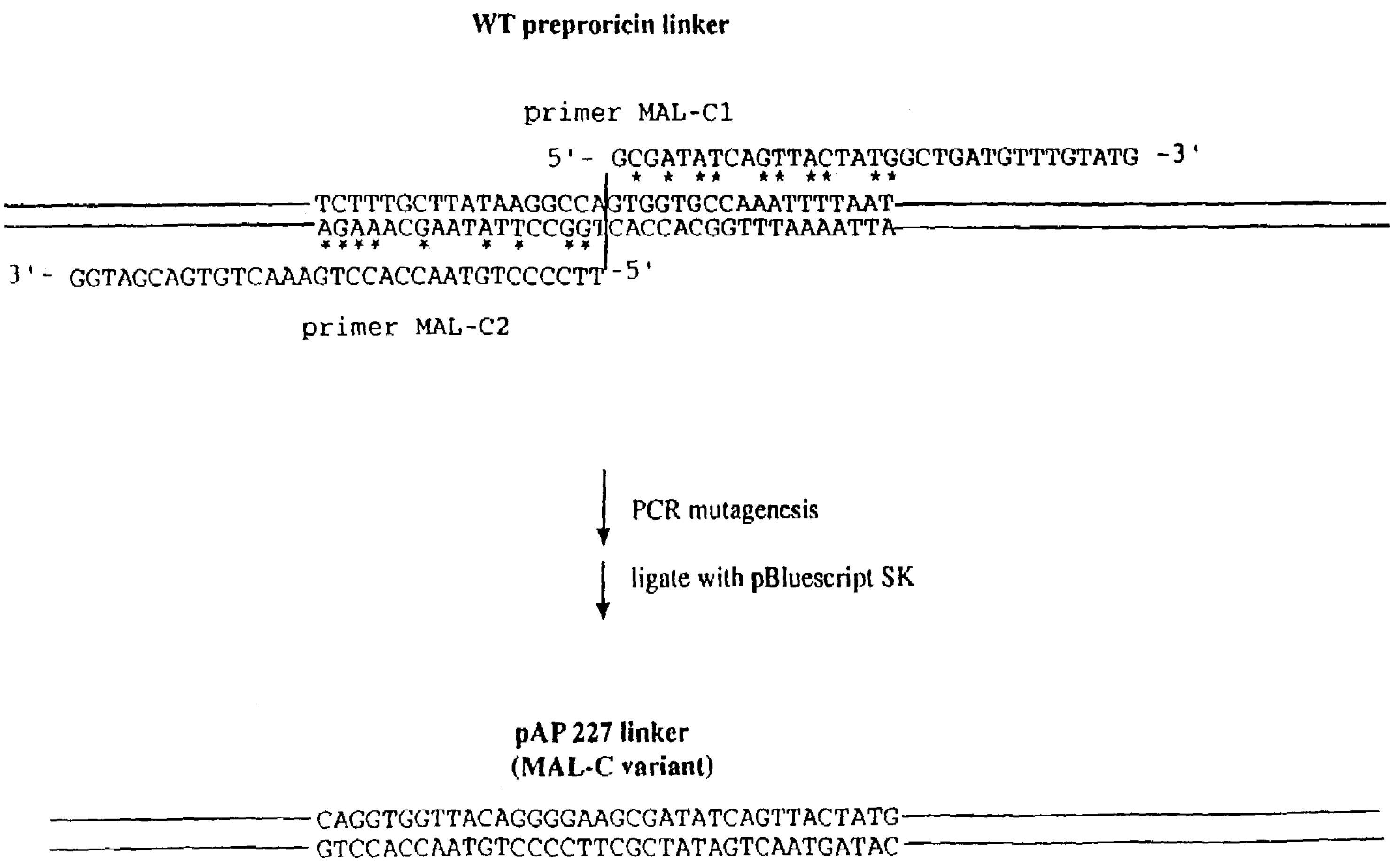
FIG. 9B shows the nucleotide sequence of the *Plasmodium falciparum*-C tinker regions of pAP-227 (SEQ ID NO: 16)
Figure 9C:
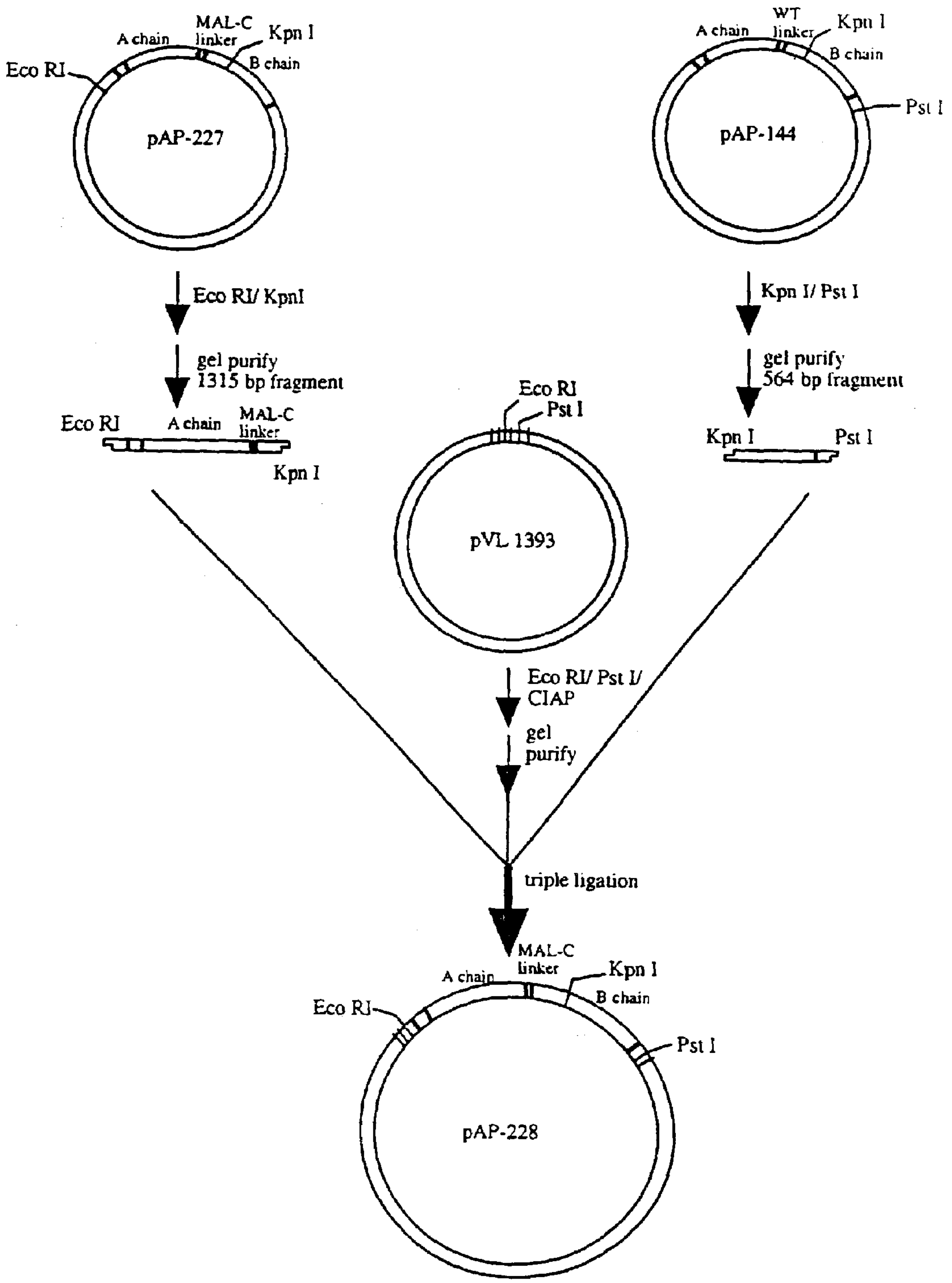
FIG. 9C shows the subcloning of the *Plasmodium falciparum*-C linker variant into a baculovirus transfer vector.
Figure 10A:
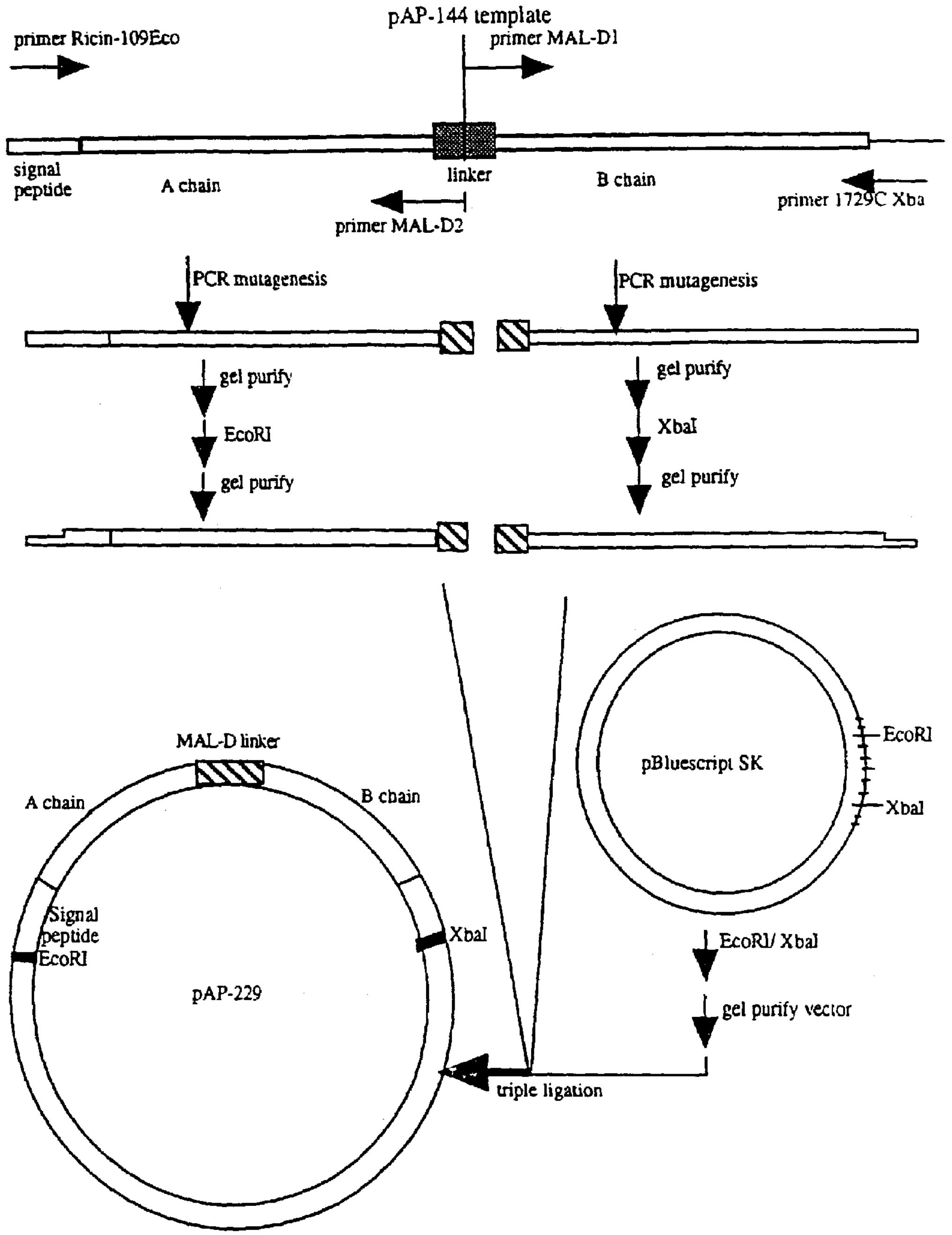
FIG. 10A summarizes the cloning strategy used to generate the pAP-229 construct.
Figure 10C:
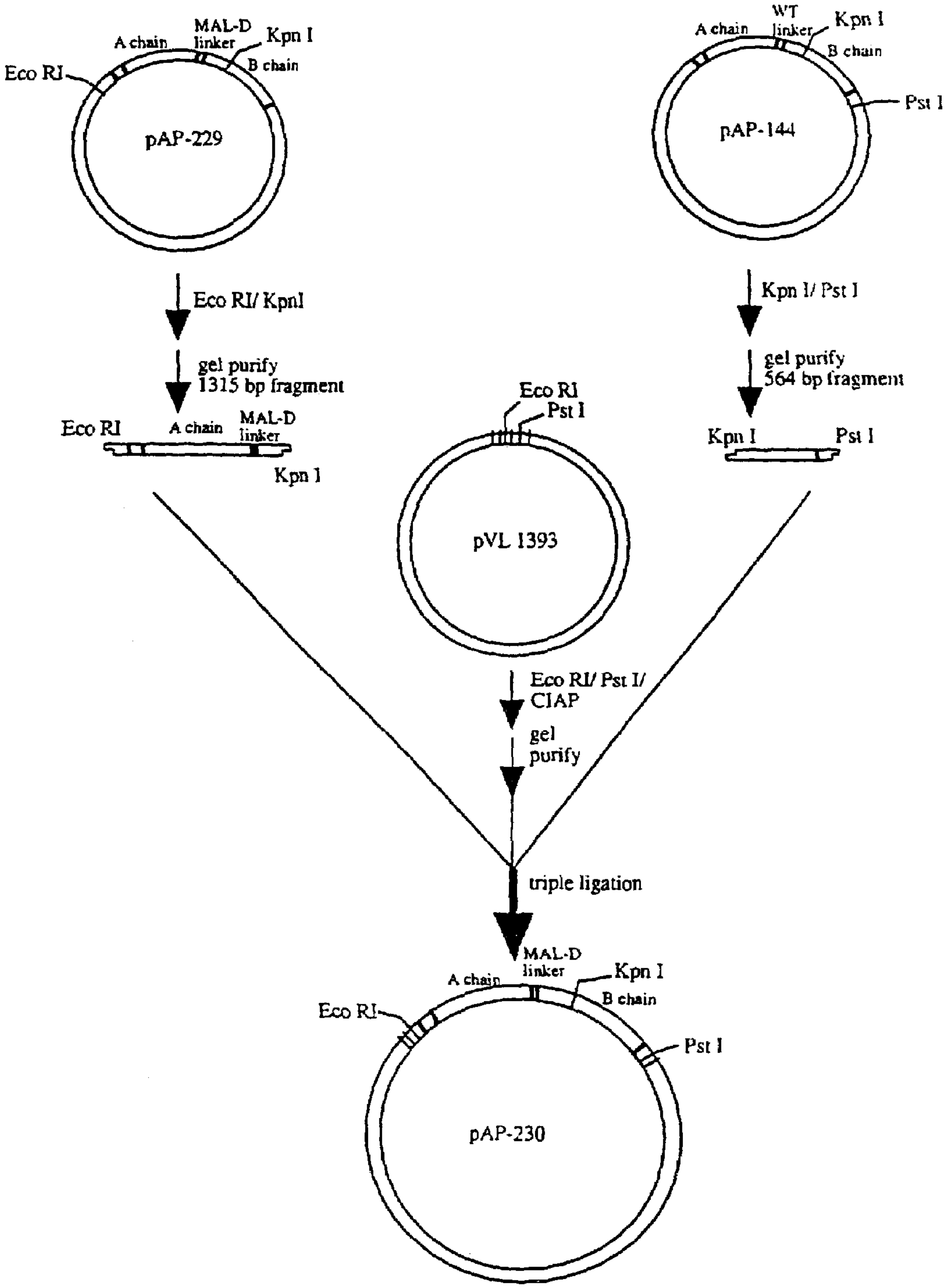
FIG. 10C shows the subcloning of the *Plasmodium falciparum*-D linker variant into a baculovirus transfer vector.
Figure 11A:
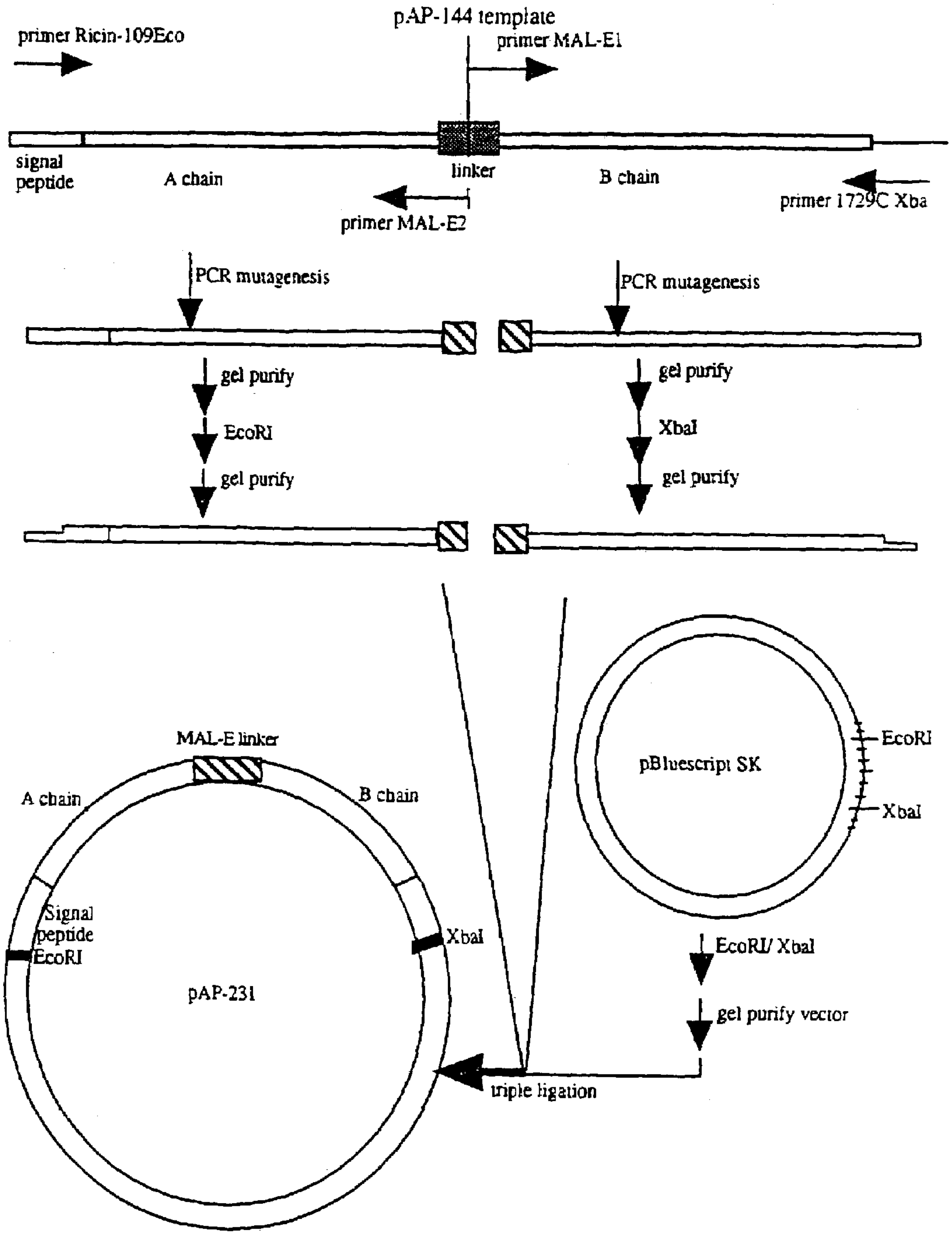
FIG. 11A summarizes the cloning strategy used to generate the pAP-231 construct.
Figure 11B:
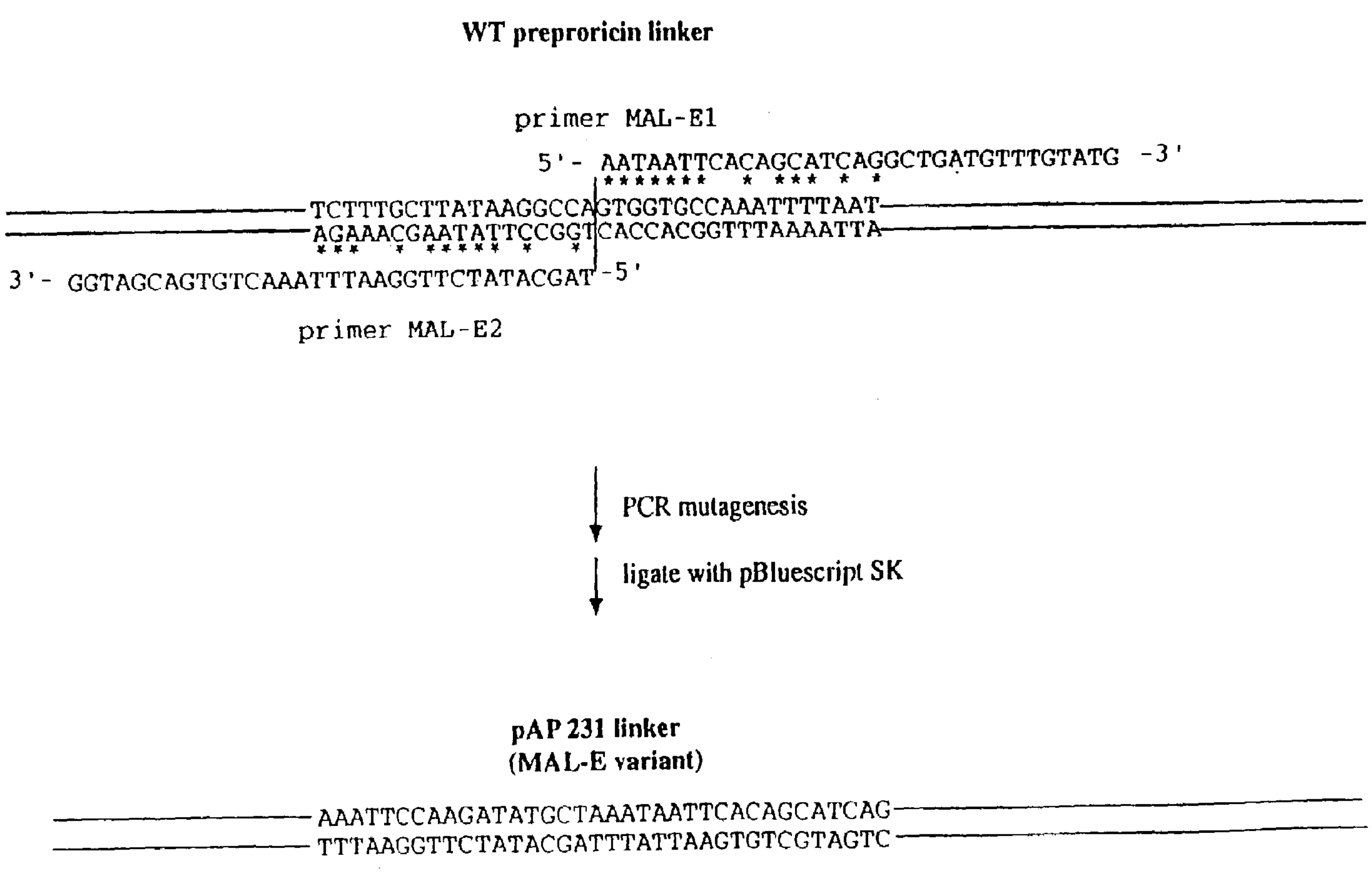
FIG. 11B shows the nucleotide sequence of the *Plasmodium falciparum*-E linker regions of pAP-231 (SEQ ID NO: 20)
Figure 11C:
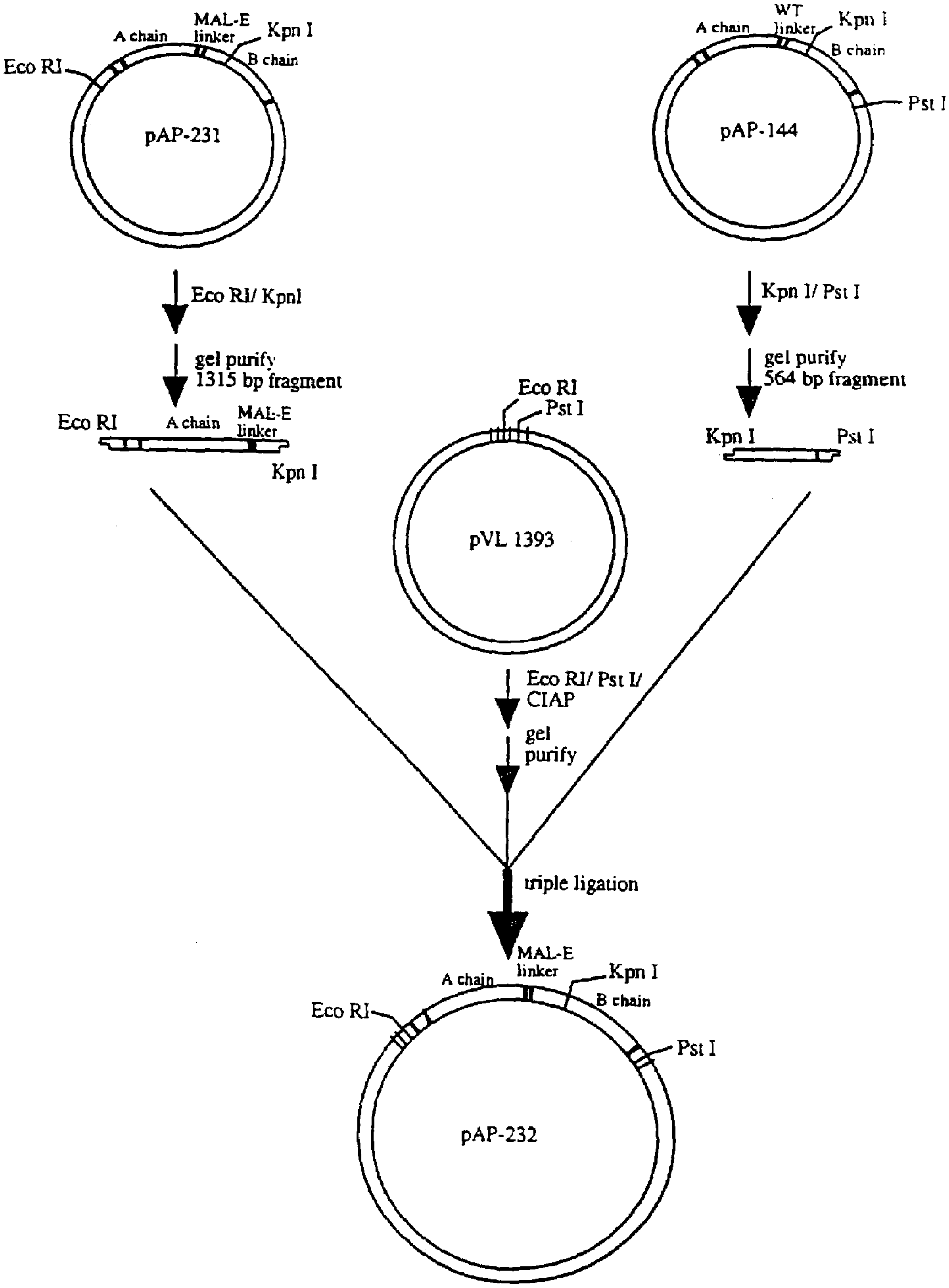
FIG. 11C shows the subcloning of the *Plasmodium falciparum*-E linker variant into a baculovirus transfer vector.
Figure 12A:
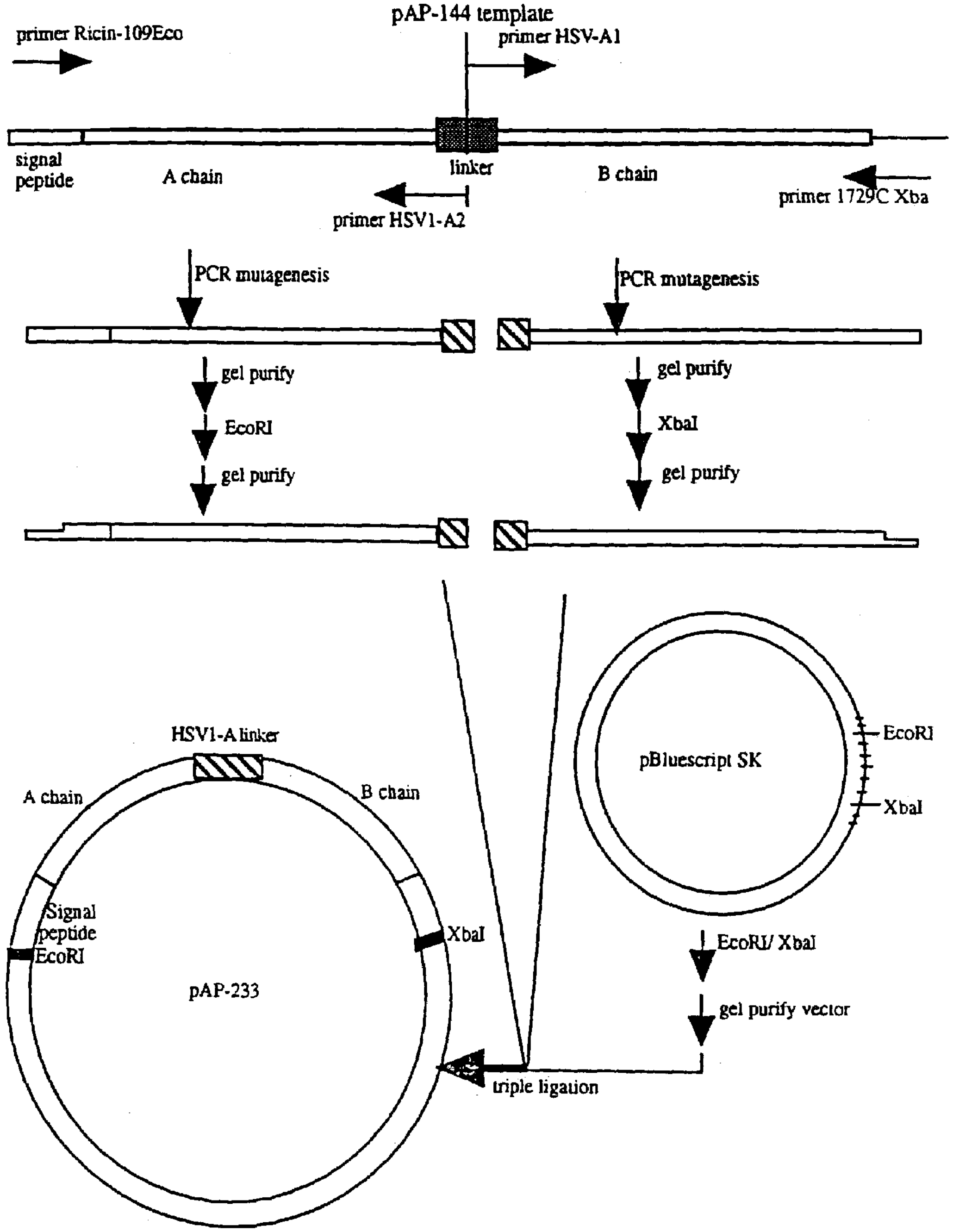
FIG. 12A summarizes the cloning strategy used to generate the pAP-233 construct.
Figure 12C:
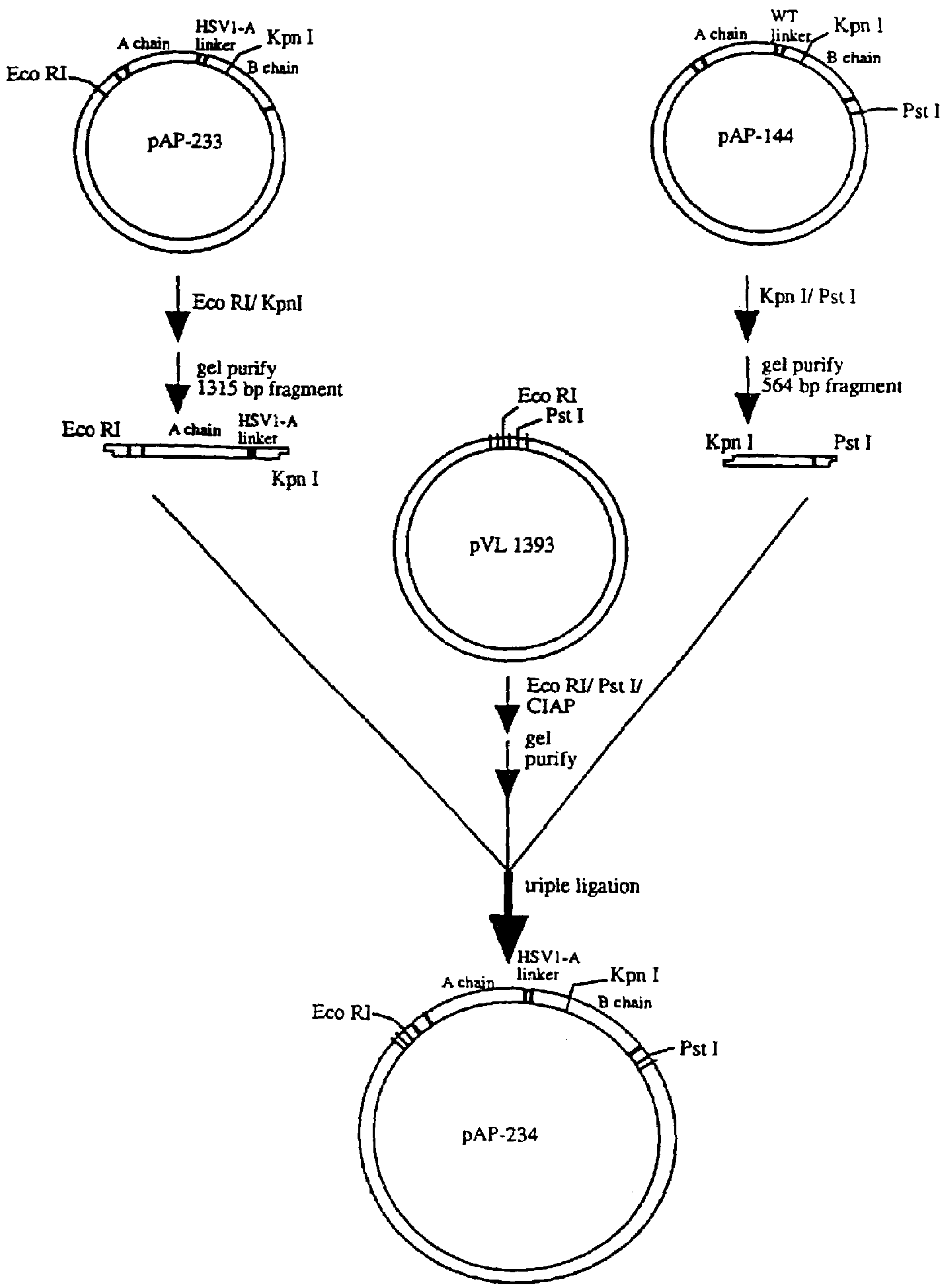
FIG. 12C shows the subcloning of the HSV-A linker variant into a baculovirus transfer vector.
Figure 13A:
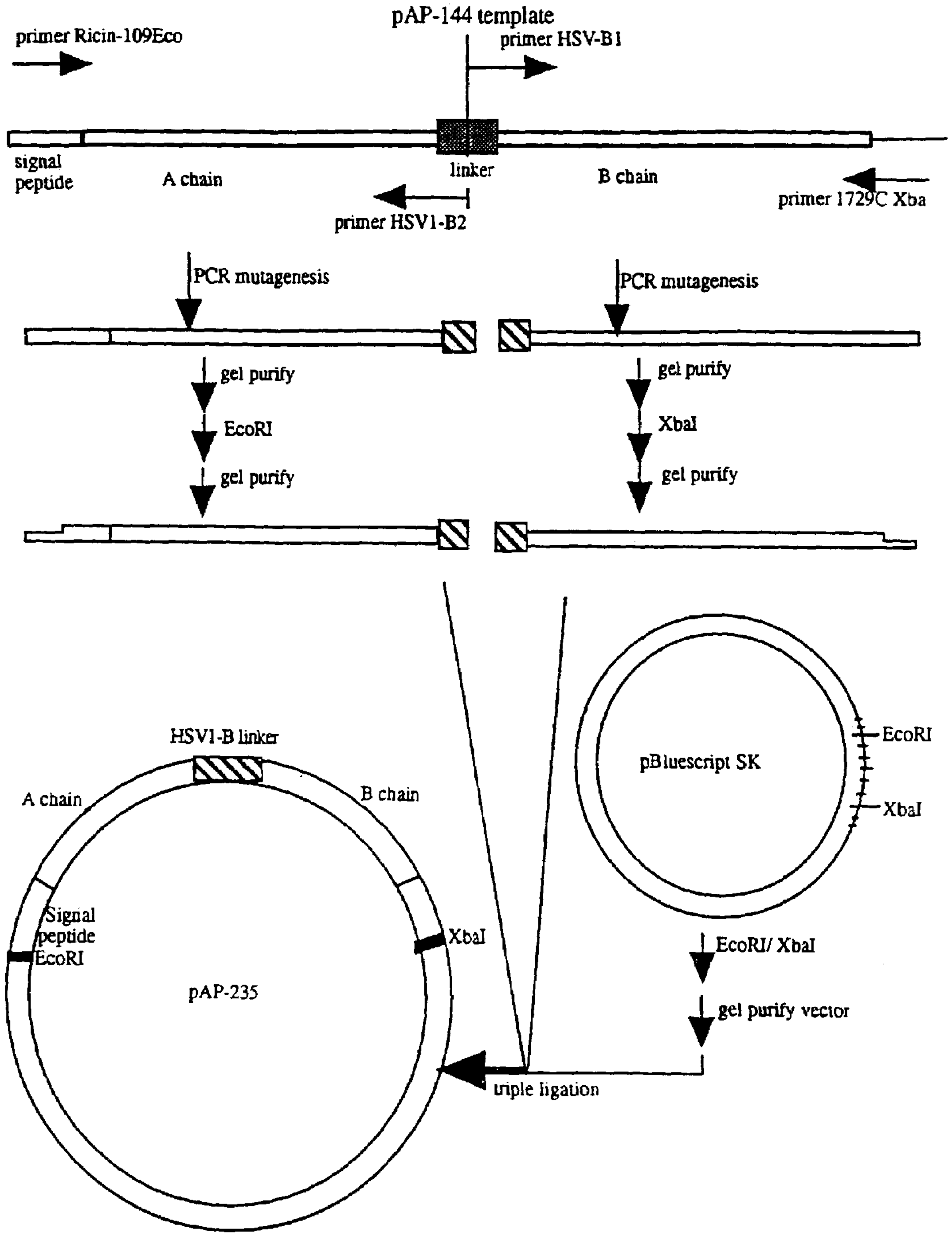
FIG. 13A summarizes the cloning strategy used to generate the pAP-235 construct.
Figure 13B:
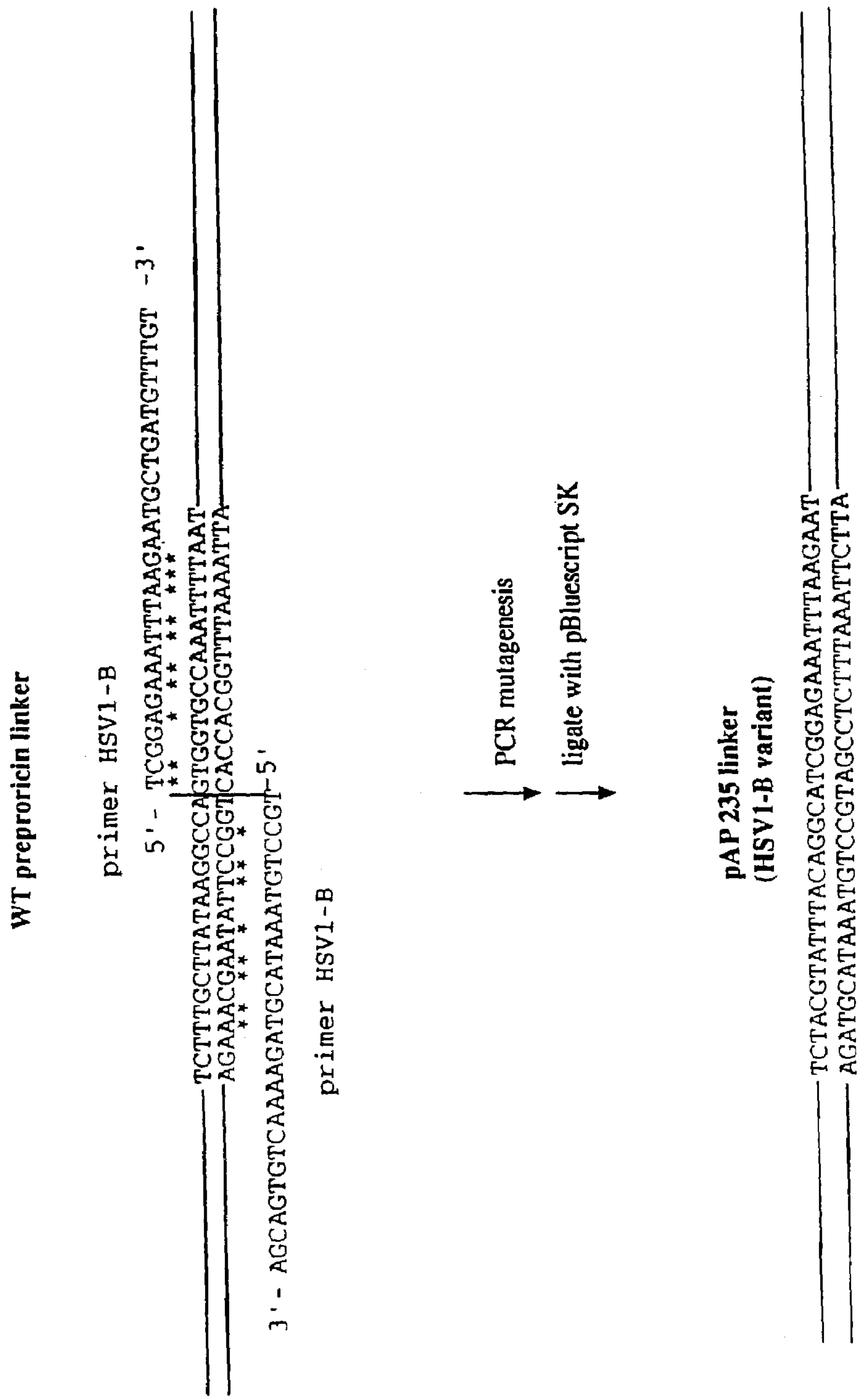
FIG. 13B shows the nucleotide sequence of the HSV-B linker regions of pAP-235 (SEQ ID NO: 24)
Figure 13C:
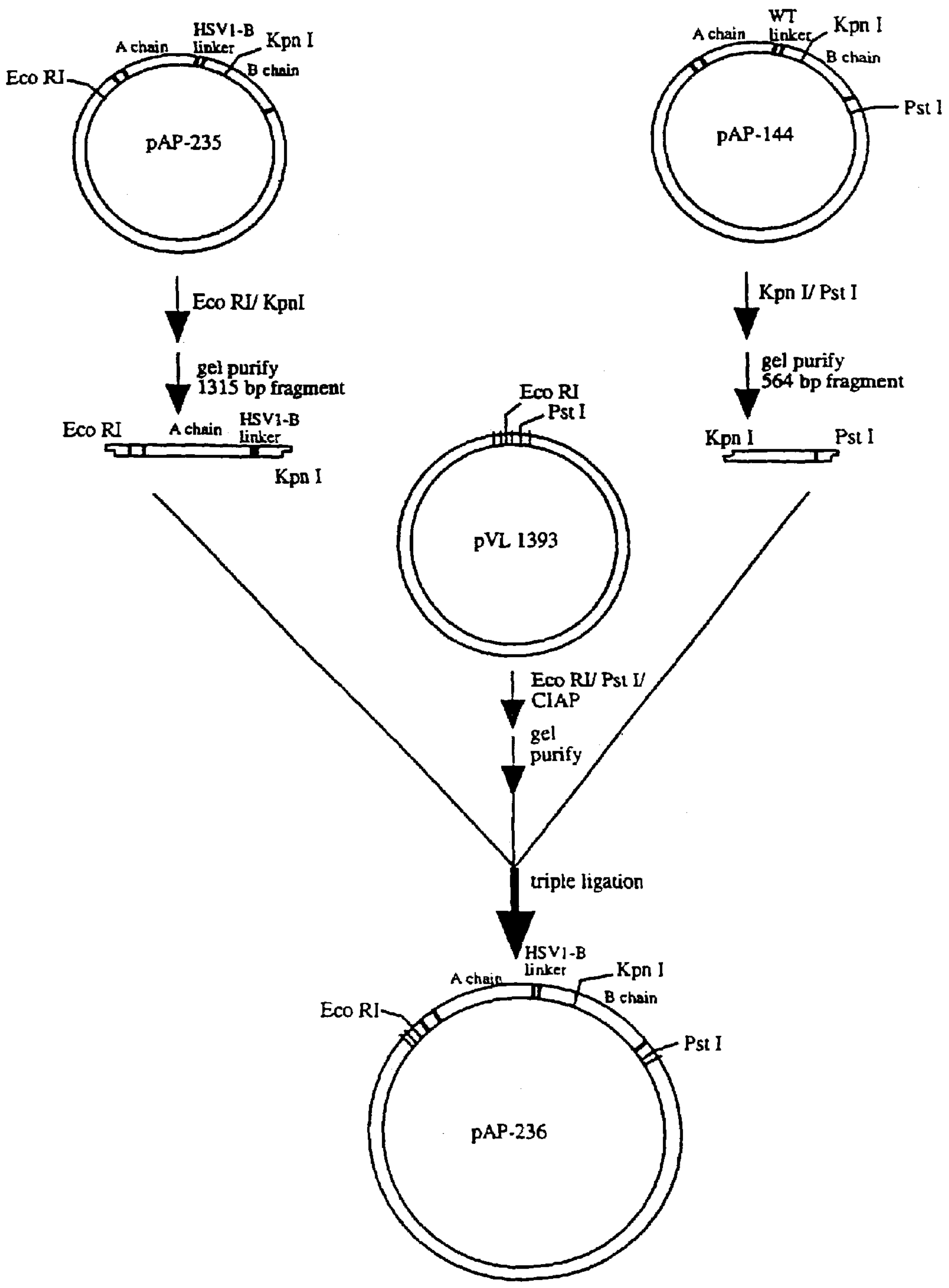
FIG. 13C shows the subcloning of the HSV-B linker variant into a baculovirus transfer vector.
Figure 14A:
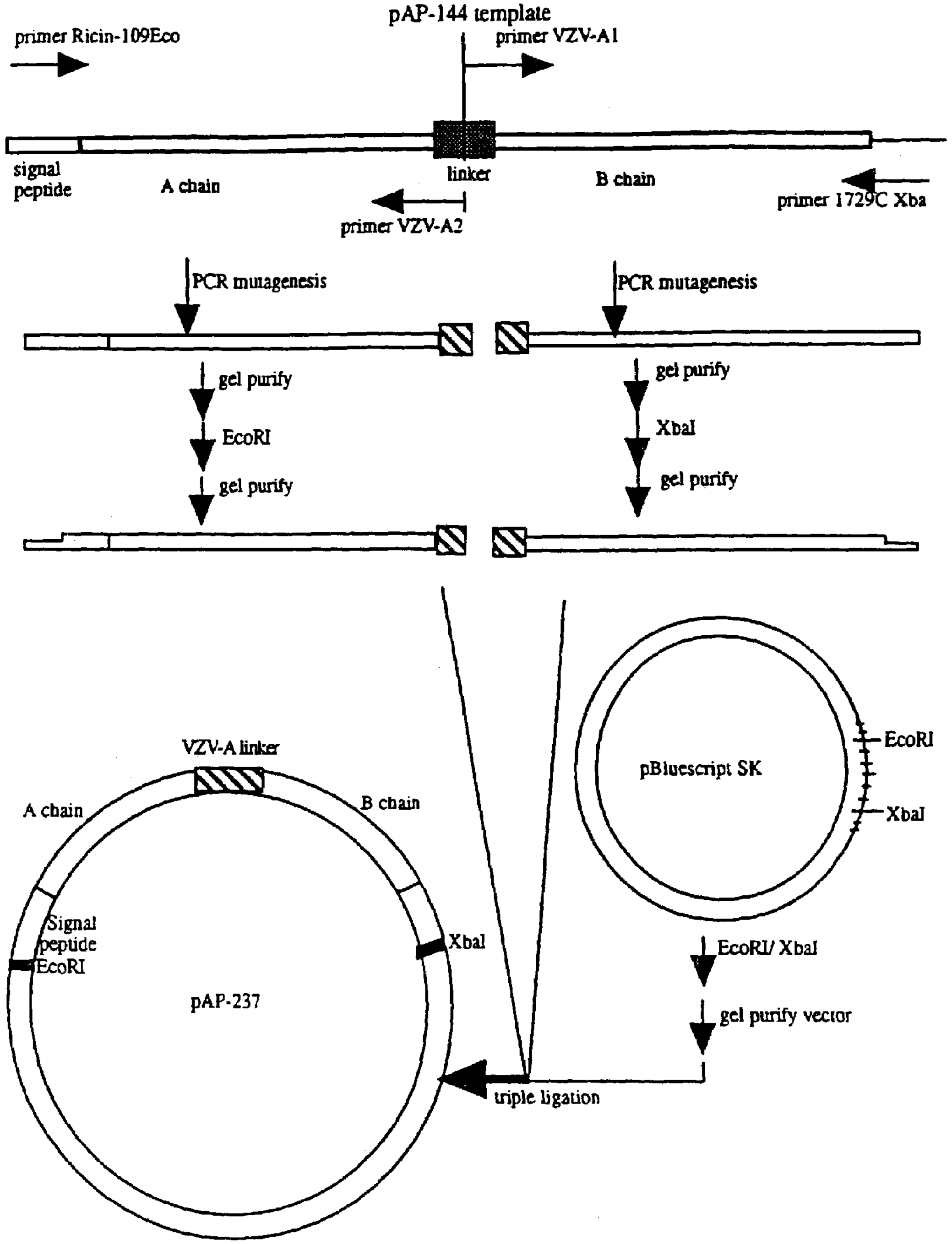
FIG. 14A summarizes the cloning strategy used to generate the pAP-237 construct.
Figure 14B:
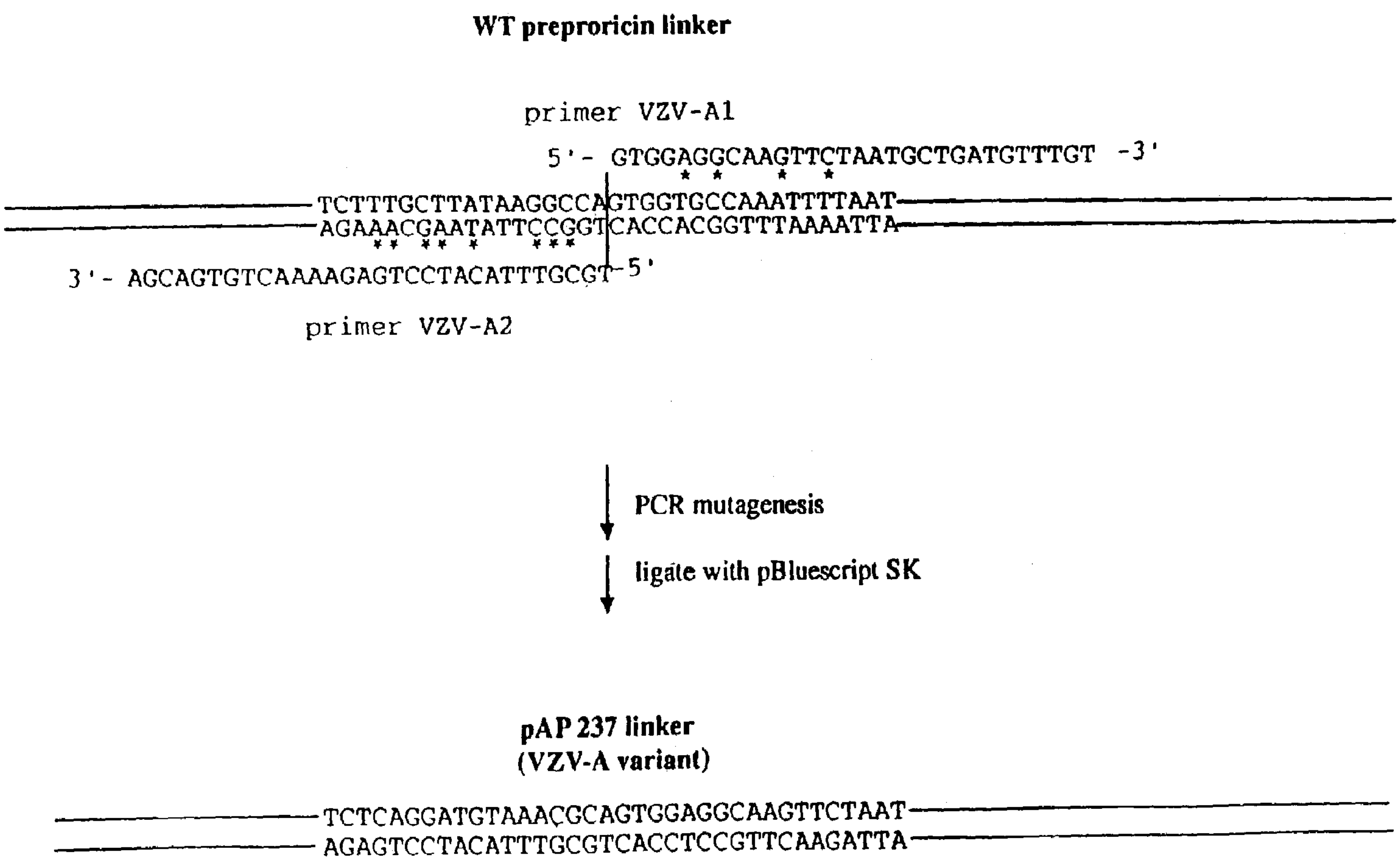
FIG. 14B shows the nucleotide sequence of the VZV-A linker regions of pAP-237 (SEQ ID NO: 26)
Figure 14C:
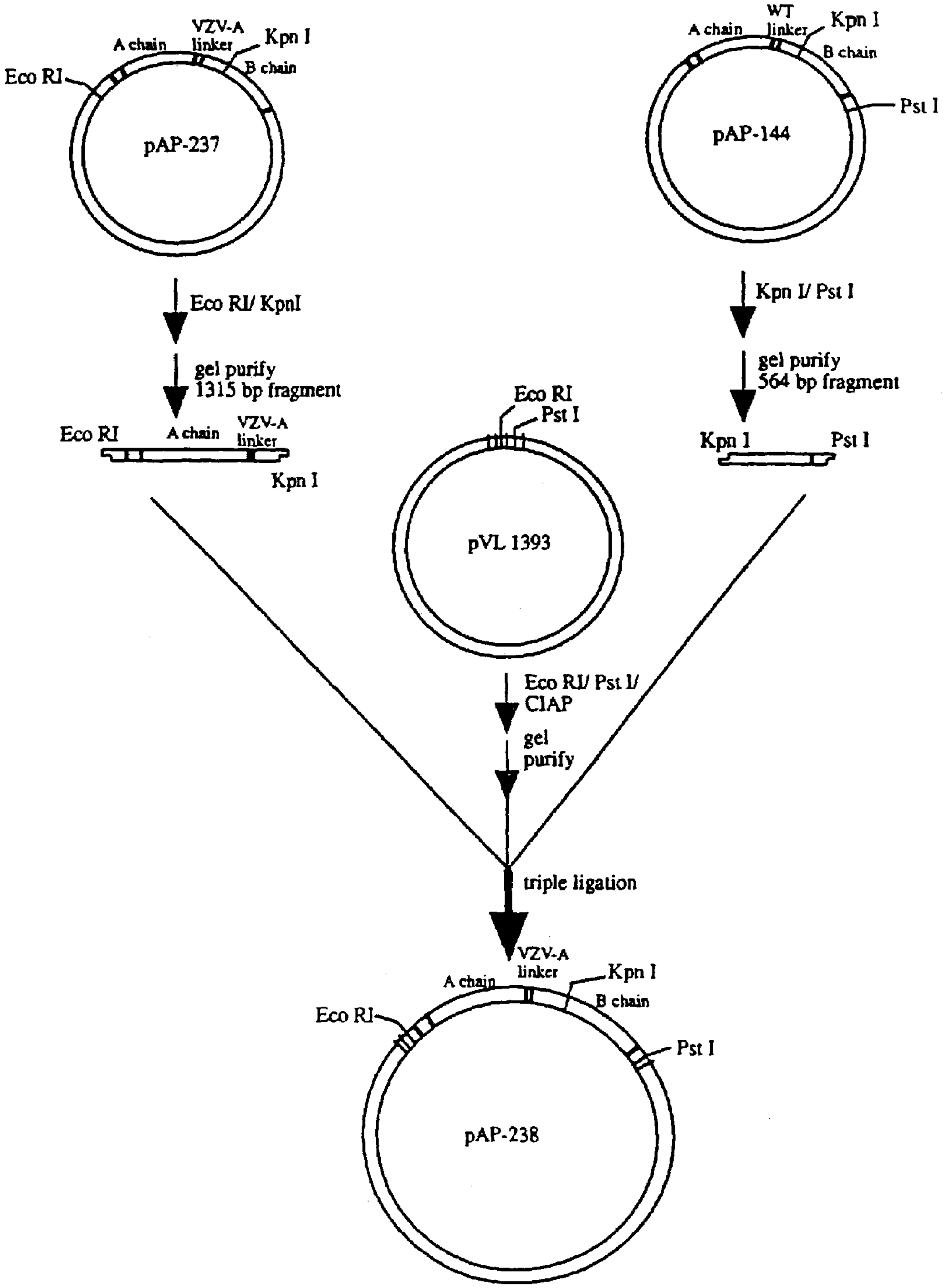
FIG. 14C shows the subcloning of the VZV-A linker variant into a baculovirus transfer vector.
Figure 15A:
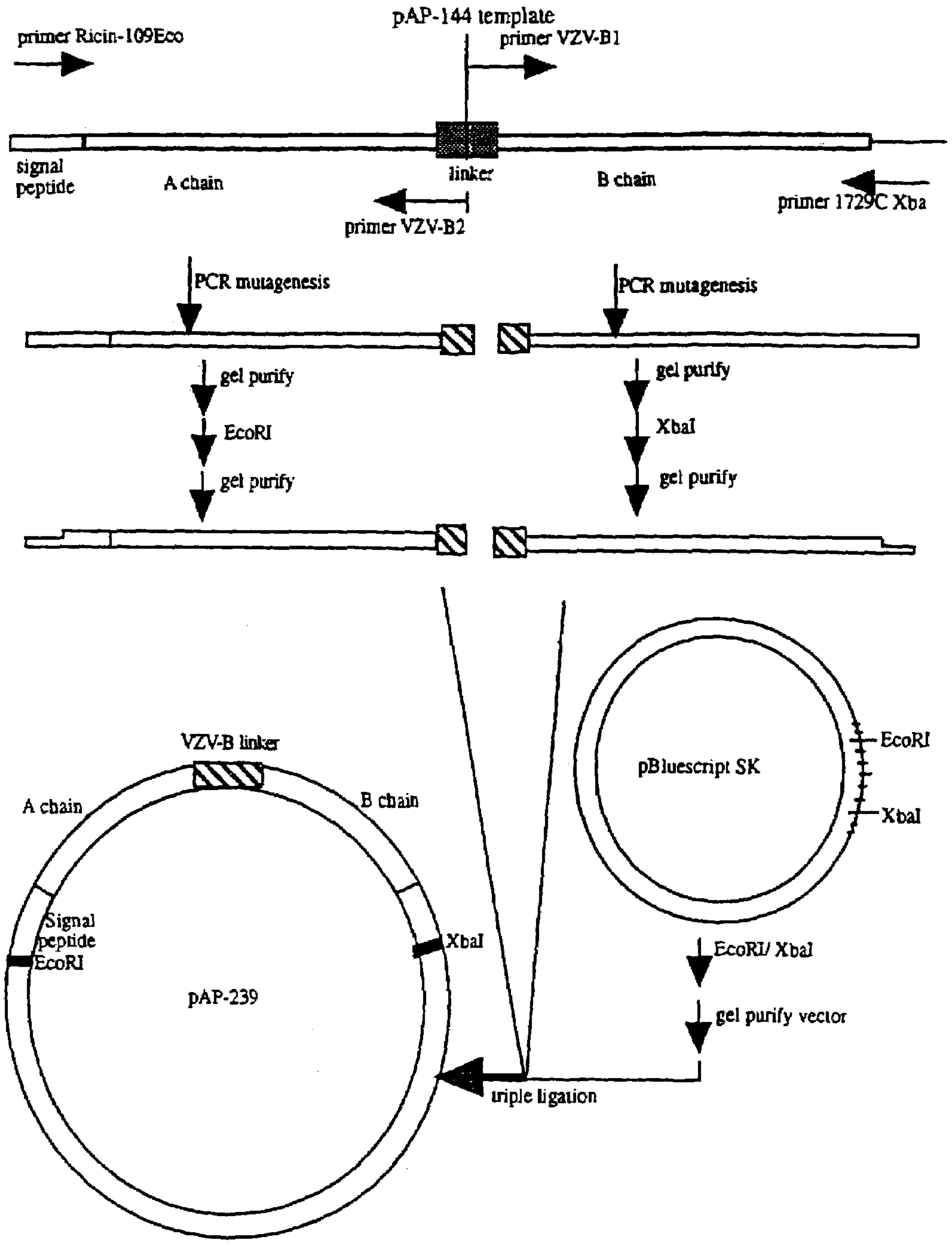
FIG. 15A summarizes the cloning strategy used to generate the pAP-239 construct.
Figure 15C:
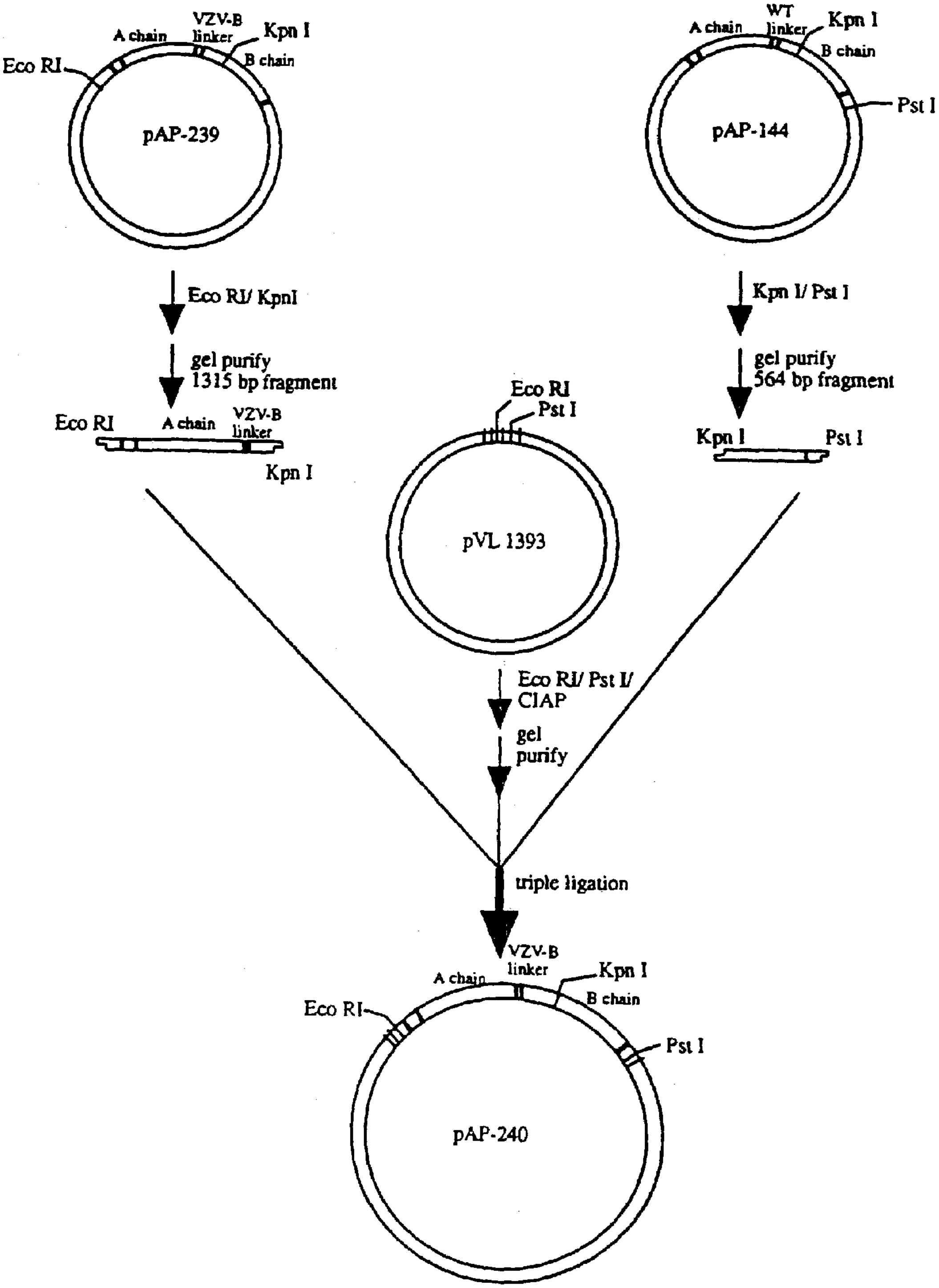
FIG. 15C shows the subcloning of the VZV-B linker variant into a baculovirus transfer vector.
Figure 16A:
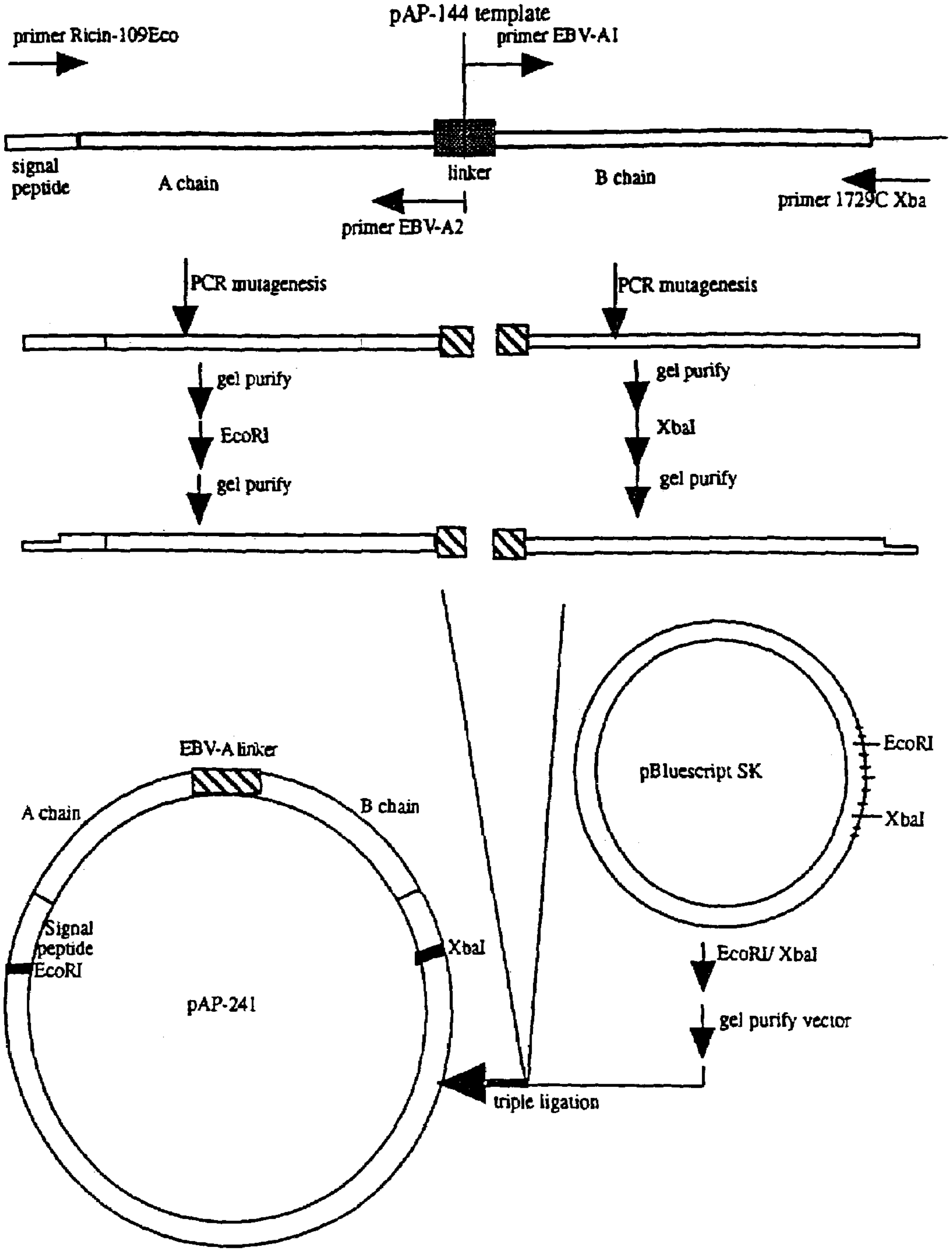
FIG. 16A summarizes the cloning strategy used to generate the pAP-241 construct.
Figure 16C:
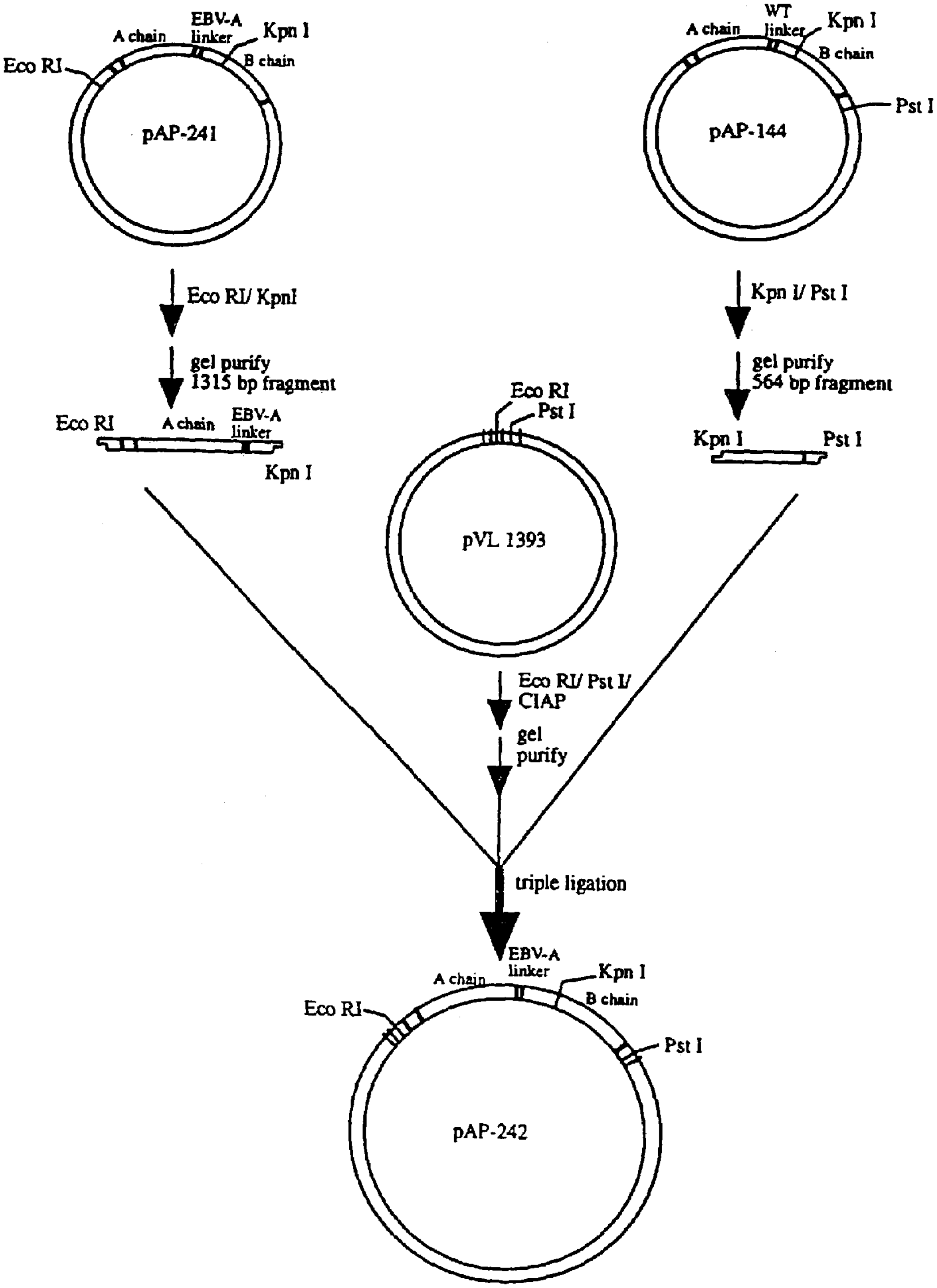
FIG. 16C shows the subcloning of the EBV-A linker variant into a baculovirus transfer vector.
Figure 17A:
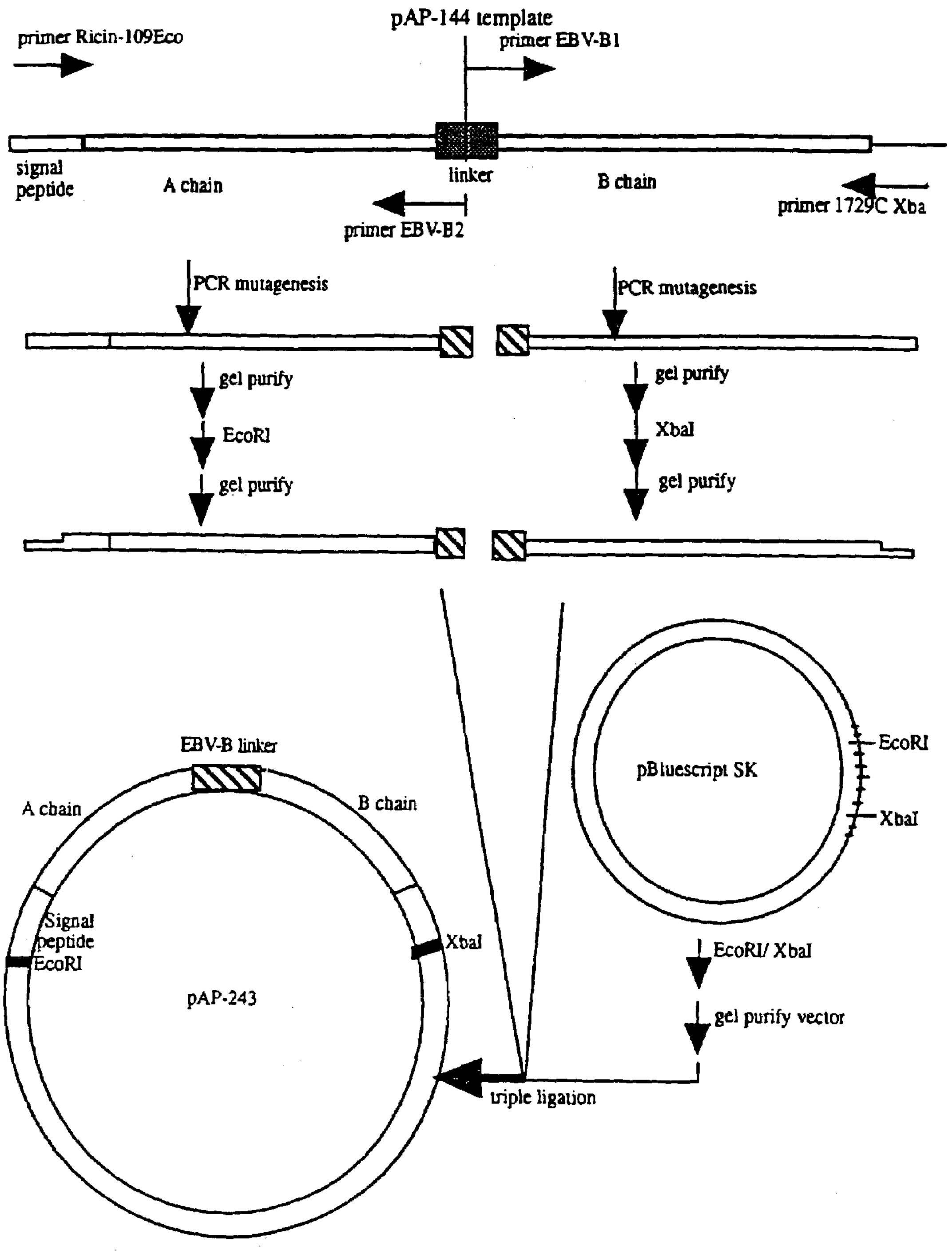
FIG. 17A summarizes the cloning strategy used to generate the pAP-243 construct.
Figure 17C:
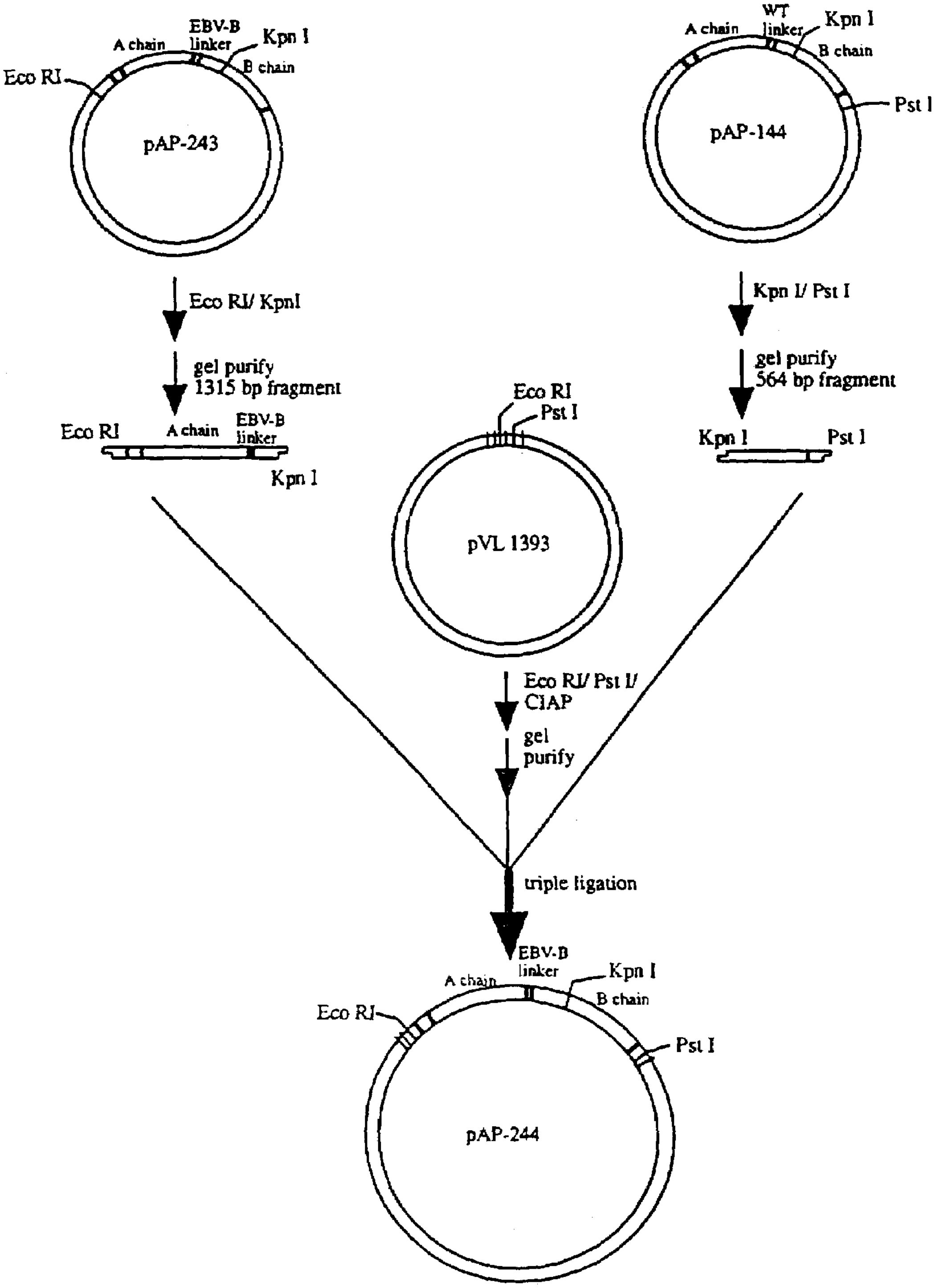
FIG. 17C shows the subcloning of the EBV-B linker variant into a baculovirus transfer vector.
Figure 18A:
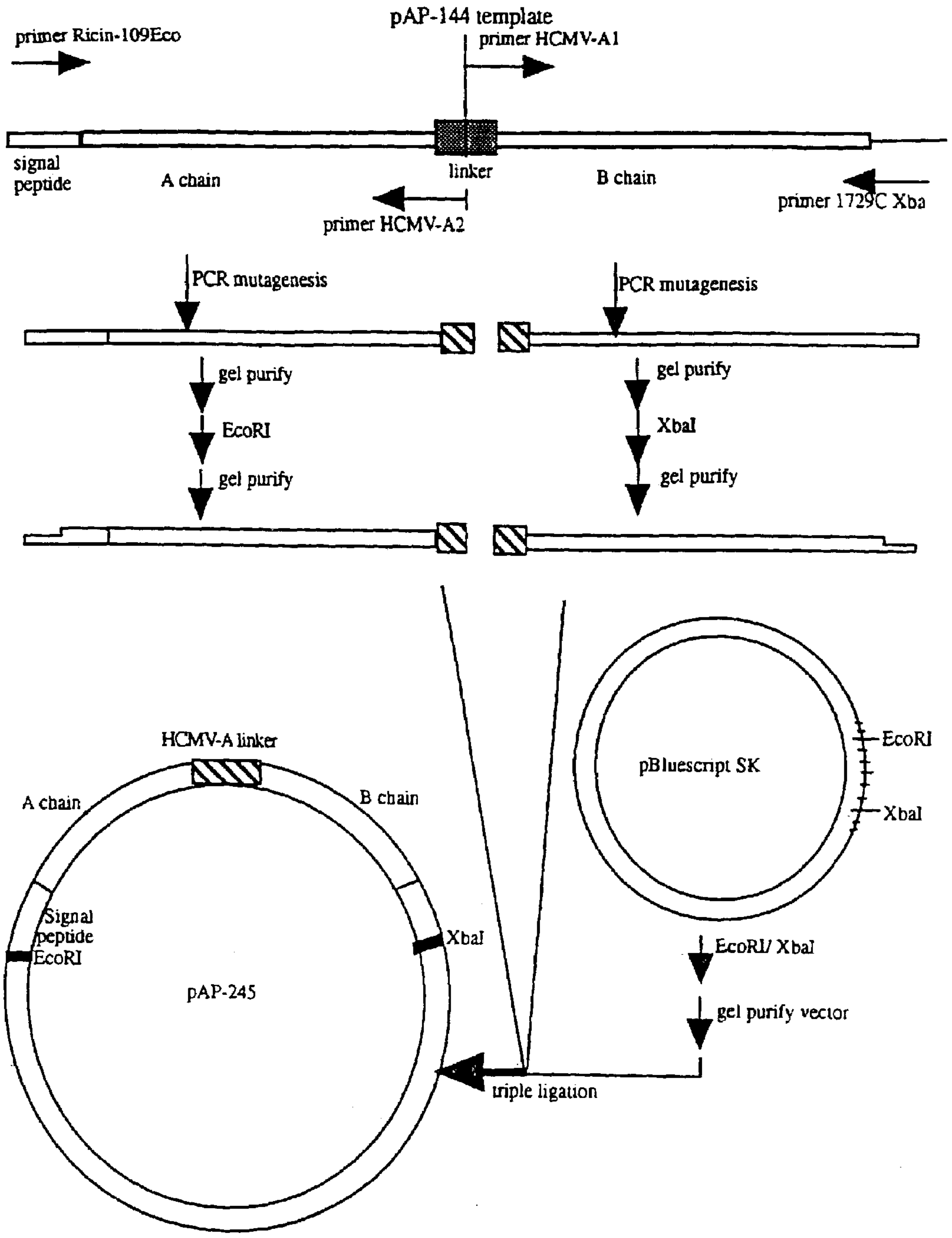
FIG. 18A summarizes the cloning strategy used to generate the pAP-245 construct.
Figure 18B:
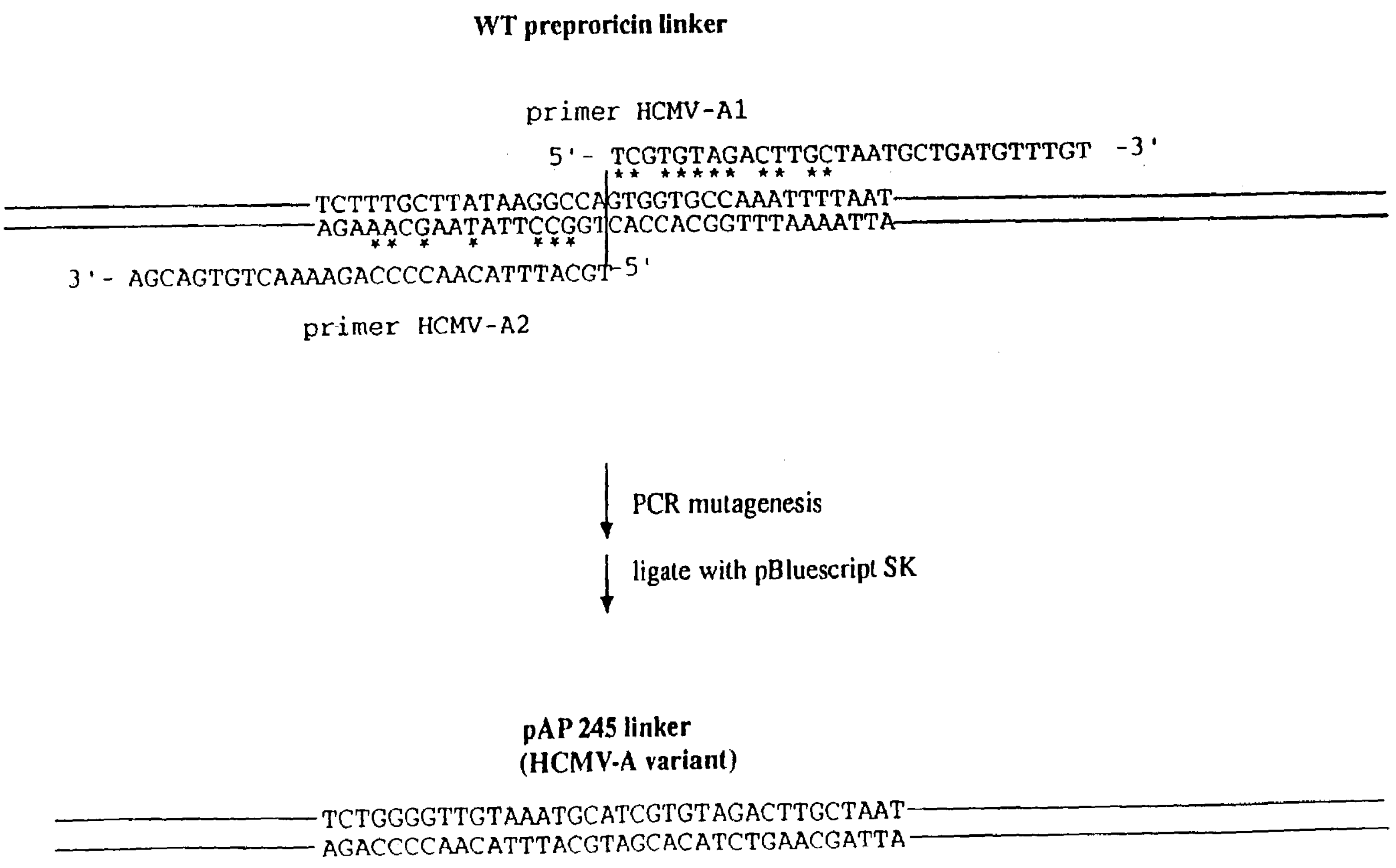
FIG. 18B shows the nucleotide sequence of the CMV-A linker regions of pAP-245 (SEQ ID NO: 34)
Figure 18C:
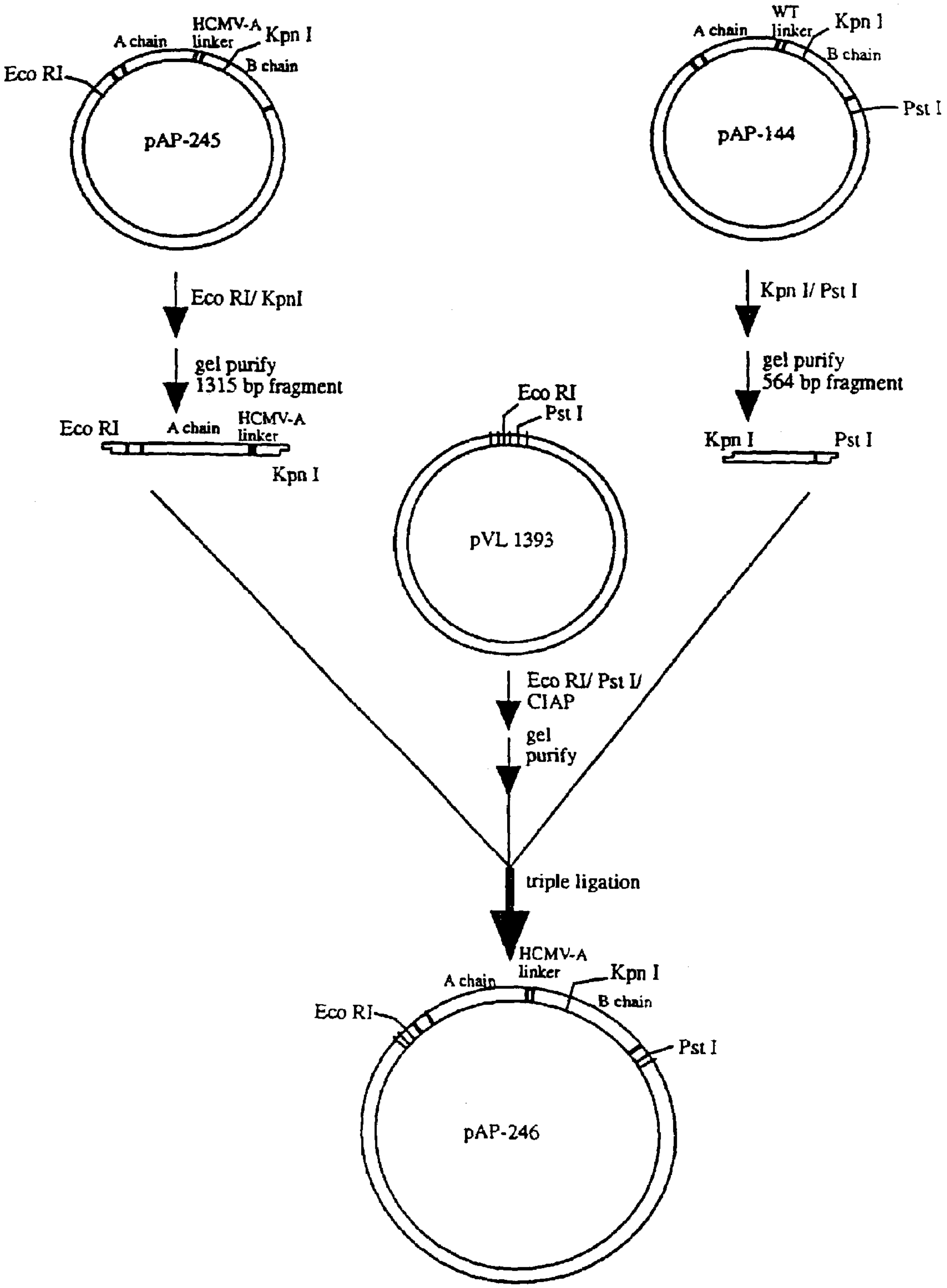
FIG. 18C shows the subcloning of the CMV-A linker variant into a baculovirus transfer vector.
Figure 19A:
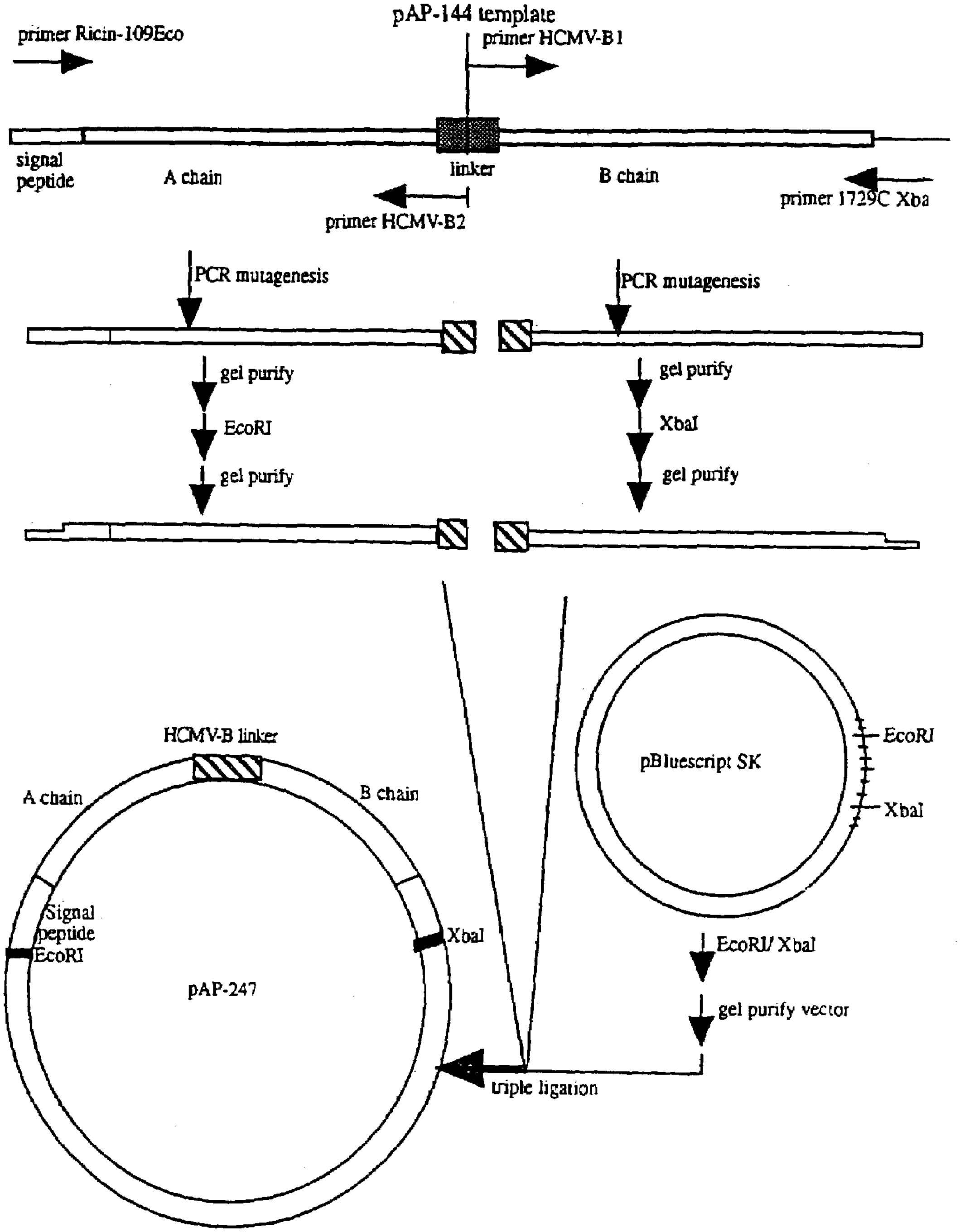
FIG. 19A summarizes the cloning strategy used to generate the pAP-247 construct.
Figure 19C:
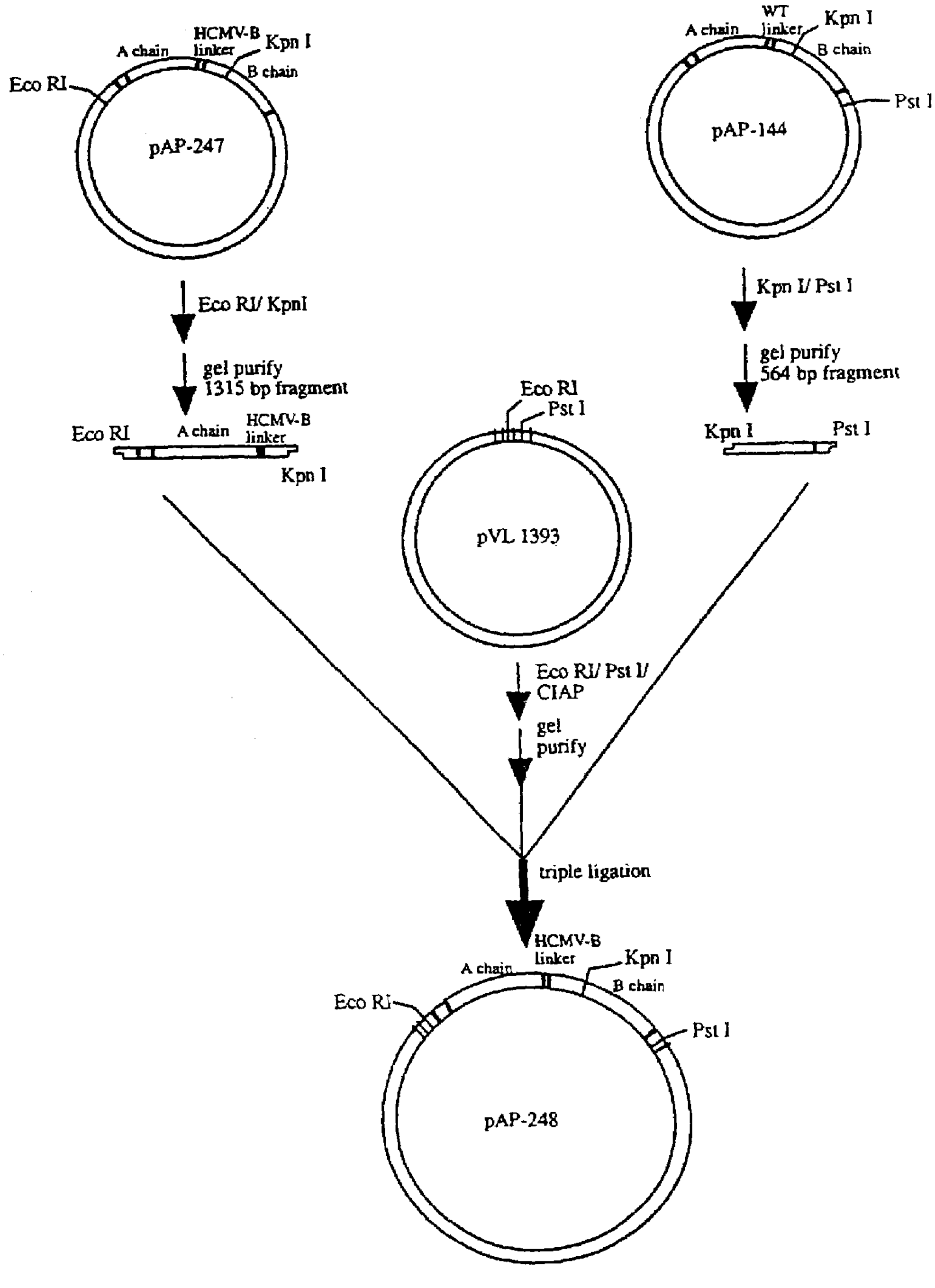
FIG. 19C shows the subcloning of the CMV-B linker variant into a baculovirus transfer vector.
Figure 20A:
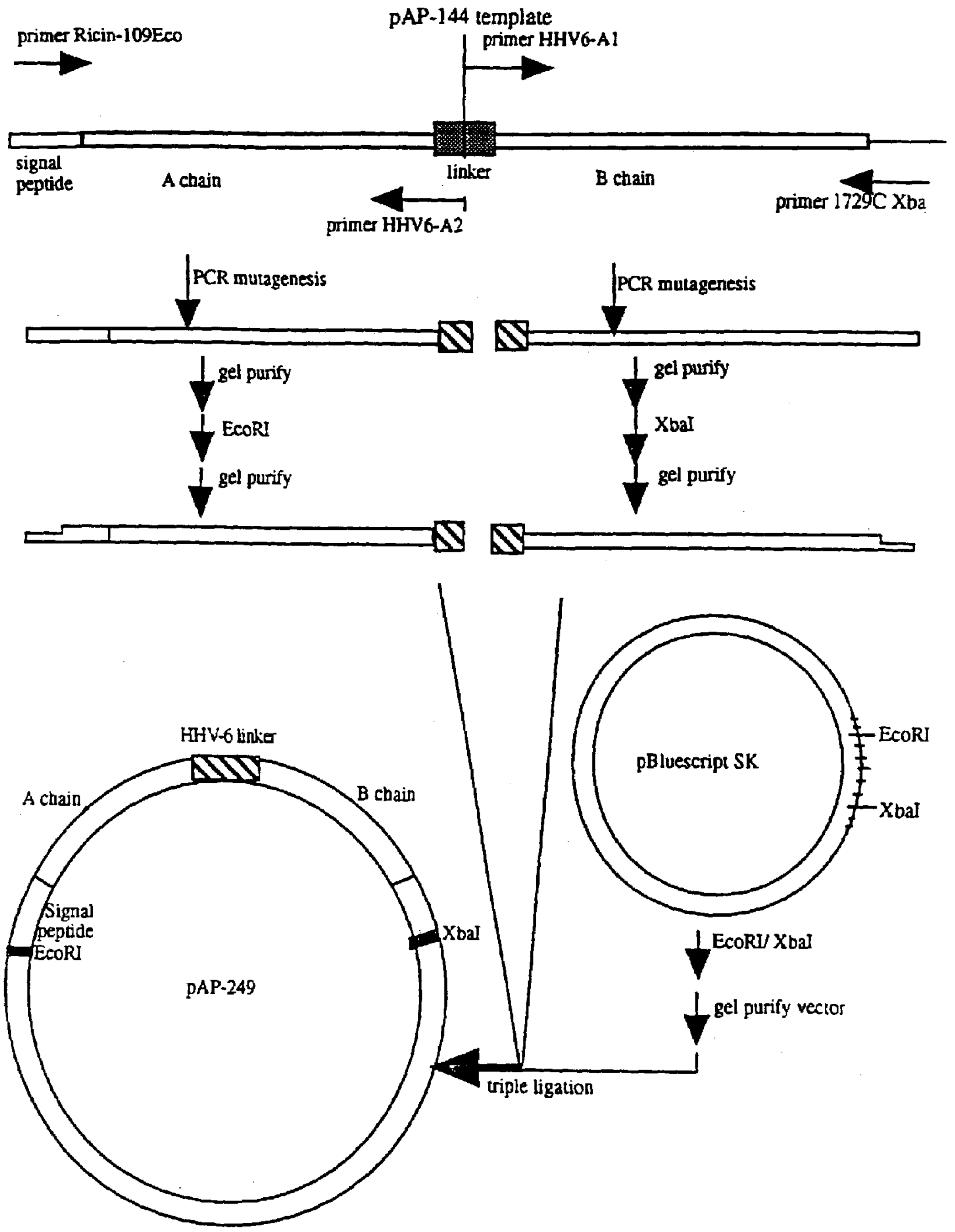
FIG. 20A summarizes the cloning strategy used to generate the pAP-249 construct.
Figure 20B:
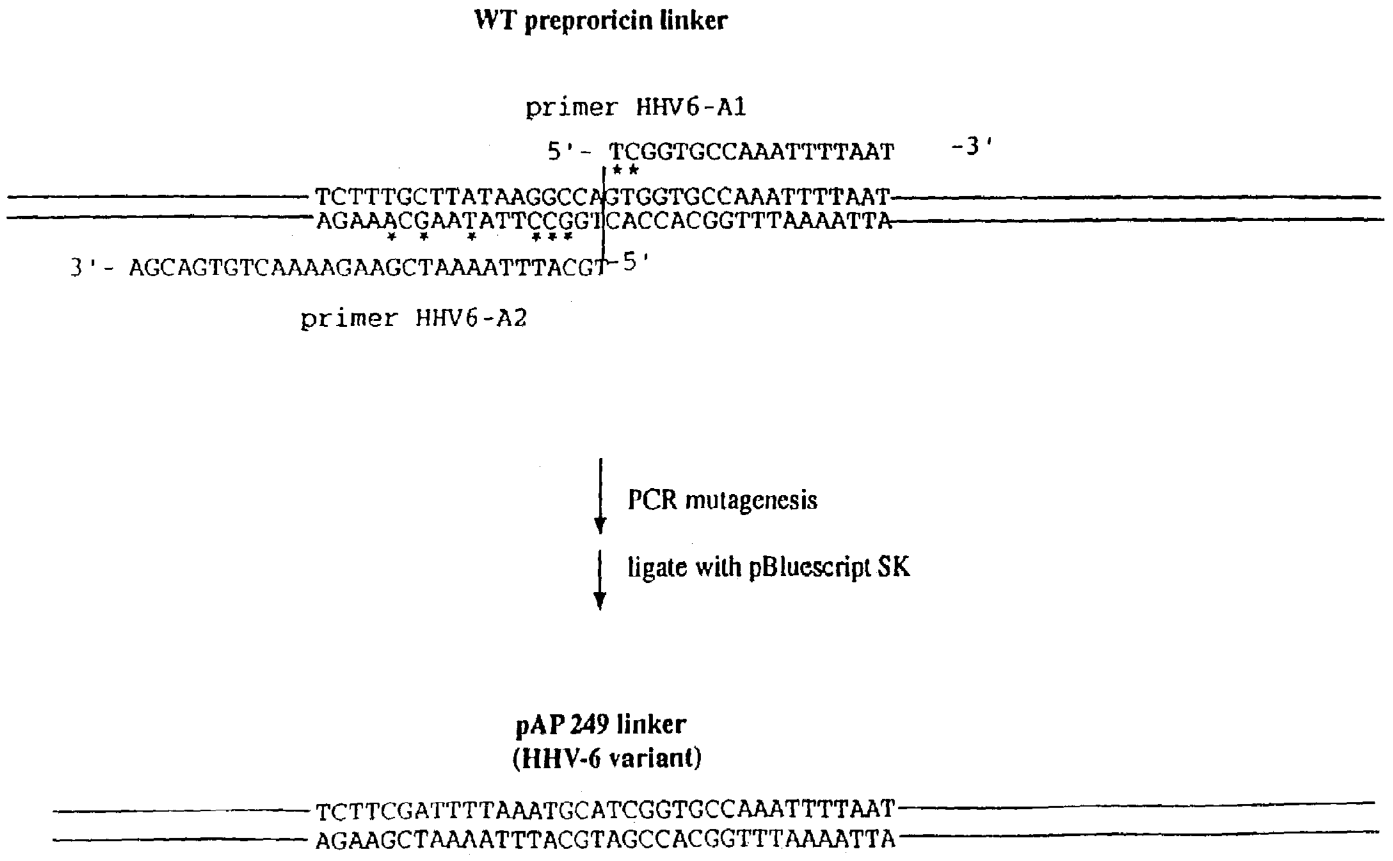
FIG. 20B shows the nucleotide sequence of the HHV-6 linker regions of pAP-249 (SEQ ID NO: 38)
Figure 20C:
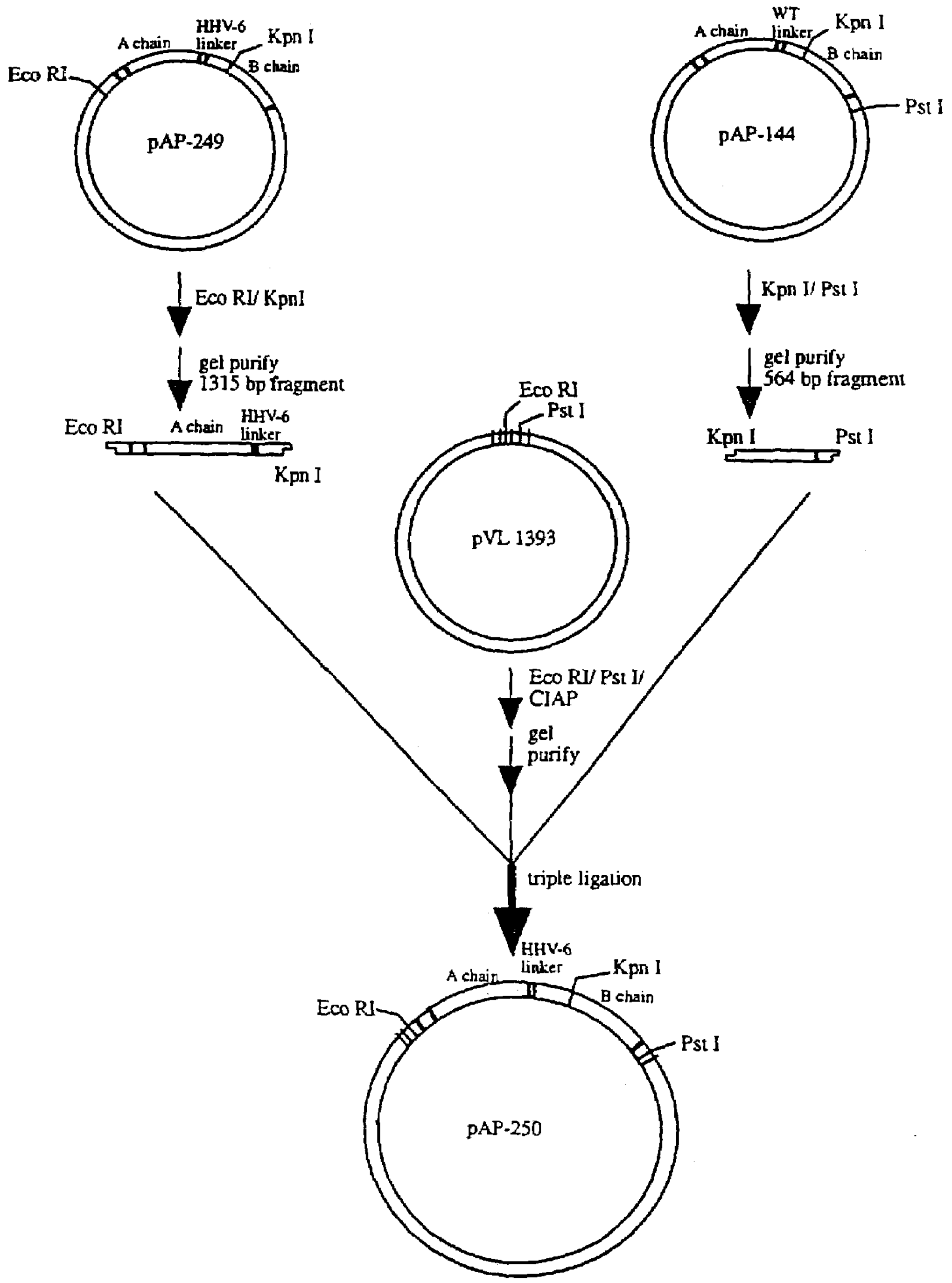
FIG. 20C shows the subcloning of the HHV-6 linker variant into a baculovirus transfer vector.
Figure 22A:
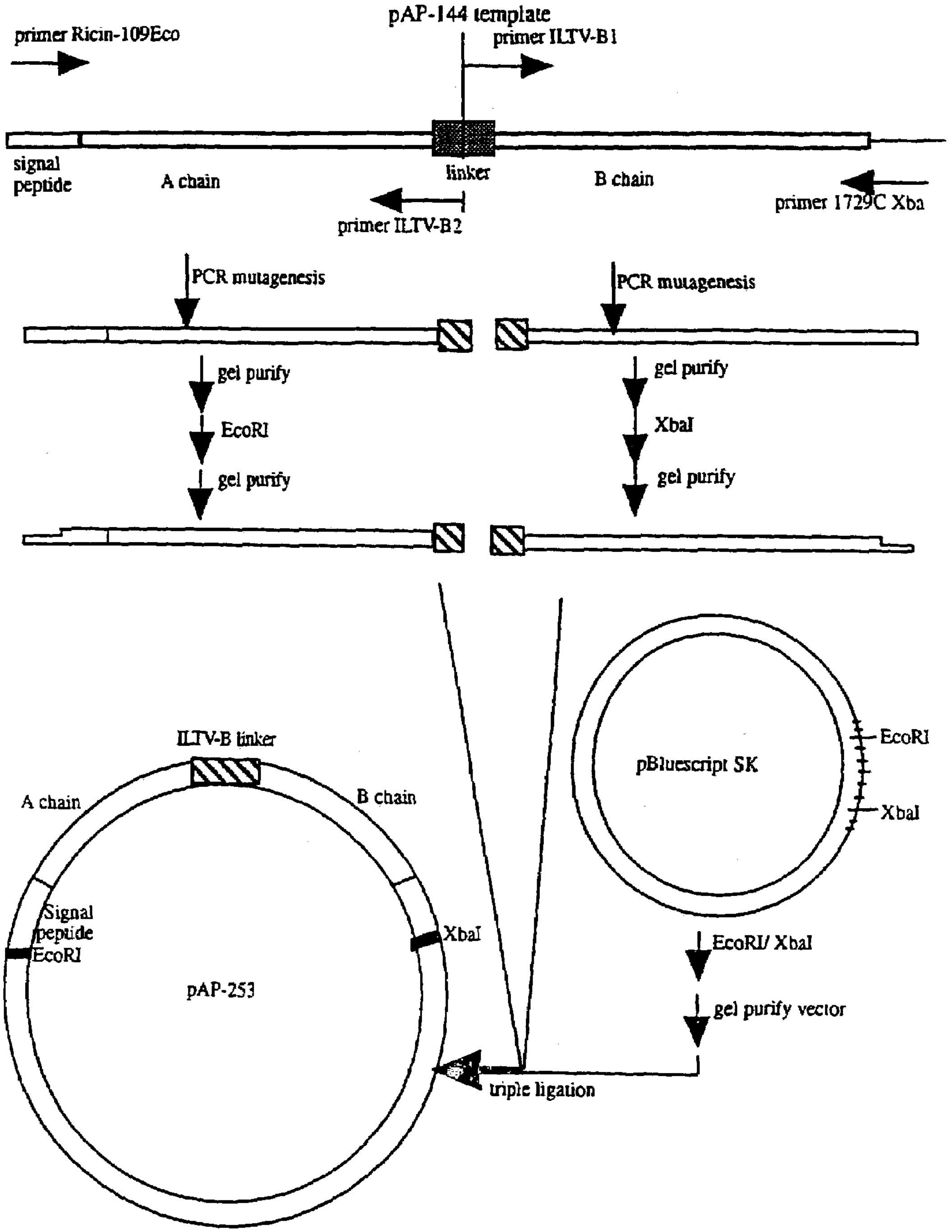
FIG. 22A summarizes the cloning strategy used to generate the pAP-253 construct.
Figure 22C:
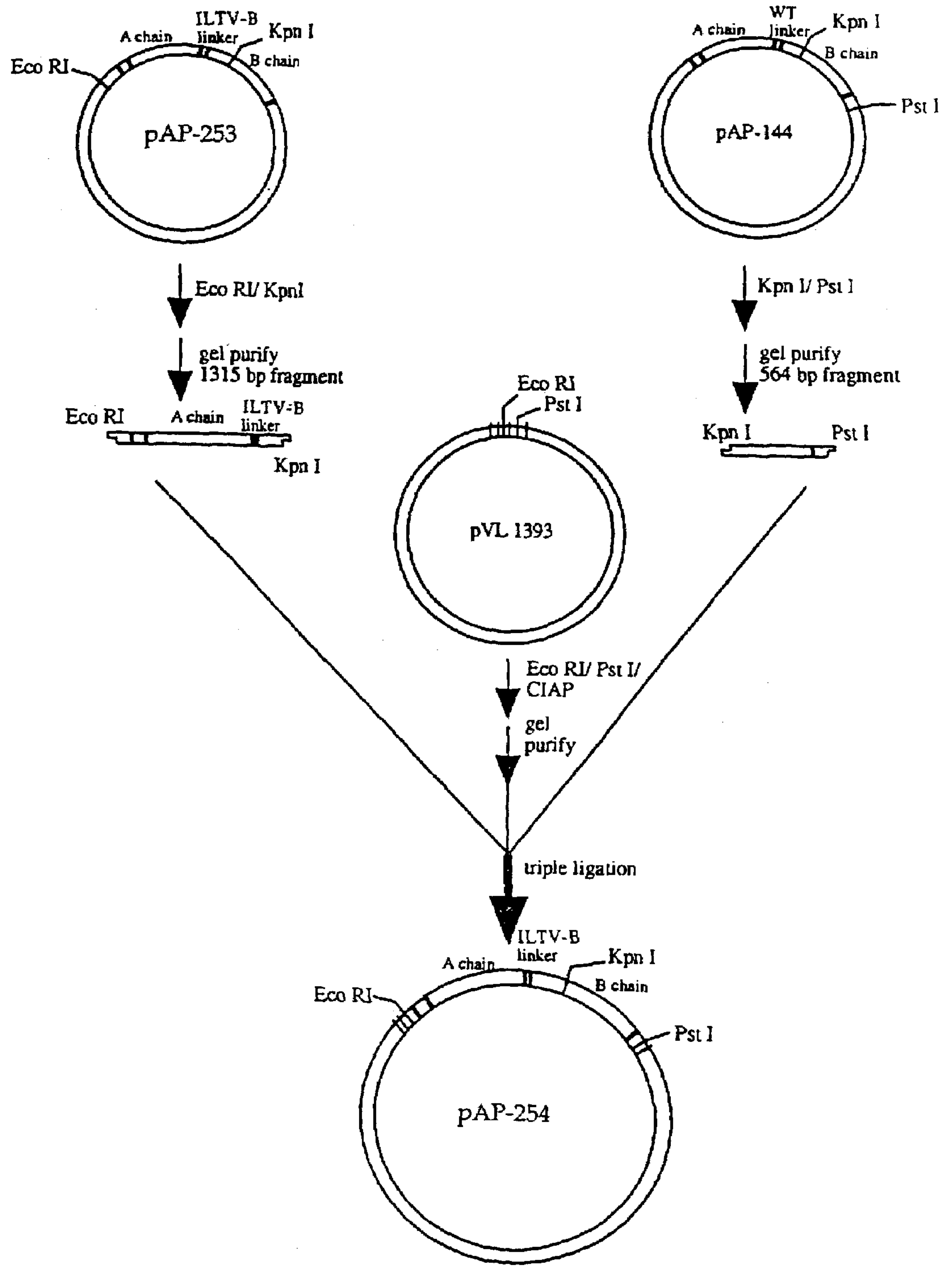
FIG. 22C shows the subcloning of the ILV linker variant into a baculovirus transfer vector.
Figure 23A:
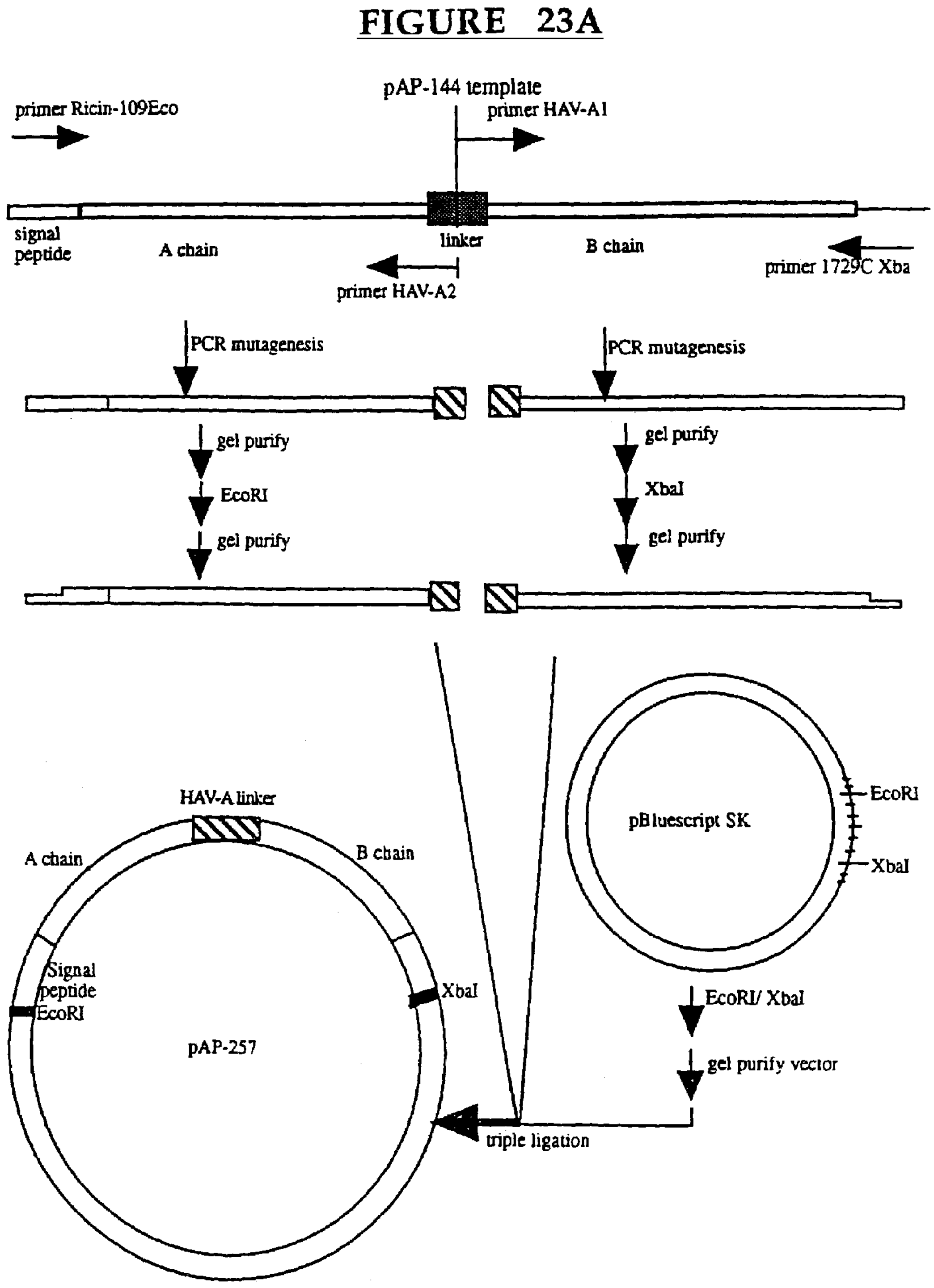
FIG. 23A summarizes the cloning strategy used to generate the pAP-257 construct.
Figure 23B:
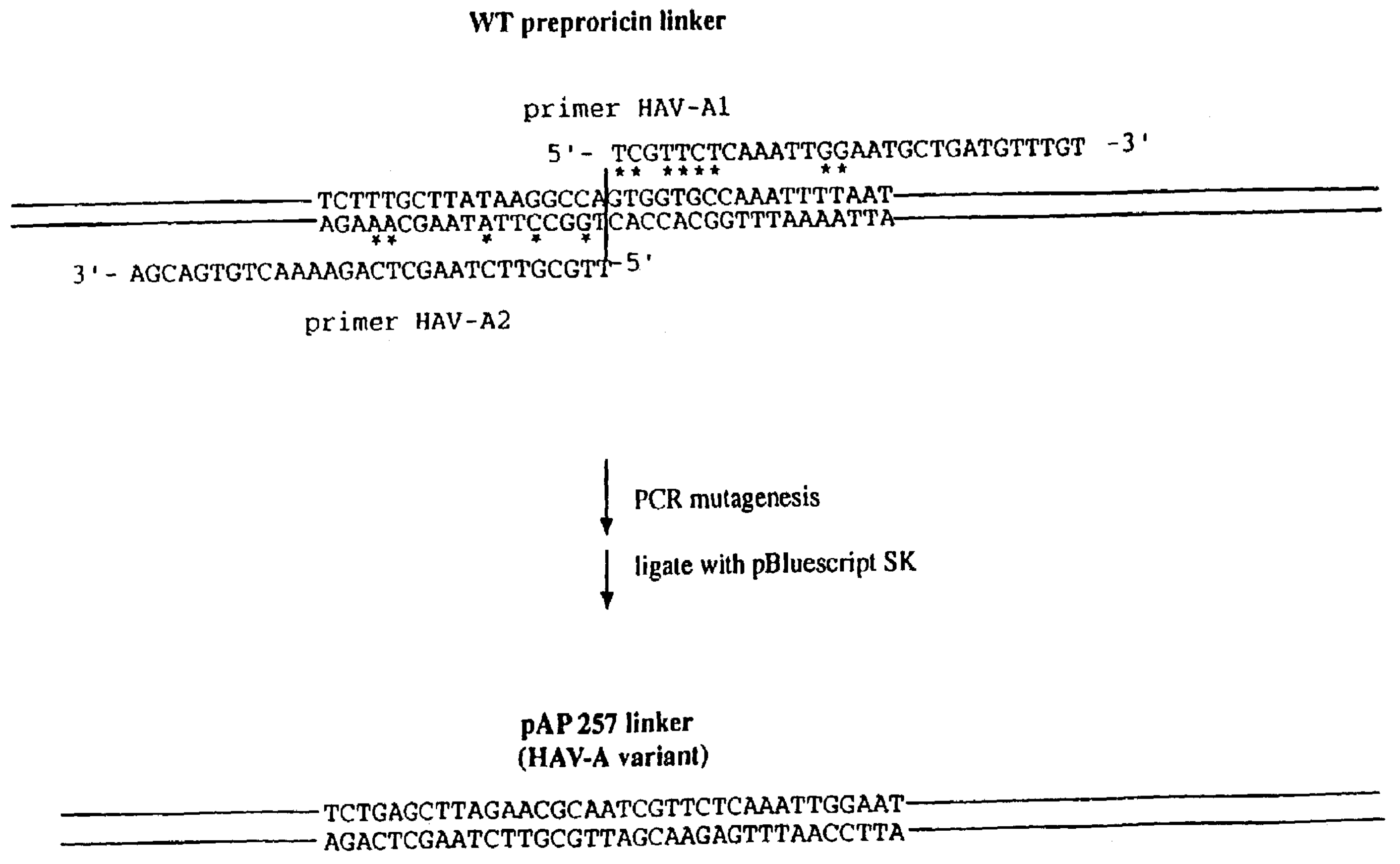
FIG. 23B shows the nucleotide sequence of the HAV-A linker regions of pAP-257 (SEQ ID NO: 49)
Figure 23C:
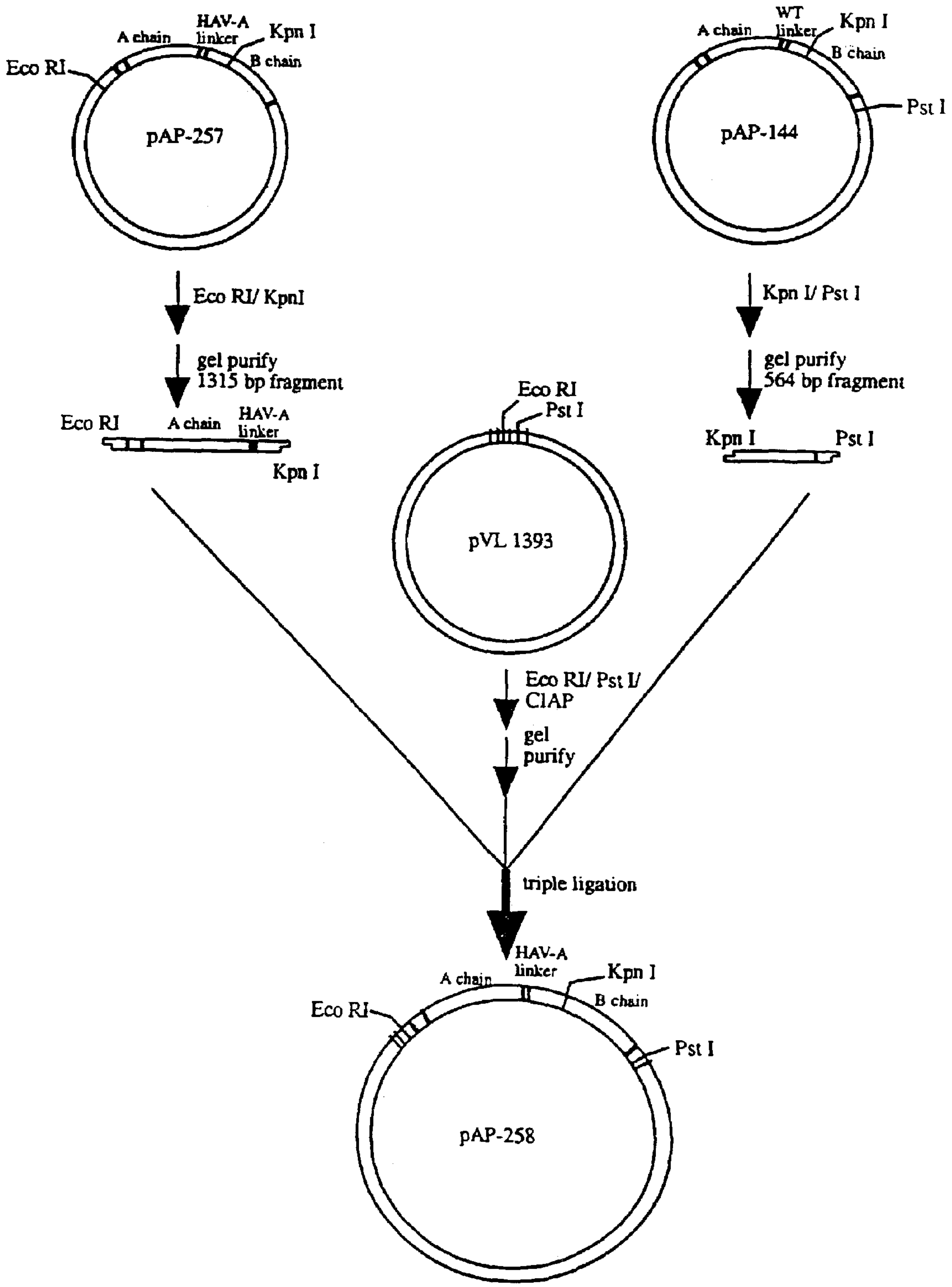
FIG. 23C shows the subcloning of the HAV-A linker variant into a baculovirus transfer vector.
Figure 24A:
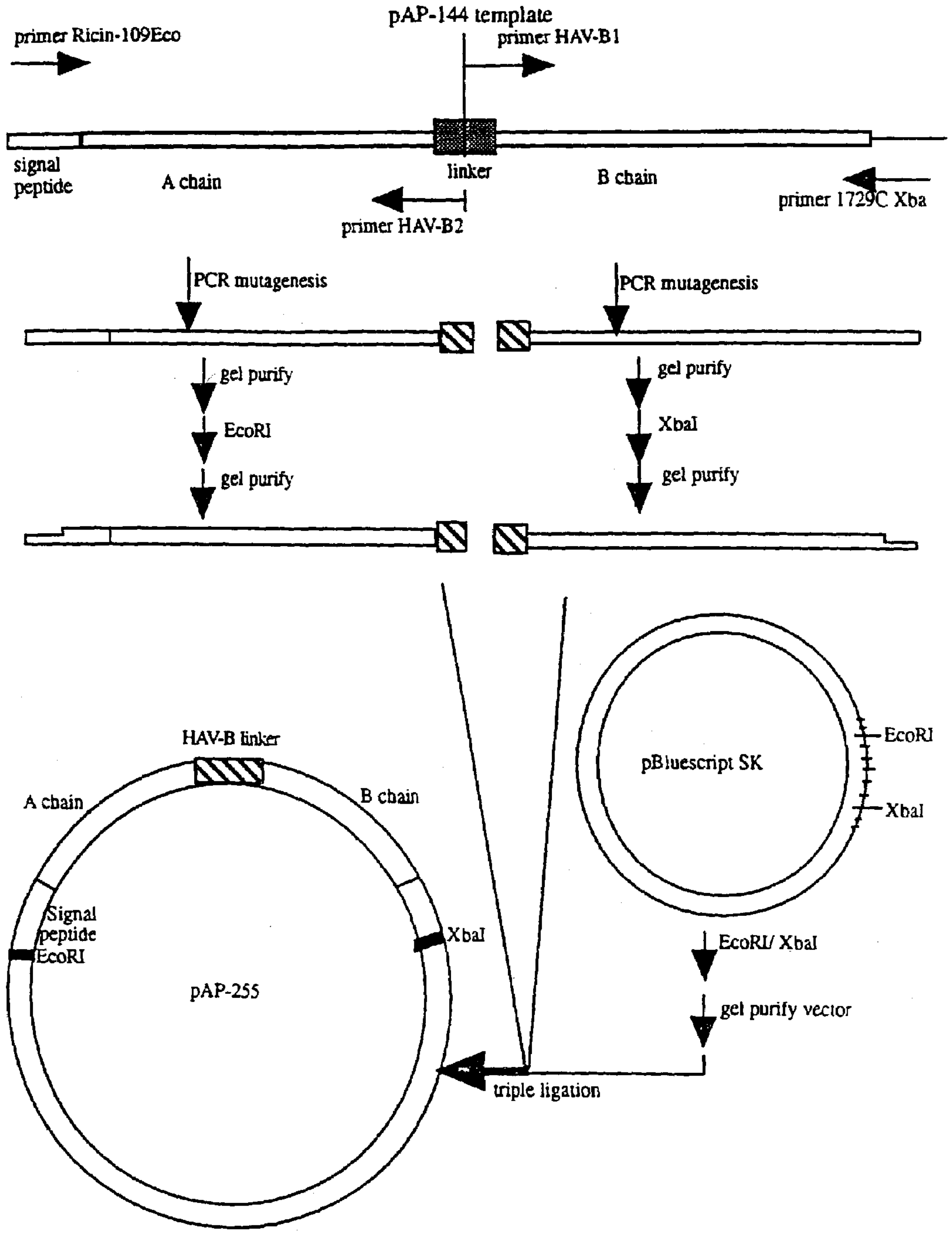
FIG. 24A summarizes the cloning strategy used to generate the pAP-255 construct.
Figure 24B:
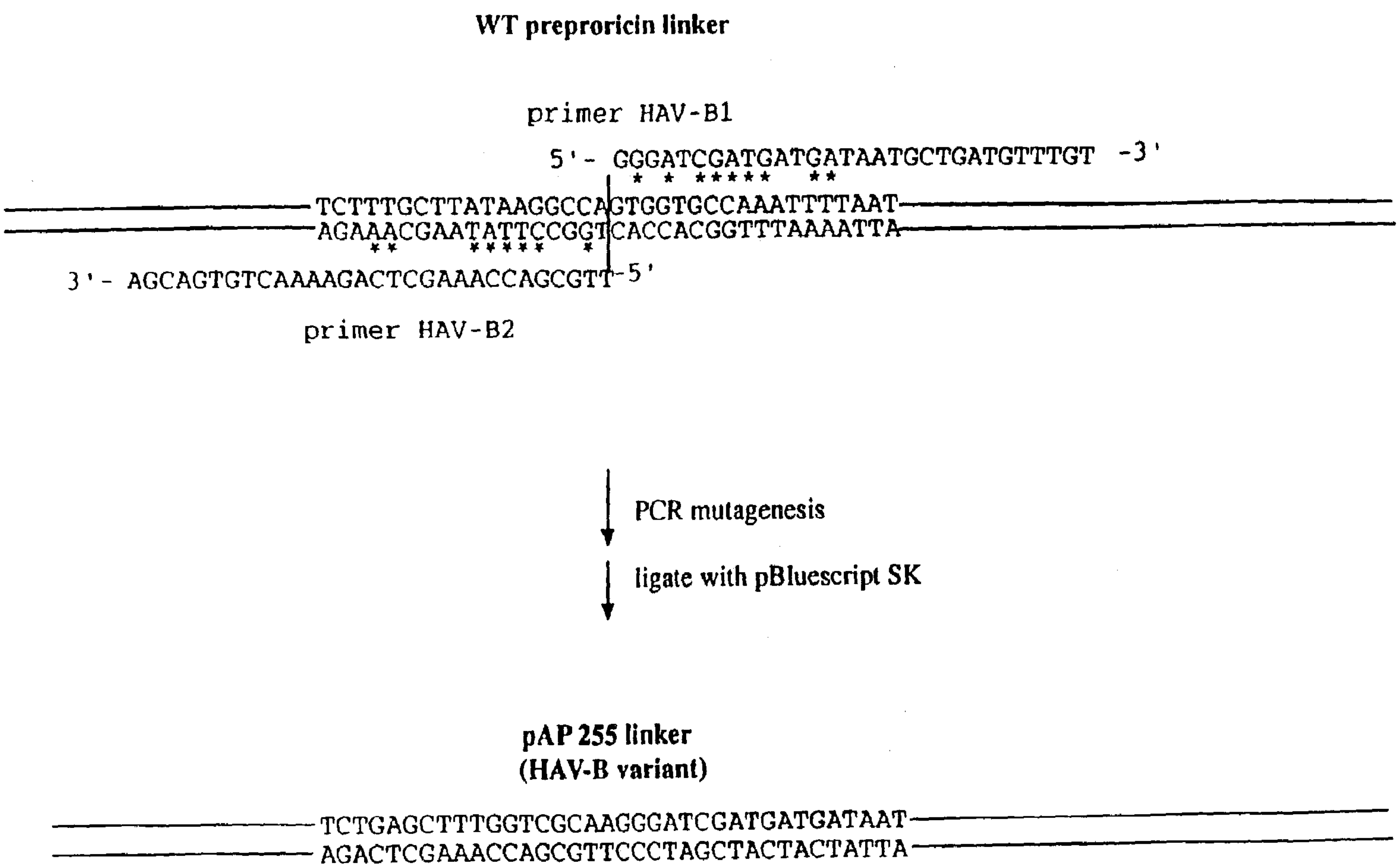
FIG. 24B shows the nucleotide sequence of the HAV-B linker regions of pAP-255 (SEQ ID NO: 51)
Figure 24C:
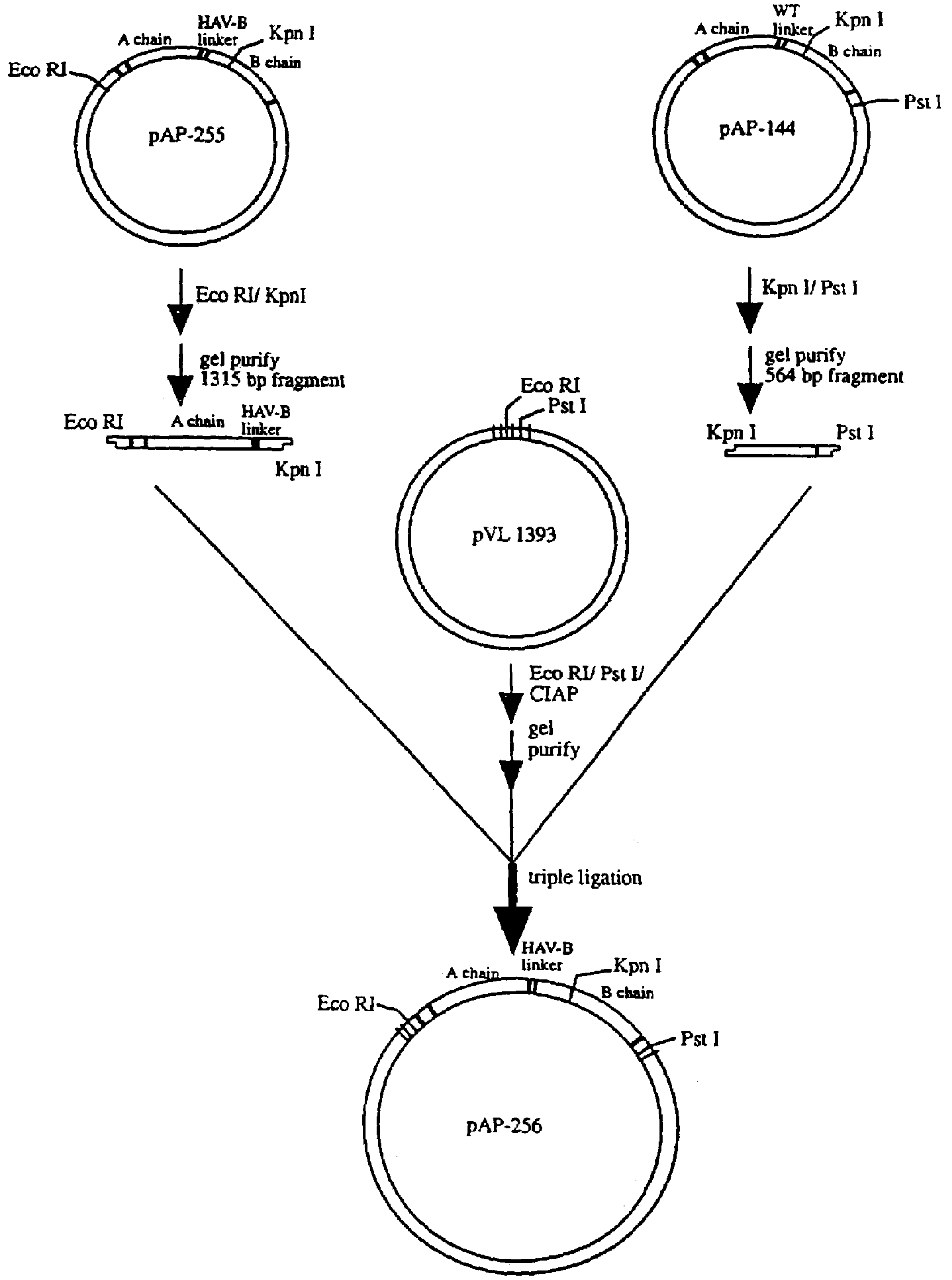
FIG. 24C shows the subcloning of the HAV-B linker variant into a baculovirus transfer vector.
Figure 25A:
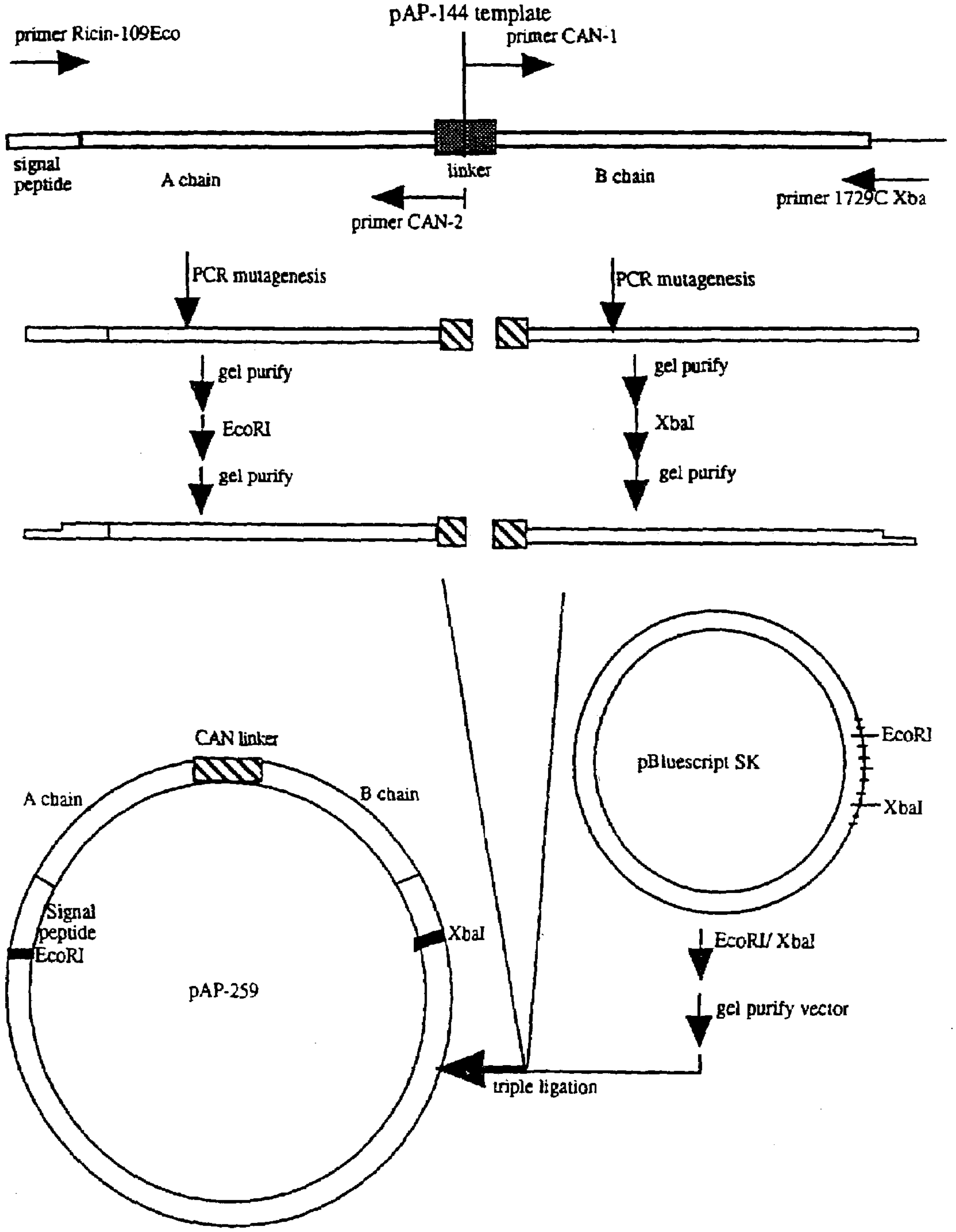
FIG. 25A summarizes the cloning strategy used to generate the pAP-259 construct.
Figure 25B:
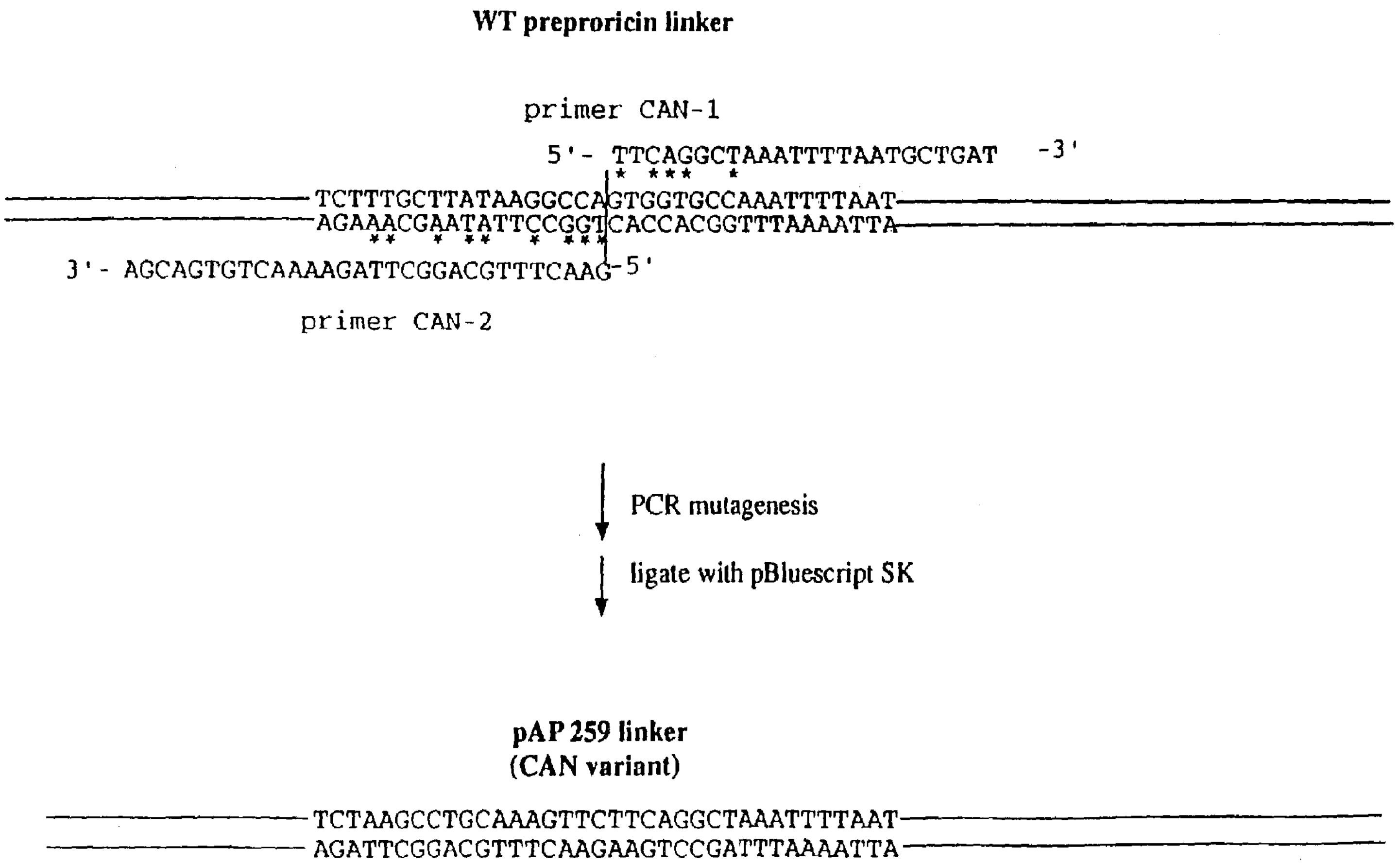
FIG. 25B shows the nucleotide sequence of the CAN linker regions of pAP-259 (SEQ ID NO: 53)
Figure 25C:
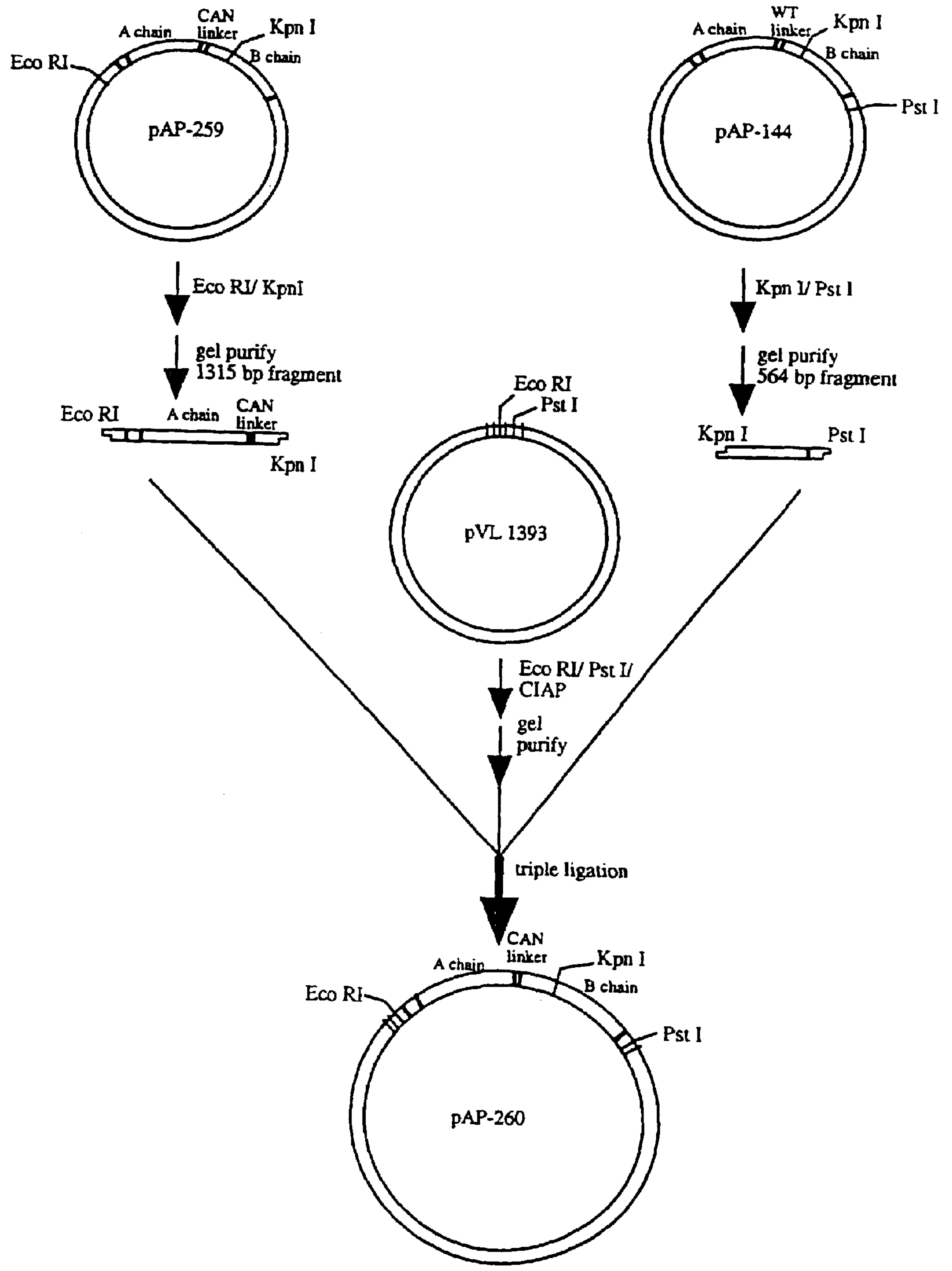
FIG. 25C shows the subcloning of the CAN linker variant into a baculovirus transfer vector.
Figure 29:
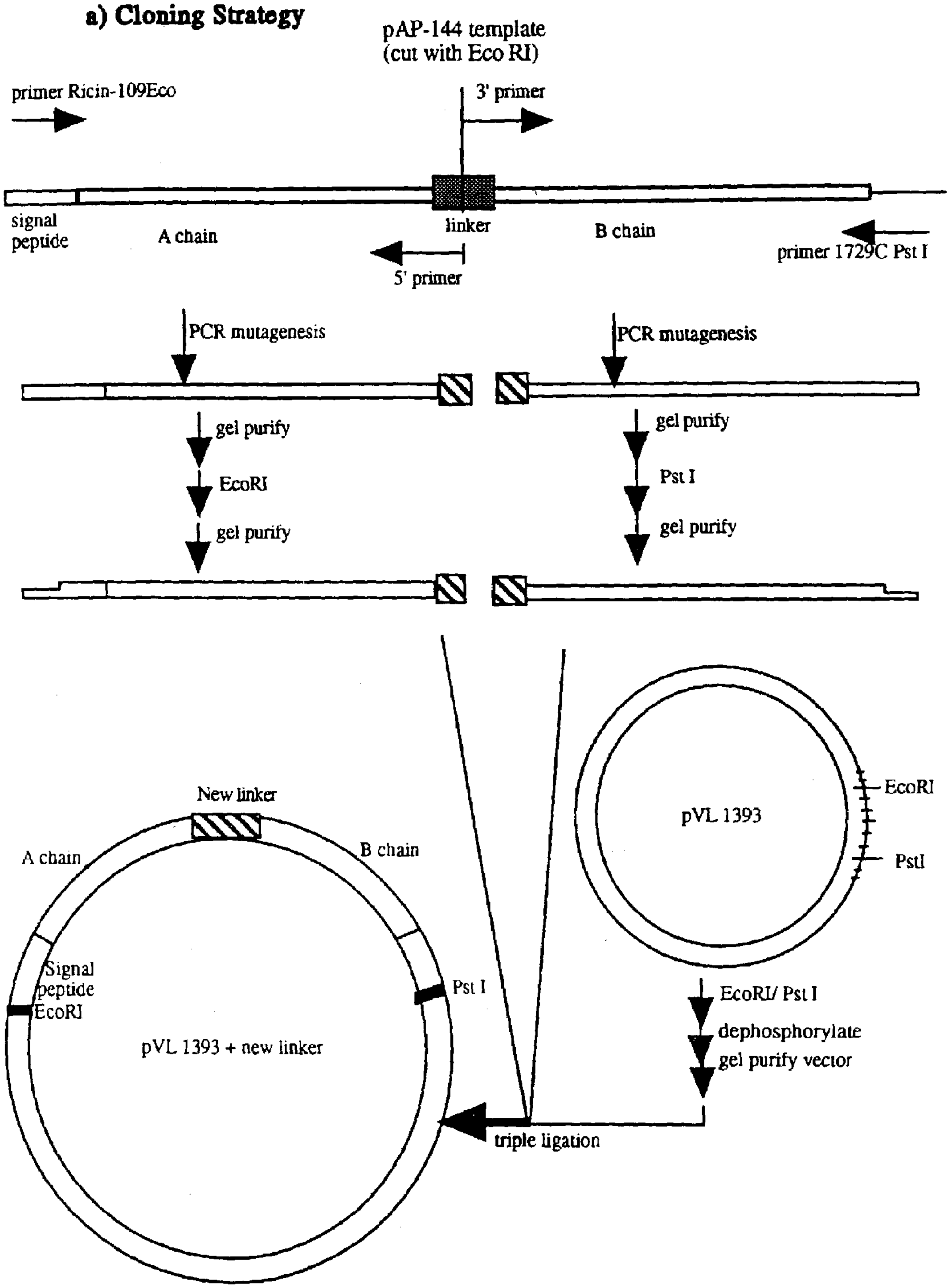
FIG. 29 describes an alternative mutagenesis and subcloning strategy to provide a baculovirus transfer vector containing the ricin-like toxin variant gene.
Figure 30A:
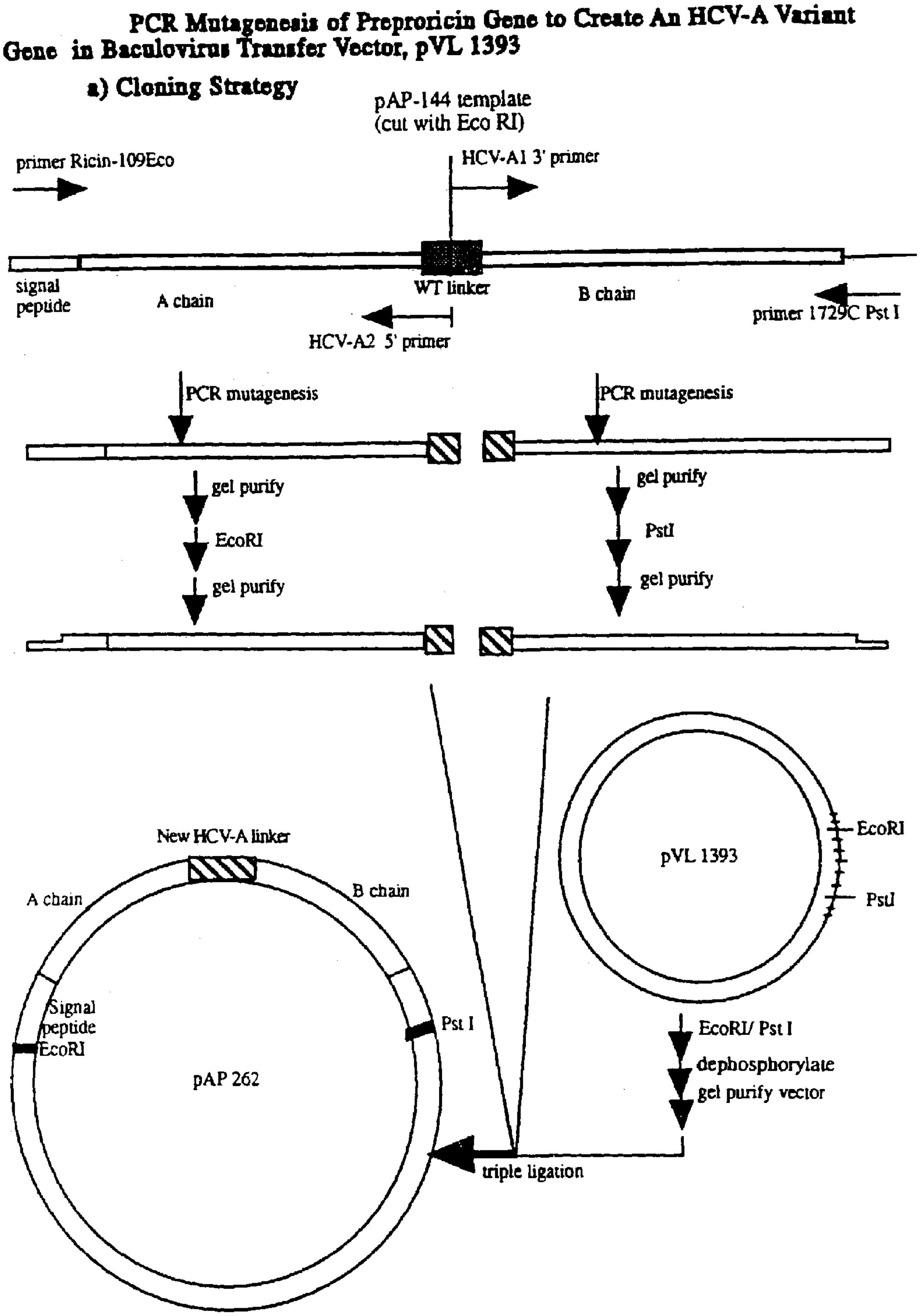
FIG. 30A summarizes the cloning strategy used to generate the pAP-262 construct.
Figure 31A:
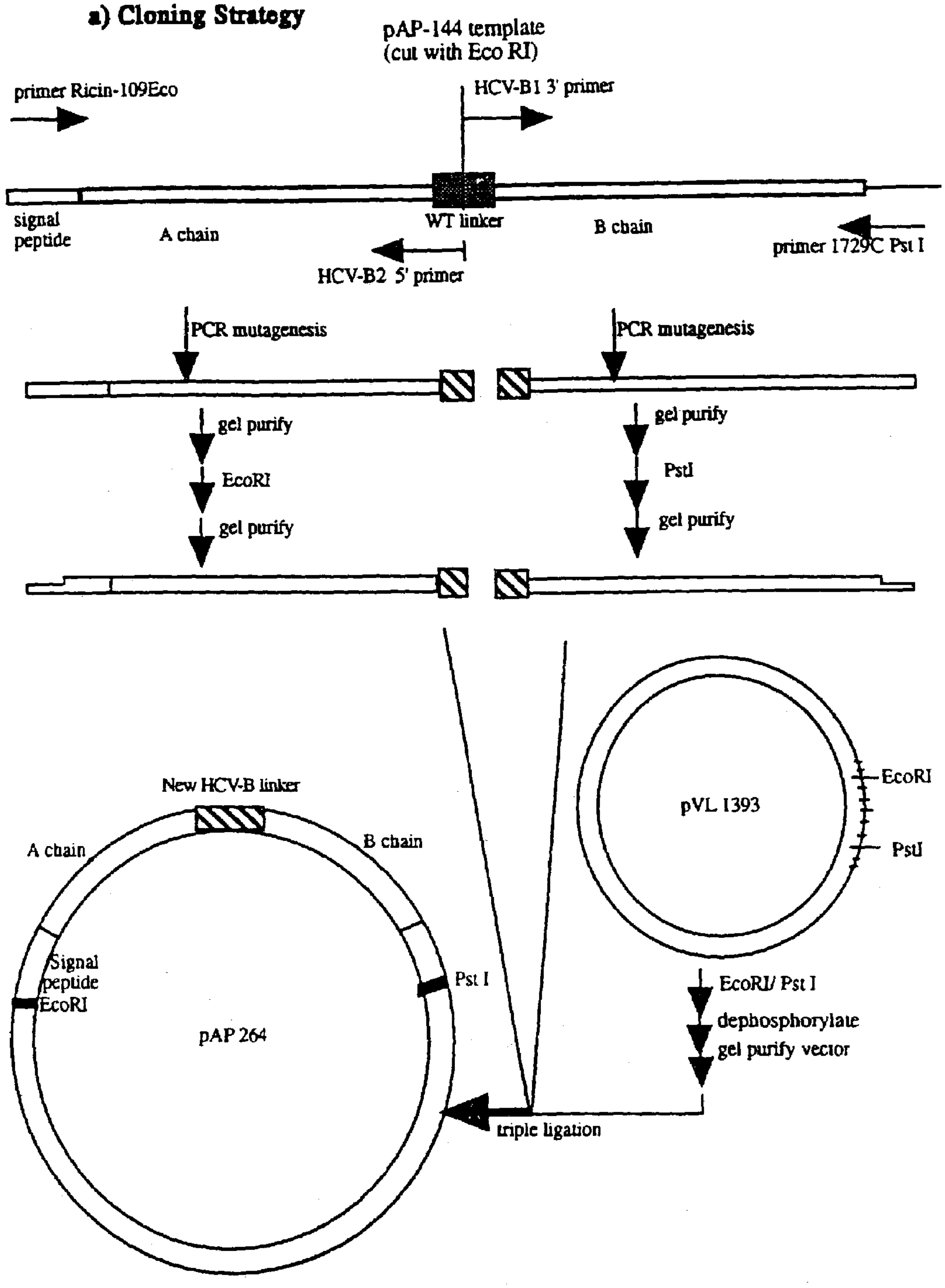
FIG. 31A summarizes the cloning strategy used to generate the pAP-264 construct.
Figure 32A:
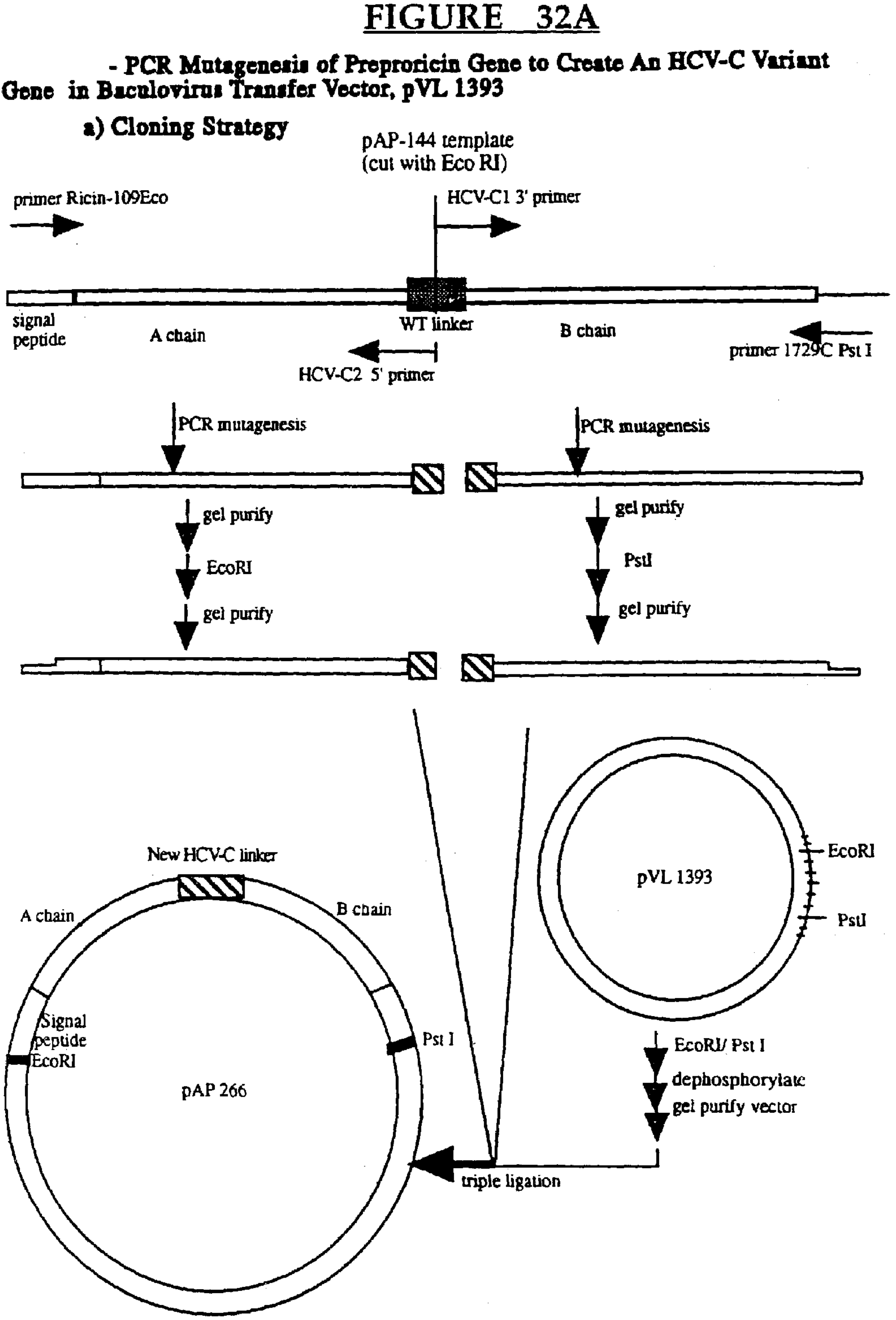
FIG. 32A summarizes the cloning strategy used to generate the pAP-266 construct.
Figure 33A:
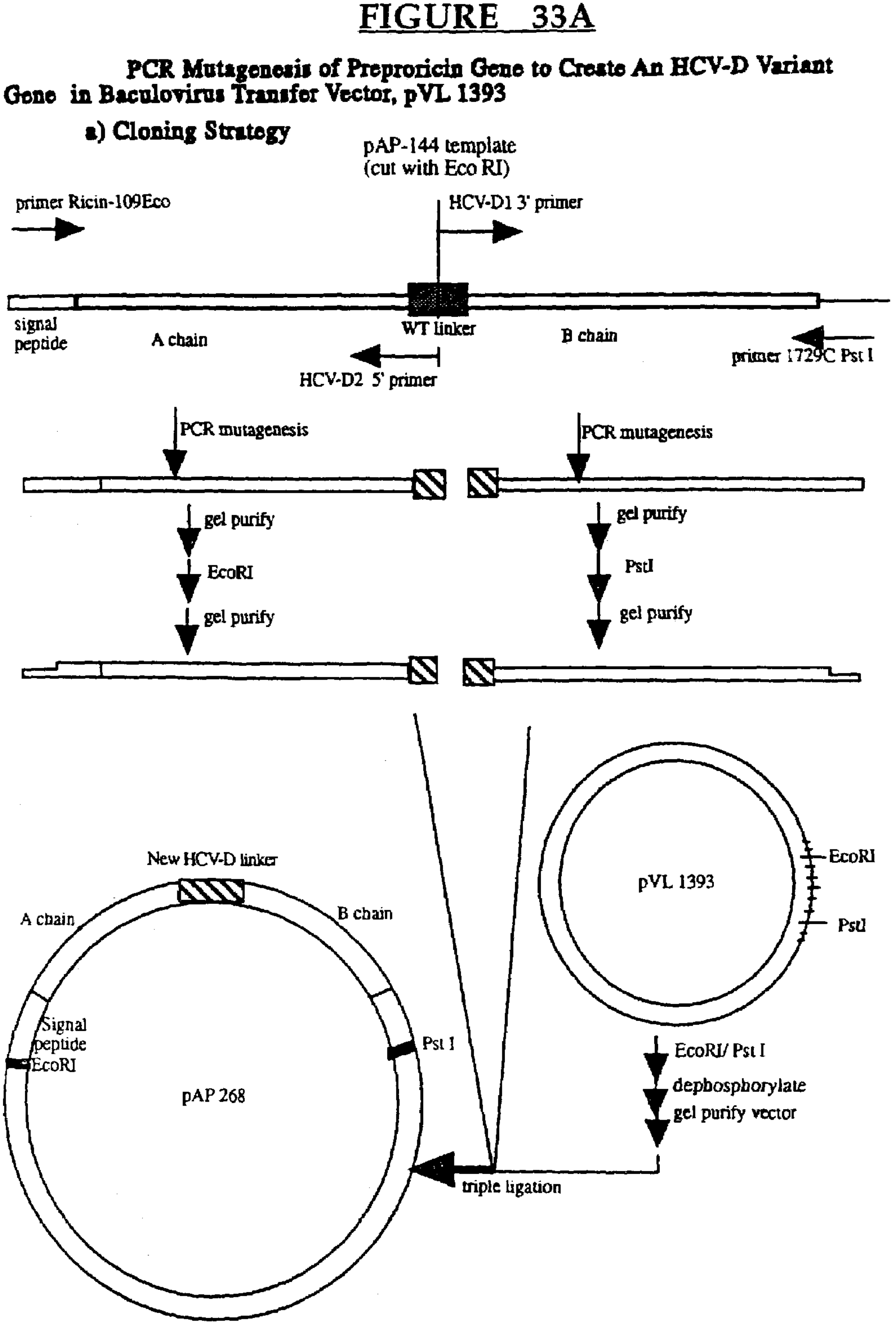
FIG. 33A summarizes the cloning strategy used to generate the pAP-268 construct.
Figure 34A:
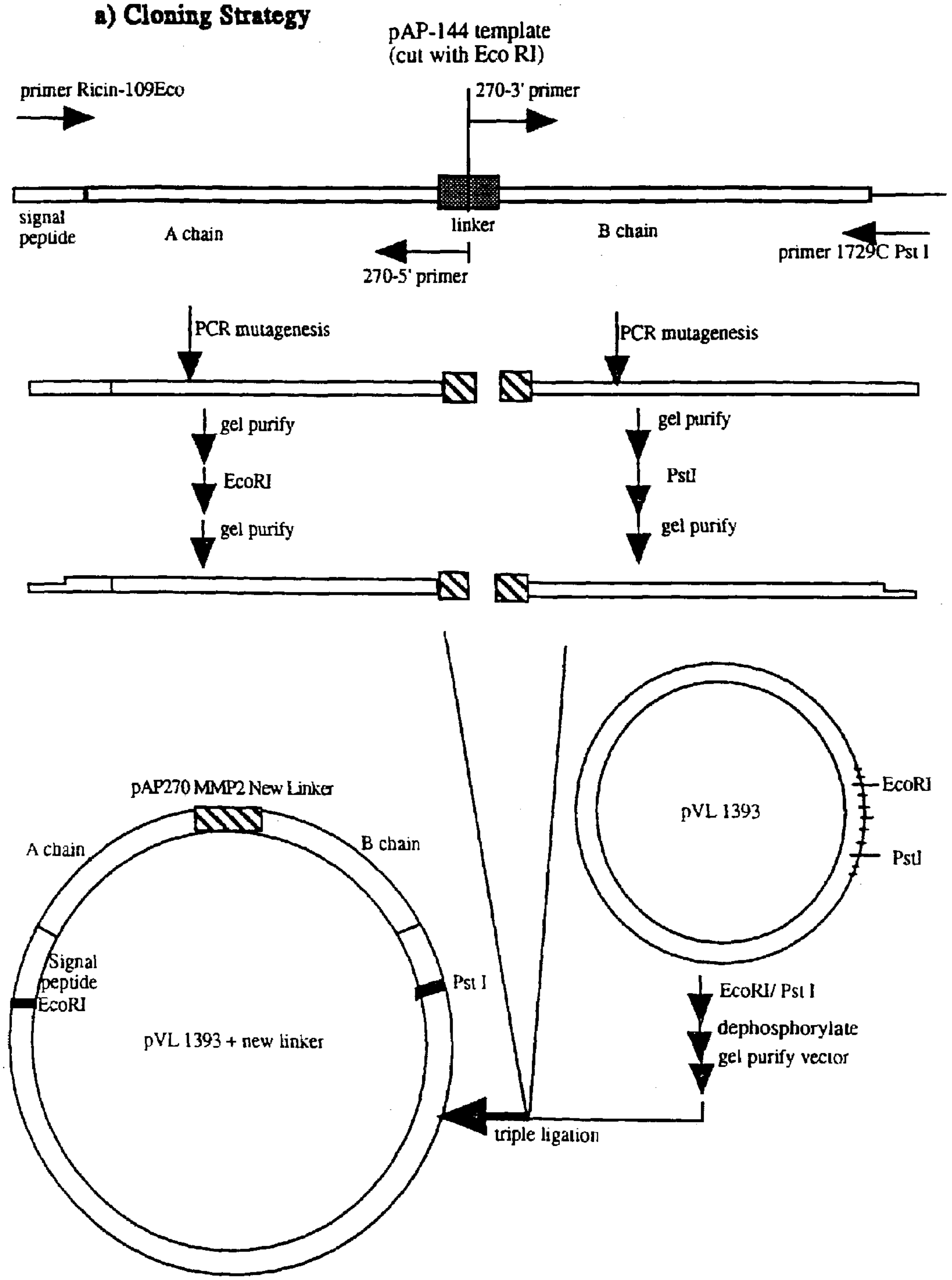
FIG. 34A summarizes the cloning strategy used to generate the pAP-270 construct.
Figure 35A:
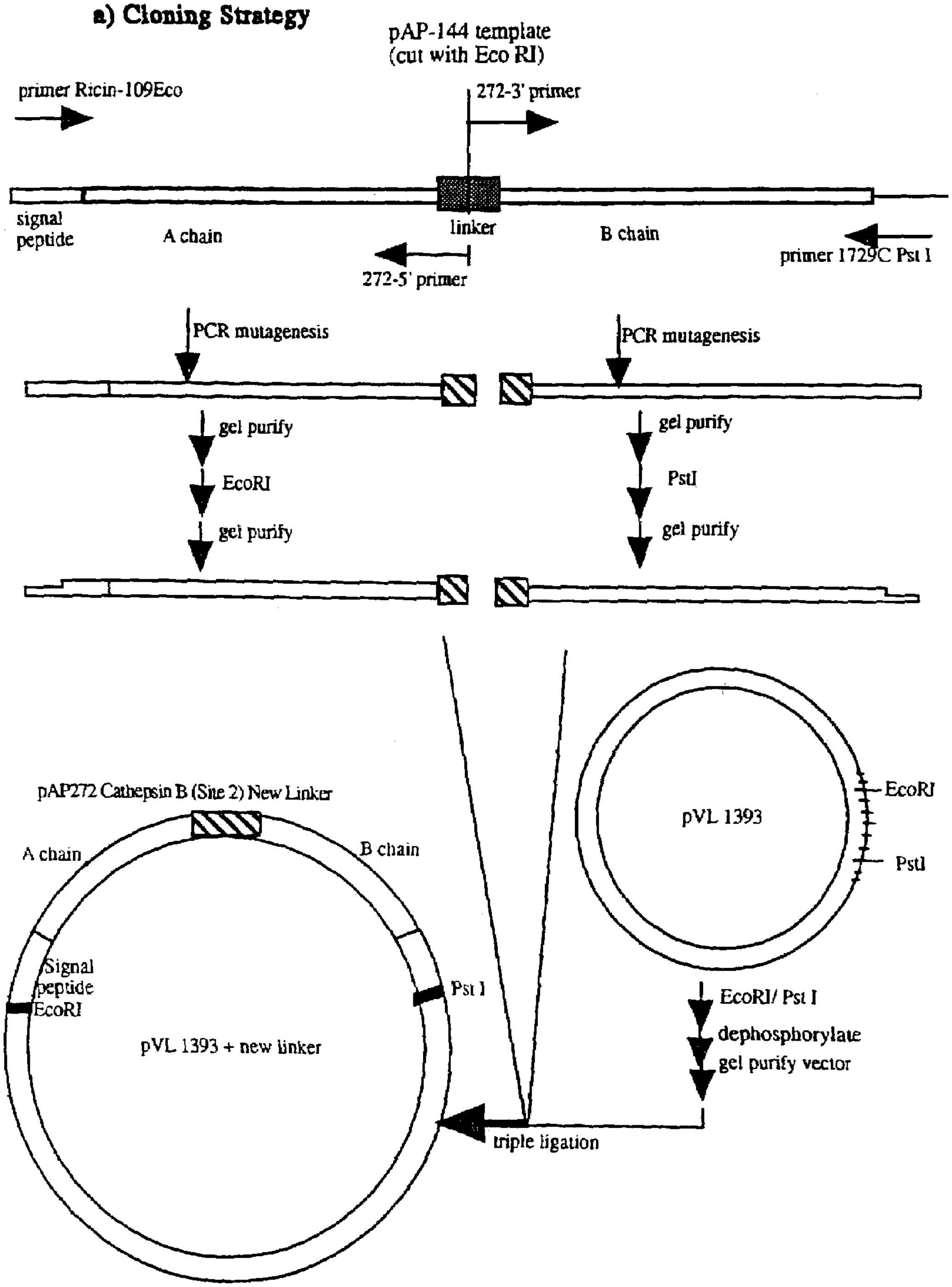
FIG. 35A summarizes the cloning strategy used to generate the pAP-272 construct.

An alternative mutagenesis and cloning strategy that can be used to generate the disease-specific protease-sensitive linker variants is summarized in FIG. 29. The first step of this method involves a DNA amplification using a set of mutagenic primers in combination with the two flanking primers Ricin-109Eco and Ricin1729Pst. Restriction digested PCR fragments (Eco RI and Pst I) are gel purified. Preproricin variants produced from this method can be subcloned directly into the baculovirus transfer vector digested with Eco RI and Pst I and intermediate ligation steps involving pBluescript SK and pSB2 are circumvented. The cloning strategies used to generate disease-specific protease-sensitive linker variants are summarized in Part A of FIGS. 30 to 47. With respect to the nucleotide sequences and amino acid sequences prepared as a result of the implementation of this strategy the following sequences have been assigned the sequence ID numbers as indicated.

The nucleotide sequence of the HCV-A linker region of pAP-262 is referred to herein as SEQ ID NO. 73.

The DNA sequence of the pAP-262 insert is referred to herein as SEQ ID NO. 74.

The amino acid sequence of the mutant preproricin linker region for HCV-A, pAP-262, is referred to herein as SEQ ID NO. 75.

The nucleotide sequence of the HCV-B linker region of pAP-264 is referred to herein as SEQ ID NO. 76.

The DNA sequence of the pAP-264 insert is referred to herein as SEQ ID NO. 77.

The amino acid sequence of the mutant preproricin linker region for HCV-B, pAP-264, is referred to herein as SEQ ID NO. 78.

The nucleotide sequence of the HCV-C linker region of pAP-266 is referred to herein as SEQ ID NO. 79.

The DNA sequence of the pAP-266 insert is referred to herein as SEQ ID NO. 80.

The amino acid sequence of the mutant preproricin linker region for HCV-C, pAP-266, is referred to herein as SEQ ID NO. 81.

The nucleotide sequence of the HCV-D linker region of pAP-268 is referred to herein as SEQ ID NO. 82.

The DNA sequence of the pAP-268 insert is referred to herein as SEQ ID NO. 83.

The amino acid sequence of the mutant preproricin linker region for HCV-D, pAP-268, is referred to herein as SEQ ID NO. 84.

The nucleotide sequence of the MMP-2 linker region of pAP-270 is referred to herein as SEQ ID NO. 85.

The DNA sequence of the pAP-270 insert is referred to herein as SEQ ID NO. 86.

The amino acid sequence of the mutant preproricin linker region for MMP-2, pAP-270, is referred to herein as SEQ ID NO. 87.

The nucleotide acid sequence of the Cathepsin B (Site 2) linker region of pAP-272 is referred to herein as SEQ ID NO. 88.

The DNA sequence of the pAP-272 insert is referred to herein as SEQ ID NO. 89.

The amino acid sequence of the mutant preproricin linker region for Cathepsin B (Site 2), pAP-272, is referred to herein as SEQ ID NO. 90.

The nucleotide sequence of the Cathepsin L linker region of pAP-274 is referred to herein as SEQ ID NO. 91.

The DNA sequence of the pAP-274 insert is referred to herein as SEQ ID NO. 92.

The amino acid sequence of the mutant preproricin linker region of Cathepsin L, pAP-274, is referred to herein as SEQ ID NO. 93.

The nucleotide sequence of Cathepsin D linker region of pAP-276 is referred to herein as SEQ ID NO. 94.

The DNA sequence of the pAP-276 insert is referred to herein as SEQ ID NO. 95.

The amino acid sequence of the mutant preproricin linker region for Cathepsin D, pAP-276, is referred to herein as SEQ ID NO. 96.

The nucleotide sequence of the MMP-1 linker region of pAP-278 is referred to herein as SEQ ID NO. 97.

The DNA sequence of the pAP-278 insert is referred to herein as SEQ ID NO. 98.

The amino acid sequence of the mutant preproricin linker region for MMP-1, pAP-278, is referred to herein as SEQ ID NO. 99.

The nucleotide sequence of the Urokinase-Type Plasminogen Activator linker region of pAP-280 is referred to herein as SEQ ID NO. 100.

The DNA sequene of the pAP-280 insert is referred to herein as SEQ ID NO. 101.

The amino acid sequence of the mutant preproricin linker region for Urokinase-Type Plasminogen Activator, pAP-280, is referred to herein as SEQ ID NO. 102.

The nucleotide sequence of MT-MMP linker region of pAP-282 is referred to herein as SEQ ID NO. 103.

The DNA sequence of the pAP-282 insert is referred to herein as SEQ ID NO. 104.

The amino acid sequence of the mutant preproricin linker region for MT-MMP, pAP-282, is referred to herein as SEQ ID NO. 105.

The nucleotide sequence of the MMP-11 linker region of pAP-284 is referred to herein as SEQ ID NO. 106.

The DNA sequence of the pAP-284 insert is referred to herein as SEQ ID NO. 107.

The amino acid sequence of the mutant preproricin linker region for MMP-11, pAP-284, is referred to herein as SEQ ID NO. 108.

The nucleotide sequence of the MMP-13 linker region of pAP-286 is referred to herein as SEQ ID NO. 109.

The DNA sequence of the pAP-286 insert is referred to herein as SEQ ID NO. 110.

The amino acid sequence of the mutant preproricin linker region for MMP-13, pAP-286, is referred to herein as SEQ ID NO. 111.

The nucleotide sequence of the Tissue-type Plasminogen Activator linker region of pAP-288 is referred to herein as SEQ ID NO. 112.

The DNA sequence of the pAP-288 insert is referred to herein as SEQ ID NO. 113.

The amino acid sequence of the mutant preproricin linker region for Tissue-type Plasminogen Activator, pAP-288, is referred to herein as SEQ ID NO. 114.

The nucleotide sequence of the human Prostate-Specific Antigen linker region of pAP-290 is referred to herein as SEQ ID NO. 115.

The DNA sequence of the pAP-290 insert is referred to herein as SEQ ID NO. 116.

The amino acid sequence of the mutant preproricin linker region for the human Prostate-Specific Antigen, pAP-290, is referred to herein as SEQ ID NO. 117.

The nucleotide sequence of the kallikrein linker region of pAP-292 is referred to herein as SEQ ID NO. 118.

The DNA sequence of the pAP-292 insert is referred to herein as SEQ ID NO. 119.

The amino acid sequence of the mutant preproricin linker region for the kallikrein, pAP-292, is referred to herein as SEQ ID NO. 120.

The nucleotide sequence of the neutrophil elastase linker region of pAP-294 is referred to herein as SEQ ID NO. 121.

The DNA sequence of the pAP-294 insert is referred to herein as SEQ ID NO. 122.

The amino acid sequence of the mutant preproricin linker region for neutrophil elastase, pAP-294, is referred to herein as SEQ ID NO. 123.

The nucleotide sequence of the calpain linker region of pAP-296 is referred to herein as SEQ ID NO. 124.

The DNA sequence of the pAP-296 insert is referred to herein as SEQ ID NO. 125.

The amino acid sequence of the mutant preproricin linker region for calpain, pAP-296, is referred to herein as SEQ ID NO. 126.

The amino acid sequence of the wild type linker region is referred to herein as SEQ ID NO. 127.

The nucleic acid molecule of the invention has sequences encoding an A chain of a ricin-like toxin, a B chain of a ricin-like toxin and a heterologous linker sequence containing a cleavage recognition site for a disease-specific protease. The nucleic acid may be expressed to provide a recombinant protein having an A chain of a ricin-like toxin, a B chain of a ricin-like toxin and a heterologous linker sequence containing a cleavage recognition site for a disease-specific protease.

The nucleic acid molecule may comprise the A and/or B chain of ricin. The ricin gene has been cloned and sequenced, and the X-ray crystal structures of the A and B chains are published (Rutenber, E., et al. Proteins 10:240-250 (1991); Weston et al., *Mol. Biol.* 244:410-422 (1994); Lamb and Lord, *Eur. J. Biochem.* 14:265 (1985); Halling, K., et al., *Nucleic Acids Res.* 13:8019 (1985)). It will be appreciated that the invention includes nucleic acid molecules encoding truncations of A and B chains of ricin like proteins and analogs and homologs of A and B chains of ricin-like proteins and truncations thereof (i.e., ricin-like proteins), as described herein. It will further be appreciated that variant forms of the nucleic acid molecules of the invention which arise by alternative splicing of an mRNA corresponding to a cDNA of the invention are encompassed by the invention.

Another aspect of the invention provides a nucleotide sequence which hybridizes under high stringency conditions to a nucleotide sequence encoding the A and/or B chains of a ricin-like protein. Appropriate stringency conditions which promote DNA hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

The nucleic acid molecule may comprise the A and/or B chain of a ricin-like toxin. Methods for cloning ricin-like toxins are known in the art and are described, for example, in E.P. 466,222. Sequences encoding ricin or ricin-like A and B chains may be obtained by selective amplification of a coding region, using sets of degenerative primers or probes for selectively amplifying the coding region in a genomic or cDNA library. Appropriate primers may be selected from the nucleic acid sequence of A and B chains of ricin or ricin-like toxins. It is also possible to design synthetic oligonucleotide primers from the nucleotide sequences for use in PCR. Suitable primers may be selected from the sequences encoding regions of ricin-like proteins which are highly conserved, as described for example in U.S. Pat. No. 5,101,025 and E.P. 466,222.

A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., *Biochemistry* 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.). It will be appreciated that the methods described above may be used to obtain the coding sequence from plants, bacteria or fungi, preferably plants, which produce known ricin-like proteins and also to screen for the presence of genes encoding as yet unknown ricin-like proteins.

A sequence containing a cleavage recognition site for a specific protease may be selected based on the disease or the pathogen which is to be targeted by the recombinant protein. The cleavage recognition site may be selected from sequences known to encode a cleavage recognition site for the cancer, viral or parasitic protease. Sequences encoding cleavage recognition sites may be identified by testing the expression product of the sequence for susceptibility to cleavage by the respective protease.

A sequence containing a cleavage recognition site for a viral, fungal, parasitic or cancer associated protease may be selected based on the retrovirus which is to be targeted by the recombinant protein. The cleavage recognition site may be selected from sequences known to encode a cleavage recognition site for the viral, fungal, parasitic or cancer associated protease. Sequences encoding cleavage recognition sites may be identified by testing the expression product of the sequence for susceptibility to cleavage by a viral, fungal, parasitic or cancer associated protease. A polypeptide containing the suspected cleavage recognition site may be incubated with a protease and the amount of cleavage product determined (DiIannit, 1990, J. Biol. Chem. 285: 17345-17354 (1990)).

The protease may be prepared by methods known in the art and used to test suspected cleavage recognition sites.

In one embodiment, the preparation of tumour-associated cathepsin B, its substrates and enzymatic activity assay methodology have been described by Sloane, B. F. et al. (*Proc. Natl. Acad. Sci. USA* 83:2483-2487 (1986)), Schwartz, M. K. (*Clin. Chim. Acta* 237:67-78 (1995)), and Panchal, R. G. et al. (*Nature Biotechnol.* 14:852-856 (1996)). The preparation of Epstein-Barr virus protease, its substrates and enzymatic activity assay methodology have been described by Welch, A. R. (*Proc. Natl. Acad. Sci. USA* 88:10792-10796 (1991)).

In another embodiment, the preparation of *Plasmodium falciparum* proteases, their substrates and enzymatic activity assay methodology have been described by Goldberg, D. E. et al. (*J. Exp. Med.* 173:961-969 (1991)), Cooper & Bujard (*Mol. Biochem. Parasitol.* 56:151-160 (1992)), Nwagwu, M. et al. (*Exp. Parasitol.* 75:399-414 (1992)), Rosenthal, P. J. et al. (*J. Clin. Invest.* 91:1052-1056 (1993)), Blackman, M. J. et al. (*Mol. Biochem. Parasitol.* 62:103-114 (1995)).

In a further embodiment, the preparation of proteases from human cytomegalovirus, human herpes virus, varicalla zoster virus and infectious laryngotracheitis virus have been taught by Liu F. & Roizman, B. (*J. Virol.* 65:5149-5156 (1991)) and Welch, A. R. (*Proc. Natl. Acad. Sci. USA* 88:10792-10796 (1991)). In addition, their respective substrates and enzymatic activity assay methodologies are also described.

In another embodiment, the preparation of hepatitis A virus protease, its substrates and enzymatic activity assay methodology have been described by Jewell, D. A. et al. (*Biochemistry* 31:7862-7869 (1992)). The preparation of poliovirus protease, its substrates and enzymatic activity assay methodology have been described by Weidner, J. R. et al. (*Arch. Biochem. Biophys.* 286:402-408 (1991)). The preparation of human rhinovirus protease, its substrates and enzymatic activity assay methodology have been described by Long, A. C. et al. (*FEBS Lett.* 258:75-78 (1989)).

In another embodiment of the invention, the preparation of proteases associated with *Candida* yeasts their substrates and enzymatic activity are contemplated, including the aspartic proteinases which have been associated specifically with numerous virulent strains of *Candida* including *Candida albican, Candida tropicalis*, and *Candida parapsilosis* (Abad-Zapatero, C. et al., *Protein Sci.* 5:640-652 (1996); Cutfield, S. M. et al., *Biochemistry* 35:398-410 (1995); Ruchel, R. et al, *Zentralbl. Bakteriol. Mikrobiol Hyg. I Abt. Orig. A.* 255:537-548 (1983); Remold, H. et al., *Biochim. Biophys. Acta* 167:399-406 (1968)).

The nucleic acid molecule of the invention may be prepared by site directed mutagenesis. For example, the cleavage site of a disease-specific protease may be prepared by site directed mutagenesis of the homologous linker sequence of a proricin-like toxin. Procedures for cloning proricin-like genes, encoding a linker sequence are described in EP 466,222. Site directed mutagenesis may be accomplished by DNA amplification of mutagenic primers in combination with flanking primers. Suitable procedures using the mutagenic primers are shown in Parts A and B of FIGS. 1-4, FIGS. 13-16, FIGS. 18-36, FIGS. 38-41, and FIGS. 50-67.

The nucleic acid molecule of the invention may also encode a fusion protein. A sequence encoding a heterologous linker sequence containing a cleavage recognition site for a disease-specific protease may be cloned from a cDNA or genomic library or chemically synthesized based on the known sequence of such cleavage sites. The heterologous linker sequence may then be fused in frame with the sequences encoding the A and B chains of the ricin-like toxin for expression as a fusion protein. It will be appreciated that a nucleic acid molecule encoding a fusion protein may contain a sequence encoding an A chain and a B chain from the same ricin-like toxin or the encoded A and B chains may be from different toxins. For example, the A chain may be derived from ricin and the B chain may be derived from abrin. A protein may also be prepared by chemical conjugation of the A and B chains and linker sequence using conventional coupling agents for covalent attachment.

An isolated and purified nucleic acid molecule of the invention which is RNA can be isolated by cloning a cDNA encoding an A and B chain and a linker into an appropriate vector which allows for transcription of the cDNA to produce an RNA molecule which encodes a protein of the invention. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

Recombinant Protein of the Invention

As previously mentioned, the invention provides novel recombinant proteins which incorporate the A and B chains of a ricin like toxin linked by a heterologous linker sequence containing a cleavage recognition site for a disease-specific protease. It is an advantage of the recombinant proteins of the invention that they are non-toxic until the A chain is liberated from the B chain by specific cleavage of the linker by the target protease.

Thus the protein may be used to specifically target cancer cells or cells infected with a virus or parasite in the absence of additional specific cell-binding components to target infected cells. It is a further advantage that the disease-specific protease cleaves the heterologous linker intracellularly thereby releasing the toxic A chain directly into the cytoplasm of the cancer cell or infected cell. As a result, said cells are specifically targeted and non-infected normal cells are not directly exposed to the activated free A chain.

Ricin is a plant derived ribosome inhibiting protein which blocks protein synthesis in eukaryotic cells. Ricin may be derived from the seeds of *Ricinus communis* (castor oil plant). The ricin toxin is a glycosylated heterodimer with A and B chain molecular masses of 30,625 Da and 31,431 Da respectively. The A chain of ricin has an N-glycosidase activity and catalyzes the excision of a specific adenine residue from the 28S rRNA of eukaryotic ribosomes (Endo, Y; & Tsurugi, K. J. Biol. Chem. 262:8128 (1987)). The B chain of ricin, although not toxic in itself, promotes the toxicity of the A chain by binding to galactose residues on the surface of eukaryotic cells and stimulating receptor-mediated endocytosis of the toxin molecule (Simmons et al., *Biol. Chem.* 261:7912 (1986)).

All protein toxins are initially produced in an inactive, precursor form. Ricin is initially produced as a single polypeptide (preproricin) with a 35 amino acid N-terminal presequence and 12 amino acid linker between the A and B chains. The pre-sequence is removed during translocation of the ricin precursor into the endoplasmic reticulum (Lord, J. M., *Eur. J. Biochem.* 146:403-409 (1985) and Lord, J. M., *Eur. J. Biochem.* 146:411-416 (1985)). The proricin is then translocated into specialized organelles called protein bodies where a plant protease cleaves the protein at a linker region between the A and B chains (Lord, J. M. et al., *FASAB Journal* 8:201-208 (1994)). The two chains, however, remain covalently attached by an interchain disulfide bond (cysteine 259 in the A chain to cysteine 4 in the B chain) and mature disulfide linked ricin is stored in protein bodies inside plant cells. The A chain is inactive in the proricin (O'Hare, M., et al., *FEBS Lett.* 273:200-204 (1990)) and it is inactive in the disulfide-linked mature ricin (Richardson, P. T. et al., *FEBS Lett.* 255:15-20 (1989)). The ribosomes of the castor bean plant are themselves susceptible to inactivation by ricin A chain; however, as there is no cell surface galactose to permit B chain recognition the A chain cannot re-enter the cell.

Ricin-like proteins include, but are not limited to, bacterial, fungal and plant toxins which have A and B chains and inactivate ribosomes and inhibit protein synthesis. The A chain is an active polypeptide subunit which is responsible for the pharmacologic effect of the toxin. In most cases the active component of the A chain is an enzyme. The B chain is responsible for binding the toxin to the cell surface and is thought to facilitate entry of the A chain into the cell cytoplasm. The A and B chains in the mature toxins are linked by disulfide bonds. The toxins most similar in structure to ricin are plant toxins which have one A chain and one B chain. Examples of such toxins include abrin which may be isolated from the seeds of Abrus precatorius and modeccin.

Ricin-like bacterial proteins include diphtheria toxin, which is produced by *Corynebacterium diphtheriae, Pseudomonas*enterotoxin A and cholera toxin. It will be appreciated that the term ricin-like toxins is also intended to include the A chain of those toxins which have only an A chain. The recombinant proteins of the invention could include the A chain of these toxins conjugated to, or expressed as, a recombinant protein with the B chain of another toxin. Examples of plant toxins having only an A chain include trichosanthin, MMC and pokeweed antiviral proteins, dianthin 30, dianthin 32, crotin II, curcin II and wheat germ inhibitor. Examples of fungal toxins having only an A chain include alpha-sarcin, restrictocin, mitogillin, enomycin, phenomycin. Examples of bacterial toxins having only an A chain include cytotoxin from *Shigella dysenteriae* and related Shiga-like toxins. Recombinant trichosanthin and the coding sequence thereof is disclosed in U.S. Pat. Nos. 5,101,025 and 5,128,460.

In addition to the entire A or B chains of a ricin-like toxin, it will be appreciated that the recombinant protein of the invention may contain only that portion of the A chain which is necessary for exerting its cytotoxic effect. For example, the first 30 amino acids of the ricin A chain may be removed resulting in a truncated A chain which retains toxic activity. The truncated ricin or ricin-like A chain may be prepared by expression of a truncated gene or by proteolytic degradation, for example with Nagarase (Funmatsu et al., *Jap. J. Med. Sci. Biol.* 23:264-267 (1970)). Similarly, the recombinant protein of the invention may contain only that portion of the B chain necessary for galactose recognition, cell binding and transport into the cell cytoplasm. Truncated B chains are described for example in E.P. 145,111. The A and B chains may be glycosylated or non-glycosylated. Glycosylated A and B chains may be obtained by expression in the appropriate host cell capable of glycosylation. Non-glycosylated chains may be obtained by expression in nonglycosylating host cells or by treatment to remove or destroy the carbohydrate moieties.

The proteins of the invention may be prepared using recombinant DNA methods. Accordingly, the nucleic acid molecules of the present invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native A and B chains and/or its flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, diethylaminoethyl-dextran (DEAE-dextran) mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include *E. coli, B. subtilis, Salmonella typhimurium*, and various species within the genus' *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615 (1978)), the trp promoter (Nichols and Yanofsky, Meth in Enzymology 101:155, (1983) and the tac promoter (Russell et al., Gene 20: 231, (1982)). Representative selectable markers include various antibiotic resistance markers such as the kanamycin or ampicillin resistance genes. Suitable expression vectors include but are not limited to bacteriophages such as lambda derivatives or plasmids such as pBR322 (Bolivar et al., *Gene* 2:9S, (1977)), the pUC plasmids pUC18, pUC19, pUC118, pUC119 (see Messing, Meth in Enzymology 101:20-77, 1983 and Vieira and Messing, *Gene* 19:259-268 (1982)), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (Amann et al., *Gene* 69:301-315 (1988)) and pET 11d (Studier et al., Gene Expression Technology: Methods in Enzymology 185, Academic Press, San Diego, Calif., 60-89 (1990)).

Yeast and fungi host cells suitable for carrying out the present invention include, but are not limited to *Saccharomyces cerevisae*, the genera *Pichia* or *Kluyveromyces* and various species of the genus *Aspergillus*. Examples of vectors for expression in yeast *S. cerivisae* include pYepSec1 (Baldari. et al., *Embo J.* 6:229-234 (1987)), pMFa (Kurjan and Herskowitz, *Cell* 30:933-943 (1982)), pJRY88 (Schultz et al., *Gene* 54:113-123 (1987)), and pYES2 (Invitrogen Corporation, San Diego, Calif.). Protocols for the transformation of yeast and fungi are well known to those of ordinary skill in the art. (see Hinnen et al., *Proc. Natl. Acad. Sci. USA* 75:1929 (1978); Itoh et al., *J. Bacteriology* 153:163 (1983), and Cullen et al. (*Bio/Technology* 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., *Nature* 329:840 (1987)) and pMT2PC (Kaufman et al., *EMBO J.* 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., *J. Biosci* (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, pAS2022, pAS2023, and pAS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., *Mol. Cell Biol.* 3:2156-2165 (1983)) and the pVL series (Lucklow, V. A., and Summers, M. D., *Virology* 170:31-39 (1989)). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. *Nature* 315:680-683 (1985); Palmiter et al. *Science* 222:809-814 (1983); Brinster et al. *Proc. Natl. Acad. Sci. USA* 82:4438-4442 (1985); Palmiter and Brinster *Cell* 41:343-345 (1985) and U.S. Pat. No. 4,736,866).

The proteins of the invention may also be prepared by chemical synthesis using techniques well known in the chemistry of proteins such as solid phase synthesis (Merrifield, *J. Am. Chem. Assoc.* 85:2149-2154 (1964)) or synthesis in homogenous solution (Houbenweyl, Methods of Organic Chemistry, ed. E. Wansch, Vol. 15 I and II, Thieme, Stuttgart (1987)).

The present invention also provides proteins comprising an A chain of a ricin-like toxin, a B chain of a ricin-like toxin and a heterologous linker amino acid sequence linking the A and B chains, wherein the linker sequence contains a cleavage recognition site for a disease-specific protease. Such a protein could be prepared other than by recombinant means, for example by chemical synthesis or by conjugation of A and B chains and a linker sequence isolated and purified from their natural plant, fungal or bacterial source. Such A and B chains could be prepared having the glycosylation pattern of the native ricin-like toxin.

N-terminal or C-terminal fusion proteins comprising the protein of the invention conjugated with other molecules, such as proteins may be prepared by fusing, through recombinant techniques. The resultant fusion proteins contain a protein of the invention fused to the selected protein or marker protein as described herein. The recombinant protein of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Utility of the Nucleic Acid Molecules and Proteins of the Invention

The proteins of the invention may be used to specifically inhibit or destroy mammalian cells affected by a disease or infection which have associated with such cells a specific protease, i.e., disease-specific, for example cancer cells or cells infected with a virus, fungus or parasite, all of which are encompassed within the term “disease-specific.” It is an advantage of the recombinant proteins of the invention that they have specificity for said cells without the need for a cell binding component. The ricin-like B chain of the recombinant proteins recognize galactose moieties on the cell surface and ensure that the protein is taken up by the diseased cell and released into the cytoplasm. When the protein is internalized into a non-infected cell, cleavage of the heterologous linker would not occur in the absence of the disease-specific protease and the A chain will remain inactive bound to the B chain. Conversely, when the protein is internalized into a diseased cell, the disease-specific protease will cleave the cleavage recognition site in the linker thereby releasing the toxic A chain.

The specificity of a recombinant protein of the invention may be tested by treating the protein with the disease-specific protease which is thought to be specific for the cleavage recognition site of the linker and assaying for cleavage products. Disease-specific proteases may be isolated from cancer cells or infected cells, or they may be prepared recombinantly, for example following the procedures in Darket et al. (*J. Biol. Chem.* 254:2307-2312 (1988)). The cleavage products may be identified for example based on size, antigenicity or activity. The toxicity of the recombinant protein may be investigated by subjecting the cleavage products to an in vitro translation assay in cell lysates, for example using Brome Mosaic Virus mRNA as a template. Toxicity of the cleavage products may be determined using a ribosomal inactivation assay (Westby et al., *Bioconjugate Chem.* 3:377-382 (1992)). The effect of the cleavage products on protein synthesis may be measured in standardized assays of in vitro translation utilizing partially defined cell free systems composed for example of a reticulocyte lysate preparation as a source of ribosomes and various essential cofactors, such as mRNA template and amino acids. Use of radiolabelled amino acids in the mixture allows quantitation of incorporation of free amino acid precursors into trichloroacetic acid precipitable proteins. Rabbit reticulocyte lysates may be conveniently used (O'Hare, *FEBS Lett.* 273:200-204 (1990)).

The ability of the recombinant proteins of the invention to selectively inhibit or destroy animal cancer cells or cells infected with a virus or parasite may be readily tested in vitro using animal cancer cell lines or cell cultures infected with the virus or parasite of interest. The selective inhibitory effect of the recombinant proteins of the invention may be determined, for example, by demonstrating the selective inhibition of viral antigen expression in infected mammalian cells, the selective inhibition of general mRNA translation and protein synthesis in diseased cells, or selective inhibition of cellular proliferation in cancer cells or infected cells.

Toxicity may also be measured based on cell viability, for example the viability of infected and non-infected cell cultures exposed to the recombinant protein may be compared. Cell viability may be assessed by known techniques, such as trypan blue exclusion assays.

In another example, a number of models may be used to test the cytotoxicity of recombinant proteins having a heterologous linker sequence containing a cleavage recognition site for a cancer-associated matrix metalloprotease. Thompson, E. W. et al. (*Breast Cancer Res. Treatment* 31:357-370 (1994)) has described a model for the determination of invasiveness of human breast cancer cells in vitro by measuring tumour cell-mediated proteolysis of extracellular matrix and tumour cell invasion of reconstituted basement membrane (collagen, laminin, fibronectin, Matrigel or gelatin). Other applicable cancer cell models include cultured ovarian adenocarcinoma cells (Young, T. N. et al. *Gynecol. Oncol.* 62:89-99 (1996); Moore, D. H. et al. *Gynecol. Oncol.* 65:78-82 (1997)), human follicular thyroid cancer cells (Demeure, M. J. et al., *World J. Surg.* 16:770-776 (1992)), human melanoma (A-2058) and fibrosarcoma (HT-1080) cell lines (Mackay, A. R. et al. *Lab. Invest.* 70:781-783 (1994)), and lung squamous (HS-24) and adenocarcinoma (SB-3) cell lines (Spiess, E. et al. *J. Histochem. Cytochem.* 42:917-929 (1994)). An in vivo test system involving the implantation of tumours and measurement of tumour growth and metastasis in athymic nude mice has also been described (Thompson, E. W. et al., *Breast Cancer Res. Treatment* 31:357-370 (1994); Shi, Y. E. et al., *Cancer Res.* 53:1409-1415 (1993)).

A further model may be used to test the cytotoxicity of recombinant proteins having a heterologous linker sequence containing a cleavage recognition site for a cancer-associated Cathepsin B protease is provided in human glioma (Mikkelsen, T. et al. J. *Neurosurge*, 83:285-290 (1995)).

Similarly, the cytotoxicity of recombinant proteins having a heterologous linker sequence containing a cleavage recognition site for a malarial protease may be tested by a *Plasmodium* invasion assay using human erythrocytes infected with mature-stage merozoite parasites as described by McPherson, R. A. et al. (*Mol. Biochem. Parasitol.* 62:233-242 (1993)). Alternatively, in vitro cultures of human hepatic parenchymal cells may be used to evaluate schizont infectivity and *Plasmodium merozoite* generation.

With respect to models of viral infection and replication, suitable animal cells which can be cultured in vitro and which are capable of maintaining viral replication can be used as hosts. The toxicity of the recombinant protein for infected and non-infected cultures may then be compared. The ability of the recombinant protein of the invention to inhibit the expression of these viral antigens may be an important indicator of the ability of the protein to inhibit viral replication. Levels of these antigens may be measured in assays using labelled antibodies having specificity for the antigens. Inhibition of viral antigen expression has been correlated with inhibition of viral replication (U.S. Pat. No. 4,869,903). Toxicity may also be assessed based on a decrease in protein synthesis in target cells, which may be measured by known techniques, such as incorporation of labelled amino acids, such as [3H] leucine (O'Hare et al., *FEBS Lett.* 273:200-204 (1990)). Infected cells may also be pulsed with radiolabelled thymidine and incorporation of the radioactive label into cellular DNA may be taken as a measure of cellular proliferation. Toxicity may also be measured based on cell death or lysis, for example, the viability of infected and non-infected cell cultures exposed to the recombinant protein may be compared. Cell viability may be assessed by known techniques, such as trypan blue exclusion assays.

Although the primary specificity of the proteins of the invention for diseased cells is mediated by the specific cleavage of the cleavage recognition site of the linker, it will be appreciated that specific cell binding components may optionally be conjugated to the proteins of the invention. Such cell binding components may be expressed as fusion proteins with the proteins of the invention or the cell binding component may be physically or chemically coupled to the protein component. Examples of suitable cell binding components include antibodies to cancer, viral or parasitic proteins.

Antibodies having specificity for a cell surface protein may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., Monoclonal Antibodies in Cancer Therapy Allen R., Bliss, Inc., pages 77-96 (1985)), and screening of combinatorial antibody libraries (Huse et al., *Science* 246:1275 (1989)). Hybridoma cells can be screened immunochemically for production of antibodies specifically reactive with the peptide and the monoclonal antibodies can be isolated.

The term "antibody" as used herein is intended to include fragments thereof which also specifically react with a cell surface component. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a cell surface antigen (See, for example, Morrison et al., *Proc. Natl Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., E.P. Pat. No. 171,496; European Patent No. 173,494, United Kingdom Patent No. GB 2177096B). It is expected that chimeric antibodies would be less immunogenic in a human subject than the corresponding non-chimeric antibody.

Monoclonal or chimeric antibodies specifically reactive against cell surface components can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g. Teng et al., *Proc. Natl. Acad. Sci. U.S.A.*, 80:7308-7312 (1983); Kozbor et al., *Immunology Today* 4:7279 (1983); Olsson et al., *Meth. Enzymol.*, 92:3-16 (1982), and PCT Publication WO92/06193 or EP 239,400). Humanized antibodies can also be commercially produced (Scotgen Limited, 2 Holly Road, Twickenham, Middlesex, Great Britain.)

Specific antibodies, or antibody fragments, reactive against cell surface components may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., *Nature* 341:544-546 (1989); Huse et al., *Science* 246:1275-1281 (1989); and McCafferty et al., *Nature* 348:552-554 (1990)). Alternatively, a SCID-hu mouse, for example the model developed by Genpharm, can be used to produce antibodies, or fragments thereof.

The proteins of the invention may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation.

The nucleic acid molecules of the invention may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, intramuscular, etc.), oral administration, inhalation, transdermal administration (such as topical cream or ointment, etc.), or suppository applications. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The pharmaceutical compositions may be used in methods for treating animals, including mammals, preferably humans, with cancer or infected with a virus or a parasite. It is anticipated that the compositions will be particularly useful for treating patients with B-cell lymphoproliferative disease, (melanoma), mononucleosis, cytomegalic inclusion disease, malaria, herpes, shingles, hepatitis, poliomyelitis, or infectious laryngotracheitis. The dosage and type of recombinant protein to be administered will depend on a variety of factors which may be readily monitored in human subjects. Such factors include the etiology and severity (grade and stage) of neoplasia, the stage of malarial infection (e.g. exoerythrocytic vs. erythrocytic), or antigen levels associated with viral load in patient tissues or circulation.

As mentioned above, the novel recombinant toxic proteins and nucleic acid molecules of the present invention are useful in treating cancerous or infected cells wherein the cells contain a specific protease that can cleave the linker region of the recombinant toxic protein. One skilled in the art can appreciate that many different recombinant toxic proteins can be prepared once a disease associated protease has been identified. For example, the novel recombinant toxic proteins and nucleic acid molecules of the invention may be used to treat CNS tumors. Muller et al. (1993) describe increased activity of Insulin-type Growth Factor Binding Protein-3 (IGFBP-3) protease in the Cerebral Spinal Fluid of patients with CNS tumors. Cohen et al. (1992) claim that prostate-specific antigen (PSA) is an IGFBP-3 protease. The pAP290 construct described above is a substrate for PSA. Conover et al. (1994) claim that cathepsin D is IGFBP-3 protease. The pAP276 described herein is a substrate for cathepsin D. Another example of a specific use of the invention is treatment of human glioma which has been shown to produce cathepsin D (Mikkelsen, T. et al. *J. Neurosurge*, 83:285-290 (1995)). The pAP 214 and 272 define herein are substrates for cathepsin B.

In addition, the novel proteins and nucleic acid molecules of the present invention may be used to treat cystic fibrosis. Hansen et al. (1995) describe how CF airway disease is characterized by neutrophil-dominated chronic inflammation with an excess of uninhibited neutrophil elastase (NE). NE levels in CF sputum are 350 times higher than that found in normal sputum. The pAP294 described herein is a substrate for neutrophil elastase.

As well, the novel proteins and nucleic acid molecules of the present invention may also be used to treat multiple sclerosis. Bever Jr. et al. (1994) implicate cathepsin B (possibly from inflammatory cells of hematogenous origin) in the demyelination found in multiple sclerosis. pAPs 214 and 272 defined herein present substrates for cathepsin B.

The term “animal” as used herein includes all members of the animal kingdom including mammals, preferably humans.

The following non-limiting examples are illustrative of the present invention:

EXAMPLES

Example 1

Cloning and Expression of Proricin Variants Activated by Disease-Specific Proteases Isolation of Total RNA The preproricin gene was cloned from new foliage of the castor bean plant. Total messenger RNA was isolated according to established procedures (Sambrook et al., *Molecular Cloning: A Lab Manual* (Cold Spring Harbour Press, Cold Spring Harbour, (1989)) and cDNA generated using reverse transcriptase.

cDNA Synthesis:

Oligonucleotides, corresponding to the extreme 5' and 3' ends of the preproricin gene were synthesized and used to polymerase chain reaction (PCR) amplify the gene. Using the cDNA sequence for preproricin (Lamb et al., Eur. J. Biochem., 145:266-270, 1985), several oligonucleotide primers were designed to flank the start and stop codons of the preproricin open reading frame. The oligonucleotides were synthesized using an Applied Biosystems Model 392 DNA/RNA Synthesizer. First strand cDNA synthesis was primed using the oligonucleotide Ricin1729C (Table 1). Three micrograms of total RNA was used as a template for oligo Ricin1729C primed synthesis of cDNA using Superscript II Reverse Transcriptase (BRL) following the manufacturer’s protocol.

DNA Amplification and Cloning

The first strand cDNA synthesis reaction was used as template for DNA amplification by the polymerase chain reaction (PCR). The preproricin cDNA was amplified using the upstream primer Ricin-99 and the downstream primer Ricin1729C with Vent DNA polymerase (New England Biolabs) using standard procedures (Sambrook et al., Molecular Cloning: A Laboratory Manual, Second Edition, (Cold Spring Harbor Laboratory Press, 1989)). Amplification was carried out in a Biometra thermal cycler (TRIO-Thermalcycler) using the following cycling parameters: denaturation 95° C. for 1 min., annealing 52° C. for 1 min., and extension 72° C. for 2 min., (33 cycles), followed by a final extension cycle at 72° C. for 10 min. The 1846bp amplified product was fractionated on an agarose gel (Sambrook et al., Molecular Cloning: A Laboratory Manual, Second Edition, (Cold Spring Harbor Laboratory Press, 1989), and the DNA purified from the gel slice using Qiaex resin (Qiagen) following the manufacturer’s protocol. The purified PCR fragment encoding the preproricin cDNA was then ligated (Sambrook et al., Molecular Cloning: A Laboratory Manual, Second Edition, (Cold Spring Harbor Laboratory Press, 1989)) into an Eco RV-digested pBluescript II SK plasmid (Stratagene), and used to transform competent XL1-Blue cells (Stratagene). Positive clones were confirmed by restriction digestion of purified plasmid DNA. Plasmid DNA was extracted using a Qiaprep Spin Plasmid Miniprep Kit (Qiagen).

DNA Sequencing

The cloned PCR product containing the putative preproricin gene was confirmed by DNA sequencing of the entire cDNA clone (pAP-144). Sequencing was performed using an Applied Biosystems 373A Automated DNA Sequencer, and confirmed by double-stranded dideoxy sequencing by the Sanger method using the Sequenase kit (USB). The oligonucleotide primers used for sequencing were as follows: Ricin267, Ricin486, Ricin725, Ricin937, Ricin1151, Ricini1399, Ricin1627, T3 primer (5'AATTAACCCTCACTAAAGGG-3') (SEQ ID NO. 128) and T7 primer (5'GTAATACGACTCACTATAGGGC-3) (SEQ ID NO. 129). Sequence data was compiled and analyzed using PC Gene software package (intelligenetics). The sequences and location of oligonucleotide primers is shown in Table 1. The oligonucleotide primers shown in Table 1 have been assigned the following sequence ID numbers:

Ricin-109 is referred to herein as SEQ ID NO. 130;
Ricin-99Eco is referred to herein as SEQ ID NO. 131;
Ricin267 is referred to herein as SEQ ID NO. 132;
Ricin486 is referred to herein as SEQ ID NO. 133;
Ricin725 is referred to herein as SEQ ID NO. 134;
Ricin 937 is referred to herein as SEQ ID NO. 135;
Ricin 1151 is referred to herein as SEQ ID NO. 136;
Ricin 1399 is referred to herein as SEQ ID NO. 137;
Ricin 1627 is referred to herein as SEQ ID NO. 138;
Ricin 1729C is referred to herein as SEQ ID NO. 139; and
Ricin 1729C Xba is referred to herein as SEQ ID NO. 140.

Production and Cloning of Linker Variants pAP144 cut with EcoRI was used as target for PCR pairs employing the Ricin109-Eco oligonucleotide (Ricin-109Eco primer: 5 GGAGGAATCCGGAGATGAAACCGGGAGGAAATACTATTGTAAT-3 (SEQ ID No. 141)) and a mutagenic primer for the 5' half of the linker as well as the Ricin1729Pstl primer (Ricin1729-Pstl: 5 GTAGGCGCTGCAGATAACTTGCTGTCCTTTCAG-3 (SEQ ID No. 142)) and a mutagenic primer for the 3' half of the linker. The cycling conditions used for the PCRs were 98° C. for 2 min.;

98° C. min., 52° C. 1 min., 72° C. 1 min. 15 sec. (30 cycles); 72° C. 10 min.; 4° C. soak. The PCR products were then digested by EcoRI and Pstl respectively, electrophoresed on an agarose gel, and the bands purified by via glass wool spin columns. Triple ligations comprising the PCR product pairs (corresponding halves of the new linker) and pVL1393 vector digested with EcoRI and Pstl were carried out. Recombinant clones were identified by restriction digests of plasmid miniprep DNA and the altered linkers confirmed by DNA sequencing. See FIG. 45 as an example of the cloning strategy. Recombinant clones were identified by restriction digests of plasmid miniprep DNA and the altered linkers confirmed by DNA sequencing. Note that since all altered linker variants were cloned directly into the pVL1393 vector odd-numbered pAPs were no longer required or produced.

Isolation of Recombinant Baculoviruses

Insect cells *S. frugiperda* (Sf9), and *Trichoplusia ni* (Tn368 and BTI-TN-581-4 (High Five)) were maintained on EX-CELL 405 medium (JRH Biosciences) supplemented with 10% total calf serum (Summers et al., A Manual of Methods of Baculovirus Vectors and Insect Cell Culture Procedures, (Texas Agricultural Experiment Station, 1987)). Two micrograms of recombinant pVL1393 DNA was co-transfected with 0.5 microgram of BaculoGold AcNPV DNA (Pharmingen) into $2\times10^6$ Tn368 insect cells following the manufacturer's protocol (Gruenwald et al., Baculovirus Expression Vector System: Procedures and Methods Manual, 2nd Edition, (San Diego, Calif., 1993)). On day 5 post-transfection, media were centrifuged and the supernatants tested in limiting dilution assays with Tn368 cells (Summers et al., A Manual of Methods of Baculovirus Vectors and Insect Cell Culture Procedures, (Texas Agricultural Experiment Station, 1987)). Recombinant viruses in the supernatants were then amplified by infecting Tn368 cells at a multiplicity of infection (moi) of 0.1, followed by collection of day 3 to 5 supernatants. A total of three rounds of amplification were performed for each recombinant following established procedures (Summers et al., A Manual of Methods of Baculovirus Vectors and Insect Cell Culture Procedures, (Texas Agricultural Experiment Station, 1987 and Gruenwald et al., Baculovirus Expression Vector System: Procedures and Methods Manual, 2nd Edition, (San Diego, Calif., 1993)).

Expression of Mutant Proricin

Recombinant baculoviruses were used to infect $1\times10^7$ Tn368 or sf9 cells at an moi of 9 in EX-CELL 405 media (JRH Biosciences) with 25 mM α-lactose in spinner flasks. Media supernatants containing mutant proricins were collected 3 or 4 days post-infection.

Example 2

Harvesting and Affinity Column Purification of Pro-ricin Variants

Protein samples were harvested three days post transfection. The cells were removed by centrifuging the media at 8288 g for ten minutes using a GS3 (Sorvall) centrifuge rotor. The supernatant was further clarified by centrifuging at 25400 g using a SLA-1500 rotor (Sorvall) for 45 minutes. Protease inhibitor phenylmethylsulfonyl fluoride (Sigma) was slowly added to a final concentration of 1 mM. The samples were further prepared by adding lactose to a concentration of 20 mM (not including the previous lactose contained in the expression medium). The samples were concentrated to 700 mL using a Prep/Scale-TFF Cartridge (2.5 ft, 10K regenerated cellulose (Millipore)) and a Masterflex pump. The samples were then dialysed for 2 days in 1× Column Buffer (50 mM Tris, 100 mM NaCl, 0.02% $NaN_3$, pH 7.5) using dialysis tubing (10 K MWCO, 32 mm flat width(Spectra/Por)). Subsequently, the samples were clarified by centrifuging at 25400 g using a SLA-1500 rotor (Sorvall) for 45 minutes.

Following centrifugation, the samples were degassed and applied at 4° C. to a XK26/20 (Pharmacia) column (attached to a Pharmacia peristaltic pump, Pharmacia Single-path Monitor UV-1 Control and Optical Units, and Bromma LKB 2210 2-Channel Recorder) containing 20 mL of a-Lactose Agarose Resin (Sigma). The column was washed for 3 hours with 1× Column buffer. Elution of pro-ricin variant was performed by eluting with buffer (1× Column buffer (0.1% NaN3), 100 mM Lactose) until the baseline was again restored. The samples were concentrated using an Amicon 8050 concentrator (Amicon) with a YM10 76 mm membrane, utilizing argon gas to pressurize the chamber. The samples were further concentrated in Centricon 10 (Millipore) concentrators according to manufacturer's specifications.

Purification of Variant pAP-Protein by Gel Filtration Chromatography

In order to purify the pro-ricin variant from processed material produced during fermentation, the protein was applied to a SUPERDEX 75 (16/60) column and SUPERDEX 200 (16/60) column (Pharmacia) connected in series equilibrated with 50 mM Tris, 100 mM NaCl, pH 7.5 containing 100 mM Lactose and 0.1% b-mercaptoethanol (bME). The flow rate of the column was 0.15 mL/min and fractions were collected every 25 minutes. The ultraviolet (UV) (280 nm) trace was used to determine the approximate location of the purified pAP-protein and thus determine the samples for Western analysis.

Western Analysis of Column Fractions

Fractions eluted from the SUPERDEX columns (Pharmacia) were analyzed for purity using standard Western blotting techniques. An aliquot of 10 μL from each fraction was boiled in 1× sample buffer (62.6 mM Tris-Cl, pH 6.8, 4.4% βME, 2% sodium dodecyl sulfate (SDS), 5% glycerol (all from Sigma) and 0.002% bromophenol blue (Biorad)) for five minutes. Denatured samples were loaded on 12% Tris-Glycine Gels (Biorad) along with 50 ng of $RCA_{60}$ (Sigma) and 5 μL of kaleidoscope prestained standards (Biorad). Electrophoresis was carried out for ninety minutes at 100V in 25 mM Tris-Cl, pH 8.3, 0.1% SDS, and 192 mM glycine using the BioRad Mini Protean II cells (Biorad).

Following electrophoresis gels were equilibrated in transfer buffer (48 mM Tris, 39 mM glycine, 0.0375% SDS, and 20% Methanol) for a few minutes. Polyvinyl diflouride (PVDF) Biorad membrane was presoaked for one minute in 100% methanol, rinsed in deionized distilled water and two minutes in transfer buffer. Whatman paper was soaked briefly in transfer buffer. Five pieces of Whatman paper, membrane, gel, and another five pieces of Whatman paper were arranged on the bottom cathode (anode) of the Pharmacia Novablot transfer apparatus (Pharmacia). Transfer was for one hour at constant current (2 mA/cm2).

Transfer was confirmed by checking for the appearance of the prestained standards on the membrane. Non-specific sites on the membrane were blocked by incubating the blot for thirty minutes in 1× Phosphate Buffered Saline (1×PBS; 137 mM NaCl, 2.7 mM KCl, 8 mM $Na_2HPO_4$, 1.5 mM $KH_2PO_4$, pH 7.4) with 5% skim milk powder (Carnation). Primary antibody (Rabbit α-ricin, Sigma) was diluted 1:3000 in 1×PBS containing 0.1% Tween 20 (Sigma) and 2.5% skim milk and incubated with blot for forty five minutes on a orbital shaker (VWR). Non-specifically bound primary antibody was removed by washing the blot for ten minutes with 1×PBS containing 0.2% Tween 20. This was repeated four times. Secondary antibody donkey anti-rabbit (Amersham) was incubated with the blot under the same conditions as the primary antibody. Excess secondary antibody was washed as described above. Blots were developed with the ECL Western Blotting detection reagents according to the manufacturer's instructions. Blots were exposed to Medtec's Full Speed Blue Film (Medtee) or Amersham's ECL Hyperfilm (Amersham) for one second to five minutes. Film was developed in a KODAK Automatic Developer.

Determination of Lectin Binding Ability of Pro-ricin Variant

An Immulon 2 plate (VDVR) was coated with 100 μl per well of 10 μg/ml of asialofetuin and left overnight at 4° C. The plate was washed with 3×300 μL per well with $ddH_2O$ using an automated plate washer (BioRad). The plate was blocked for one hour at 37° C. by adding 300 μL per well of PBS containing 1% ovalbumin. The plate was washed again as above. Pro-ricin variant pAP-protein was added to the plate in various dilutions in 1× Baculo. A standard curve of $RCA_{60}$ (Sigma) from 1-10 ng was also included. The plate was incubated for 1 h at 37° C. The plate was washed as above. Anti-ricin monoclonal antibody (Sigma) was diluted 1:3000 in 1×PBS containing 0.5% ovalbumin and 0.1% tween-20, added at 100 μL per well and incubated for 1 h at 37° C. The plate was washed as above. Donkey-anti rabbity polyclonal antibody was diluted 1:3000 in 1×PBS containing 0.5% ovalbumin, 0.1% Tween-20, and added at 100 μL per well and incubated for 1 h at 37° C. The plate was given a final wash as described above. Substrate was added to plate at 100 μL per well (1 mg/ml o-phenylenediamine (Sigma), 1 μL/ml $H_2O_2$, 25 μL of stop solution (20% $H_2SO_4$) was added and the absorbance read (A490 nm-A630 nm) using a SPECTRA MAX 340 plate reader (Molecular Devices).

Determination of pAP-Protein Activity Using the Rabbit Reticulocyte Assay

Ricin samples were prepared for reduction.

A) $RCA_{60}$=3,500 ng/μL of $RCA_{60}$+997 μL 1×Endo buffer (25 mM Tris, 25 mM KCl, 5 mM $MGCl_2$, pH 7.6)

Reduction=95 μL of 10 ng/μL+5 μL β-mercaptoethanol

B) Ricin variants

Reduction=40 μL variant+2 μL β-mercaptoethanol

The ricin standard and the variants were incubated for 30 minutes at room temperature.

Ricin—Rabbit Reticulocyte Lysate Reaction

The required number of 0.5 mL tubes were labelled. (2 tubes for each sample, + and −aniline). To each of the sample tubes 20 μL of 1×endo buffer was added, and 30 μL of buffer was added to the controls. To the sample tubes either 10 μL of 10 ng/μL Ricin or 10 μL of variant was added. Finally, 30 μL of rabbit reticulocyte lysate was added to all the tubes. The samples were incubated for 30 minutes at 30° C. using the thermal block. Samples were removed from the eppendorf tube and contents added into a 1.5 mL tube containing 1 mL of TRIZOL (Gibco). Samples were incubated for 15 minutes at room temperature. After the incubation, 200 μL of chloroform was added, and the sample was vortexed and spun at 12,000 g for 15 minutes at 4° C. The top aqueous layer from the samples was removed and contents added to a 1 mL tube containing 500 μL of isopropanol. Samples were incubated for 15 minutes at room temperature and then centrifuged at 12,000 for 15 minutes at 4° C. Supernatant was removed and the pellets were washed with 1 mL of 70% ethanol. Centrifugation at 12,000 g for 5 minutes at 4° C. precipitated the RNA. All but approximately 20 μL of the supernatant was removed and air dried. Pellets from the other samples (+aniline samples) were dissolved in 20 μL of DEPC treated $ddH_2O$. An 80 μL aliquot of 1 M aniline (distilled) with 2.8 M acetic acid was added to these RNA samples and transferred to a fresh 0.5 mL tube. The samples were incubated in the dark for 3 minutes at 60° C. RNA was precipitated by adding 100 μL of 95% ethanol and 5 μL of 3M sodium acetate, pH 5.2 to each tube and centrifuging at 12,000 g for 30 minutes at 4° C. Pellets were washed with 1 mL 70% ethanol and centrifuged again at 12,000 g for 5 minutes at 4° C. to precipitate RNA. The supernatant was removed and air dried. These pellets were dissolved in 10 μL of 0.1×E buffer. To all samples, 10 μL of formamide loading dye was added. The RNA ladder (8 μL of ladder+8 μL of loading dye) was also included. Samples were incubated for 2 minutes at 70° C. on the thermal block. Electrophoresis was carried out on the samples using 1.2% agarose, 50% formamide gels in 0.1×E buffer+0.2% SDS. The gel was run for 90 minutes at 75 watts. RNA was visualized by staining the gel in 1 μg/μL ethidium bromide in running buffer for 45 minutes. The gel was examined on a 302 nm UV box, photographed using the gel documentation system and saved to a computer disk.

Results:

Protein Expression Yields

Aliquots were taken at each stop of the harvesting/purification and tested. Yields of functional ricin variant were determined by ELISA. Typical results of an 2400 mL prep of infected *T. ni* cells are given below.

| Aliquot | μg pAP 220 |
|---|---|
| Before concentration and dialysis | 6000 |
| After concentration and dialysis | 4931 |
| alpha-Lactose agarose column flow through | 219 |
| alpha-Lactose agarose column elution | 1058 |

Yield: 1058/6000 = 17.6%

Purification of pAP-Protein and Western Analysis of Column Fractions

Partially purfied pAP-protein was applied to Superdex 75 and 200 (16/60) columns connected in series in order to remove the contaminating non-specifically processed pAP-protein. Eluted fractions were tested via Western analysis as described above and the fractions containing the most pure protein were pooled, concentrated and re-applied to the column. The variant was applied a total of three times to the column. Final purified pAP-protein has less than 1% processed variant.

The purified pAP-protein was tested for susceptibility to cleavage by the particular protease and for activation of the A-chain of the pro-ricin variant, (inhibition of protein synthesis). Typically, pAP-protein was incubated with and without protease for a specified time period and then electrophoresed and blotted. Cleaved pAP will run as two 30 kDa proteins (B is slightly larger) under reducing (SDS-PAGE) conditions. Unprocessed pAP-protein, which contains the linker region, will run at 60 kDa.

Activation of pAP-Protein Variant with Specific Protease

Activation of protease treated pAP-protein is based on the method of May et al. (EMBO Journal. 8 301-8, 1989).

Activation of ricin A chain upon cleavage of the intermediary linker results in catalytic depurination of the adenosine 4325 residue of 28S or 26S rRNA. This depurination renders the molecule susceptible to amine-catalyzed hydrolysis by aniline of the phosphodiester bond on either side of the modification site. The result is a diagnostic 390 base band. As such, reticulocyte ribosomes incubated with biochemically purified ricin A chain, released the characteristic RNA fragment upon aniline treatment of isolated rRNA (May, M. J. et al. Embo. Journal, 8:301-308 at 302-303 (1989)). It is on this basis that the assay allows for the determination of activity of a ricin A chain which has been cleaved from the intact unit containing a particular variant linker sequence.

Example 3

In Vitro Protease Digestion of Proricin Variants:

Affinity-purified proricin variant is treated with individual disease-specific proteases to confirm specific cleavage in the linker region. Ricin-like toxin variants are eluted from the lactose-agarose matrix in protease digestion buffer (50 mM NaCl, 50 mM Na-acetate, pH 5.5, 1 mM dithiothreitol) containing 100 mM lactose. Proricin substrate is then incubated at 37° C. for 60 minutes with a disease-specific protease. The cleavage products consisting ricin A and B chains are identified using SDS/PAGE (Sambrook et al., Molecular Cloning: a Laboratory Manual, 2nd. ed., Cold Spring Harbor Press, 1989), followed by Western blot analysis using anti-ricin antibodies (Sigma).

Cathepsin B may be obtained from Medcor or Calbiochem. Matrix metalloproteinases may be prepared substantially as described by Lark, M. W. et al. (*Proceedings of the 4th International Conference of the Imflammation Research Association* Abstract 145 (1988)) and Welch, A. R. et al. (*Arch. Biochem. Biophys*. 324:59-64 (1995)). *Candida* acid protease may be prepared substantially as described in Remold, H. H. et al. (*Biochim. Biophys. Acta* 167:399-406 (1968)), Ray, T. L. and Payne, C. D. (*Infect. Immunol*. 58:508-514 (1990)) and Fusek, M. et al. (*FEBS Lett*. 327: 108-112 (1993)). Hepatitis A protease may be prepared as described in Jewell, D. A. et al. (*Biochemistry* 31:7862-7869 (1992)). *Plasmodium* proteases may be prepared as described in Goldberg, D. E. et al. (*J. Exp. Med*. 173:961-969 (1991)) and Cooper, J. A. and Bujard, H. (*Mol. Biochem. Parasitol*. 56:151-160 (1992)).

In Vitro Cytotoxicity Assay:

Human ovarian cancer cells (e.g. MA148) are seeded in 96-well flat-bottom plates and are exposed to ricin-like toxin variants or control medium at 37° C. for 16 h. The viability of the cancer cells is determined by measuring [$^{35}$S]methionine incorporation and is significantly lower in wells treated with the toxin variants than those with control medium.

In Vivo Tumour Growth Inhibition Assay:

Human breast cancer (e.g. MCF-7) cells are maintained in suitable medium containing 10% fetal calf serum. The cells are grown, harvested and subsequently injected subcutaneously into ovariectomized athymic nude mice. Tumour size is determined at intervals by measuring two right-angle measurements using calipers. In animals that received ricin-like toxin variants containing the matrix metalloproteinase-sensitive linkers, tumour size and the rate of tumour growth are lower than animals in the control group.

In Vivo Tumour Metastasis Assay:

The metastasis study is performed substantially as described in Honn, K. V. et al. (*Biochem. Pharmacol*. 34:235-241 (1985)). Viable B16a melanoma tumour cells are prepared and injected subcutaneously into the left axillary region of syngeneic mice. The extent of tumour metastasis is measured after 4 weeks. The lungs are removed from the animals and are fixed in Bouin's solution and macroscopic pulmonary metastases are counted using a dissecting microscope. In general without therapeutic intervention, injection of $10^5$ viable tumour cells forms approximately 40-50 pulmonary metastases. The number of metastases in animal treated with proricin variants containing cathepsin B-sensitive linkers is substantially lower.

Example 4

In Vitro Protease Digestion of Proricin Variants by Cancer Proteases Cathepsin B or MMP-9

The general protocol for proricin digestion by cancer proteases is described in Examples 2 and 3.

In Vitro Protease Digestion of Cathepsin B Proricin Variant

Affinity-purified mutant proricin is treated with individual disease-specific proteases to confirm specific cleavage in the linker region. The proricin substrate is digested in a Cathepsin B protease buffer (50 mM Sodium acetate, 2 mM EDTA, 0.05% Triton) at 40° C. Two hours and overnight (16 hr) digestion reactions are carried out using 100 ng of proricin substrate and 100 and 618 ng of Cathepsin B protease per reaction (CALBIOCHEM, USA). The cleavage products of proricin (ricin A and B chains) are identified using SDS/PAGE (Sambrook et al., Molecular cloning: a laboratory Manual, 2nd. ed., Cold Spring Harbor Press, 1989), followed by Western blot analysis using anti-ricin antibodies (Sigma).

In Vitro Protease Digestion of MMP-9 Proricin Variant

Affinity-purified mutant proricin is treated with individual disease-specific proteases to confirm specific cleavage in the linker region. The proricin substrate is digested in 1× column buffer (100 mM NaCl, 50 mM Tris, PH 7.5) at 37° C. Two hours and overnight (16 hr) digestion reactions are set up using 50 ng of MMP-9 proricin substrate and 20 and 200 ng of MMP-9 protease per reaction (CALBIOCHEM, USA). The cleavage products of proricin (ricin A and B chains) are identified using SDS/PAGE (Sambrook et al., Molecular cloning: a laboratory Manual, 2nd. ed., Cold Spring Harbor Press, 1989), followed by Western blot analysis using anti-ricin antibodies (Sigma).

The protocol for Western analysis of ricin chains is described in Example 2.

Results

FIGS. 48 and 49 illustrate Western blots showing the cleavage of the protease-sensitive linkers by cathepsin B (pAP 214) and MMP-9 (pAP 220) respectively. Without protease digestion, the proricin variant appears as a single band at approximately 60 kDa (Lane B of FIG. 48 and Lane A of FIG. 49). Wild type ricin A chain and B chain appear as two disparate bands at approximately 30 kDa (Lane A of FIG. 48 and Lane E of FIG. 49). Increasing extent of proricin cleavage can clearly be observed with increasing protease concentration (Lanes C and D of FIG. 48 and Lanes B-C of FIG. 49).

Example 5

In Vitro Protease Digestion of Various Proricin Variants by Their Corresponding Proteases.

The general protocol for proricin digestion by corresponding proteases was as desribed in Examples 2 and 3 and should be considered in connection with the digestions described below.

Cleavage of pAP-222 Protein with the Matrix Metalloproteinase 2 (MMP-2)

Affinity-purified mutant proricin is treated with individual disease-specific proteases to confirm specific cleavage in the linker region.

The pAP-222 protein sample (1.0 ug) was digested with the MMP-2 protease (1.0 ug) overnight at 37° C. The total volume of the digestion reaction was 21.5 ul, and 0.250 ug of the reaction sample was loaded on a protein gel. The MMP-2 protease was purchased from Calbiochem-Novabiochem Corporation, USA.

Cleavage of pAP-248 Protein with the Human Cytomegalovirus (HCMV) Protease

Affinity-purified mutant proricin is treated with individual disease-specific proteases to confirm specific cleavage in the linker region.

The pAP-248 protein sample (1.19 ug) was digested with the HCMV protease (1.13 ug) overnight at 37° C. The total volume of the digestion was 10.5 ul, and 0.279 ug of the reaction sample was loaded on a protein gel. The HCMV was purchased from BACHEM Bioscience Inc., USA.

Cleavage of pAP-256 Protein with the Hepatitis A Virus 3C (HAV 3C) Protease

Affinity-purified mutant proricin is treated with individual disease-specific proteases to confirm specific cleavage in the linker region.

The pAP-256 protein sample (1.26 ug) was digested with the HAV 3C protease (5 ug) overnight at 37° C. The total volume of the digestion was 12.5 ul, and 0.302 ug of the digestion sample was loaded on a protein gel. The HAV 3C protease was a gift from Dr. G. Lawson from Bates Collage, Me., USA.

Cleavage of pAP-270 Protein with the Matrix Metalloproteinase 2 (MMP-2)

Affinity-purified mutant proricin is treated with individual disease-specific proteases to confirm specific cleavage in the linker region.

The pAP-270 protein sample (0.120 ug) was digested with the MMP-2 protease (0.25 ug) overnight at 37° C. The total volume of the digestion reaction was 22.5 ul, and 0.106 ug of the reaction sample was loaded on a protein gel. The MMP-2 protease was purchased from Calbiochem-Novabiochem Corporation, USA.

Cleavage of pAP-288 Protein with tPA Plasminogen Tissue Activator

Affinity-purified mutant proricin is treated with individual disease-specific proteases to confirm specific cleavage in the linker region. The pAP-288 protein sample (1.65 ug) was digested with the t-PA protease (0.5 ug) overnight at 37° C. The total volume of the digestion reaction was 55 ul, and 0.6 ug of the reaction sample was loaded on a protein gel. The t-PA was purchased from Sigma Chemical Co., USA.

Cleavage of pAP-294 Protein with Human Neutraphil Elastase

Affinity-purified mutant proricin is treated with individual disease-specific proteases to confirm specific cleavage in the linker region.

The pAP-256 protein sample (0.6 ug) was digested with the Elastase protease (5 ug) at 25° C. for one hour. The total volume of the digestion reaction was 52.5 ul, and 0.171 ug of the digestion sample was loaded on a protein gel. The Human Neutrophil Elastase protease was purchased from Cedarlane Laboratories Limited, Canada.

Cleavage of pAP-296 Protein with Calpain

Affinity-purified mutant proricin is treated with individual disease-specific proteases to confirm specific cleavage in the linker region. The pAP-296 protein sample (2.05 ug) was digested with the Calpain protease (10 ug) overnight at 37° C. The total volume of the digestion reaction was 35 ul and 0.761 ug of the reaction sample was loaded on a protein gel. The Calpain protease was purchased from Sigma Chemical Co., USA Results FIGS. 52, 54, 58 & 66 (MMP-2), 60, 64 and 62 show the cleavage of proteases of linkers by HCMV, HAV 3C, MMP-2, t-PA, calpain, and human neutraphil elastase respectively. Without protease digestion, the proricin variants appear as a single band at approximately 60 kDA (Lane A in connection with FIG. 52; Lane B of FIG. 54; Lane A of FIG. 58; Lane B of FIG. 60; and Lane C of FIG. 62; lane B of FIG. 64 and lane B of FIG. 66). Wild type ricin chain A and B appear as two bands at approximately 30 kDA (see for example Lanes C and D of FIG. 52) proricin cleavage can clearly be obvserved with the appearance of 30 kDA bands in connection with the protein which has been digested by the respective protease (see Lane B of FIG. 52; Lane C of FIG. 54; or Lane B of FIG. 58 for examples).

Example 6

In Vitro Translation Assay (Activation by Cancer Proteases Cathepsin B or MMP-9

The general protocol for the rabbit retoculocyte lysate reaction to test the cytotoxicity of cancer protease-activiated proricin is described briefly in Example 3 and is described in more detail in Example 2.

Results

Activation of pAP 214 and pAP 220 proricin variants by cathepsin B and MMP-9, based on the method of May et al. (EMBO J. 8:301-308, 1989), is illustrated in FIGS. 50 and 51 respectively. The appearance of the 390 base pair product (positive control) is observed in Lane F of FIG. 50 and Lane G of FIG. 51. This 390 base pair product is absent in the negative control lanes. Without cathepsin or MMP-9 activation, no or minimal N-glycosidase activity in the pAP 214 variant (Lanes H to L, FIG. 50) or the pAP 220 variant (Lanes A to E, FIG. 51) was observed. When the pAP 214 variant and the pAP 220 variant were activated by cathepsin or MMP-9 respectively, appearance of the 390 base pair product was observed in a proricin concentration-dependent manner (Lanes A to E of FIG. 50 and Lanes H to L of FIG. 51). The present experimental series demonstrated the successful and selective activation of proricin variants by cancer-associated proteases.

Example 7

The general protocol for the rabbit retoculocyte lysate reaction is described briefly in Example 3 and is described in more detail in Example 2, all of which compliments the description below.

Depurination of Rabbit Reticulocyte 28S Ribosomal RNA by Digested and Undigested Ricin Variants Affinity-purified mutant proricin mutants which were previously digested with the disease-specific protease, were reduced with 5% 2-mercaptoethanol then diluted to 10 ng, 14.2 ng, 2.0 ng, 291 pg, and 41.7 pg with 1×ENDO buffer(25 mM Tris pH 7.6, 25 mM KCl, 5 mM $MgCl_2$) and incubated with rabbit reticulocyte lysate, untreated (Promega) for 30 minutes at 30° C. To compare the digested with the undigested proricin variant, the proricin in digestion buffer (according to the specific digestion protocol) was treated in the same manner as the digested sample. As a positive and negative control, 10 ng of ricin A chain and 1×ENDO buffer consecutively, was incubated with rabbit reticulocyte lysate, untreated, for 30 mm at 30° C.

Aniline Cleavage of rRNA and Gel Fractionation

Total RNA was then extracted from reticulocyte lysate translation mixtures with Trizol reagent (Gibco-BRL) as per manufacturer's instructions. The RNA was incubated with 80 ul of 1M aniline (distilled) with 2.8M acetic acid for 3 min at 60° C. in the dark. Ethanol-precipitated RNA samples were dissolved in 20 ul of 50% formamide, 0.1×E buffer (3.6 mM Tris, 3 mM NaH2PO4, 0.2 mM EDTA), and 0.05% xylene cyanol. 10 ul of this was heated to 70° C. for 2 minutes, loaded and electrophoresed in 1.2% agarose, 0.1×E buffer, and 50% formamide gel with RNA running buffer (0.1×E buffer, 0.2% SDS).

Results

Activation of pAP-248 proricin variant by HCMV; pAP-256 by HAV3C protease; pAP-270 by MMP-2 protease; pAP-288 by t-PA protease; pAP-294 by human neutrophil elastase; pAP-296 by calpain; and pAP-222 by MMP-2 is illustrated in FIGS. 52, 55, 59, 61, 63, 65, and 67 respectively. The appearance of the 390 base pair product (deposit of control) is obverved in lane L of FIG. 53, 55, 61, 63, 65 and 67. The 390 base pair product is observed in lane A of FIGS. 59 (activation of pAP-270 by MMP-2). This 390 base pair product is absent in the negative control lanes. Without the specific protease activation, no or minimal activity is seen in the lanes which contained only the proricin variant without digestion (see lane A, B, C, D, and E of FIGS. 53, 55, 61, 63, 65, and 67). The same observation is made in connection with pAP-270 in FIG. 59, however, the undigested lanes appear as H, I, J, K and L. When the variant was activated by its respective protease, there is an appearance of the 390 base pair product in a proricin concentration-dependent manner (see Lanes H, I, J, K and L of FIGS. 53, 55, 61, 63, 65, and 67 and Lanes A, B, C, D, and E of FIG. 59). The present experimental series demonstrate the successful and selective activation of the identified proricin variants by selective corresponding proteases.

Example 8

Procedure for Examining the Cytotoxicity of Ricin and Ricin Variants on the COS-1 Cell Line Cell Preparation After washing with 1×PBS (0.137 M NaCl, 2.68 mM KCl, 8.10 mM $Na_2HPO_4$, 1.47 mM $KH_2PO_4$), cells in log phase growth were removed from plates with 1× trypsin/EDTA (Gibco/BRL). The cells were centrifuged at 1100 rpm for 3 mm, resuspended in Dulbecco's Modified Eagle Medium containing 10% FBS and 1× pen/strep, and then counted using a haemocytometer. They were adjusted to a concentration of $5\times10^4$ cells·ml$^{-1}$. One hundred microliters per well of cells was added to wells 2B-2G through to wells 9B-9G of a Falcon 96 well tissue culture plate. A separate 96 well tissue culture plate was used for each sample of Ricin or Ricin variant. The plates were incubated at 37° C. with 5% $CO_2$ for 24 hours.

Toxin Preparation

The Ricin and Ricin variants were sterile filtered using a 0.22 μm filter (Millipore). The concentration of the sterile samples were then quantified by $A_{280}$ and confirmed by BCA measurements (Pierce). For the variants digested with the protease in vitro, the digests were carried out as described in the digestion procedure for each protease. The digests were then diluted in the 1000 ng·ml$^{-1}$ dilution and sterile filtered. The Ricin and the undigested pAP214 in the pAP 214 cytotoxicity data were treated in the same manner but without the Cathepsin B treatment. Ricin and Ricin variants were serially diluted to the following concentrations: 1000 ng·ml$^{-1}$, 100 ng·ml$^{-1}$, 10 ng·ml$^{-1}$, 1 ng·ml$^{-1}$, 0.1 ng·ml$^{-1}$, 0.01 ng·ml$^{-1}$, 0.001 ng·ml$^{-1}$ with media containing 10% FBS and 1× pen/strep.

Application of Toxin or Variants to Plates

Columns 2 to 9 were labeled: control, 1000 ng·ml−1, 100 ng·ml$^{-1}$, 10 ng·ml$^{-1}$, 1 ng·ml$^{-1}$, 0.1 ng·ml$^{-1}$, 0.01 ng·ml$^{-1}$, 0.001 ng·ml$^{-1}$ consecutively. The media was removed from all the sample wells with a multichannel pipettor. For each plate of variant and toxin, 50 μl of media was added to wells 2B to 2G as the control, and 50 μl of each sample dilution was added to the corresponding columns. For the pAP220+MMP-9 data, the plates were incubated for one hour at 37° C. with 5% CO2, then washed once and replaced with media, then incubated for 48 hours at 37° C. with 5% $CO_2$. For the pAP 214+Cathepsin B data, the toxin was left on the plates and incubated for 24 hours at 37° C. with 5% $CO_2$, then 50 μl of media was added to the wells with the toxin and incubated for another 24 hours at 37° C. with 5% $CO_2$.

Sample Application

The whole amount of media (and/or toxin)was removed from each well with a multichannel pipettor, and replaced with 100 μl of the substrate mixture (Promega Cell Titer 96 Aqueous Non-Radioactive Cell Proliferation Assay Kit). The plates were incubated at 37° C. with 5% $CO_2$ for 2 to 4 hours, and subsequently read with a Spectramax 340 96 well plate reader at 490 nm. The $IC_{50}$ values were calculated using the GRAFIT software program.

Results

In experiments with pAP-214 and Cathepsin B incubated with COS-1 cells, it may be seen that cells incubated with pAP-214 alone, pAP-214 was ineffective at causing cell death (see FIG. 56). However, the cytotoxicity of pAP-214 digested with Cathepsin B behaves similarly to the ricin control in COS-1 cells. This is also illustrated in FIG. 56. Similarily, the cytotoxicity of undigested pAP-220 when incubated with COS-1 cells is lower than the cytotoxicity observed with COS-1 cells incubated with pAP-220 digested with MMP-9. Indeed the results suggest that the toxicity of digested pAP-220 is greater than that of ricin. (See FIG. 57).

Example 9

Procedure for Examining the Cytotoxicity of Ricin and Ricin Variants on Various Tissue Culture Cell Lines Cell Preparation After washing with 1×PBS (1.37M NaCl, 26.8 mM KCl, 81 mM Na2HPO4, 14.7 mM $KH_2PO_4$), cells in log phase growth were removed from plates with 1× trypsin/EDTA (Gibco/BRL). The cells were centrifuged at 1100 rpm for 3 mm, resuspended in media containing 10% FBS and 1× pen/strep (media used depended on the cell line being tested), and then counted using a haemocytometer. They were adjusted to a concentration of $5\times10^4$ cell·ml$^{-1}$ (faster growing cell lines were adjusted to $2\times10^4$ cells·ml$^{-1}$). One hundred microliters per well of cells was added to wells 2B-2G through to wells 9B-9G of a Falcon 96 well tissue culture plate. A separate 96 well tissue culture plate was used for each sample of Ricin or Ricin variant. The plates were incubated at 37° C. with 5% $CO_2$ for 24 hours.

Toxin Preparation

The Ricin and Ricin variants were sterile filtered using a 0.22 μm filter (Millipore). The concentration of the sterile samples were then quantified by $A_{280}$ and confirmed by a BCA measurement (Pierce). Ricin and Ricin variants were serially diluted to the following concentrations: 3000 ng·ml$^{-1}$, 300 ng·ml$^{-1}$, 30 ng·ml$^{-1}$, 3 ng·ml$^{-1}$, 0.3 ng·ml$^{-1}$, 0.03 ng·ml$^{-1}$, 0.003 ng·ml$^{-1}$ with media containing 10% FBS and 1× pen/strep.

Application of Toxin or Variants to Plates

Columns 2 to 9 were labeled: control, 0.001 ng·ml$^{-1}$, 0.01 ng·ml$^{-1}$, 0.1 ng·ml$^{-1}$, 1 ng·ml$^{-1}$, 10 ng·ml$^{-1}$, 100 ng·ml$^{-1}$, 1000 ng·mL$^{-1}$ consecutively. For each plate of variant and toxin, 50 μl of media was added to wells 2B to 2G as the control, and 50 μL of each sample dilution was added to the corresponding columns containing 100 μl per well of cells (i.e. 50 μl of the 3000 ng·m$^{-1}$ dilution added to the wells B-G in column 9, labeled 1000 ng·ml$^{-1}$). The plates were incubated for 48 hours at 37° C. with 5% $CO_2$.

Sample Application

An amount of 140 μl was removed from each well with a multichannel pipettor, and replaced with 100 μl of the substrate mixture (Promega Cell Titer 96 Aqueous Non-Radioactive Cell Proliferation Assay Kit). The plates were incubated at 37° C. with 5% $CO_2$ for 2 to 4 hours, and subsequently read with a Spectramax 340 96 well plate reader at 490 nm. The $IC_{50}$ values were calculated using the GRAFIT software program.

Results

Referring to Table 2, it may be seen that the survival of cells is correlated with the proricin variant and the cell specific protease produced by the cell type. For example, in the HT1080 cell line, both pAP-214 and pAP-220 required only 2-½ times the amount of ricin to achieve the same level of cytotoxicity. On the other hand, pAP-224 required 193 times the amount of ricin to achieve the same level of cell death. As well, it may be seen that in the cells where expression of Cathepsin D is found, pAP-214 and 220 were more effective at causing cell death than ricin and more effective than pAP-224. Details concerning the various cells types used in these experiments are outlined below.

COS-1 (African Green Monkey Kidney Cells)

This is an SV40 transformed cell line which was prepared from established simian cells CV-1. (Reference: Gluzman, Y. (1975) Cell, 23, 175-182)(ATCC CRL 1650)

HT-1080 Human Fibrosarcoma (ATCC CCL 121) This cell line was shown to produce active MMP-9 in tissue culture. References: Moore et al. (1997) Gynecologic Oncology 65, 83-88.

9L Rat Glioblastoma

Glioblastomas are generally associated with cathepsin B expression. Levels of cathepsin B expression correspond to the extent of progression of malignancy i.e. highest levels for glioblastomas over anaplastic astrocytomas over low-grade gliomas and normal brain tissue. The 9L cell line was provided by Dr. William Jia of the B.C. Cancer Agency. References: Mikkelsen et al. (August 1995) Journal of Neurosurgery 83(2), 285-290. Nakano et al. (1995) J. of Neurosurgery 83(2), 298-307.

MCF-7 Human Breast Cancer Cell Line (Epithilial)

(ATCC CRL 1555) In the absence of estrogen cathepsin B has not been shown to be elevated relative to normal cells. It can be induced with estrogen to produce Cathepsin D. Production of MMP-9 is unknown.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

FULL CITATIONS FOR CERTAIN REFERENCES REFERRED TO IN THE SPECIFICATION

Bever Jr., C. T., Panitch, H. S., and Johnson, K. P. (1994) Neurology 44(4), 745-8. Increased cathepsin B activity in peripheral blood mononuclear cells of multiple sclerosis patients.

Cohen, P., Graves, H. C., Peehl, D. M., Kamarei, M., Giudice, L. C., and Rosenfeld, R. G. (1992) Journal of Clinal Endocrinology and Metabolism 75(4), 1046-53. Prostate-specific antigen (PSA) is an insulin-like growth factor binding protein-3 protease found in seminal plasma.

Conover, C. A. and De Leon, D. D. (1994) J. Biol. Chem. 269(10), 7076-80. Acid activated insulin-like growth factor-binding protein-3 proteolysis in normal and transformed cells. Role of cathepsin D.

Hansen, G., Schuster, A., Zubrod, C., and Wahn, V. (1995) Respiration 62(3), 117-24. Alpha 1-proteinase inhibitor abrogates proteolytic and secretagogue activity of cystic fibrosis sputum.

Muller, H. L., Oh, Y., Gargosky, S. E., Lehrnbecher, T., Hintz, R. L., and Rosenfeld, R. G. (1993) Journal of Clinical Endocrinology and Metabolism 77(5), 1113-9. Concentrations of insulin-like growth factor (IGF)-binding protein-3 (IGFBP-3), IGF, and IGFBP-3 protease activity in cerebrospinal fluid of children with leukemia, central nervous system tumor, or meningitis.

TABLE 1

Table I - Sequence and Location of Oligonucleotide Primers

| Name of Primer | Primer Sequence† | SEQ ID NO: | Corresponds to preproricin nucleotide numbers: (see FIGS. 8-10) |
|---|---|---|---|
| Ricin-109 | 5'- GGAGATGAAACCGGGAGGAAATACTATTGTAAT -3' | 130 | 27 to 59 |
| Ricin-99Eco | 5'- GCGGAATTCCGGGAGGAAATACTATTGTAAT -3' | 131 | 37 to 59 |
| Ricin267 | 5'- ACGGTTTATTTTAGTTGA -3' | 132 | 300 to 317 |
| Ricin486 | 5'- ACTTGCTGGTAATCTGAG -3' | 133 | 519 to 536 |
| Ricin725 | 5'- AGAATAGTTGGGGGAGAC -3' | 134 | 758 to 775 |
| Ricin937 | 5'- AATGCTGATGTTTGTATG -3' | 135 | 970 to 987 |
| Ricin1151 | 5'- CGGGAGTCTATGTGATGA -3' | 136 | 1184 to 1201 |
| Ricin1399 | 5'- GCAAATAGTGGACAAGTA -3' | 137 | 1432 to 1449 |
| Ricin1627 | 5'- GGATTGGTGTTAGATGTG -3' | 138 | 1660 to 1677 |
| Ricin1729C | 5'- ATAACTTGCTGTCCTTTCA -3' | 139 | 1864 to 1846 |
| Ricin1729C Xba | 5'- CGCTCTAGATAACTTGCTGTCCTTTCA -3' | 140 | 1864 to 1846 |

† underlined sequences inserted for subcloning purposes and not included in final preproricin sequences

TABLE 2

Comparative Toxicities to Selected Cell Lines of Ricin and Ricin Provariants

| Cell Line | $IC50_{Ricin}$ (ng/ml) | $\frac{IC50_{pAP214}}{IC50_{Ricin}}$ | $\frac{IC50_{pAP220}}{IC50_{Ricin}}$ | $\frac{IC50_{pAP224}}{IC50_{Ricin}}$ |
|---|---|---|---|---|
| COS-1 | 0.1 | 17 | 22 | 150 |
| HT1080 | 0.5 | 2.46 | 2.14 | 193 |

TABLE 2-continued

Comparative Toxicities to Selected Cell Lines of Ricin and Ricin Provariants

| Cell Line | $IC50_{Ricin}$ (ng/ml) | $\frac{IC50_{pAP214}}{IC50_{Ricin}}$ | $\frac{IC50_{pAP220}}{IC50_{Ricin}}$ | $\frac{IC50_{pAP224}}{IC50_{Ricin}}$ |
|---|---|---|---|---|
| 9L | 10.8 | 1.3 | 1.7 | 32.3 |
| MCF-7 (without estrogen) | 0.09 | 27.8 | 40 | 742 |

I claim:

1. A recombinant protein comprising an A chain of a ricin-like toxin, a B chain of a ricin-like toxin and a heterologous linker amino acid sequence, linking the A and B chains, wherein the linker sequence contains a cleavage recognition site for a cancer associated protease selected from the group consisting of cathepsin B, an Epstein-Barr virus specific protease, a matrix metalloproteinase, cathepsin L, cathepsin D, urokinase-type plasminogen activator, tissue-type plasminogen activator, human prostate-specific antigen, kallikrein, neutrophil elastase, and calpain.

2. The recombinant protein of claim 1 wherein the A chain is ricin A chain, abrin toxin A chain, diphtheria toxin A chain, or Domain II/III of *Pseudomonas* exotoxin.

3. The recombinant protein of claim 1 wherein the A chain is volkensin toxin A chain, cholera toxin A chain, modeccin toxin A chain or shiga toxin A chain.

4. The recombinant protein of claim 1 wherein the B chain is ricin B chain, abrin toxin B chain, diphtheria toxin B chain, or Domain I of *Pseudomonas* exotoxin.

5. The recombinant protein of claim 1 wherein the B chain is volkensin toxin B chain, cholera toxin B chain, modeccin toxin B chain or shiga toxin B chain.

6. The recombinant protein of claim 1, wherein the A chain is ricin A chain, the B chain is ricin B chain, and the heterologous linker contains a cleavage recognition site for a matrix metalloproteinase.

7. The recombinant protein of claim 6, wherein the heterologous linker contains a cleavage recognition site for matrix metalloproteinase-9.

8. The recombinant protein of claim 1, wherein the A chain is ricin A chain, the B chain is ricin B chain, and the heterologous linker contains a cleavage recognition site for human prostate-specific antigen.

9. The recombinant protein of claim 1 having the linker amino acid sequence according to SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 87; SEQ ID NO: 90; SEQ ID NO: 93; SEQ ID NO: 96; SEQ ID NO: 99; SEQ ID NO: 102; SEQ ID NO: 105; SEQ ID NO: 108; SEQ ID NO: 111; SEQ ID NO: 114; SEQ ID NO: 117; SEQ ID NO: 120; SEQ ID NO: 123; or SEQ ID NO: 126.

10. A recombinant protein comprising an A chain of a ricin-like toxin, a B chain of a ricin-like toxin and a heterologous linker amino acid sequence, linking the A and B chains, wherein the linker sequence contains a cleavage recognition site for a viral protease selected from the group consisting of human cytomegalovirus, human herpes virus, varicella zoster virus, hepatitis A virus, hepatitis C virus and infectious laryngotracheitis virus.

11. The recombinant protein of claim 10 wherein the A chain is ricin A chain, abrin toxin A chain, diphtheria toxin A chain, or Domain II/III of *Pseudomonas* exotoxin.

12. The recombinant protein of claim 10 wherein the A chain is volkensin toxin A chain, cholera toxin A chain, modeccin toxin A chain or shiga toxin A chain.

13. The recombinant protein of claim 10 wherein the B chain is ricin B chain, abrin toxin B chain, diphtheria toxin B chain, or Domain I of *Pseudomonas* exotoxin.

14. The recombinant protein of claim 10 wherein the B chain is volkensin toxin B chain, cholera toxin B chain, modeccin toxin B chain or shiga toxin B chain.

15. The recombinant protein of claim 10, wherein the chain is ricin A chain, the B chain is ricin B chain, and the heterologous linker contains a cleavage recognition site for hepatitis C virus.

16. The recombinant protein of claim 10 having the linker amino acid sequence according to SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 75; SEQ ID NO: 78; SEQ ID NO: 81; or SEQ ID NO: 84.

17. A recombinant protein comprising an A chain of a ricin-like toxin, a B chain of a ricin-like toxin and a heterologous linker amino acid sequence linking the A and B chains, wherein the linker sequence contains a cleavage recognition site for a *Candida* acid protease.

18. The recombinant protein of claim 17 wherein the A chain is ricin A chain, abrin toxin A chain, diphtheria toxin A chain, or Domain II/III of *Pseudomonas* exotoxin.

19. The recombinant protein of claim 17 wherein the A chain is volkensin toxin A chain, cholera toxin A chain, modeccin toxin A chain or shiga toxin A chain.

20. The recombinant protein of claim 17 wherein the B chain is ricin B chain, abrin toxin B chain, diphtheria toxin B chain, or Domain I of *Pseudomonas* exotoxin.

21. The recombinant protein of claim 17 wherein the B chain is volkensin toxin B chain, cholera toxin B chain, modeccin toxin B chain or shiga toxin B chain.

22. The recombinant protein of claim 17 having the linker amino acid sequence according to SEQ ID NO: 70; SEQ ID NO: 71; or SEQ ID NO: 72.

23. A recombinant protein comprising an A chain of a ricin-like toxin, a B chain of a ricin-like toxin and a heterologous linker amino acid sequence, linking the A and B chains, wherein the linker sequence contains a cleavage recognition site for a *Plasmodium falciparum* protease.

24. The recombinant protein of claim 23 wherein the A chain is ricin A chain, abrin toxin A chain, diphtheria toxin A chain, or Domain II/III of *Pseudomonas* exotoxin.

25. The recombinant protein of claim 23 wherein the A chain is volkensin toxin A chain, cholera toxin A chain, modeccin toxin A chain or shiga toxin A chain.

26. The recombinant protein of claim 23 wherein the B chain is ricin B chain, abrin toxin B chain, diphtheria toxin B chain, or Domain I of *Pseudomonas* exotoxin.

27. The recombinant protein of claim 23 wherein the B chain is volkensin toxin B chain, cholera toxin B chain, modeccin toxin B chain or shiga toxin B chain.

28. The recombinant protein of claim 23 having the linker amino acid sequence according to SEQ ID NO: 55; SEQ ID NO: 56; SEQ ID NO: 57; SEQ ID NO: 58; or SEQ ID NO: 59.

* * * * *